United States Patent
Cha et al.

(10) Patent No.: US 10,730,812 B2
(45) Date of Patent: Aug. 4, 2020

(54) DOUBLE SPIRO COMPOUND AND ORGANIC LIGHT-EMITTING ELEMENT COMPRISING SAME

(71) Applicant: LG Chem, Ltd., Seoul (KR)

(72) Inventors: Yongbum Cha, Daejeon (KR); Jin Joo Kim, Daejeon (KR); Sang Duk Suh, Daejeon (KR)

(73) Assignee: LG Chem, Ltd. (KR)

( * ) Notice: Subject to any disclaimer, the term of this patent is extended or adjusted under 35 U.S.C. 154(b) by 222 days.

(21) Appl. No.: 15/558,713

(22) PCT Filed: Jul. 5, 2016

(86) PCT No.: PCT/KR2016/007232
§ 371 (c)(1),
(2) Date: Sep. 15, 2017

(87) PCT Pub. No.: WO2017/007213
PCT Pub. Date: Jan. 12, 2017

(65) Prior Publication Data
US 2018/0111887 A1   Apr. 26, 2018

(30) Foreign Application Priority Data

Jul. 7, 2015 (KR) .................. 10-2015-0096574

(51) Int. Cl.
| | | |
|---|---|---|
| *H01L 51/50* | (2006.01) | |
| *C07C 13/72* | (2006.01) | |
| *C07C 211/61* | (2006.01) | |
| *C09K 11/06* | (2006.01) | |
| *C07C 211/54* | (2006.01) | |
| *C07C 211/55* | (2006.01) | |

(Continued)

(52) U.S. Cl.
CPC ............ *C07C 13/72* (2013.01); *C07C 211/54* (2013.01); *C07C 211/55* (2013.01); *C07C 211/61* (2013.01); *C09K 11/06* (2013.01); *H01L 51/50* (2013.01); *H01L 51/52* (2013.01); *H01L 51/56* (2013.01)

(58) Field of Classification Search
None
See application file for complete search history.

(56) References Cited

U.S. PATENT DOCUMENTS

| | | | |
|---|---|---|---|
| 2004/0023060 A1* | 2/2004 | Kim .................. | C07C 13/72 428/690 |
| 2004/0170863 A1* | 9/2004 | Kim .................. | C07C 13/72 428/690 |
| 2004/0251816 A1 | 12/2004 | Leo et al. | |

(Continued)

FOREIGN PATENT DOCUMENTS

| | | |
|---|---|---|
| JP | 2015124207 A | 7/2015 |
| KR | 20020083615 A | 11/2002 |

(Continued)

OTHER PUBLICATIONS

Search report from International Application No. PCT/KR2016/007232, dated Apr. 14, 2017.

*Primary Examiner* — Gregory D Clark
(74) *Attorney, Agent, or Firm* — Lerner, David, Littenberg, Krumholz & Mentlik, LLP

(57) ABSTRACT

The present specification relates to a double spiro structure compound and an organic light emitting device including the same.

16 Claims, 1 Drawing Sheet

(51) Int. Cl.
*H01L 51/52* (2006.01)
*H01L 51/56* (2006.01)

(56) References Cited

U.S. PATENT DOCUMENTS

2007/0018569 A1* 1/2007 Kawamura ........... C07C 211/61
                                                    313/504
2016/0163991 A1   6/2016 Suzuki et al.

FOREIGN PATENT DOCUMENTS

| KR | 2013129543   | * 11/2013 | ............ C09K 11/06 |
| KR | 20130129543 A |  11/2013 | |
| KR | 20140118849 A |  10/2014 | |
| KR | 20150010016 A |  1/2015  | |
| WO | 2003012890 A2 |  2/2003  | |
| WO | 2015009076 A1 |  1/2015  | |
| WO | 2015086108 A1 |  6/2015  | |

* cited by examiner

【FIG. 1】
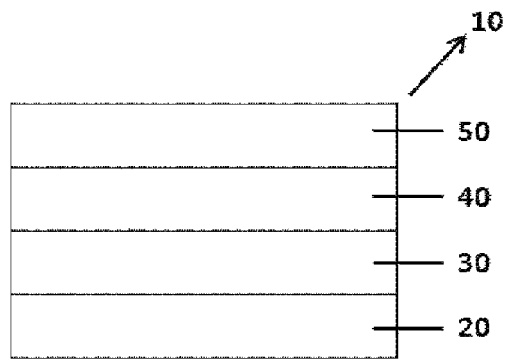
【FIG. 2】
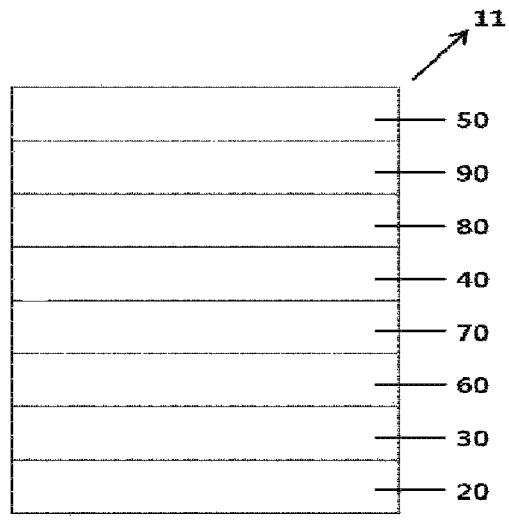

DOUBLE SPIRO COMPOUND AND ORGANIC LIGHT-EMITTING ELEMENT COMPRISING SAME

The present application is a national phase entry under 35 U.S.C. § 371 of International Application No. PCT/KR2016/007232 filed Jul. 5, 2016, published in Korean, which claims priority from Korean Patent Application No. 10-2015-0096574, filed Jul. 7, 2015, all of which are incorporated herein by reference.

TECHNICAL FIELD

This application claims priority to and the benefits of Korean Patent Application No. 10-2015-0096574, filed with the Korean Intellectual Property Office on Jul. 7, 2015, the entire contents of which are incorporated herein by reference.

The present specification relates to a double spiro structure compound and an organic light emitting device including the same.

BACKGROUND ART

An organic light emission phenomenon generally refers to a phenomenon converting electrical energy to light energy using an organic material. An organic light emitting device using an organic light emission phenomenon normally has a structure including an anode, a cathode, and an organic material layer therebetween. Herein, the organic material layer is often formed in a multilayer structure formed with different materials in order to increase efficiency and stability of the organic light emitting device, and for example, may be formed with a hole injection layer, a hole transfer layer, a light emitting layer, an electron transfer layer, an electron injection layer and the like. When a voltage is applied between the two electrodes in such an organic light emitting device structure, holes and electrons are injected to the organic material layer from the anode and the cathode, respectively, and when the injected holes and electrons meet, excitons are formed, and light emits when these excitons fall back to the ground state.

Development of new materials for such an organic light emitting device has been continuously required.

PRIOR ART DOCUMENTS

Patent Documents

International Patent Application Laid-Open Publication No. 2003-012890

DISCLOSURE

Technical Problem

The present specification provides a double spiro structure compound and an organic light emitting device including the same.

Technical Solution

One embodiment of the present specification provides a double spiro structure compound represented by the following Chemical Formula 1.

[Chemical Formula 1]

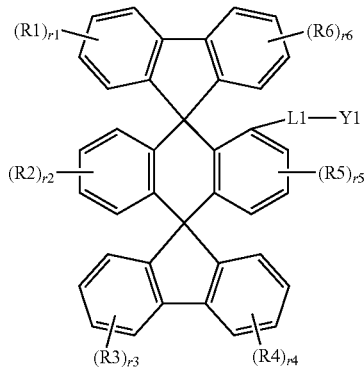

In Chemical Formula 1,

L1 is a direct bond; a substituted or unsubstituted arylene group; or a substituted or unsubstituted heteroarylene group, R1 to R6 are the same as or different from each other, and each independently hydrogen; deuterium; a nitrile group; a nitro group; a hydroxyl group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group, or adjacent groups may bond to each other to form a substituted or unsubstituted ring, Y1 is selected from the group consisting of a substituted or unsubstituted amine group; a substituted or unsubstituted silyl group; a substituted or unsubstituted aryl group; and a substituted or unsubstituted heteroaryl group, r1, r2, r3, r4 and r6 are each an integer of 1 to 4, r5 is an integer of 1 to 3, and when r1, r2, r3, r4, r5 and r6 are each 2 or more, the structures in the two or more parentheses are the same as or different from each other.

Another embodiment of the present specification provides an organic light emitting device including a first electrode; a second electrode provided opposite to the first electrode; and one, two or more organic material layers provided between the first electrode and the second electrode, wherein one or more layers of the organic material layers include the double spiro structure compound represented by Chemical Formula 1.

Advantageous Effects

An organic light emitting device including a double spiro structure compound according to one embodiment of the present specification has excellent thermal stability, and is capable of accomplishing efficiency enhancement, a low driving voltage and/or lifespan property enhancement.

3
DESCRIPTION OF DRAWINGS

FIG. 1 is a diagram showing an organic light emitting device (10) according to one embodiment of the present specification.

FIG. 2 is a diagram showing an organic light emitting device (11) according to another embodiment of the present specification.

MODE FOR DISCLOSURE

Hereinafter, the present specification will be described in more detail.

The present specification provides a double spiro structure compound represented by Chemical Formula 1.

In the present specification, a description of a certain part "including" certain constituents means capable of further including other constituents, and does not exclude other constituents unless particularly stated on the contrary.

In the present specification, a description of one member being placed "on" another member includes not only a case of the one member adjoining the another member but a case of still another member being present between the two members.

In the present specification, examples of the substituents are described below, however, the substituents are not limited thereto.

The term "substitution" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

The term "substituted or unsubstituted" in the present specification means being substituted with one, two or more substituents selected from the group consisting of deuterium; a halogen group; a nitrile group; a nitro group; an imide group; an amide group; a carbonyl group; an ester group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; and a substituted or unsubstituted heterocyclic group, or being substituted with a substituent linking two or more substituents among the substituents illustrated above, or having no substituents. For example, "a substituent linking two or more substituents" may include a biphenyl group. In other words, a biphenyl group may be an aryl group, or interpreted as a substituent linking two phenyl groups.

In the present specification,

means a site bonding to other substituents or bonding sites.

In the present specification, the halogen group may include fluorine, chlorine, bromine or iodine.

In the present specification, the number of carbon atoms of the imide group is not particularly limited, but is preferably from 1 to 30. Specifically, compounds having structures such as below may be included, but the imide group is not limited thereto.

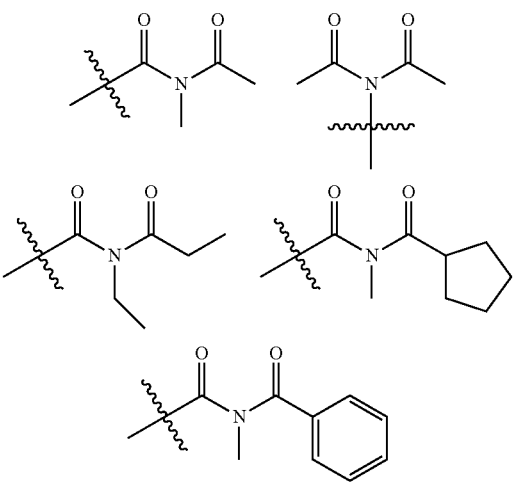

In the present specification, in the amide group, the nitrogen of the amide group may be substituted with hydrogen, a linear, branched or cyclic alkyl group having 1 to 30 carbon atoms or an aryl group having 6 to 30 carbon atoms. Specifically, compounds having the following structural formulae may be included, but the amide group is not limited thereto.

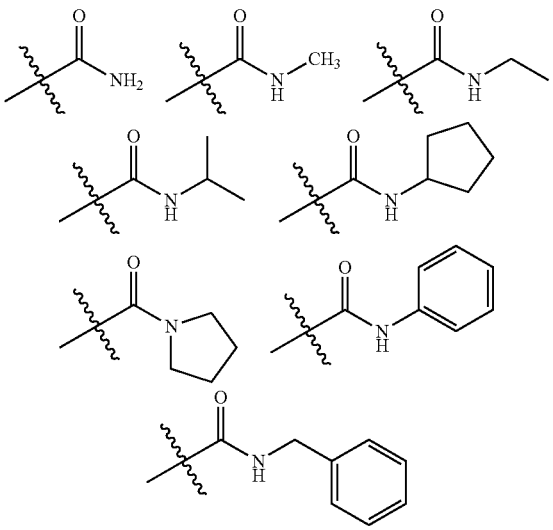

In the present specification, the number of carbon atoms of the carbonyl group is not particularly limited, but is preferably from 1 to 30. Specifically, compounds having structures such as below may be included, but the carbonyl group is not limited thereto.

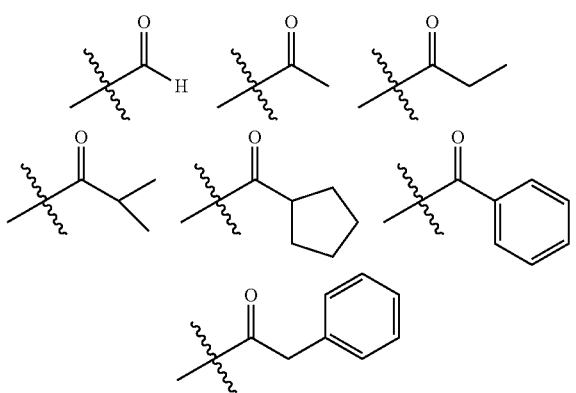

In the present specification, in the ester group, the oxygen of the ester group may be substituted with a linear, branched or cyclic alkyl group having 1 to 25 carbon atoms or an aryl group having 6 to 30 carbon atoms. Specifically, compounds having the following structural formulae may be included, but the ester group is not limited thereto.

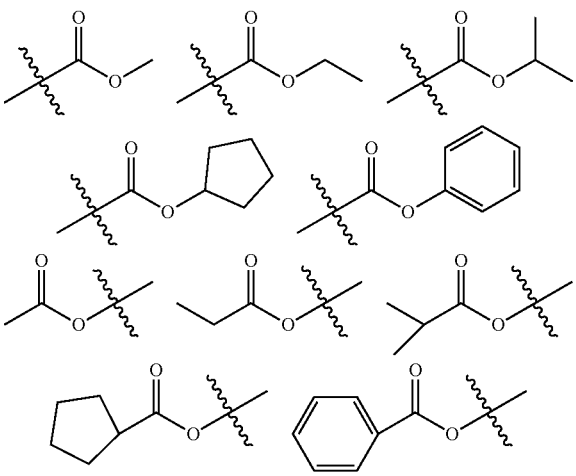

In the present specification, the alkyl group may be linear or branched, and the number of carbon atoms is not particularly limited, but is preferably from 1 to 30. Specific examples thereof may include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl and the like, but are not limited thereto.

In the present specification, the cycloalkyl group is not particularly limited, but preferably has 3 to 30 carbon atoms, and specific examples thereof may include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, the alkoxy group may be linear, branched or cyclic. The number of carbon atoms of the alkoxy group is not particularly limited, but is preferably from 1 to 30. Specific examples thereof may include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benxyloxy, p-methylbenxyloxy and the like, but are not limited thereto.

In the present specification, the amine group may be selected from the group consisting of —$NH_2$; an alkylamine group; an N-alkylarylamine group; an arylamine group; an N-arylheteroarylamine group; an N-alkylheteroarylamine group and a heteroarylamine group, and the number of carbon atoms is, although not particularly limited thereto, preferably from 1 to 30. Specific examples of the amine group may include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, an N-phenylnaphthylamine group, a ditolylamine group, an N-phenyltolylamine group, a triphenylamine group, an N-phenylbiphenylamine group; an N-phenylnaphthylamine group; an N-biphenylnaphthylamine group; an N-naphthylfluorenylamine group; an N-phenylphenanthrenylamine group; an N-biphenylphenanthrenylamine group; an N-phenylfluorenylamine group; an N-phenylterphenylamine group; an N-phenanthrenylfluorenylamine group; an N-biphenylfluorenylamine group and the like, but are not limited thereto.

In the present specification, the N-alkylarylamine group means an amine group in which N of the amine group is substituted with an alkyl group and an aryl group.

In the present specification, the N-arylheteroarylamine group means an amine group in which N of the amine group is substituted with an aryl group and a heteroaryl group.

In the present specification, the N-alkylheteroarylamine group means an amine group in which N of the amine group is substituted with an alkyl group and a heteroaryl group.

In the present specification, the alkyl group in the alkylamine group, the N-arylalkylamine group, the alkylthioxy group, the alkylsulfoxy group and the N-alkylheteroarylamine group is the same as the examples of the alkyl group described above. Specifically, the alkylthioxy group may include a methylthioxy group, an ethylthioxy group, a tert-butylthioxy group, a hexylthioxy group, an octylthioxy group and the like, and the alkylsulfoxy group may include a methylsulfoxy group, an ethylsulfoxy group, a propylsulfoxy group, a butylsulfoxy group and the like, however, the examples are not limited thereto.

In the present specification, the alkenyl group may be linear or branched, and although not particularly limited thereto, the number of carbon atoms is preferably from 2 to 30. Specific examples thereof may include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group and the like, but are not limited thereto.

In the present specification, specific examples of the silyl group may include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the boron group may be —$BR_{100}R_{101}$, and $R_{100}$ and $R_{101}$ are the same as or different from each other, and may be each independently selected from the group consisting of hydrogen; deuterium; halogen; a nitrile group; a substituted or unsubstituted monocyclic or multicyclic cycloalkyl group having 3 to 30 carbon atoms; a substituted or unsubstituted linear or branched alkyl group having 1 to 30 carbon atoms; a substituted or unsubstituted monocyclic or multicyclic aryl group having 6 to 30 carbon atoms; and a substituted or unsubstituted monocyclic or multicyclic heteroaryl group having 2 to 30 carbon atoms.

In the present specification, specific examples of the phosphine oxide group may include a diphenylphosphine oxide group, a dinaphthylphosphine oxide group and the like, but are not limited thereto.

In the present specification, the aryl group is not particularly limited, but preferably has 6 to 30 carbon atoms, and the aryl group may be monocyclic or multicyclic.

When the aryl group is a monocyclic aryl group, the number of carbon atoms is not particularly limited, but is preferably from 6 to 30. Specific examples of the monocyclic aryl group may include a phenyl group, a biphenyl group, a terphenyl group and the like, but are not limited thereto.

When the aryl group is a multicyclic aryl group, the number of carbon atoms is not particularly limited, but is preferably from 10 to 30. Specific examples of the multicyclic aryl group may include a naphthyl group, an anthracenyl group, a phenanthryl group, a triphenyl group, a pyrenyl group, a perylenyl group, a crycenyl group, a fluorenyl group and the like, but are not limited thereto.

In the present specification, the fluorenyl group may be substituted, and adjacent groups may bond to each other to form a ring.

When the fluorenyl group is substituted,

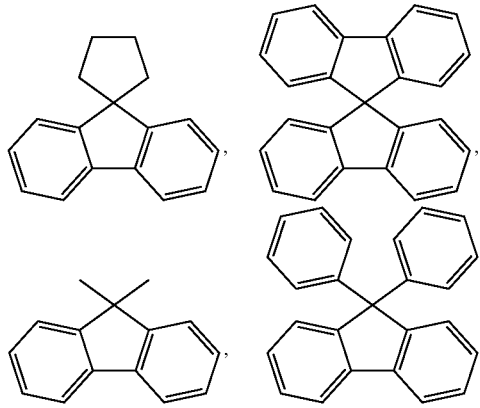

and the like may be included. However, the compound is not limited thereto.

In the present specification, an "adjacent" group may mean a substituent substituting an atom directly linking to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

In the present specification, the aryl group in the aryloxy group, the arylthioxy group, the arylsulfoxy group, the N-alkylarylamine group, the N-arylheteroarylamine group and the arylphosphine group may be same as the examples of the aryl group described above. Specific examples of the aryloxy group may include a phenoxy group, a p-tolyloxy group, a m-tolyloxy group, a 3,5-dimethyl-phenoxy group, a 2,4,6-trimethylphenoxy group, a p-tert-butylphenoxy group, a 3-biphenyloxy group, a 4-biphenyloxy group, a 1-naphthyloxy group, a 2-naphthyloxy group, a 4-methyl-1-naphthyloxy group, a 5-methyl-2-naphthyloxy group, a 1-anthryloxy group, a 2-anthryloxy group, a 9-anthryloxy group, a 1-phenanthryloxy group, a 3-phenanthryloxy group, a 9-phenanthryloxy group and the like, and specific examples of the arylthioxy group may include a phenylthioxy group, a 2-methylphenylthioxy group, a 4-tert-butylphenylthioxy group and the like, and specific examples of the arylsulfoxy group may include a benzenesulfoxy group, a p-toluenesulfoxy group and the like, however, the examples are not limited thereto.

In the present specification, examples of the arylamine group may include a substituted or unsubstituted monoarylamine group, a substituted or unsubstituted diarylamine group, or a substituted or unsubstituted triarylamine group. The aryl group in the arylamine group may be a monocyclic aryl group or a multicyclic aryl group. The arylamine group including two or more aryl groups may include monocyclic aryl groups, multicyclic aryl groups, or both a monocyclic aryl group and a multicyclic aryl group. For example, the aryl group in the arylamine group may be selected from the examples of the aryl group described above.

In the present specification, the heteroaryl group is a group including one or more atoms that are not carbon, that is, heteroatoms, and specifically, the heteroatom may include one or more atoms selected from the group consisting of O, N, Se, S and the like. The number of carbon atoms is not particularly limited, but is favorably from 2 to 30, and the heteroaryl group may be monocyclic or multicyclic. Examples of the heteroaryl group may include a thiophene group, a furanyl group, a pyrole group, an imidazolyl group, a triazolyl group, an oxazolyl group, an oxadiazolyl group, a pyridyl group, a bipyridyl group, a pyrimidyl group, triazinyl group, a triazolyl group, an acridyl group, a pyridazinyl group, a pyrazinyl group, a qinolinyl group, a quinazolinyl group, a quinoxalinyl group, a phthalazinyl group, a pyridopyrimidyl group, a pyridopyrazinyl group, a pyrazinopyrazinyl group, an isoquinolinyl group, an indolyl group, a carbazolyl group, a benzoxazolyl group, a benxzimidazolyl group, a benzothiazolyl group, a benzocarbazolyl group, a benzothiophene group, a dibenzothiophene group, a benzofuranyl group, a phenanthrolinyl group, an isoxazolyl group a thiadiazolyl group, a phenothiazinyl group, a dibenzofuranyl group and the like, but are not limited thereto.

In the present specification, examples of the heteroarylamine group may include a substituted or unsubstituted monoheteroarylamine group, a substituted or unsubstituted diheteroarylamine group, or a substituted or unsubstituted triheteroarylamine group. The heteroarylamine group including two or more heteroaryl groups may include monocyclic heteroaryl groups, multicyclic heteroaryl groups, or both a monocyclic heteroaryl group and a multicyclic heteroaryl group. For example, the heteroaryl group in the heteroarylamine group may be selected from the examples of the heteroraryl group described above.

In the present specification, examples of the heteroaryl group in the N-arylheteroarylamine group and the N-alkylheteroarylamine group are the same as the examples of the heteroaryl group described above.

In the present specification, the arylene group means an aryl group having two bonding sites, that is, a divalent group. Descriptions on the aryl group made above may be applied except for those that are each a divalent group.

In the present specification, the heteroarylene group means a heteroaryl group having two bonding sites, that is, a divalent group. Descriptions on the heteroaryl group made above may be applied except for those that are each a divalent group.

In the present specification, in a substituted or unsubstituted ring formed by adjacent groups bonding to each other, the "ring" means a substituted or unsubstituted hydrocarbon ring; or a substituted or unsubstituted heteroring.

In the present specification, the hydrocarbon ring may be aromatic, aliphatic or a fused ring of aromatic and aliphatic, and may be selected from the examples of the cycloalkyl group or the aryl group except for those that are not monovalent.

In the present specification, the aromatic ring may be monocyclic or multicyclic, and may be selected from the examples of the aryl group except for those that are not monovalent.

In the present specification, the heteroring is a group including one or more atoms that are not carbon, that is, heteroatoms, and specifically, the heteroatom may include one or more atoms selected from the group consisting of O, N, Se, S and the like. The heteroring may be monocyclic or multicyclic, may be aromatic, aliphatic or a fused ring of aromatic and aliphatic, and may be selected from the examples of the heteroaryl group except for those that are not monovalent.

According to one embodiment of the present specification, in Chemical Formula 1, R1 to R6 are hydrogen.

According to one embodiment of the present specification, Chemical Formula 1 is represented by the following Chemical Formula 1-1.

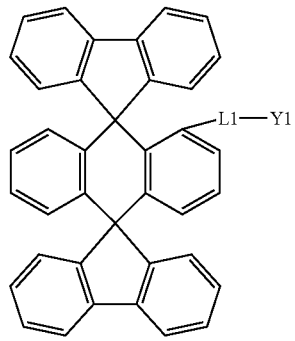

[Chemical Formula 1-1]

In Chemical Formula 1-1,
definitions of L1 and Y1 are the same as in Chemical Formula 1.

According to one embodiment of the present specification, in Chemical Formula 1, Y1 is selected from the group consisting of a substituted or unsubstituted diarylamine group; a substituted or unsubstituted diheteroarylamine group; a substituted or unsubstituted silyl group; a substituted or unsubstituted aryl group; and a substituted or unsubstituted heteroaryl group.

According to one embodiment of the present specification, in Chemical Formula 1, Y1 is selected from the group consisting of a substituted or unsubstituted diarylamine group; a substituted or unsubstituted diheteroarylamine group; a substituted or unsubstituted silyl group; a substituted or unsubstituted monocyclic or multicyclic aryl group having 6 to 30 carbon atoms; and a substituted or unsubstituted monocyclic or multicyclic heteroaryl group having 2 to 30 carbon atoms.

According to one embodiment of the present specification, in Chemical Formula 1, Y1 is selected from the group consisting of a substituted or unsubstituted phenyl group; a substituted or unsubstituted biphenyl group; a substituted or unsubstituted phenanthrenyl group; a substituted or unsubstituted naphthyl group; a substituted or unsubstituted terphenyl group; a substituted or unsubstituted fluorenyl group; a substituted or unsubstituted an anthracenyl group; a substituted or unsubstituted crycenyl group; a substituted or unsubstituted quaterphenyl group; a substituted or unsubstituted spirobifluorenyl group; a substituted or unsubstituted pyrenyl group; a substituted or unsubstituted triphenylenyl group; a substituted or unsubstituted perylenyl group; a substituted or unsubstituted triazinyl group; a substituted or unsubstituted pyrimidyl group; a substituted or unsubstituted pyridyl group; a substituted or unsubstituted quinolinyl group; a substituted or unsubstituted quinazolinyl group; a substituted or unsubstituted benzoquinolinyl group; a substituted or unsubstituted phenanthrolinyl group; a substituted or unsubstituted quinoxalinyl group; a substituted or unsubstituted dibenzofuranyl group; a substituted or unsubstituted dibenzothiophene group; a substituted or unsubstituted benzonaphthofuranyl group; a substituted or unsubstituted benzonaphthothiophene group; a substituted or unsubstituted benzoxazolyl group; a substituted or unsubstituted benzothiazolyl group; a substituted or unsubstituted benzimidazolyl group; a substituted or unsubstituted triphenylsilyl group; a substituted or unsubstituted phenothiazinyl group; a substituted or unsubstituted phenoxazinyl group; a substituted or unsubstituted thiophene group; a substituted or unsubstituted diphenylamine group; a substituted or unsubstituted N-phenylnaphthylamine group; a substituted or unsubstituted N-phenylbiphenylamine group; a substituted or unsubstituted N-phenylphenanthrenylamine group; a substituted or unsubstituted N-biphenylnaphthylamine group; a substituted or unsubstituted dibiphenylamine group; a substituted or unsubstituted N-biphenylphenanthrenylamine group; a substituted or unsubstituted dinaphthylamine group; a substituted or unsubstituted N-quaterphenylfluorenylamine group; a substituted or unsubstituted N-terphenylfluorenylamine group; a substituted or unsubstituted N-biphenylterphenylamine group; a substituted or unsubstituted N-biphenylfluorenylamine group; a substituted or unsubstituted N-phenylfluorenylamine group; a substituted or unsubstituted N-naphthylfluorenylamine group; a substituted or unsubstituted N-phenanthrenylfluorenylamine group; a substituted or unsubstituted difluorenylamine group; a substituted or unsubstituted N-phenylterphenylamine group; a substituted or unsubstituted N-phenylcarbazolylamine group; a substituted or unsubstituted N-biphenylcarbazolylamine group; a substituted or unsubstituted N-phenylbenzocarbazolylamine group; a substituted or unsubstituted N-biphenylbenzocarbazolylamine group; a substituted or unsubstituted N-fluorenylcarbazolylamine group; a substituted or unsubstituted benzocarbazolyl group; a substituted or unsubstituted dibenzocarbazolyl group; a substituted or unsubstituted carbazolyl group; a substituted or unsubstituted

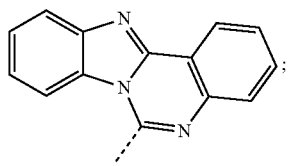
;

a substituted or unsubstituted

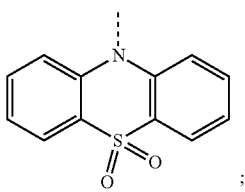
;

and structures represented by the following Chemical Formula a, and

---- means a site bonding to L1 of Chemical Formula 1.

[Chemical Formula a]

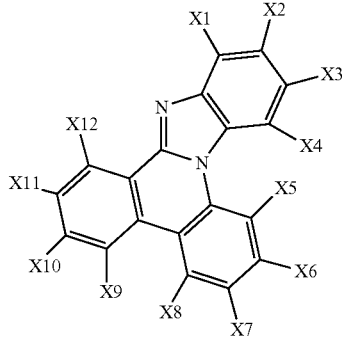

In Chemical Formula a, any one of X1 to X12 is a site bonding to Chemical Formula 1, and the remaining atoms are the same as or different from each other, and each independently hydrogen; a substituted or unsubstituted alkyl group; a substituted or unsubstituted aryl group; or a substituted or unsubstituted heteroaryl group, or adjacent groups bond to each other to form a substituted or unsubstituted ring.

According to one embodiment of the present specification, in Chemical Formula a, any one of X1 to X12 is a site bonding to Chemical Formula 1, and the remaining atoms are hydrogen.

According to one embodiment of the present specification, in Chemical Formula a, X11 and X12 bond to each other to form a substituted or unsubstituted monocyclic or multicyclic hydrocarbon ring having 6 to 20 carbon atoms.

According to one embodiment of the present specification, in Chemical Formula a, X11 and X12 bond to each other to form a substituted or unsubstituted monocyclic or multicyclic hydrocarbon ring having 6 to 10 carbon atoms.

According to one embodiment of the present specification, in Chemical Formula a, X11 and X12 bond to each other to form a substituted or unsubstituted benzene ring.

According to one embodiment of the present specification, in Chemical Formula a, X11 and X12 bond to each other to form a benzene ring.

According to one embodiment of the present specification, in Chemical Formula 1, Y1 is selected from the group consisting of a phenyl group; a biphenyl group; a phenanthrenyl group; a naphthyl group; a terphenyl group; a fluorenyl group; an anthracenyl group; a crycenyl group; a quaterphenyl group; a spirobifluorenyl group; a pyrenyl group; a triphenylenyl group; a perylenyl group; a triazinyl group; a pyrimidyl group; a pyridyl group; a quinolinyl group; a quinazolinyl group; a benzoquinolinyl group; a phenanthrolinyl group; a quinoxalinyl group; a dibenzofuranyl group; a dibenzothiophene group; a benzonaphthofuranyl group; a benzonaphthothiophene group; a benzoxazolyl group; a benzothiazolyl group; a benzimidazolyl group; a triphenylsilyl group; a phenothiazinyl group; a phenoxazinyl group; a thiophene group; a diphenylamine group; an N-phenylnaphthylamine group; an N-phenylbiphenylamine group; an N-phenylphenanthrenylamine group; an N-biphenylnaphthylamine group; a dibiphenylamine group; an N-biphenylphenanthrenylamine group; a dinaphthylamine group; an N-quaterphenylfluorenylamine group; an N-terphenylfluorenylamine group; an N-biphenylterphenylamine group; an N-biphenylfluorenylamine group; a N-phenylfluorenylamine group; an N-naphthylfluorenylamine group; an N-phenanthrenylfluorenylamine group; a difluorenylamine group; an N-phenylterphenylamine group; an N-phenylcarbazolylamine group; an N-biphenylcarbazolylamine group; an N-phenylbenzocarbazolylamine group; an N-biphenylbenzocarbazolylamine group; an N-fluorenylcarbazolylamine group; a benzocarbazolyl group; a dibenzocarbazolyl group; a carbazolyl group;

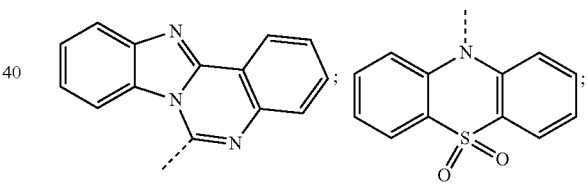

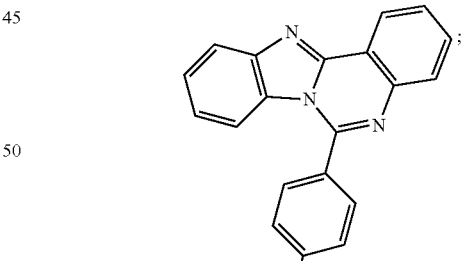

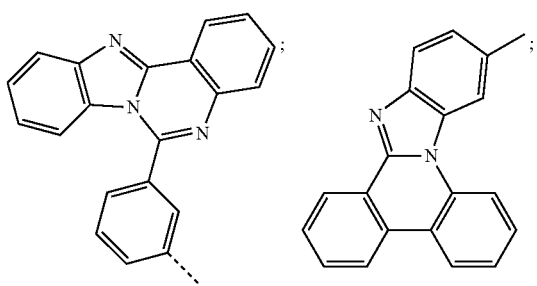

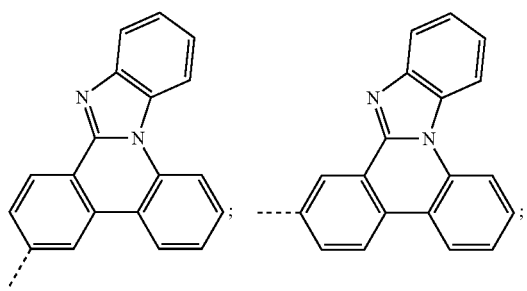

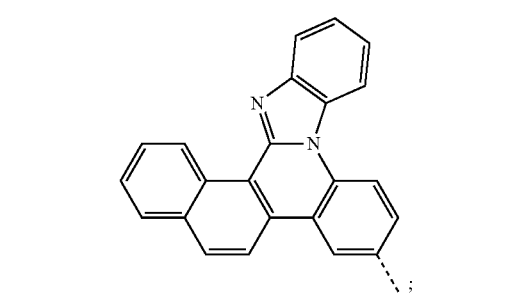

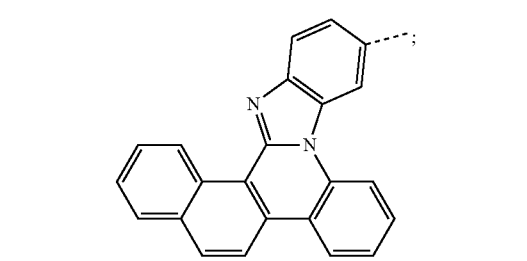

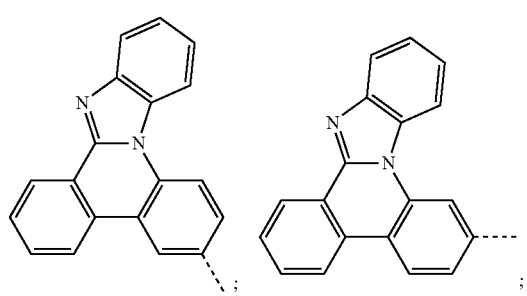

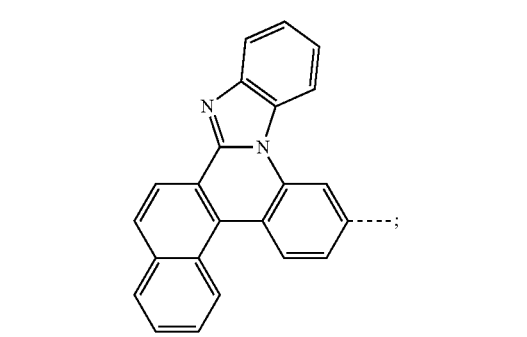

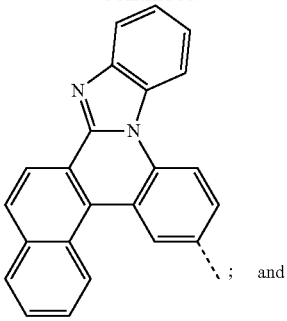

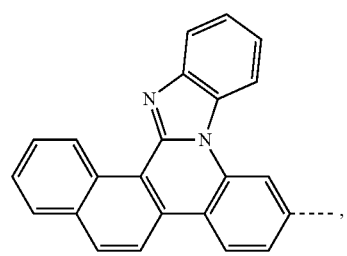

Y1 may be unsubstituted or substituted with one or more selected from the group consisting of deuterium; a fluorine group; a nitrile group; a methyl group; a t-butyl group; a phenyl group; a biphenyl group; a naphthyl group; a fluorenyl group; a phenanthrenyl group; a carbazolyl group; a benzocarbazolyl group; a pyridyl group; a triazinyl group; a triphenylenyl group; a pyrimidyl group; a quinolinyl group; a dibenzofuranyl group; a dibenzothiophene group; a benzimidazolyl group; a benzothiazolyl group; a benzoxazolyl group; a thiophene group; a trimethylsilyl group; a triphenylsilyl group; a diphenylamine group; a dibiphenylamine group; an N-phenylbiphenylamine group; an N-phenylnaphthylamine group; an N-biphenylnaphthylamine group; an N-naphthylfluorenylamine group; an N-phenylphenanthrenylamine group; an N-biphenylphenanthrenylamine group; an N-phenylfluorenylamine group; an N-phenylterphenylamine group; an N-biphenylterphenylamine group; an N-phenanthrenylfluorenylamine group; an N-biphenylfluorenylamine group; and

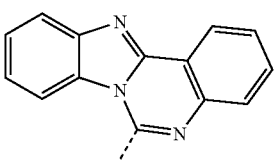

---- means a site bonding to L1 of Chemical Formula 1.

According to one embodiment of the present specification, in Chemical Formula 1, Y1 is represented by any one of the following Structural Formulae [A-1] to [A-5].

[A-1]
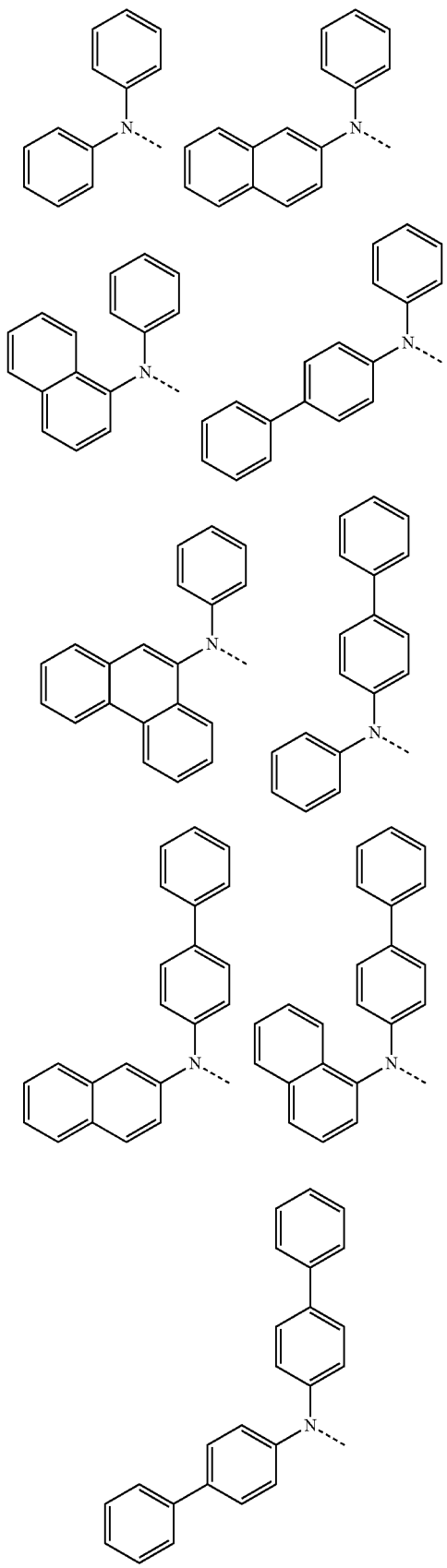
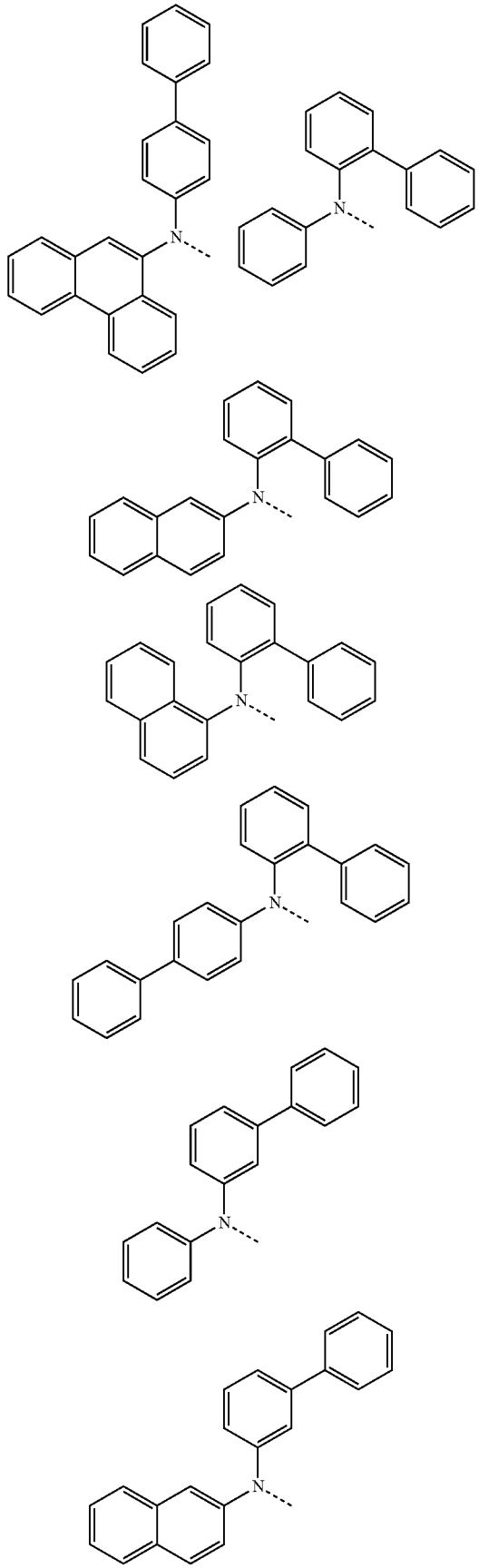
-continued

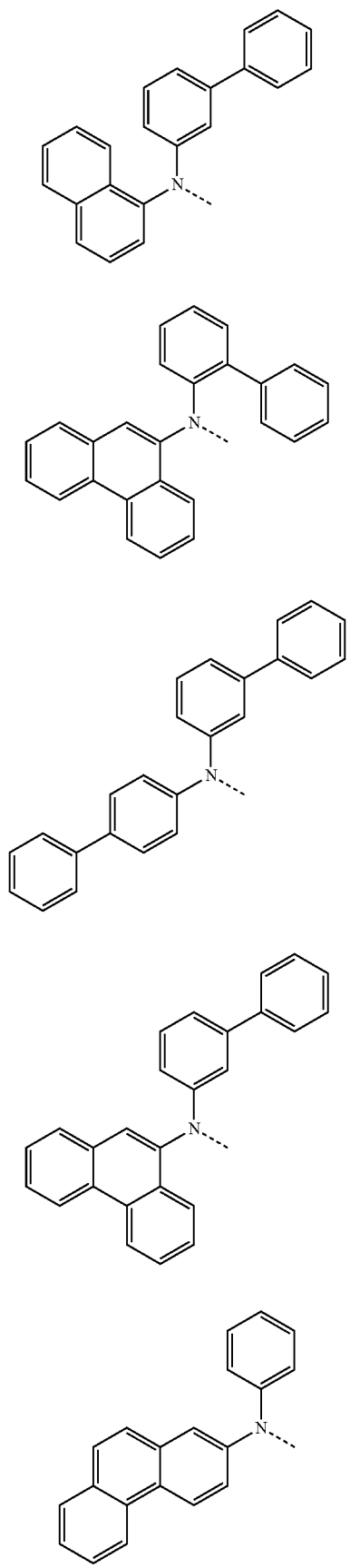
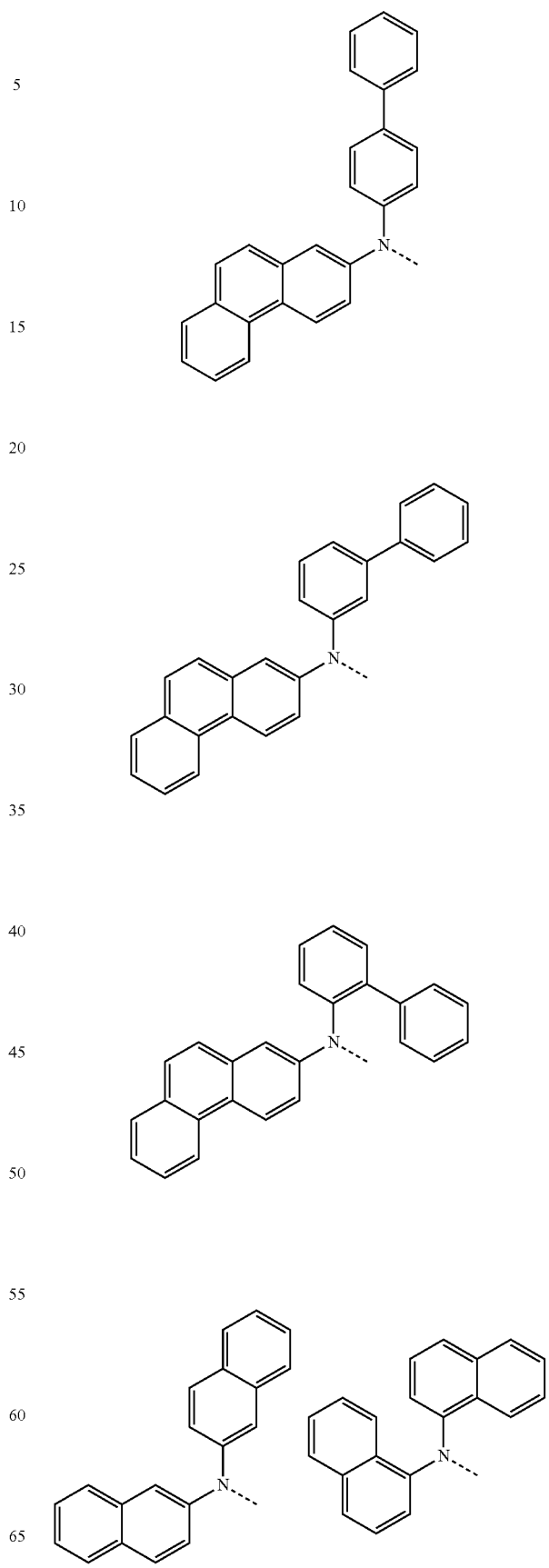

19
-continued
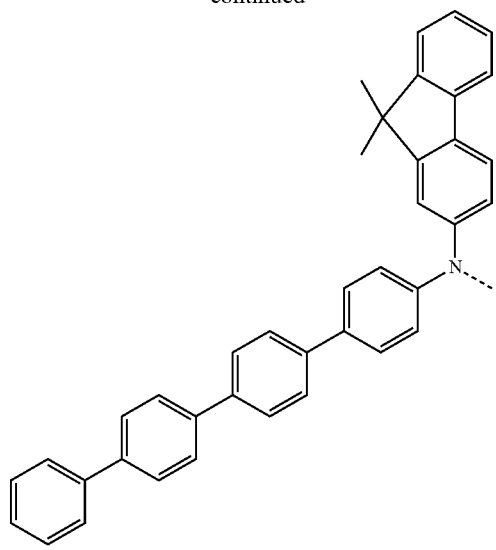
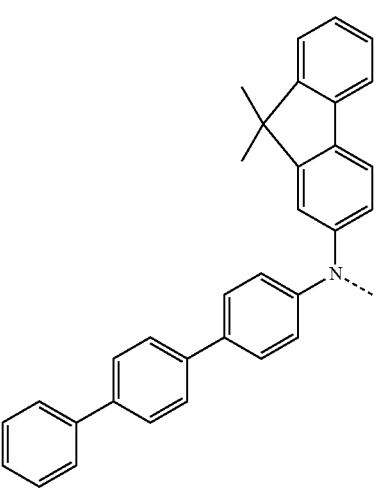
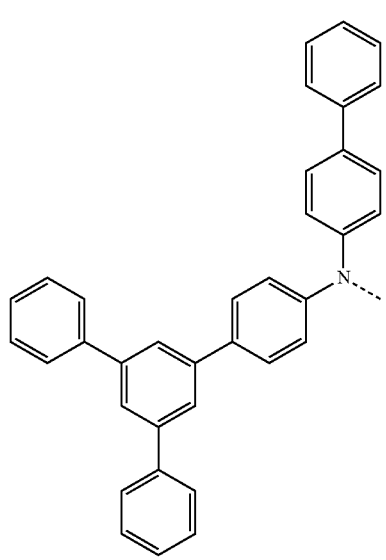
20
-continued
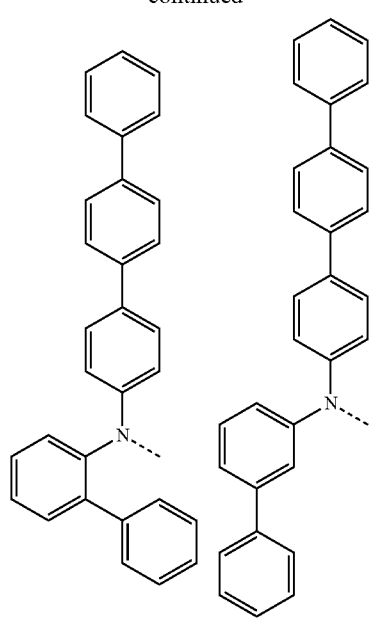
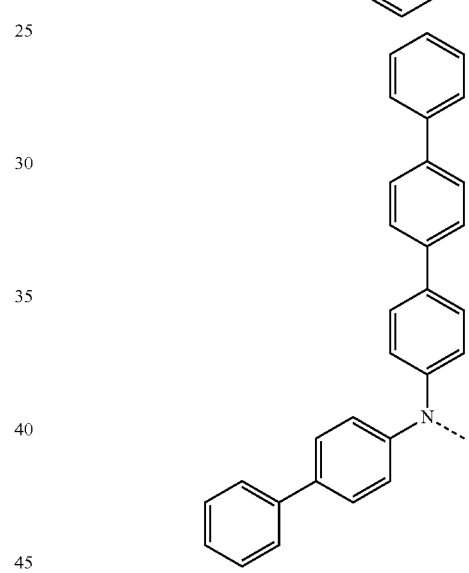
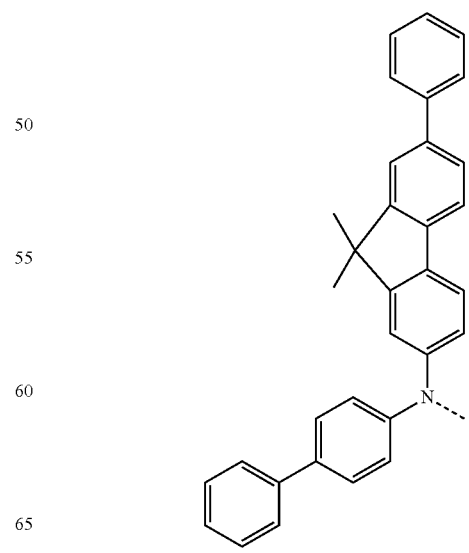

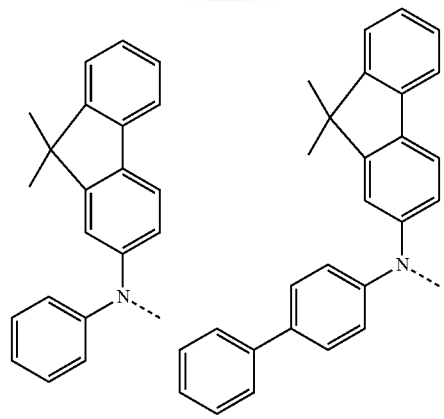
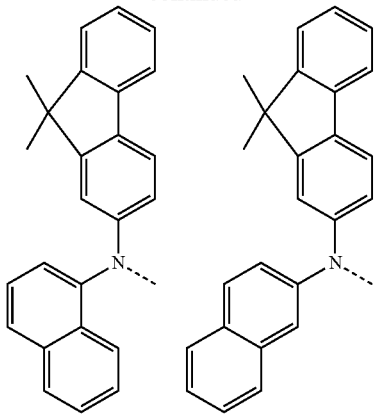
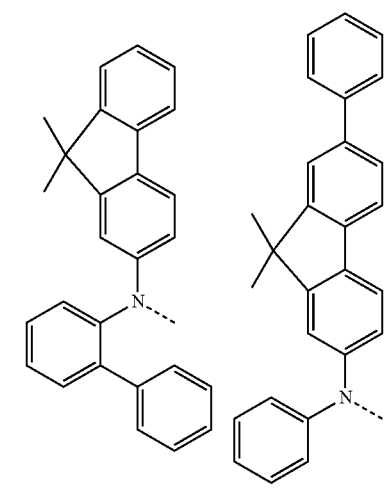
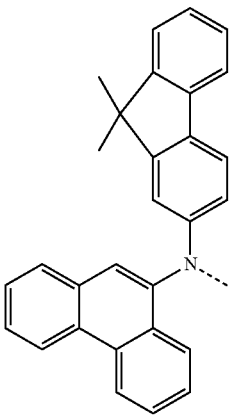
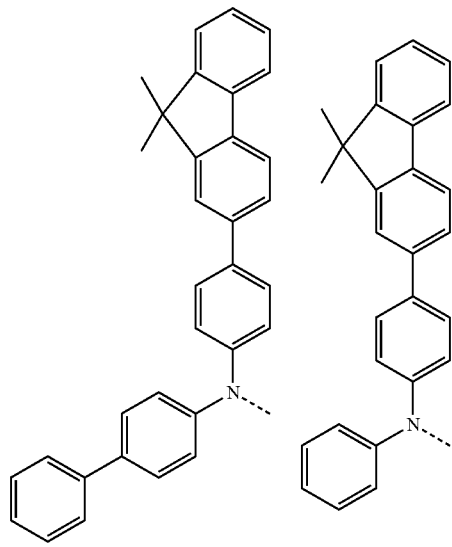
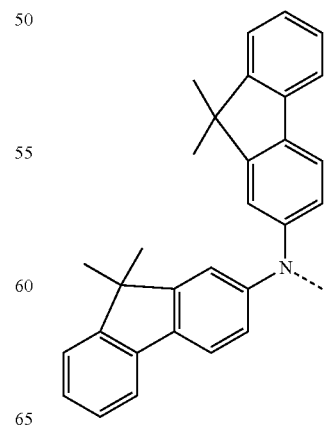
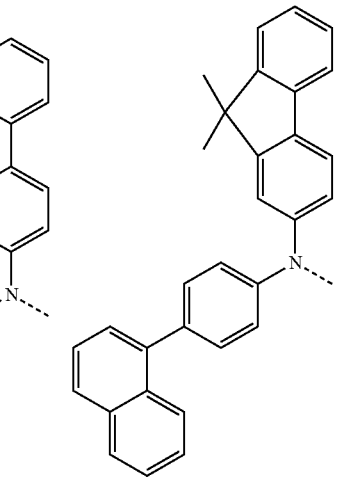

23
-continued
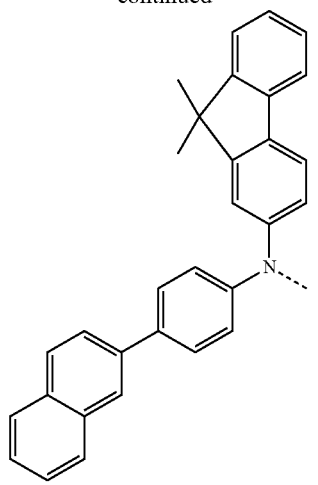
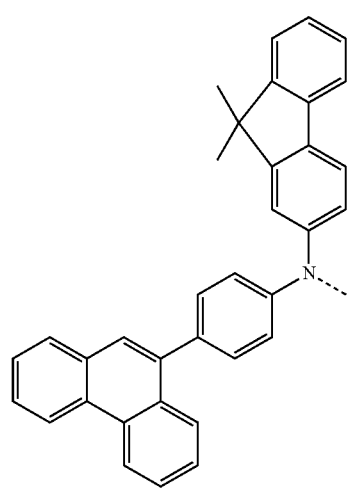
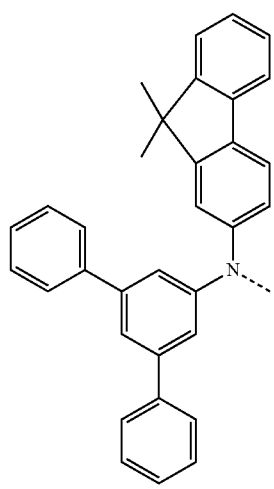
24
-continued
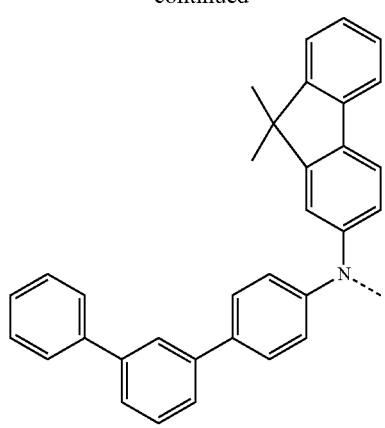
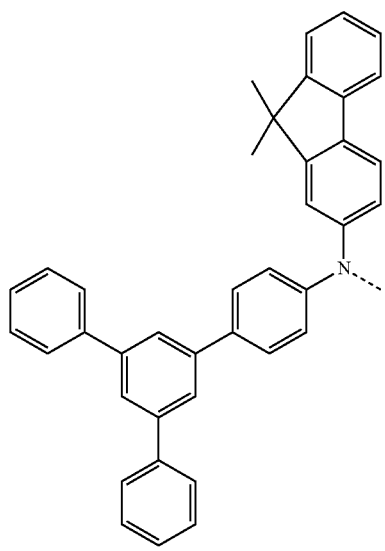
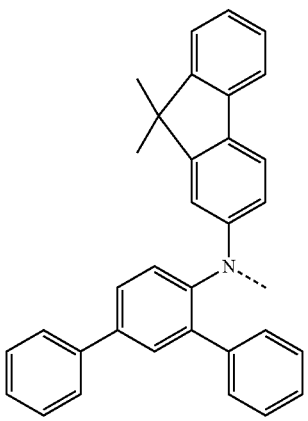


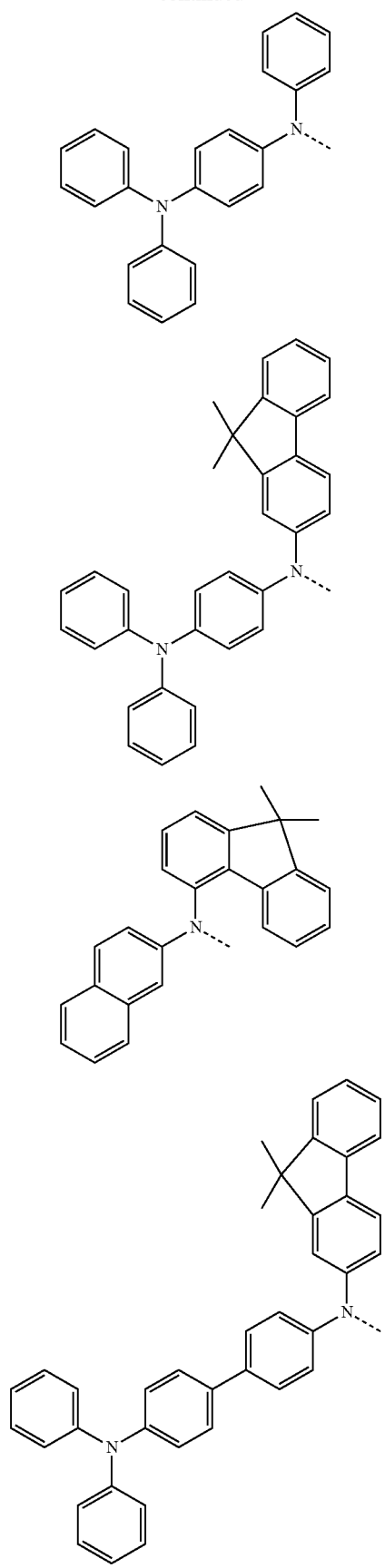
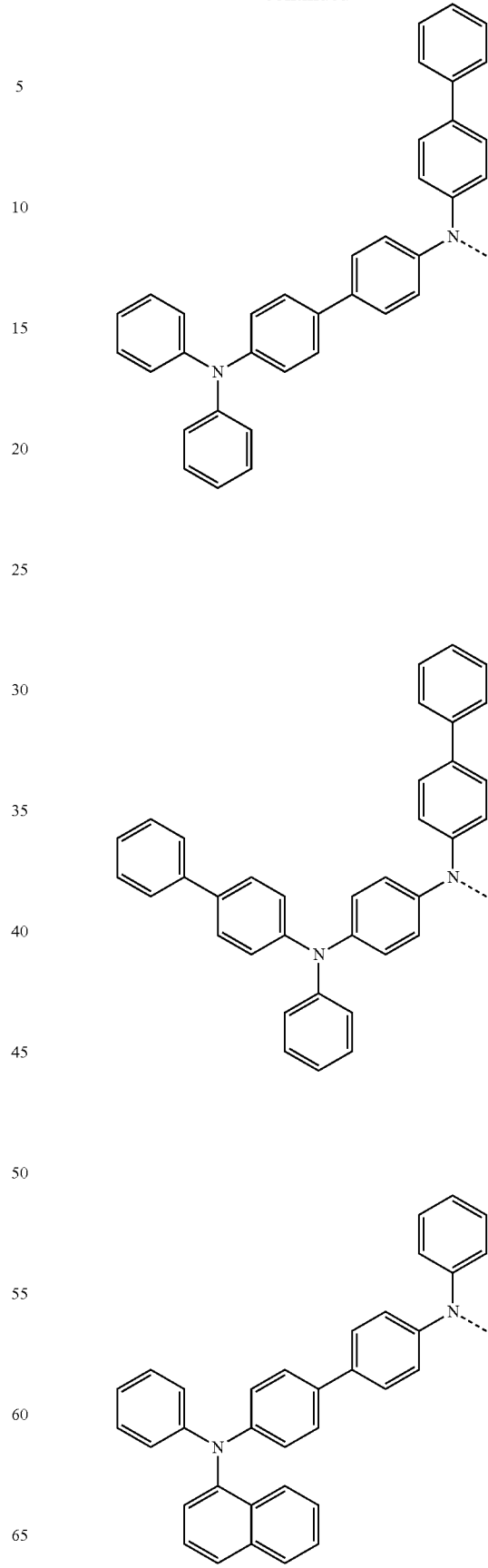

-continued
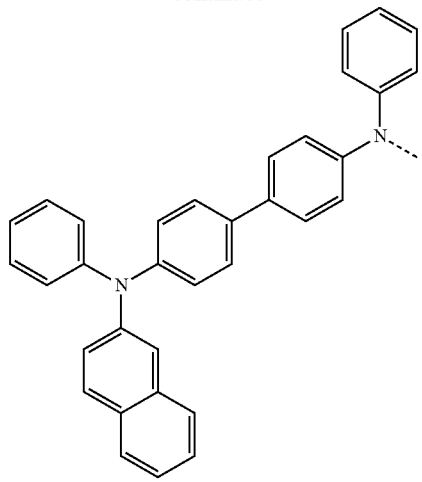
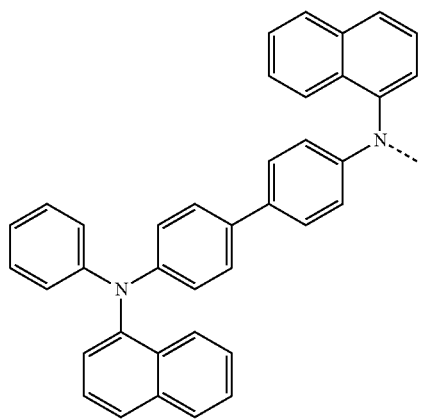
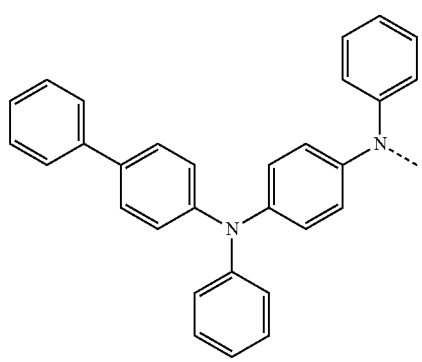
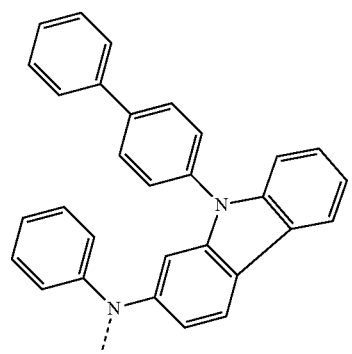
-continued
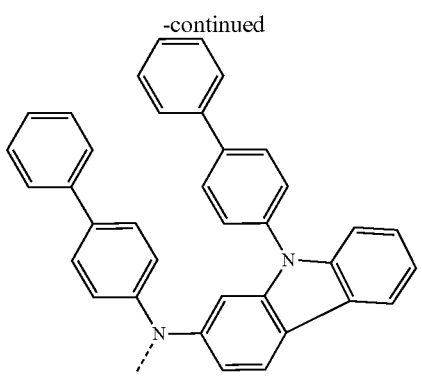
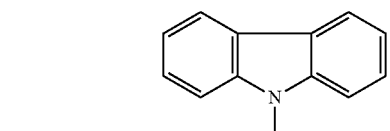
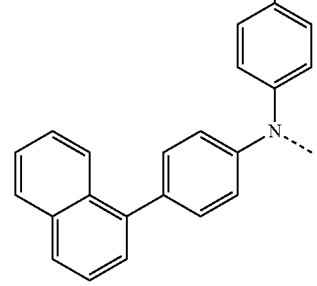
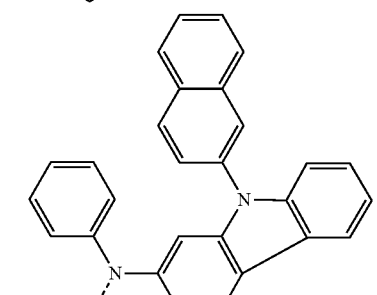
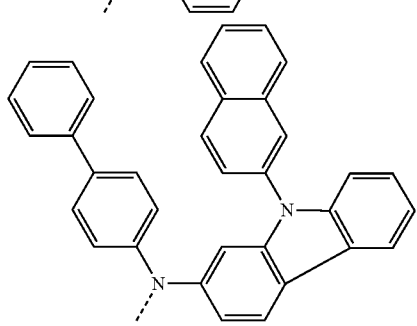
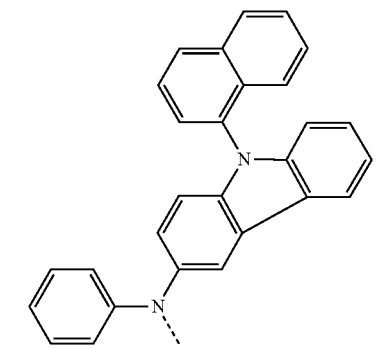

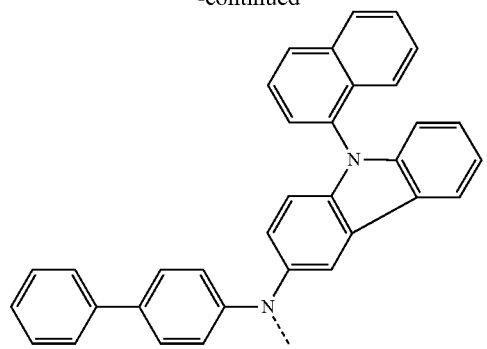
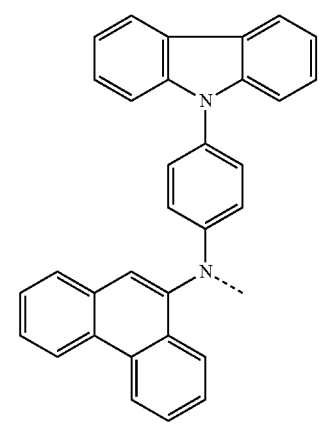
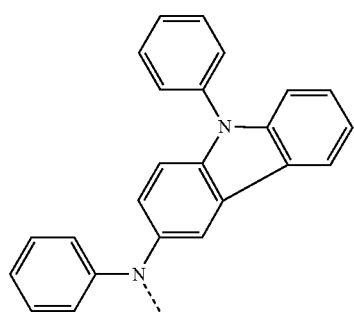
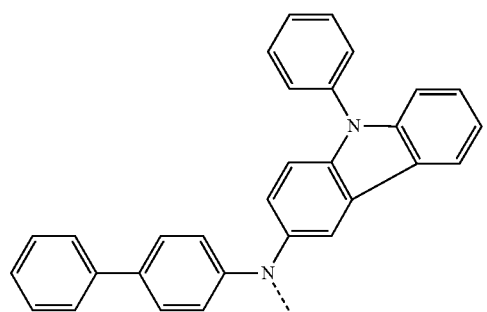
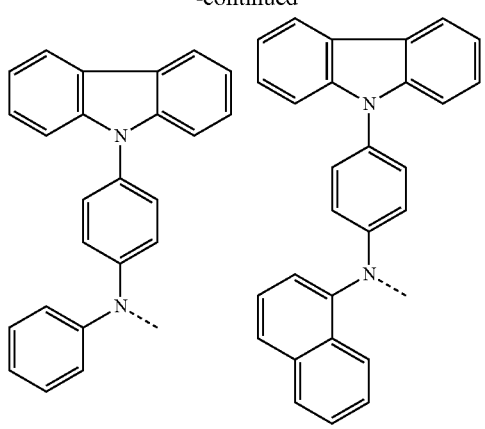
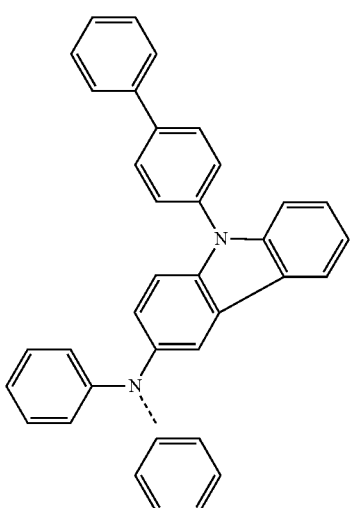
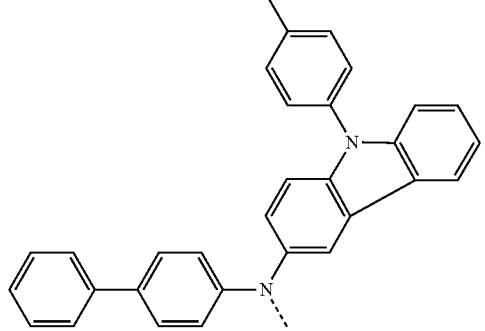
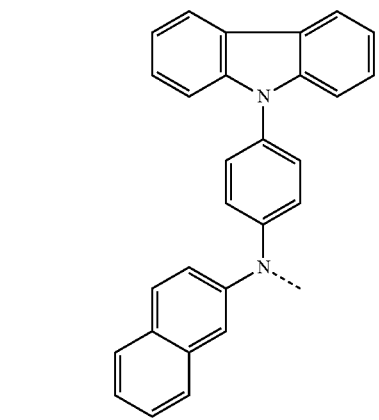

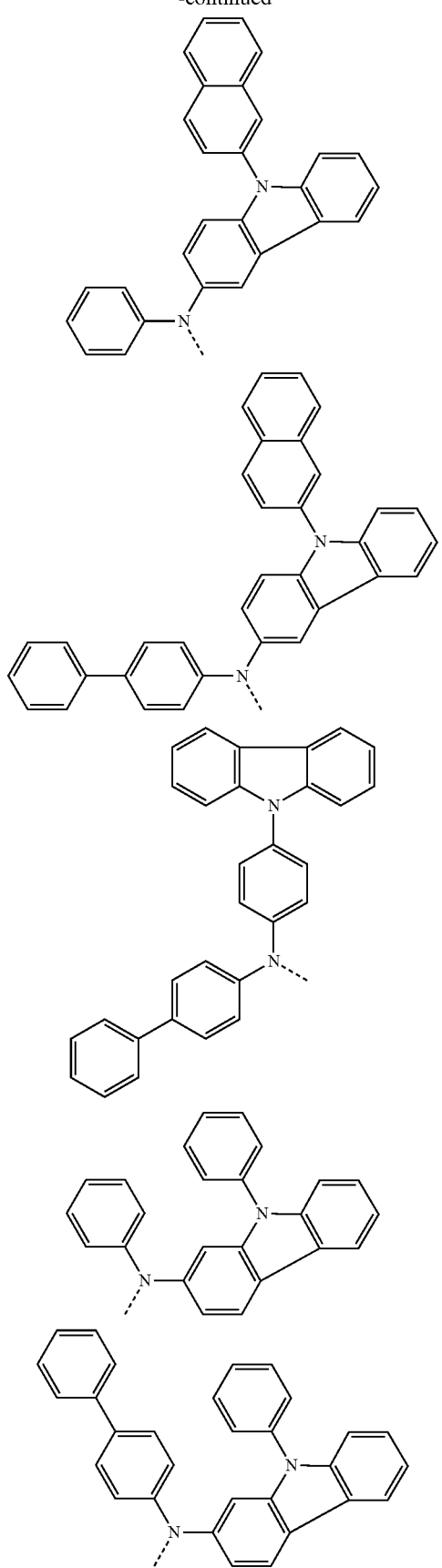
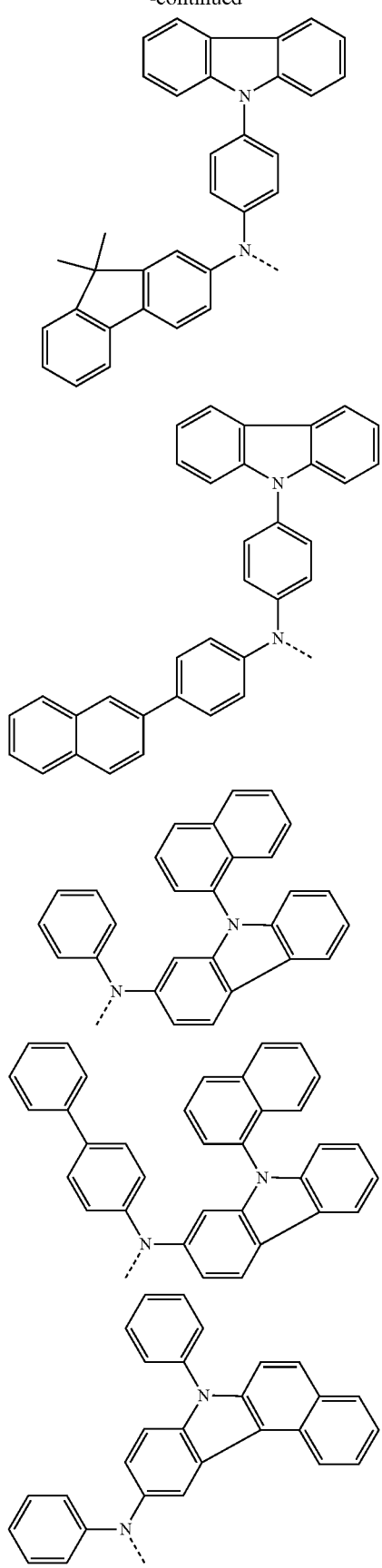

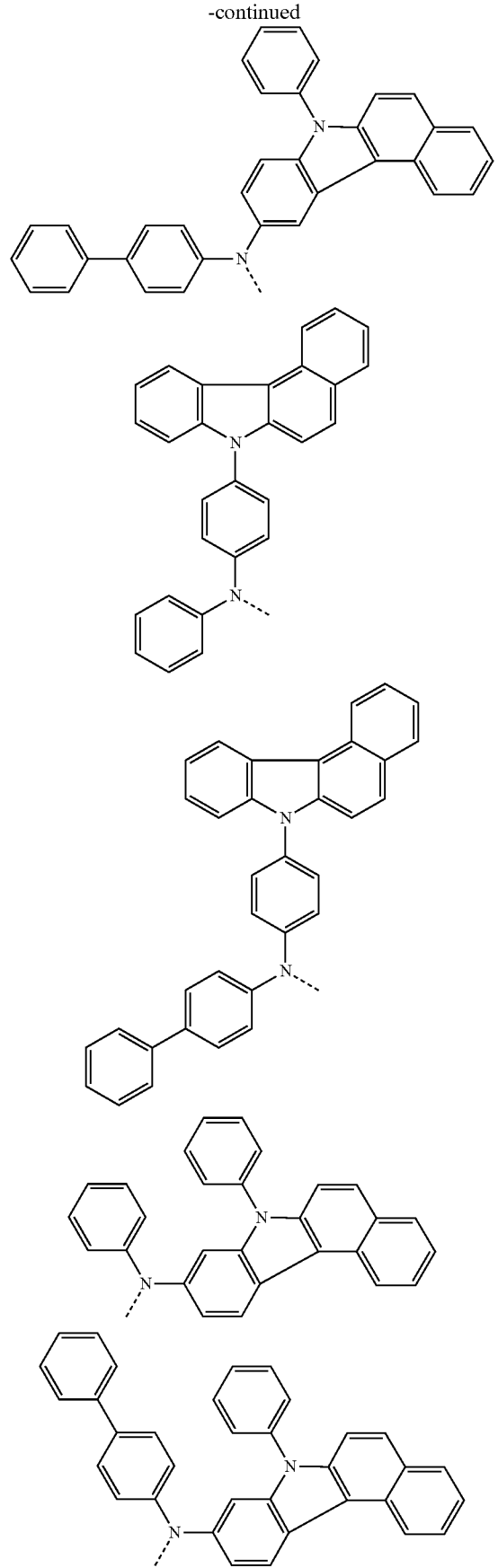
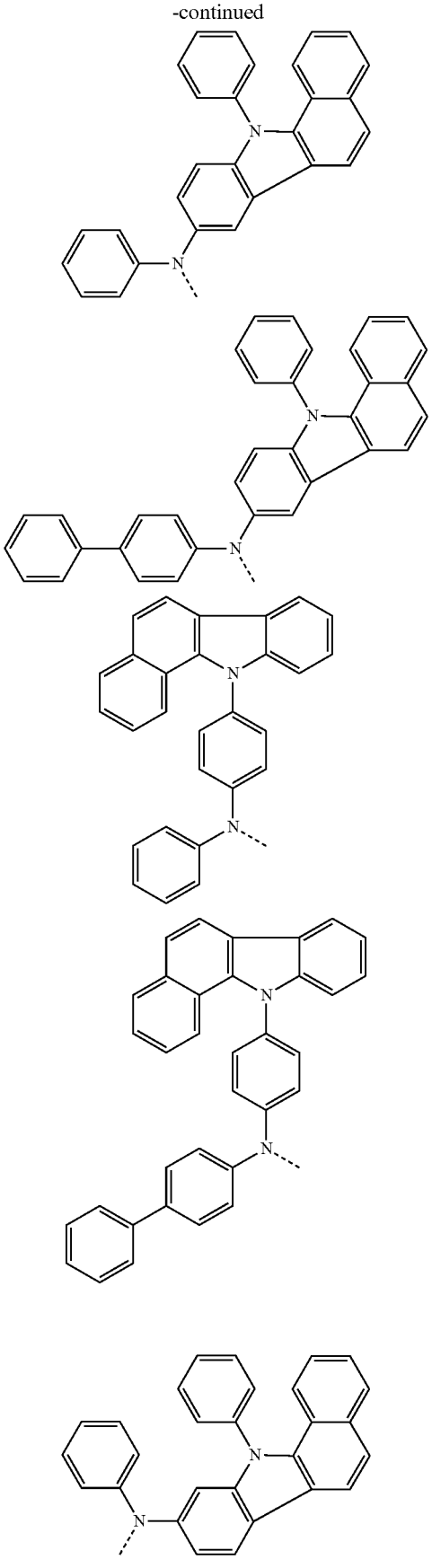

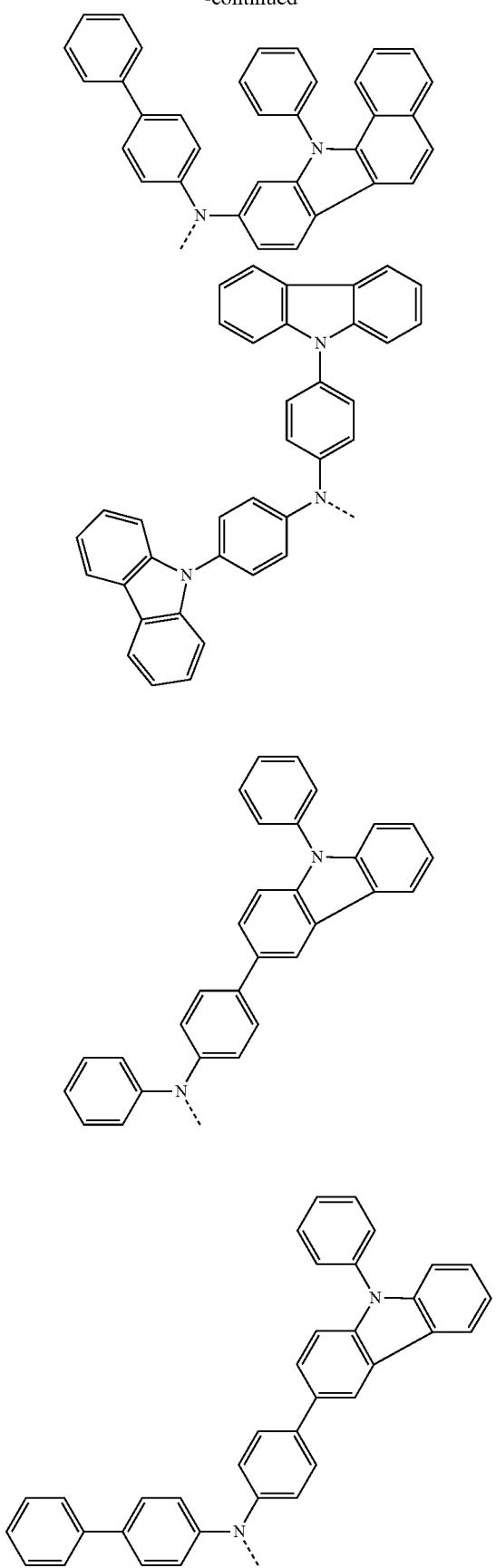
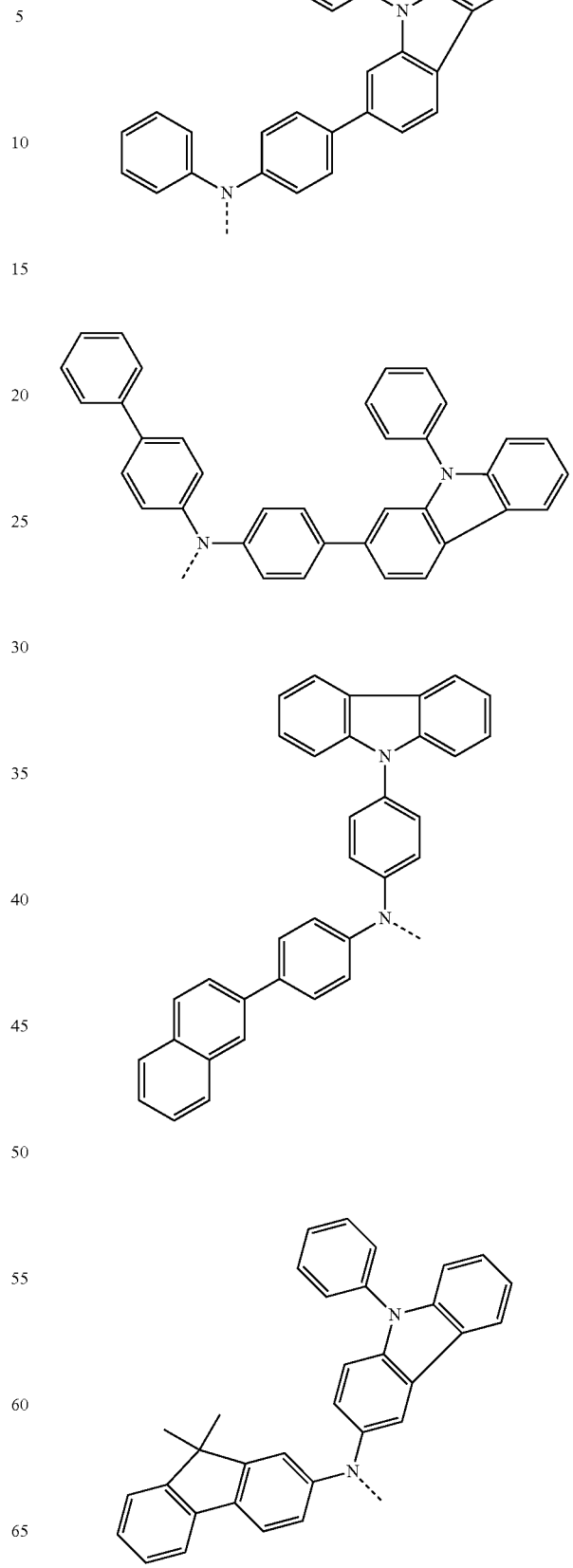

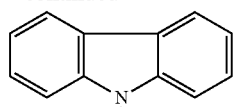
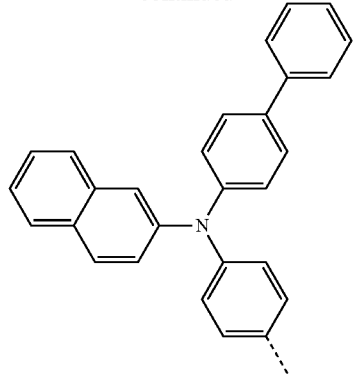
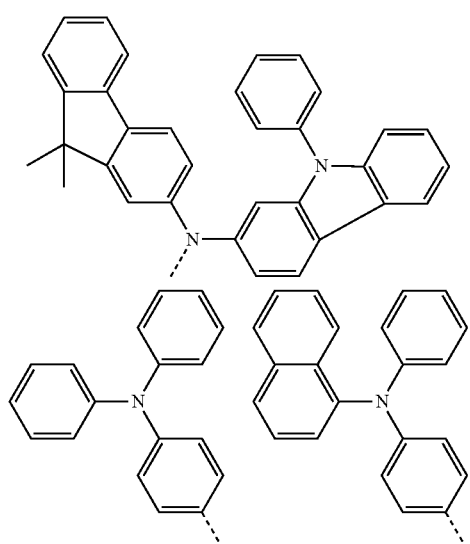
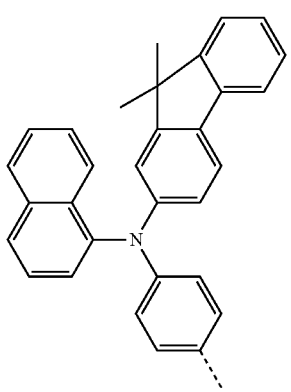
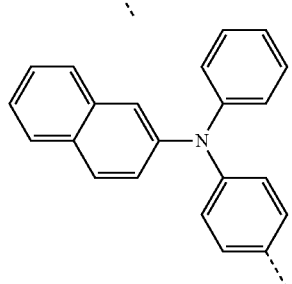
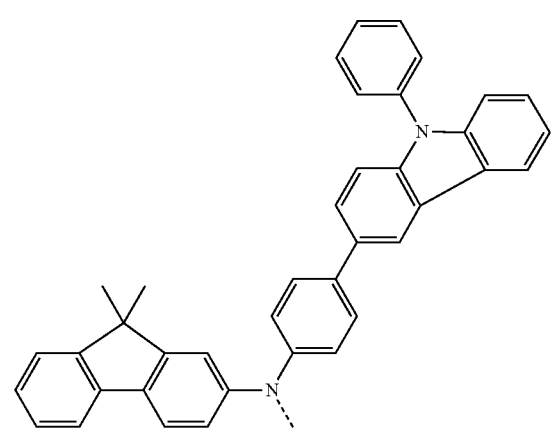
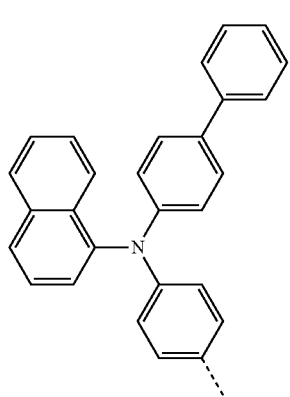
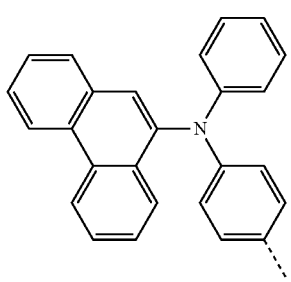

-continued
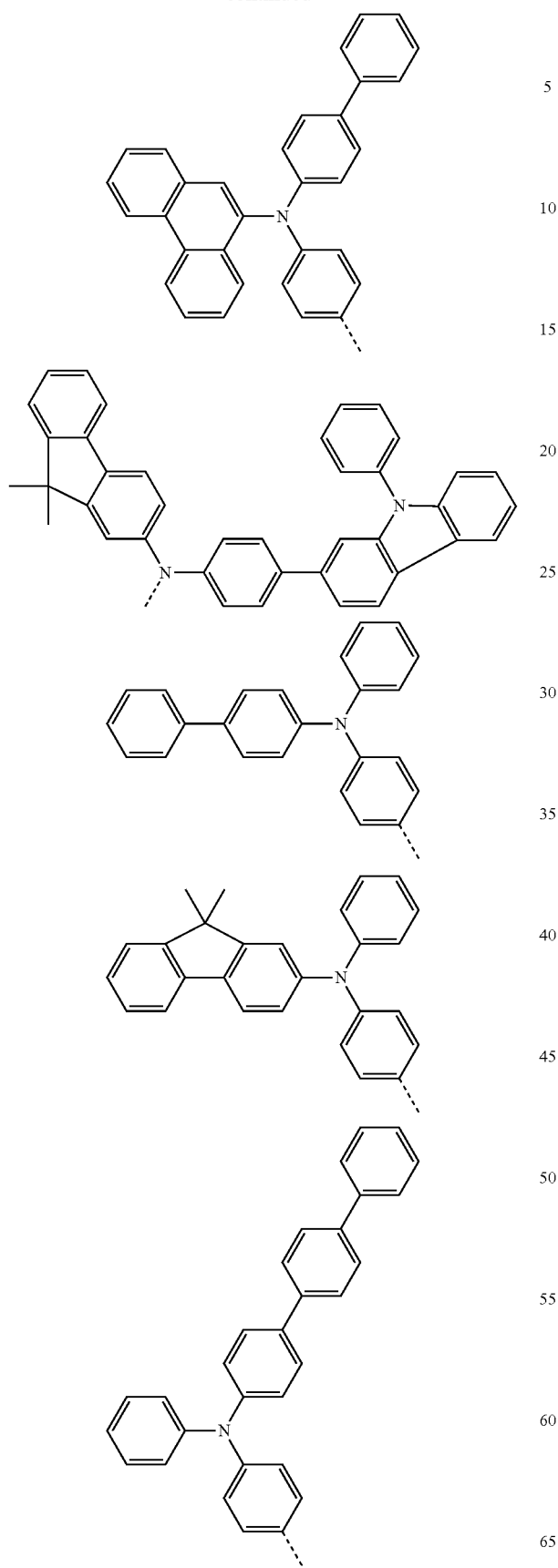
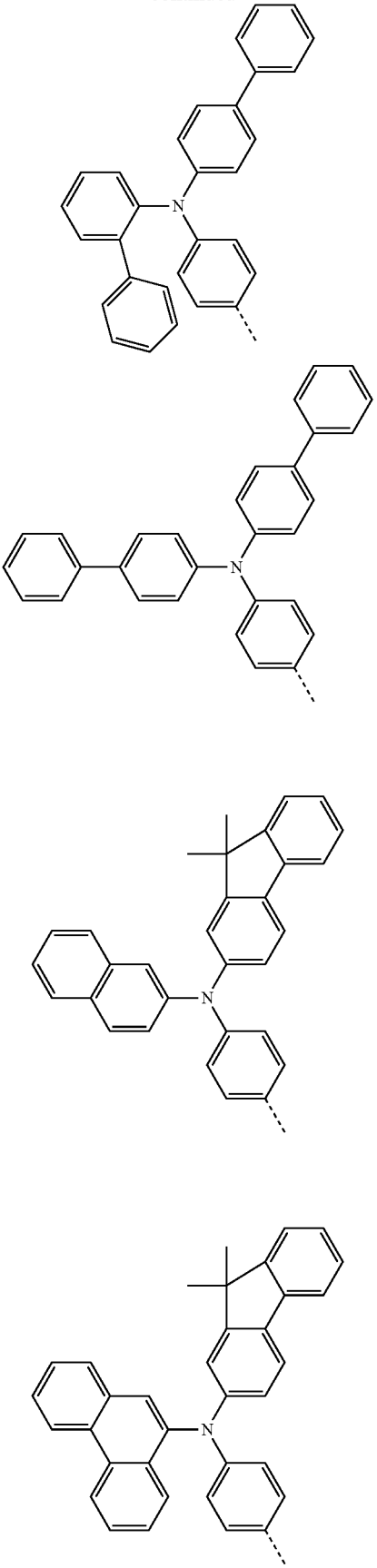

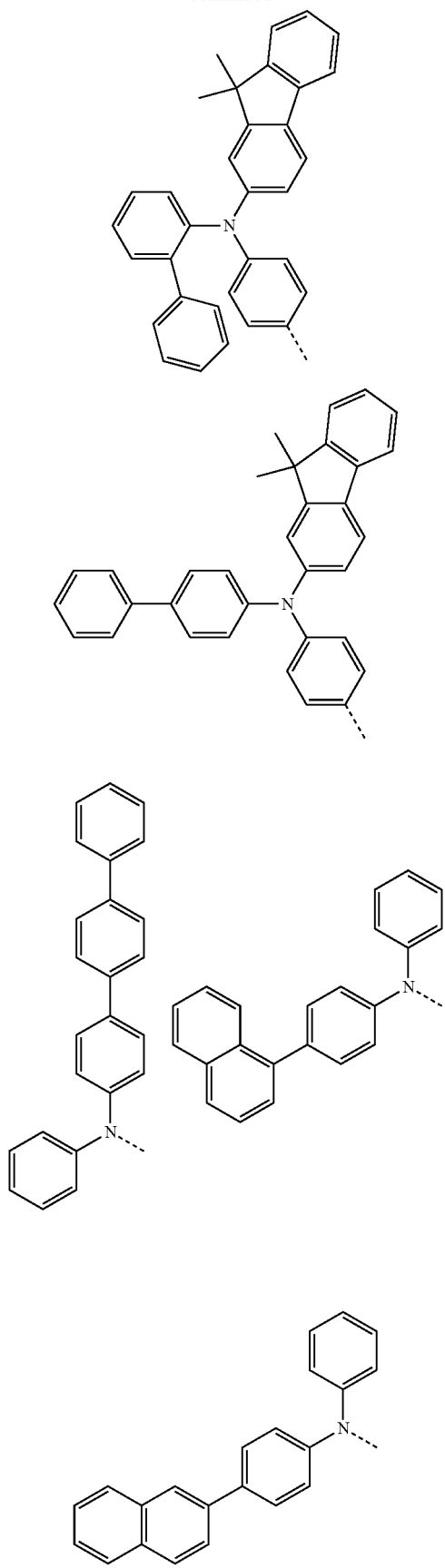
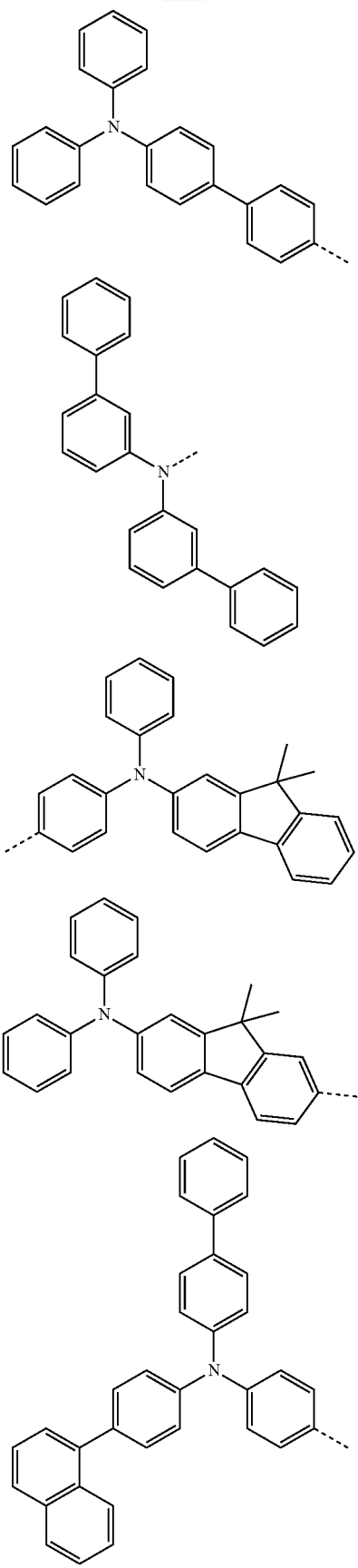

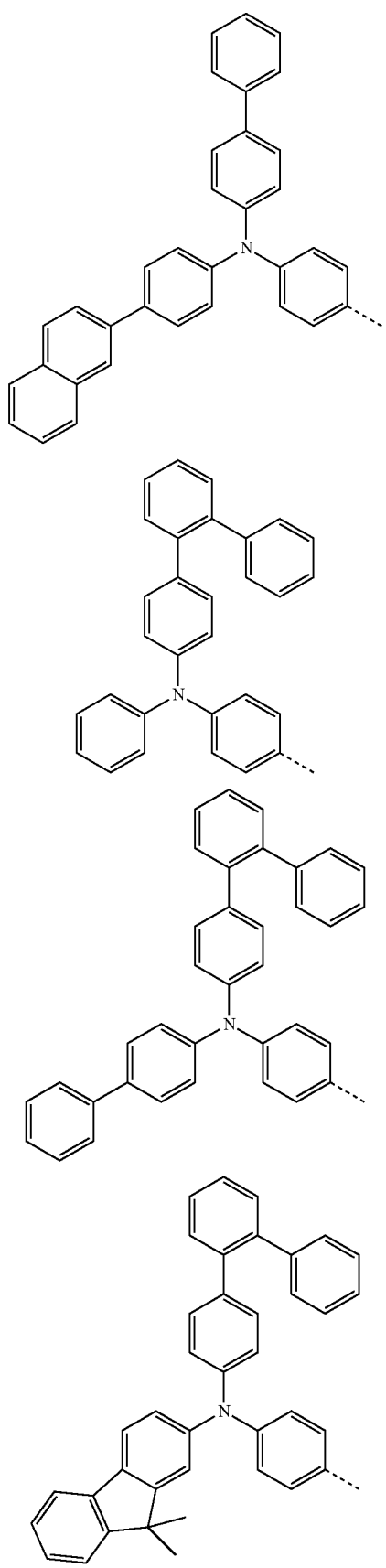
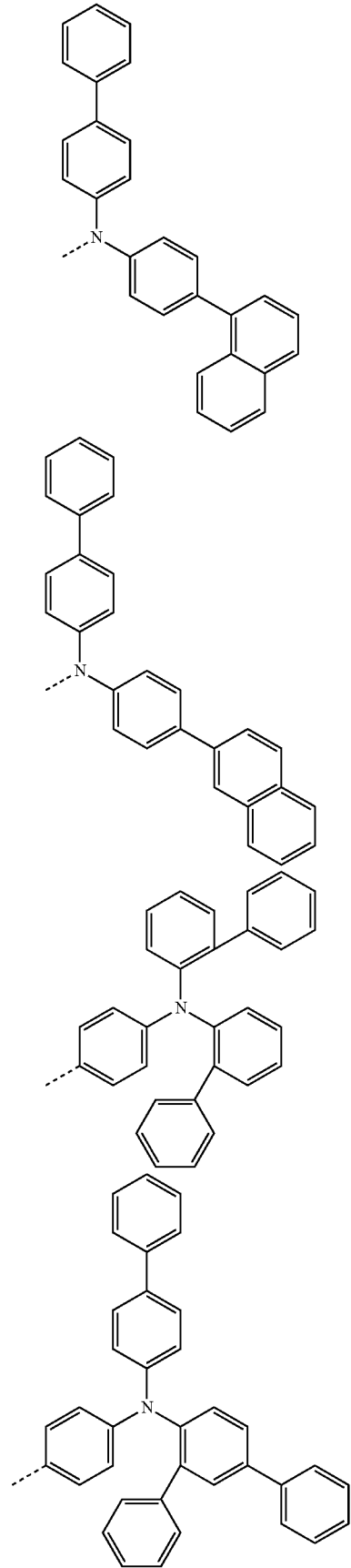

-continued
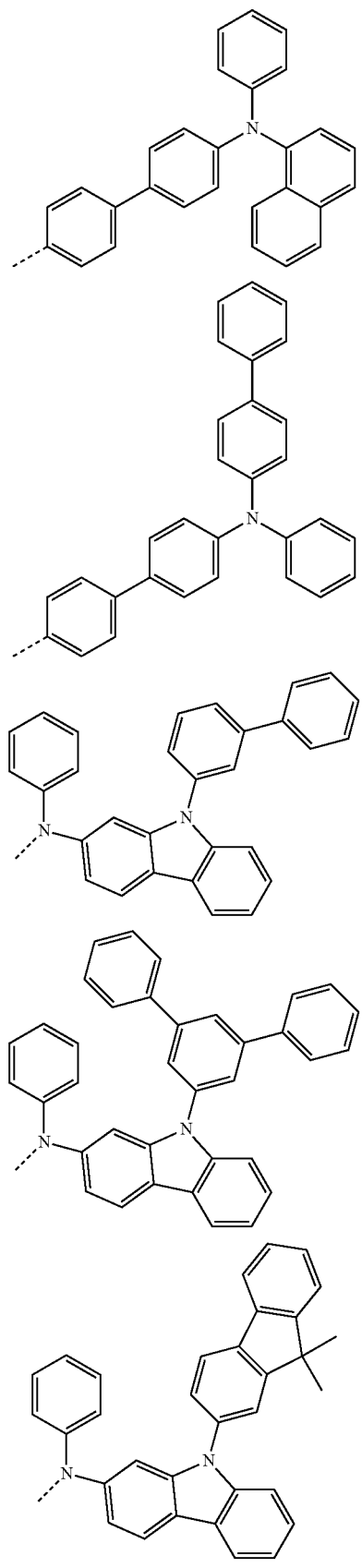
-continued
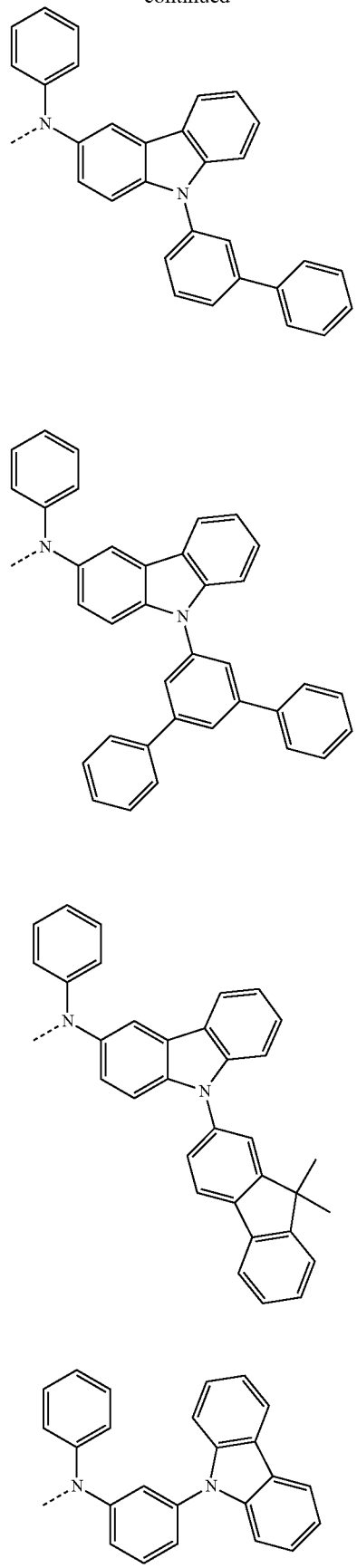

[A-2]
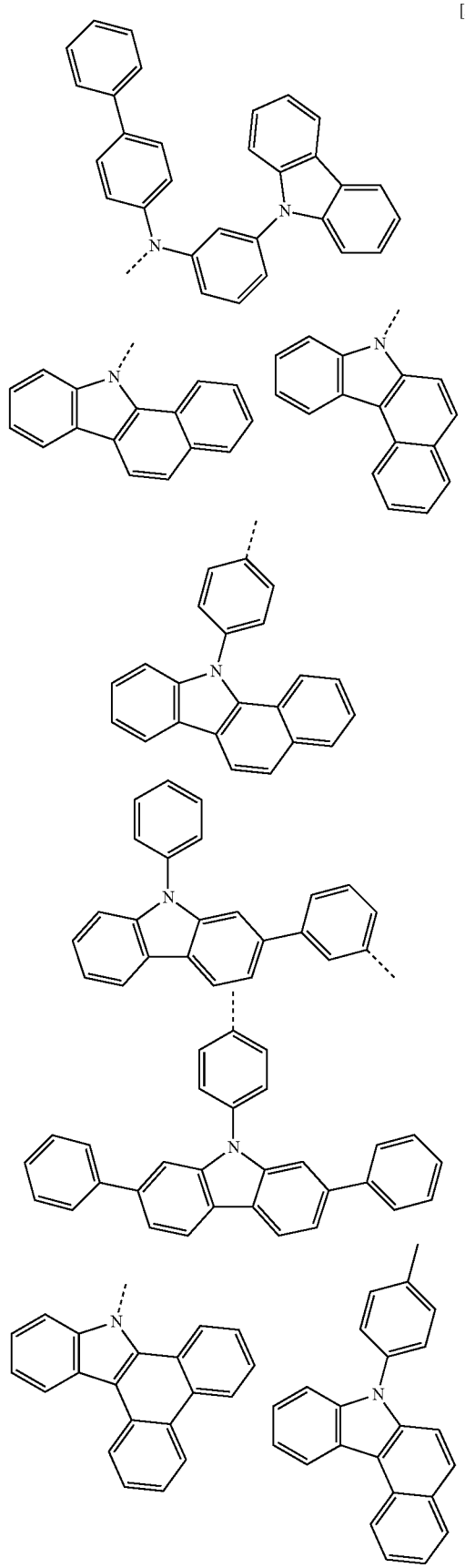

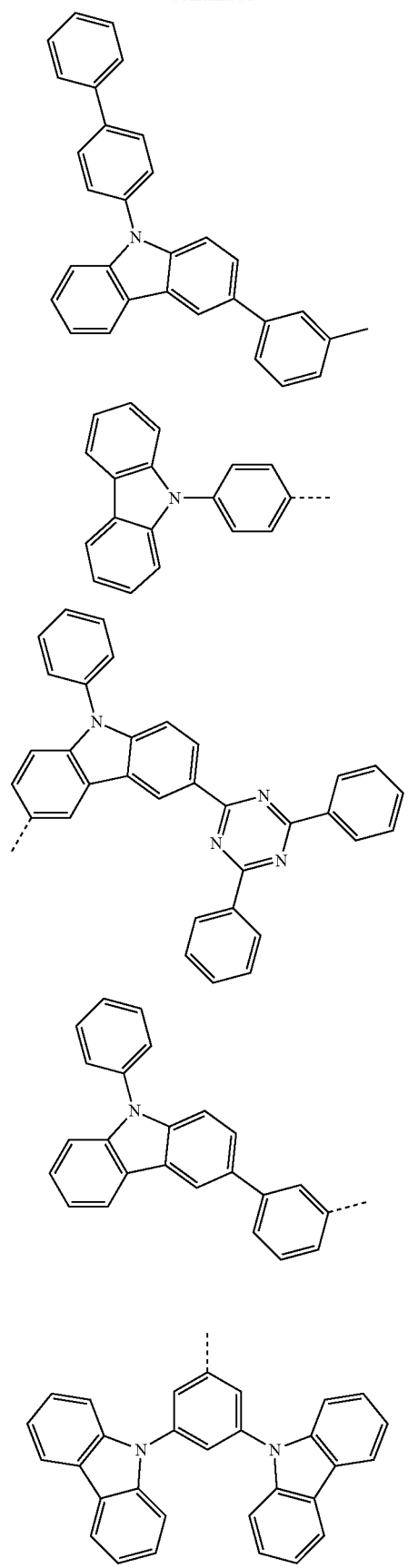
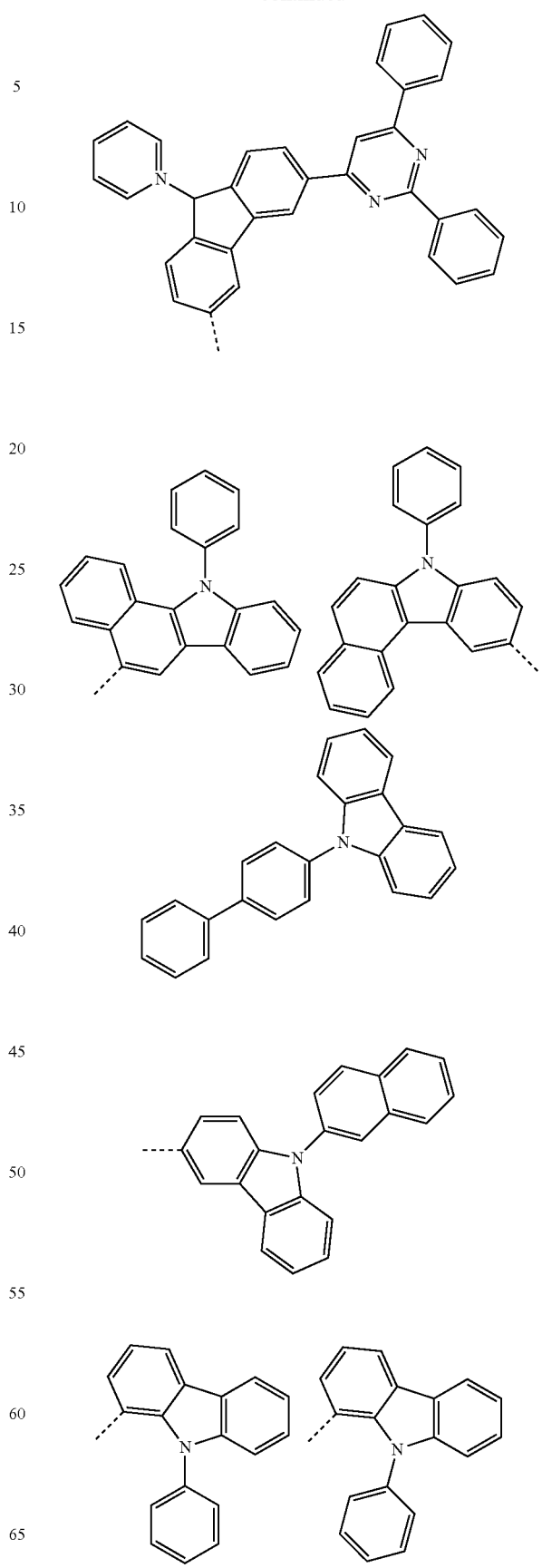

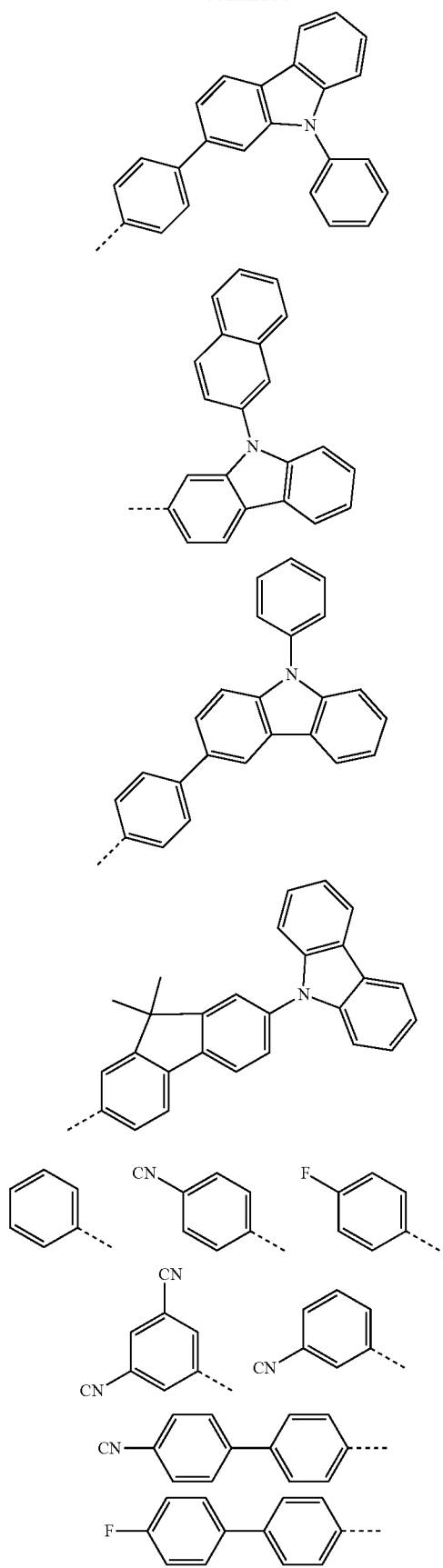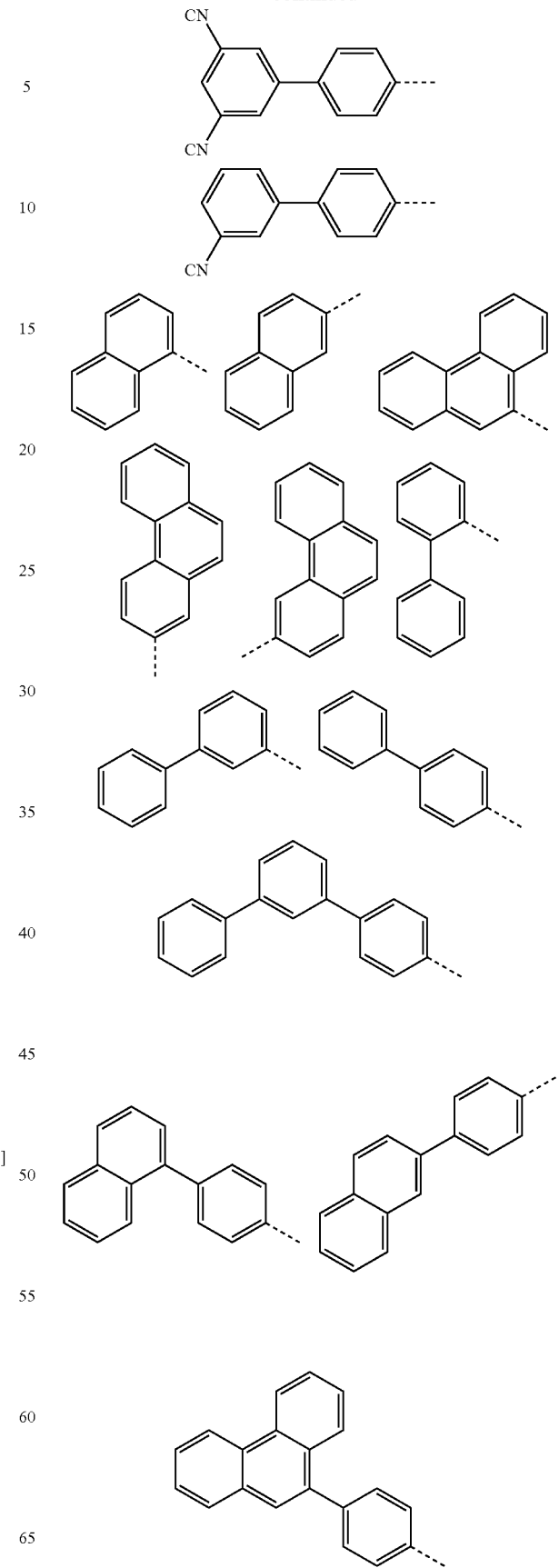

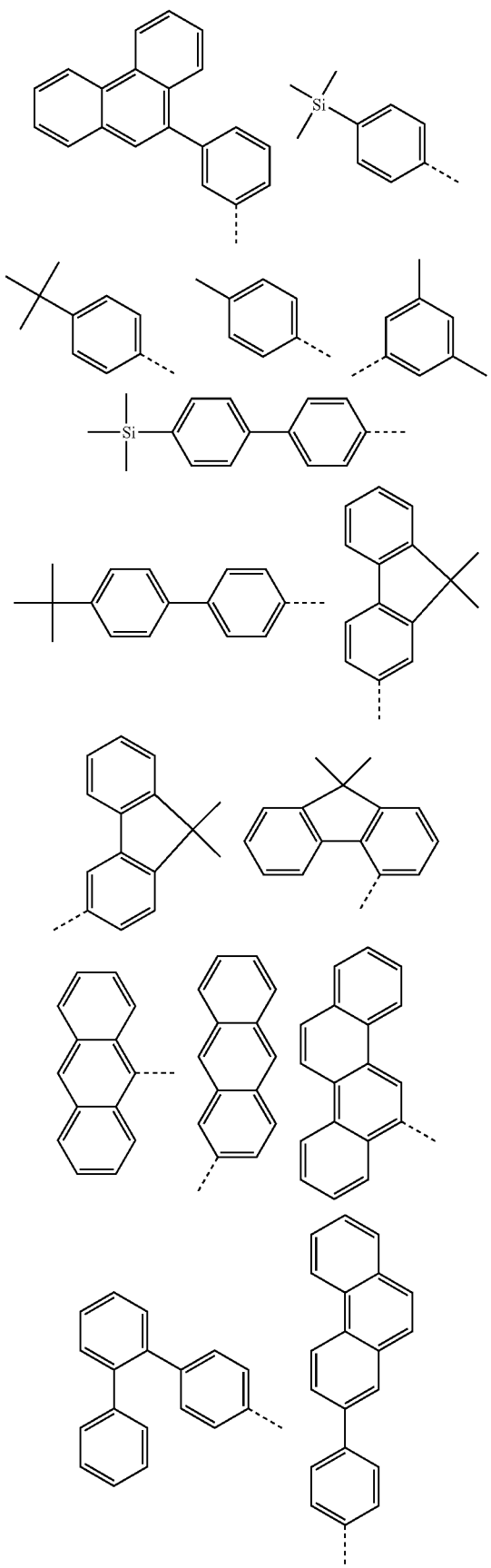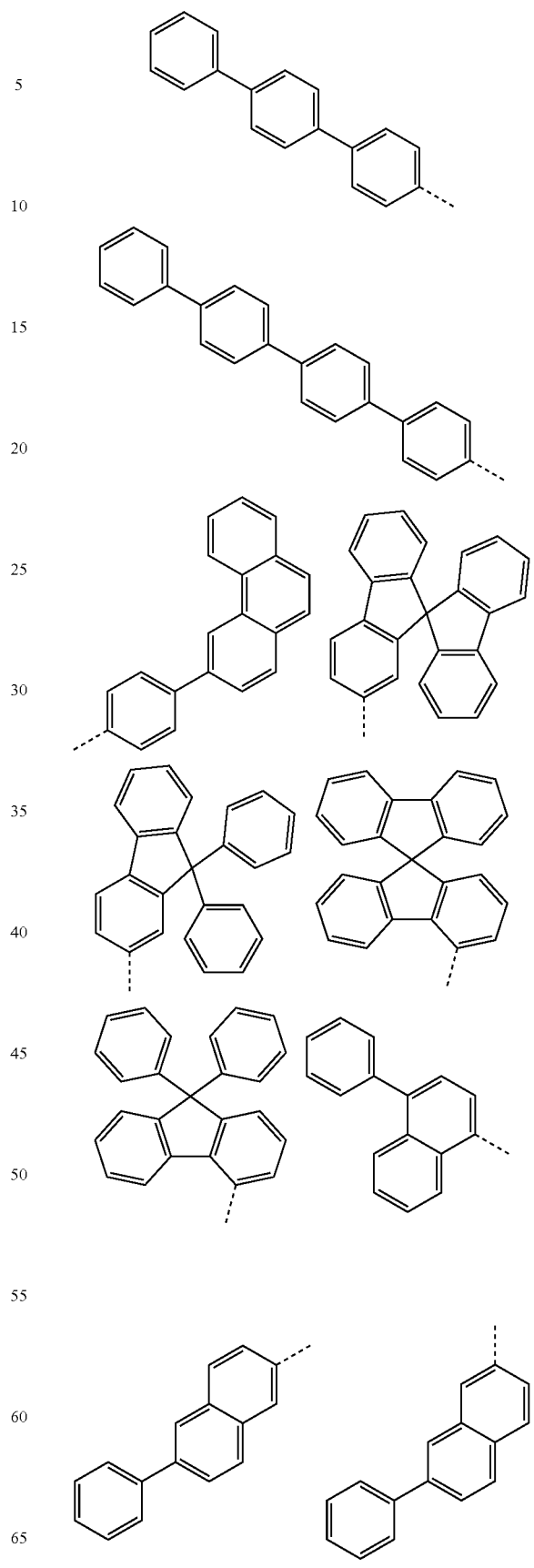

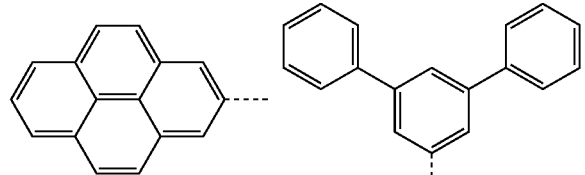
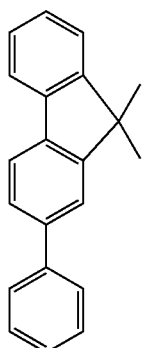
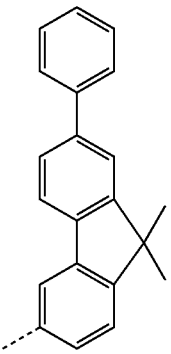
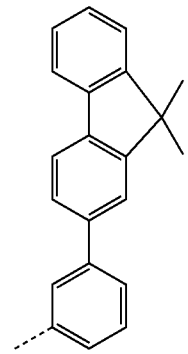
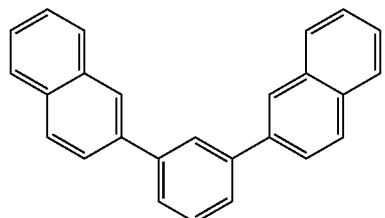
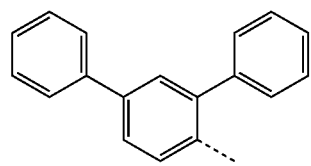
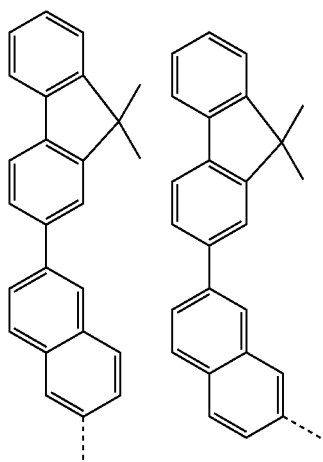
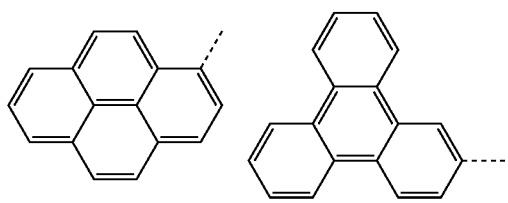
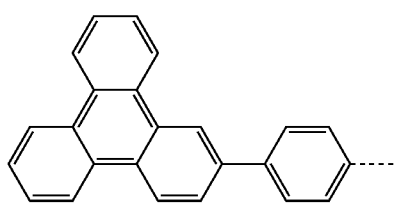
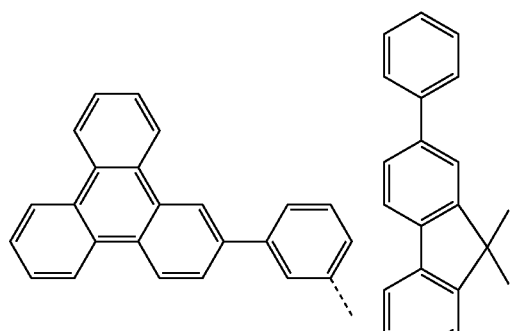
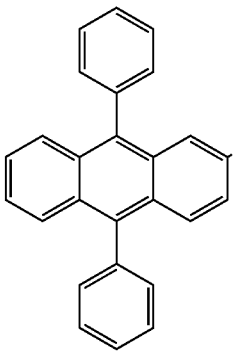
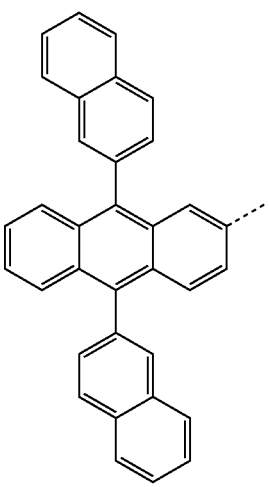

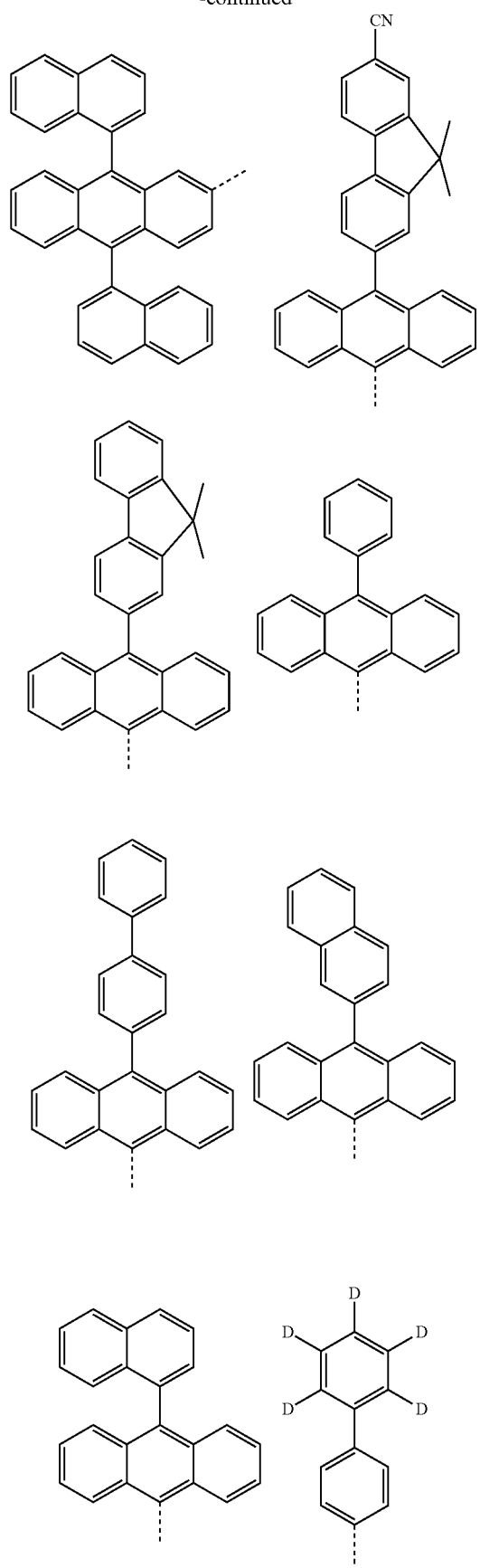
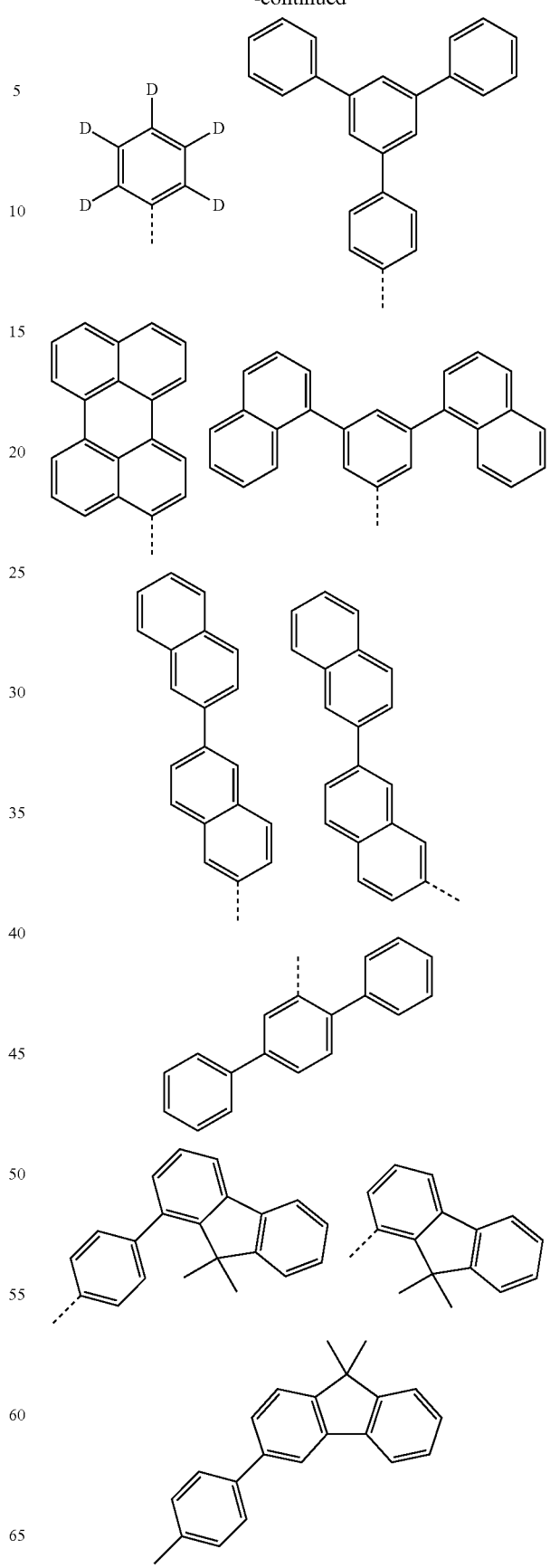

[A-4]
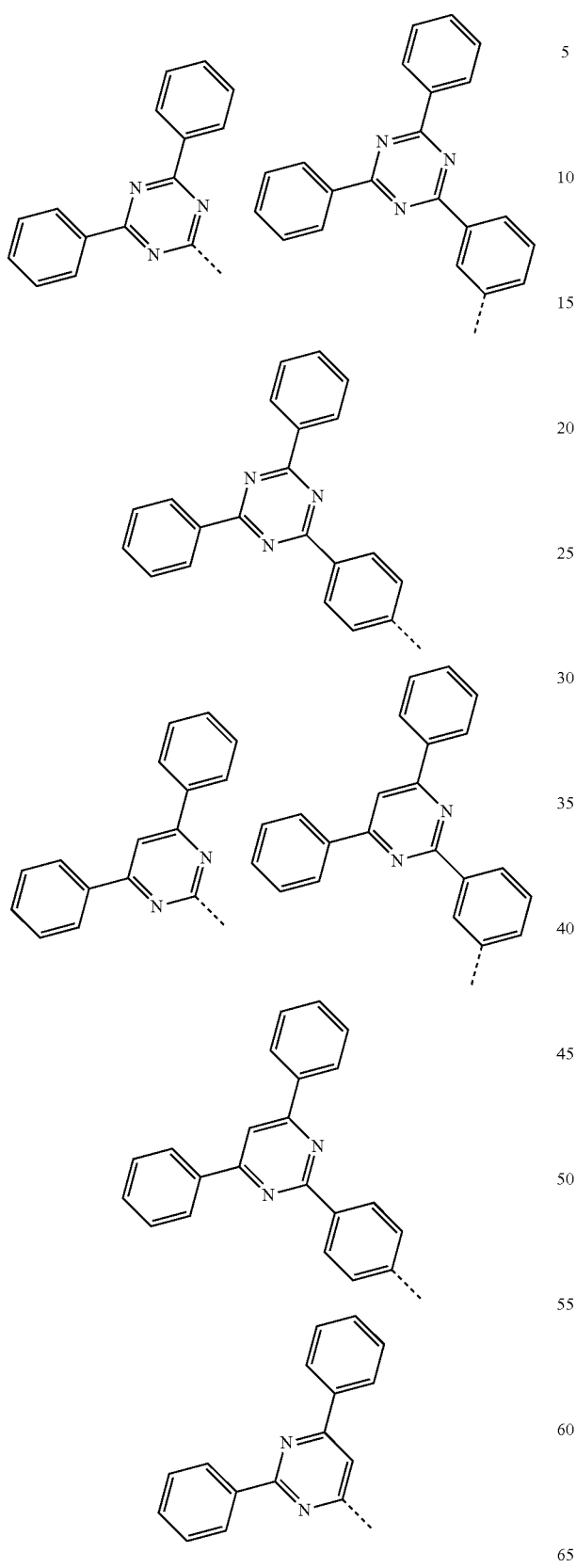
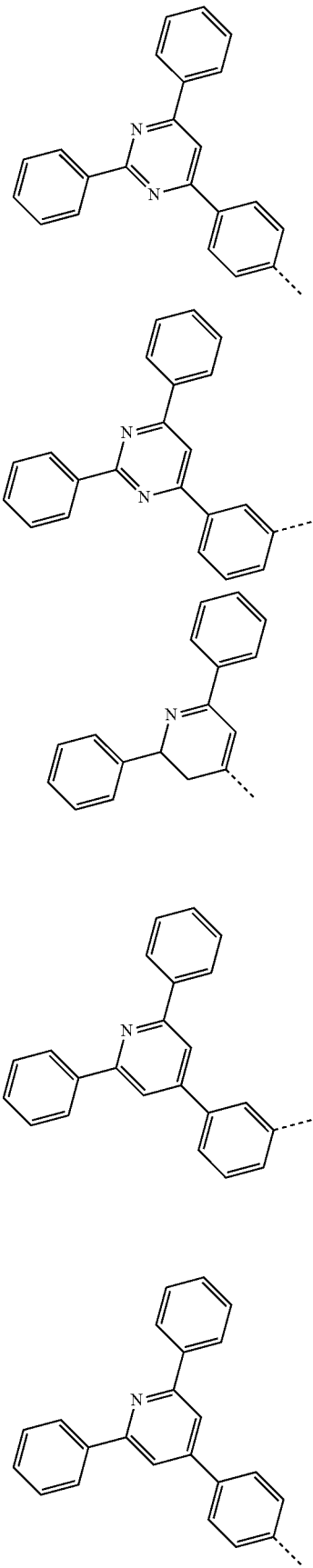

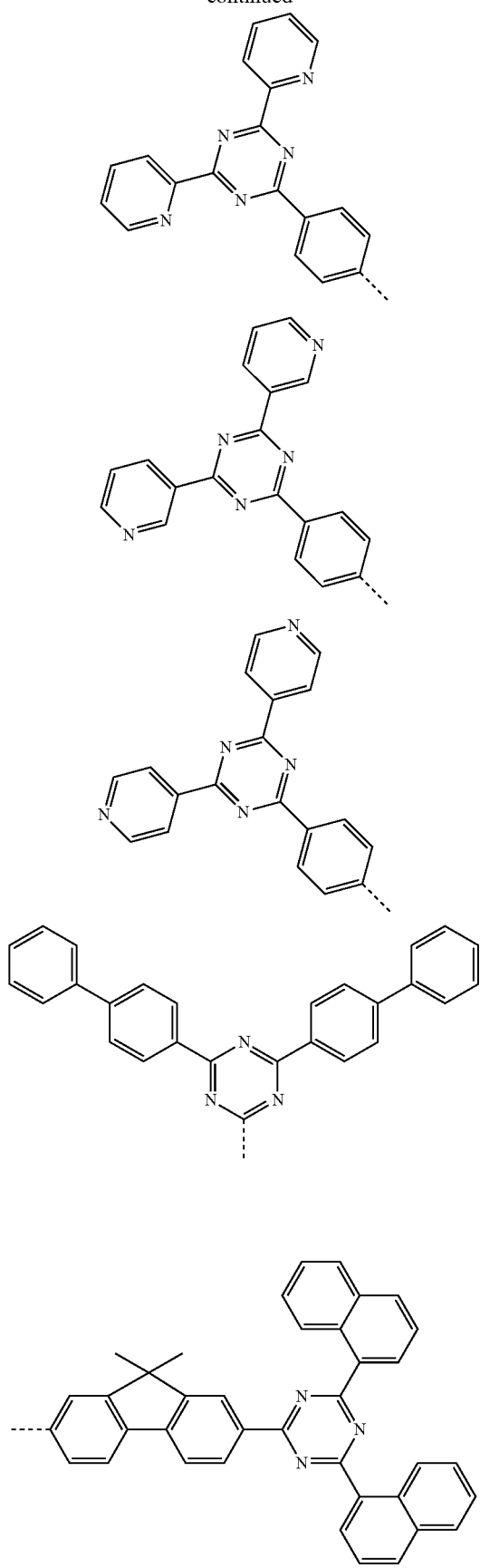
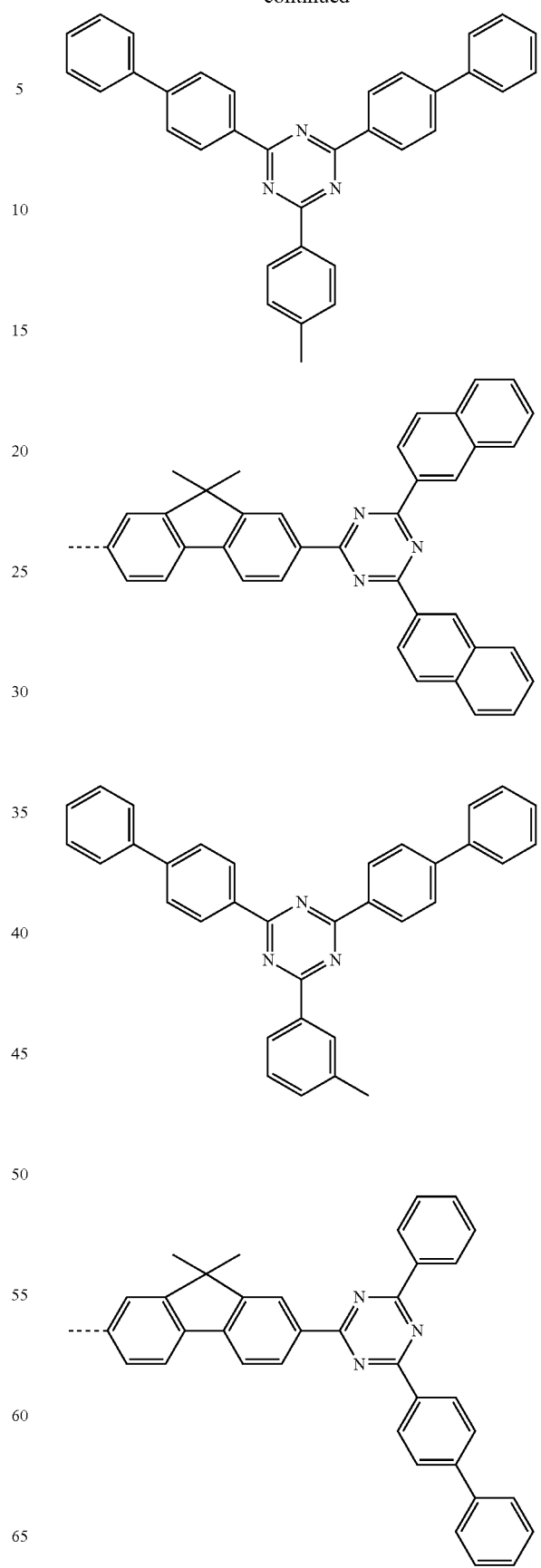

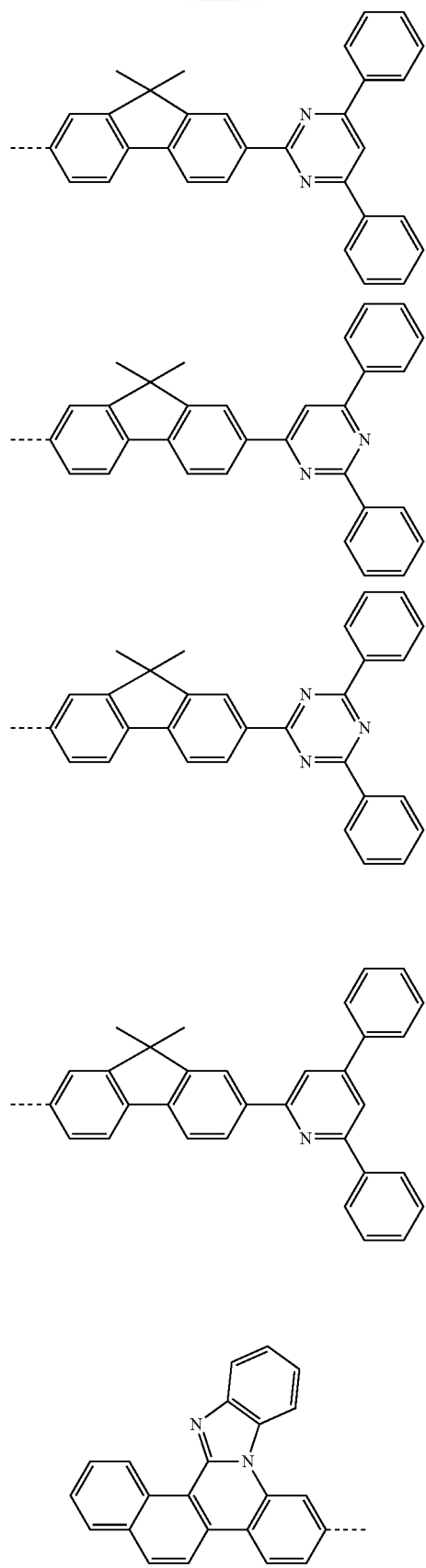
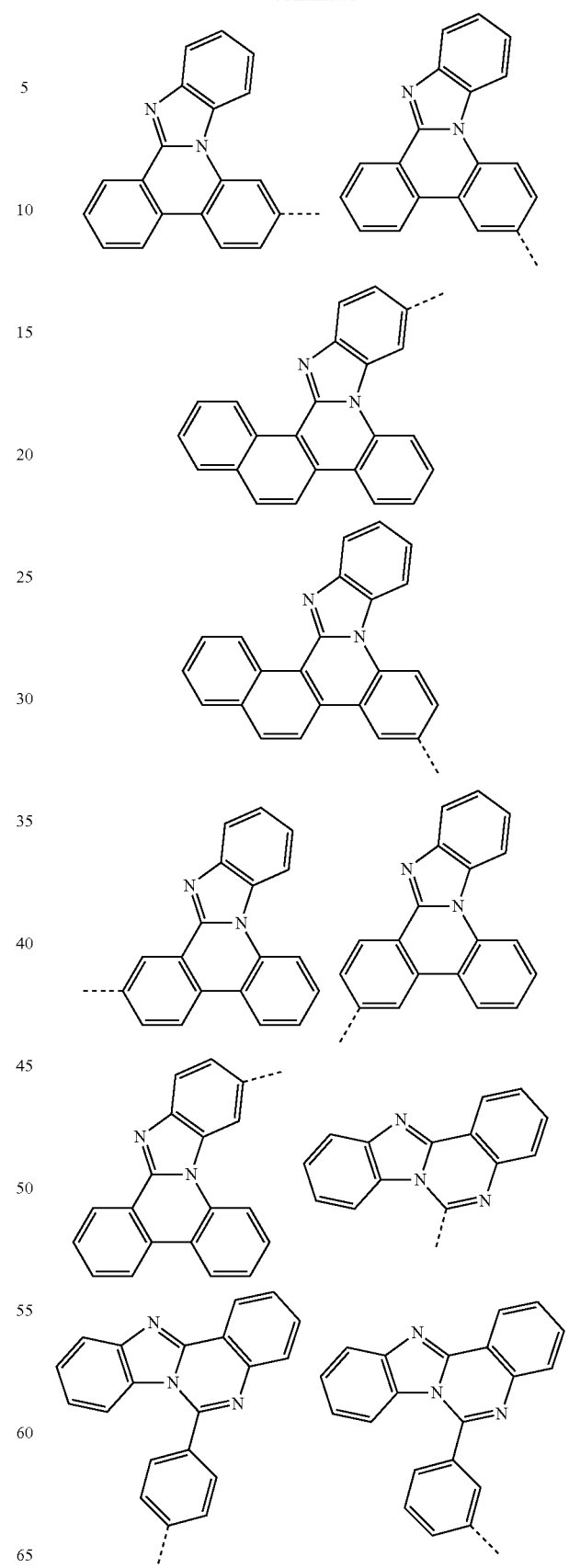

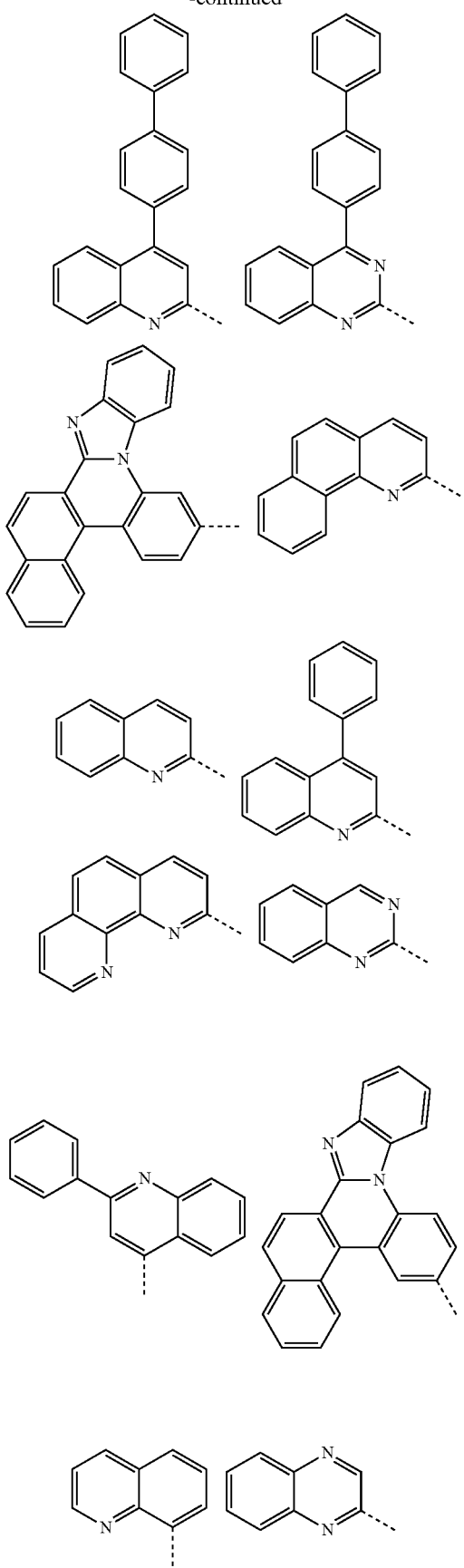
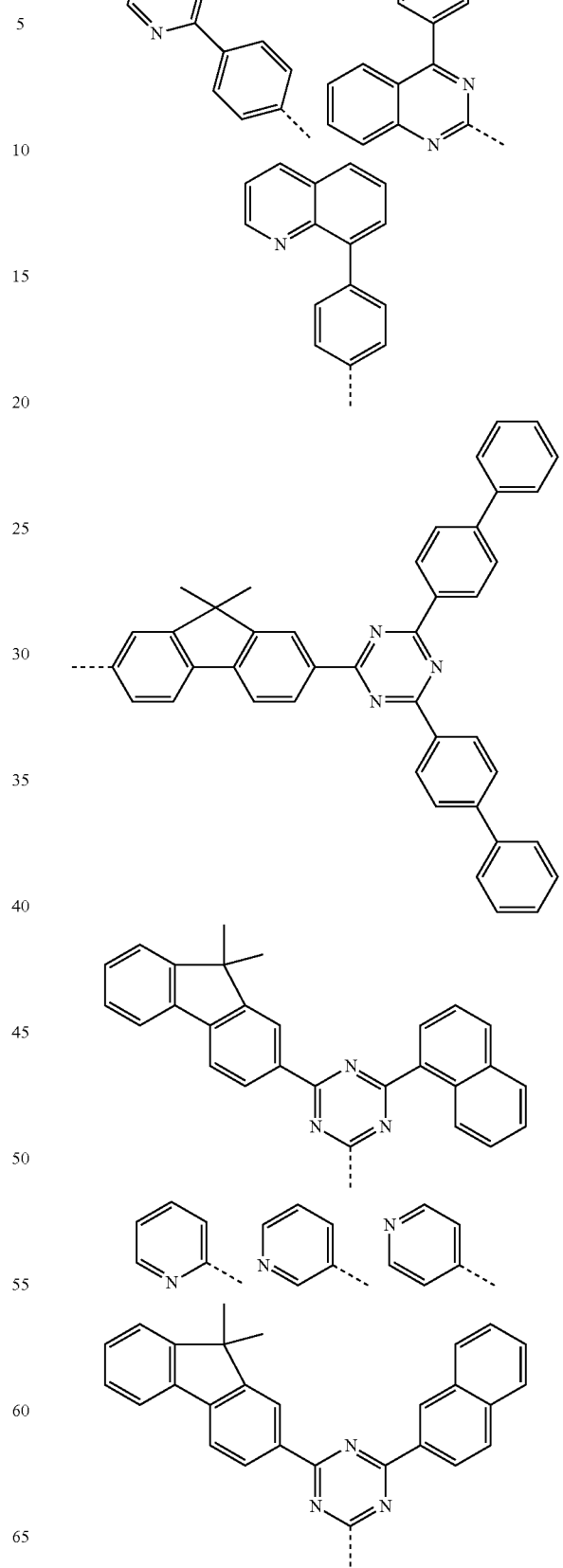

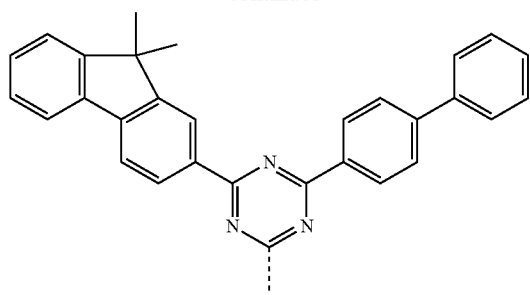
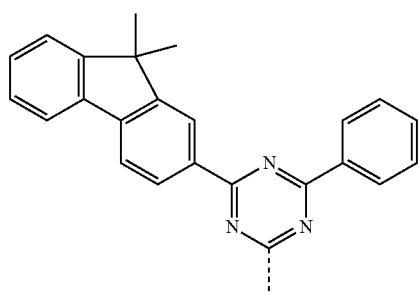
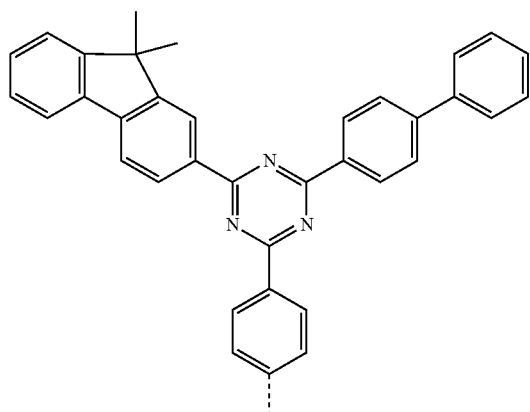
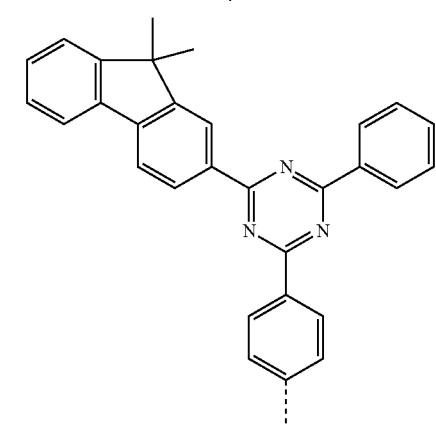
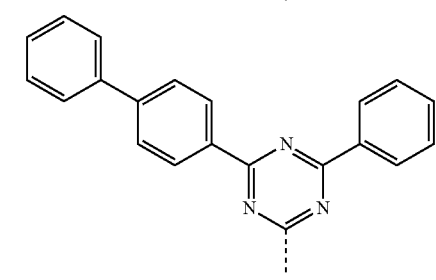
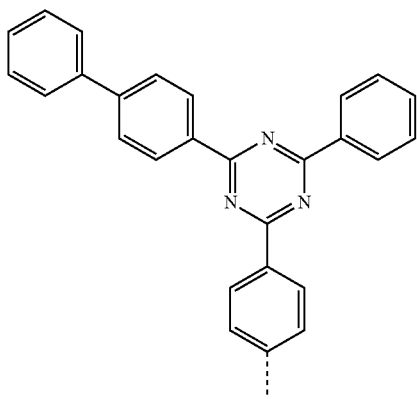
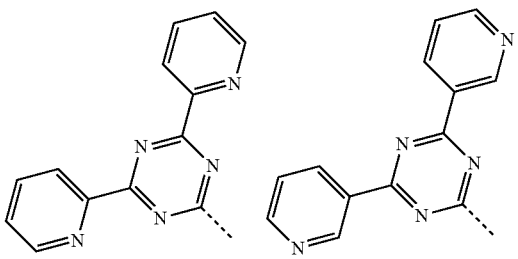
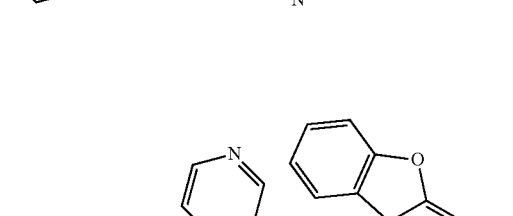
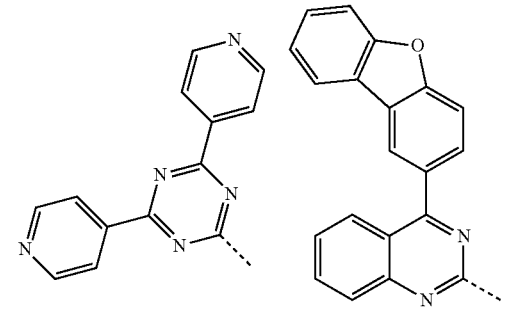
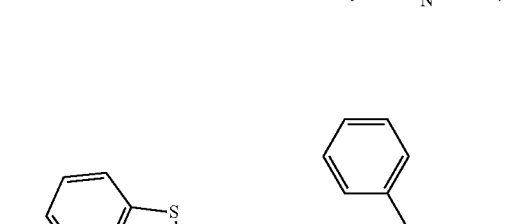
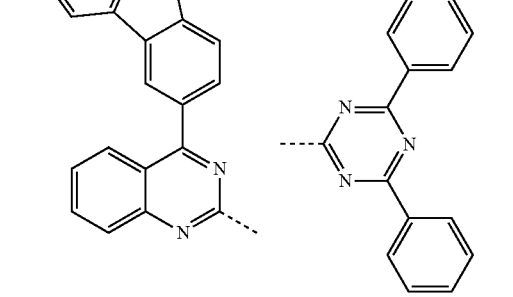

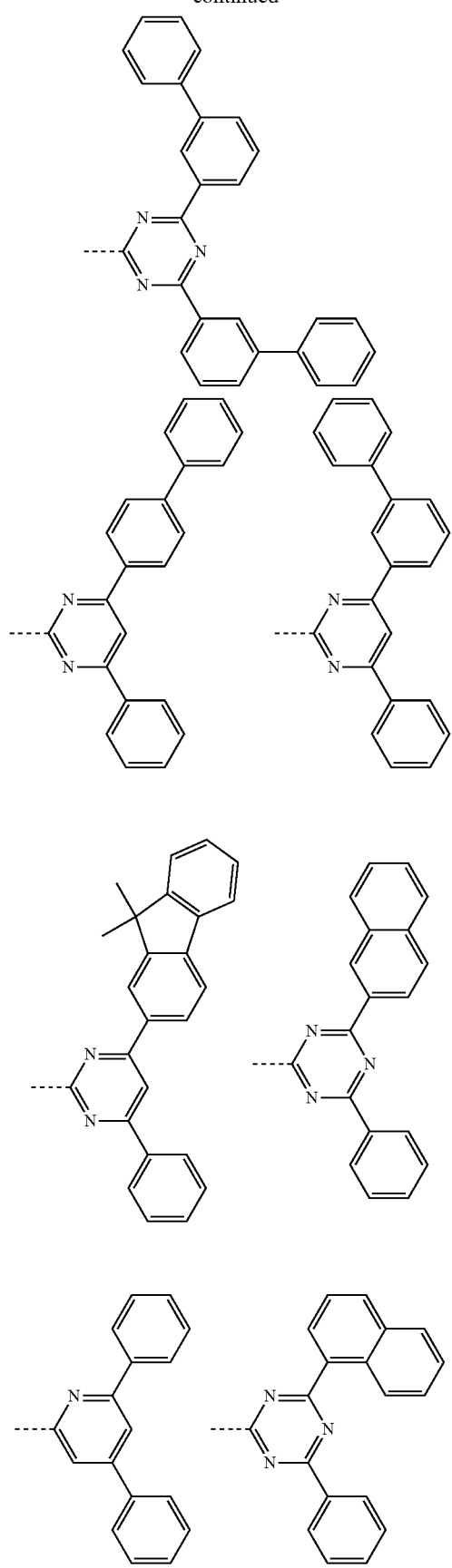
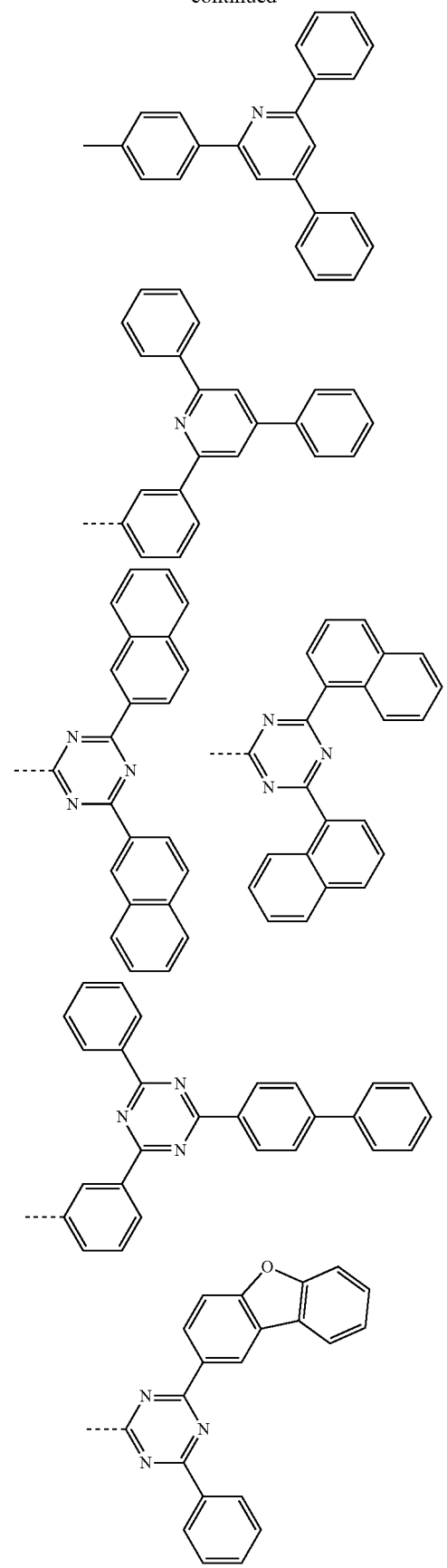

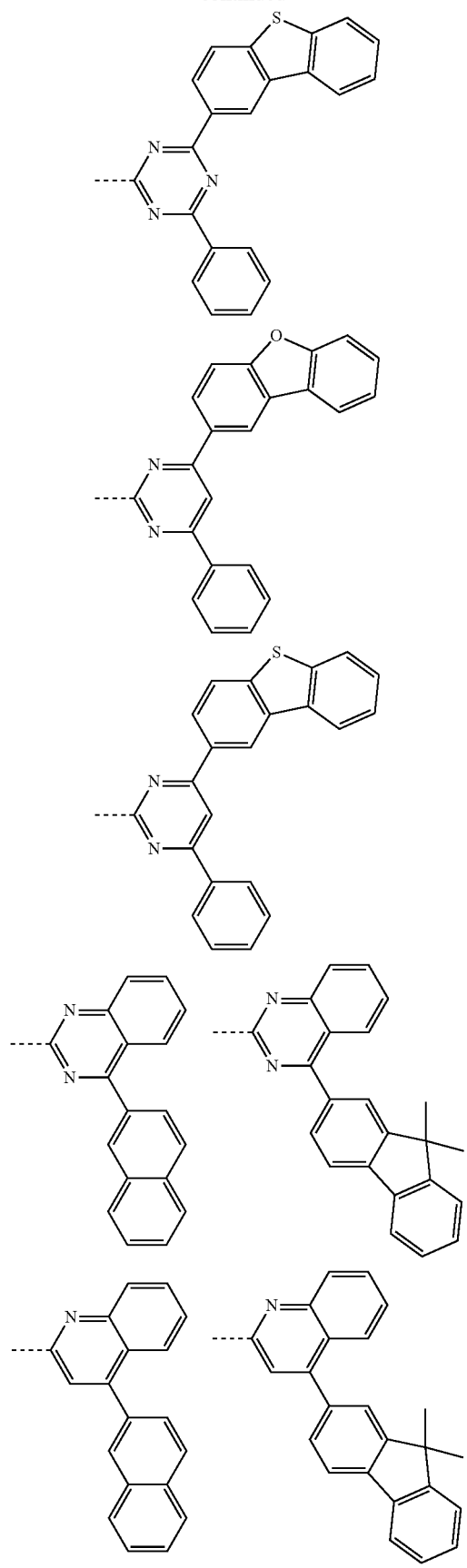
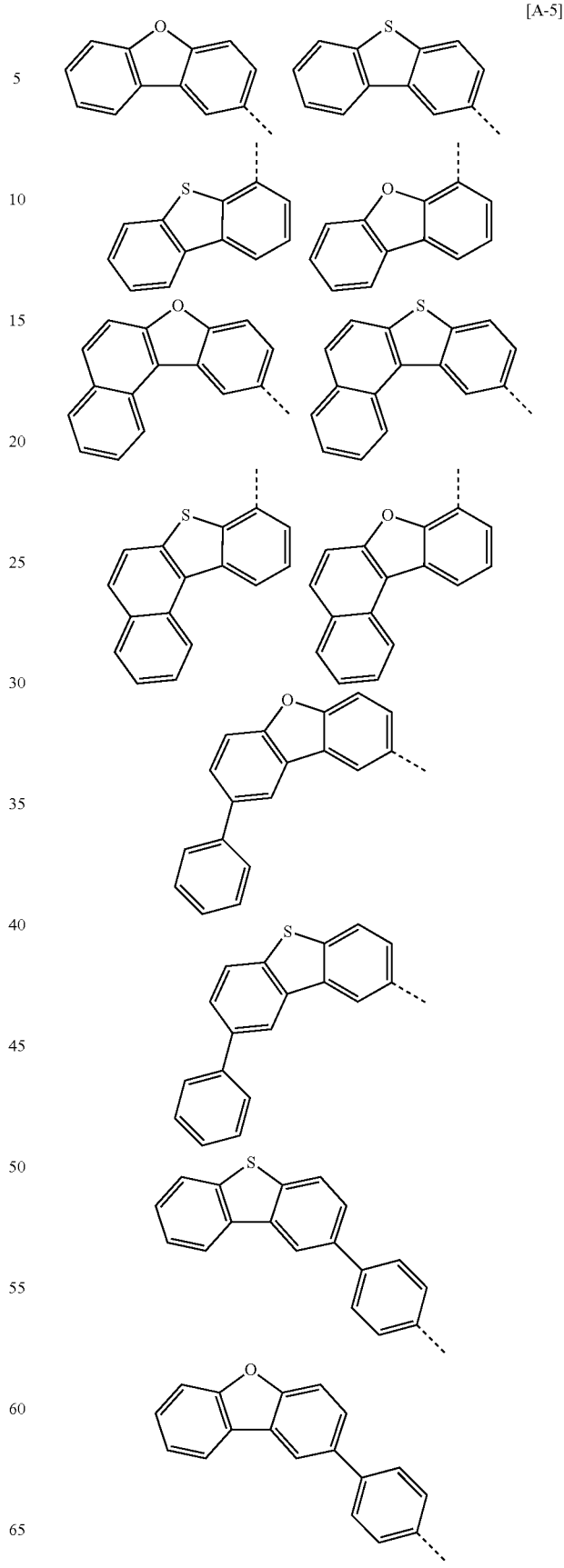
[A-5]

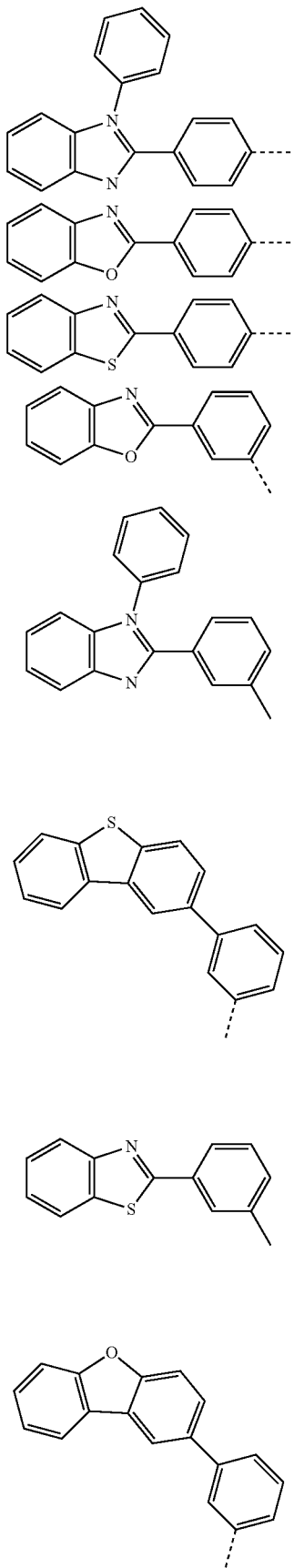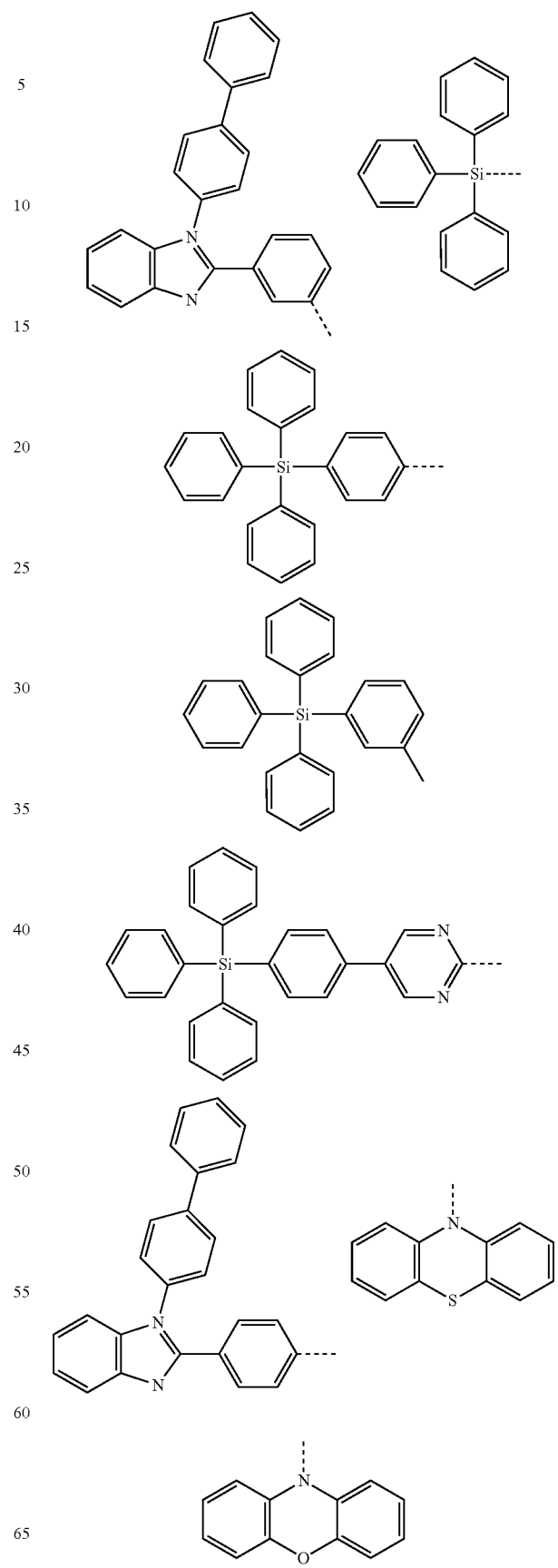

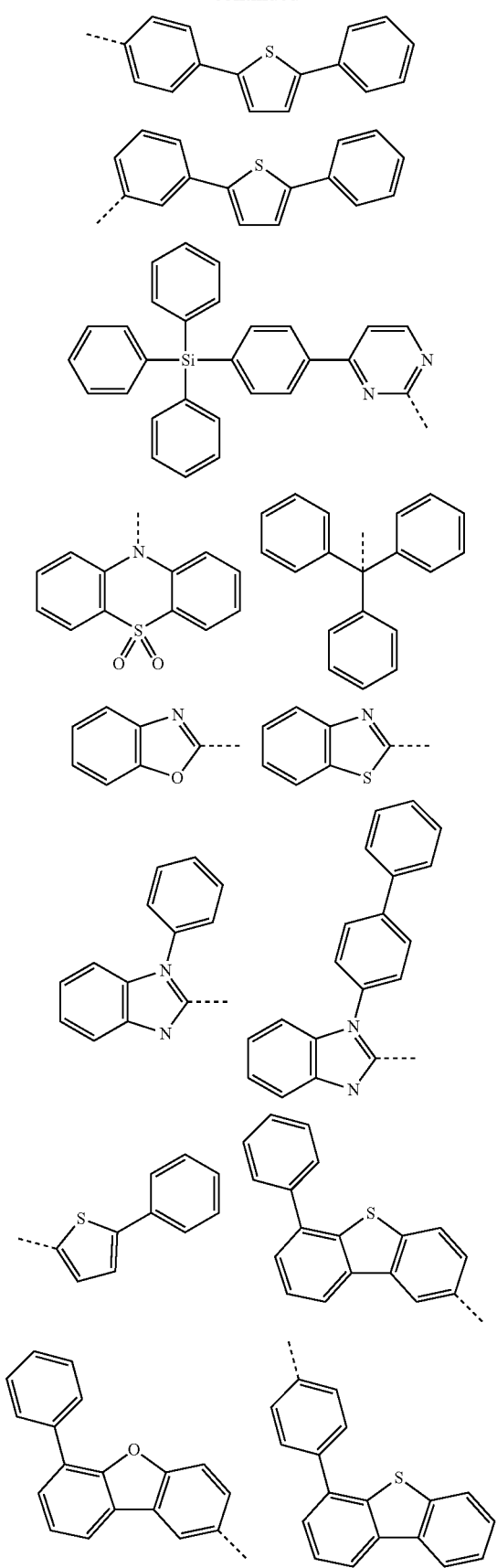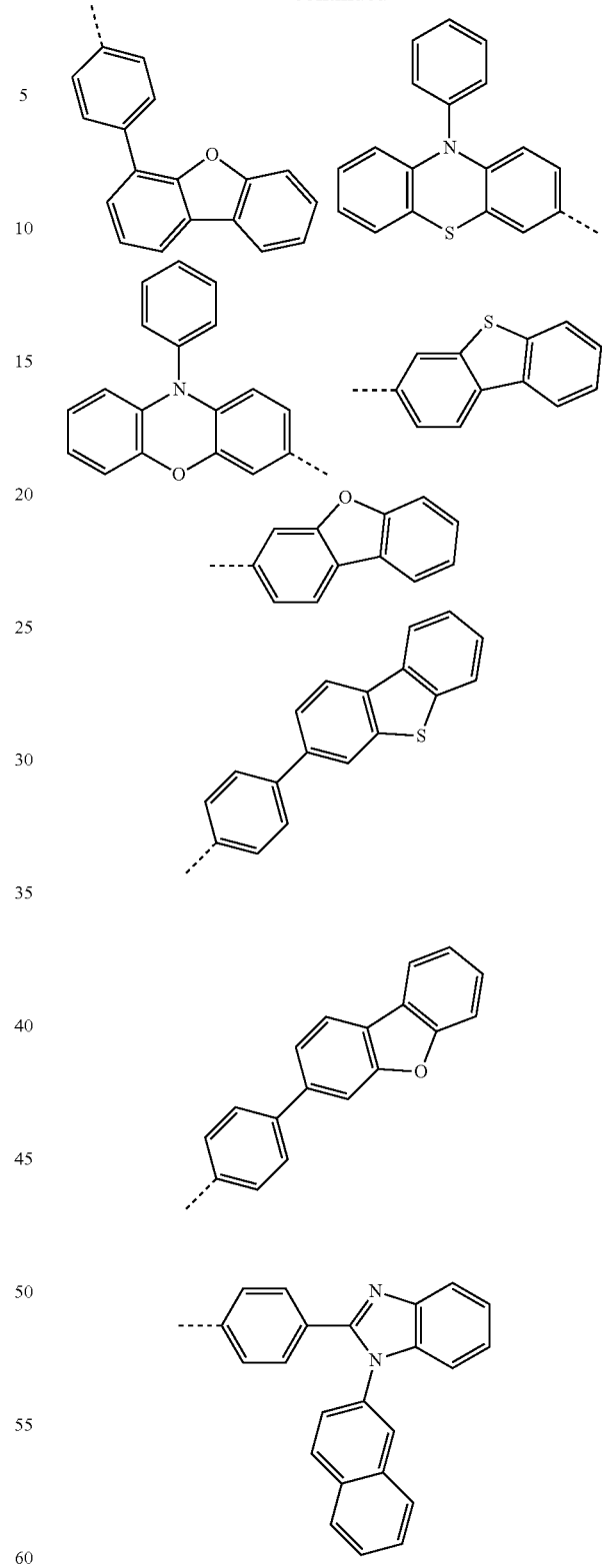
In the structural formulae, --- means a site bonding to L1 of Chemical Formula 1.
According to one embodiment of the present specification, Chemical Formula 1 is represented by any one of the following Chemical Formulae 1-2 to 1-6.

[Chemical Formula 1-2]

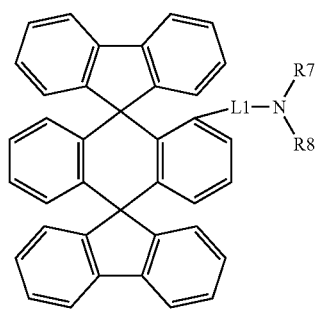

[Chemical Formula 1-3]

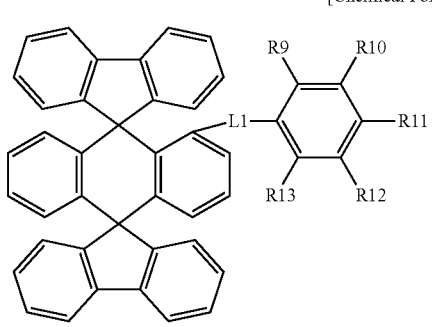

[Chemical Formula 1-4]

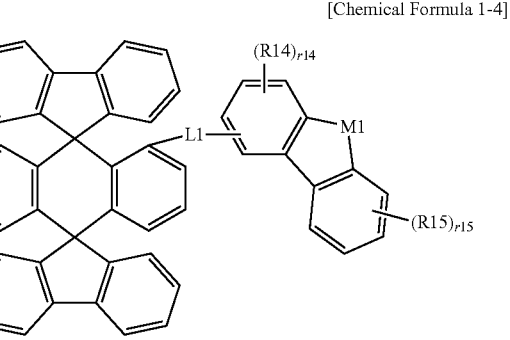

[Chemical Formula 1-5]

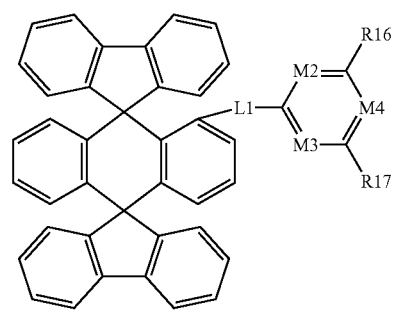

[Chemical Formula 1-6]

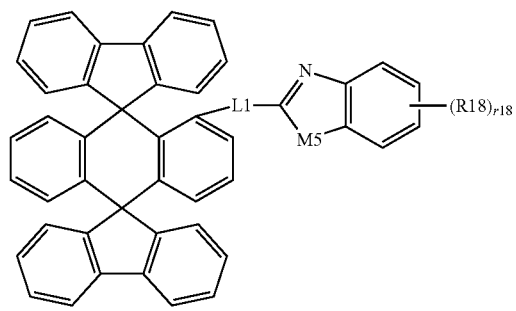

In Chemical Formulae 1-2 to 1-6, a definition of L1 is the same as in Chemical Formula 1, M1 and M5 are the same as or different from each other, and each independently O, S, NR19 or CR20R21, M2 is N or CR22, M3 is N or CR23, and M4 is N or CR24, at least one of M2 to M4 is N, R7 to R24 are the same as or different from each other, and each independently hydrogen; deuterium; a nitrile group; a substituted or unsubstituted alkyl group; a substituted or unsubstituted silyl group; a substituted or unsubstituted amine group; a substituted or unsubstituted aryl group; or a substituted or unsubstituted heteroaryl group, or adjacent groups may bond to each other to form a substituted or unsubstituted ring, r14, r15 and r18 are each an integer of 1 to 4, and when r14, r15 and r18 are each 2 or more, the structures in the two or more parentheses are the same as or different from each other.

According to one embodiment of the present specification, Chemical Formula 1 is represented by any one of the following compounds.

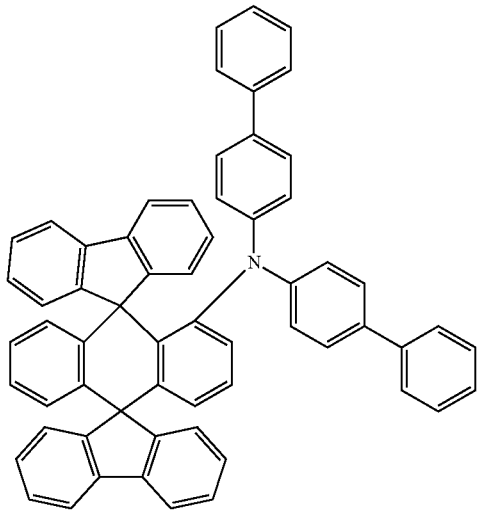

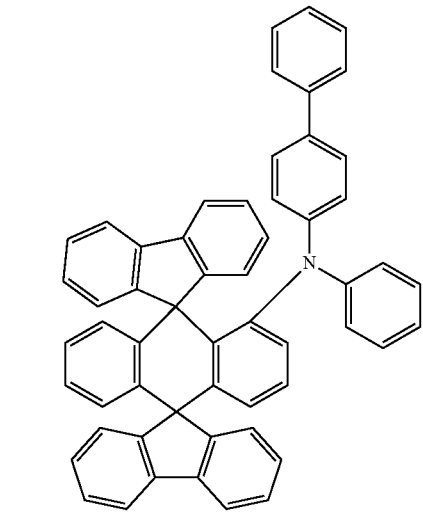

81
-continued
82
-continued
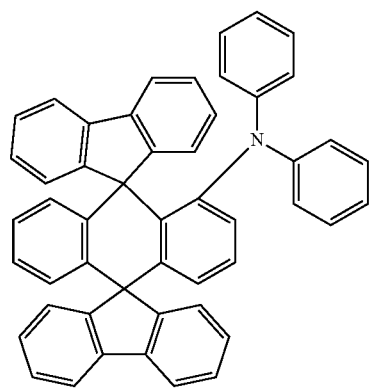
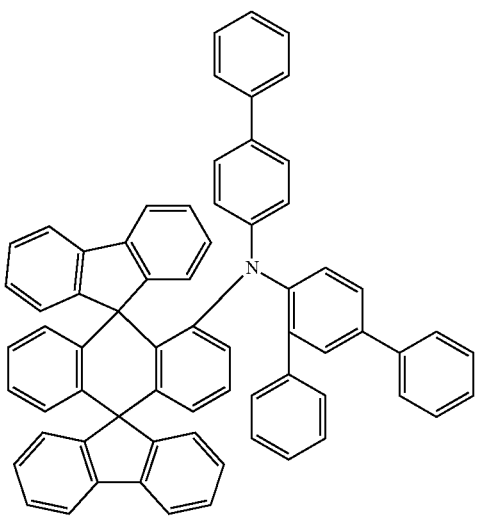
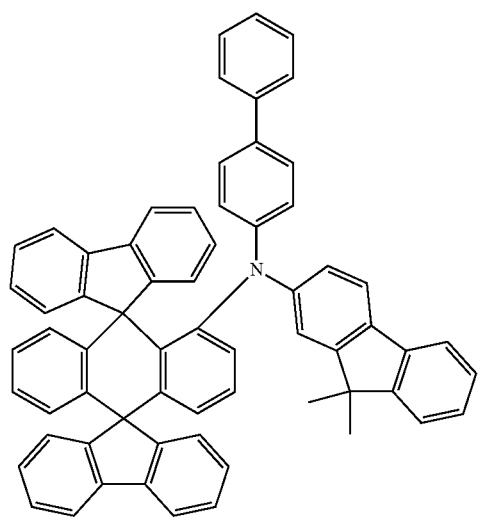
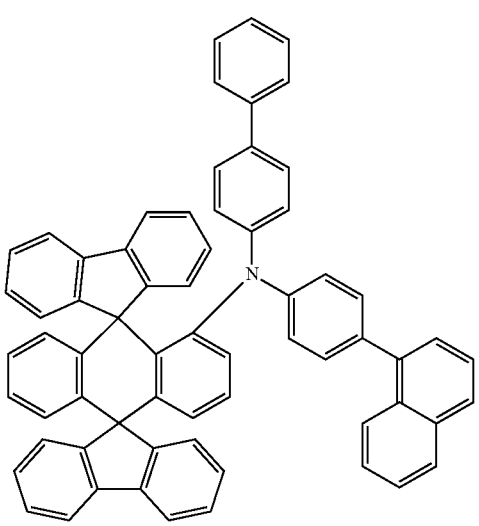
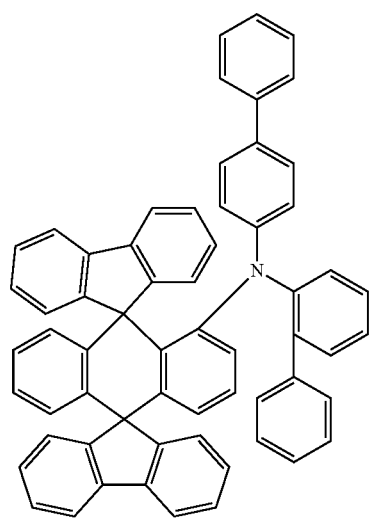
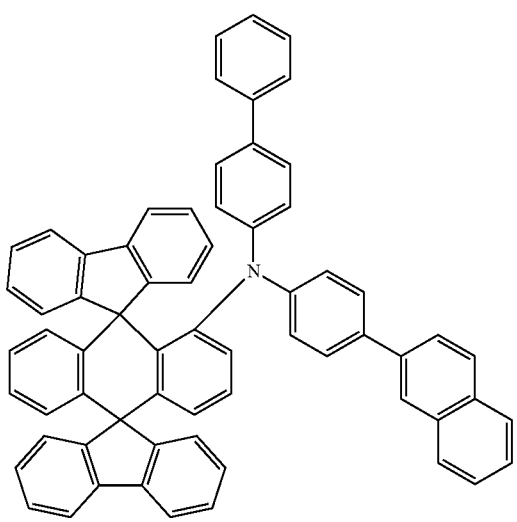

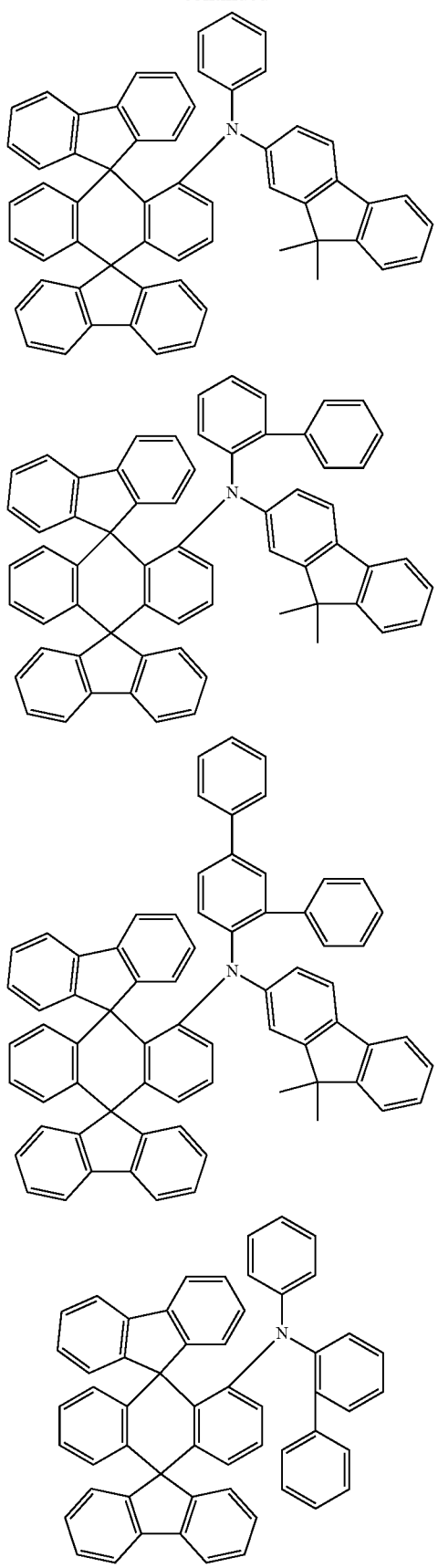
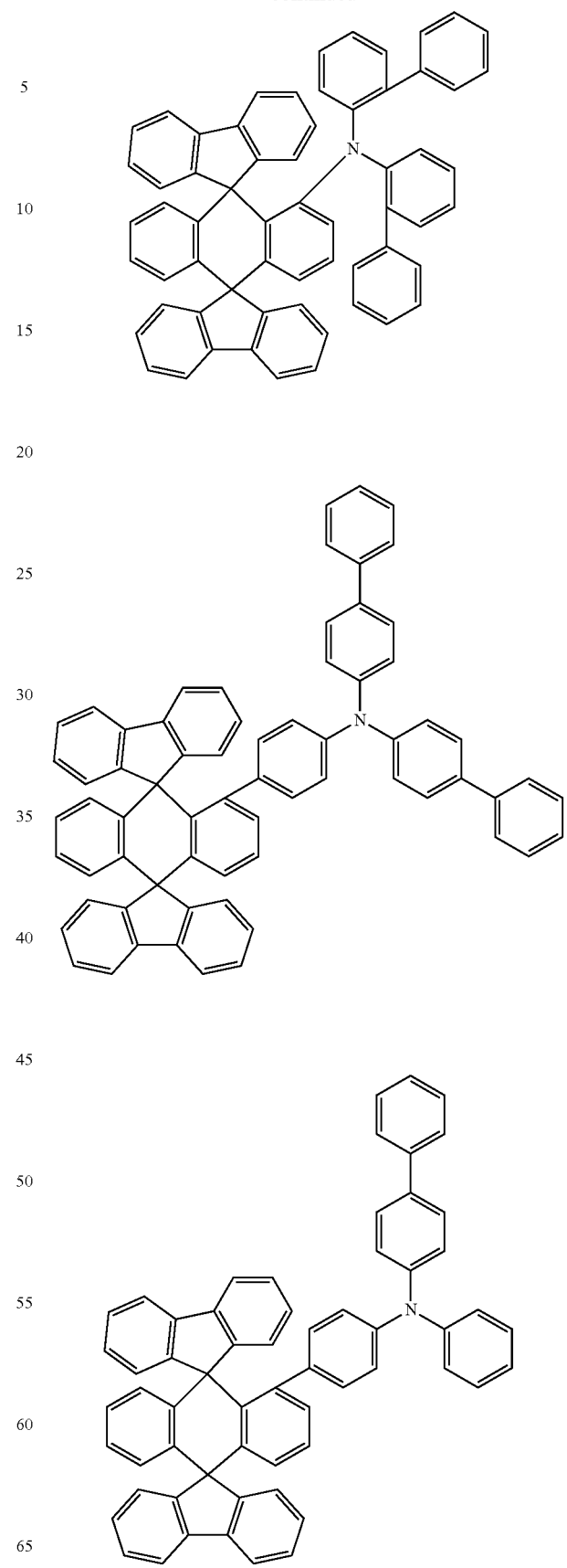

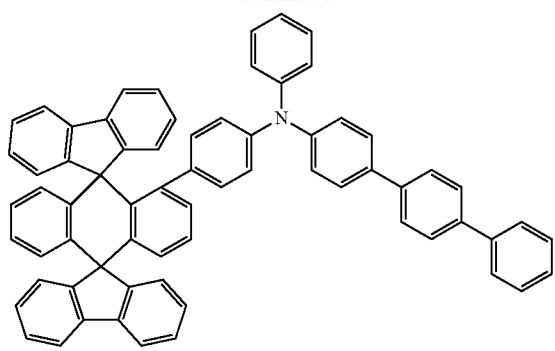
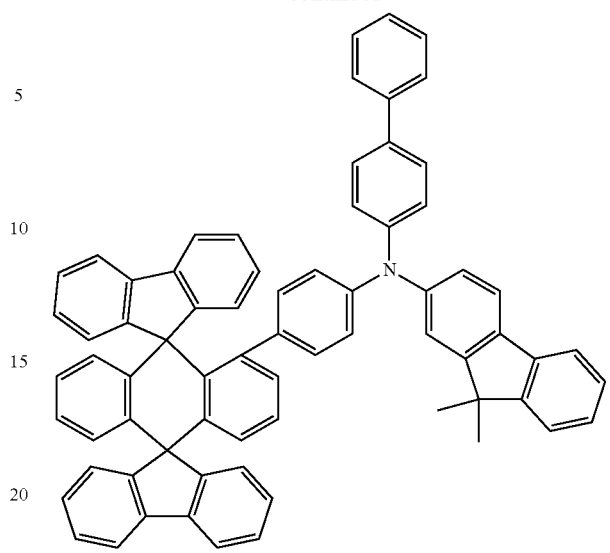
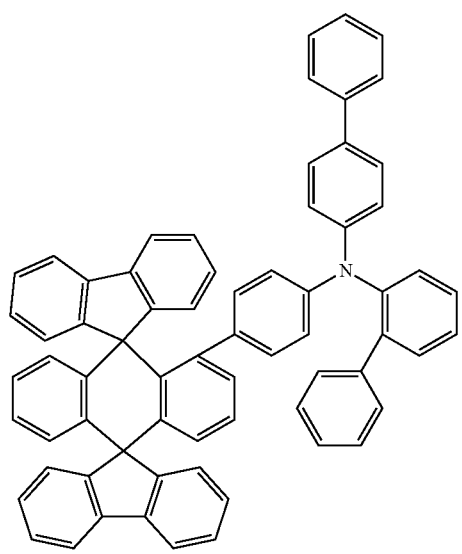
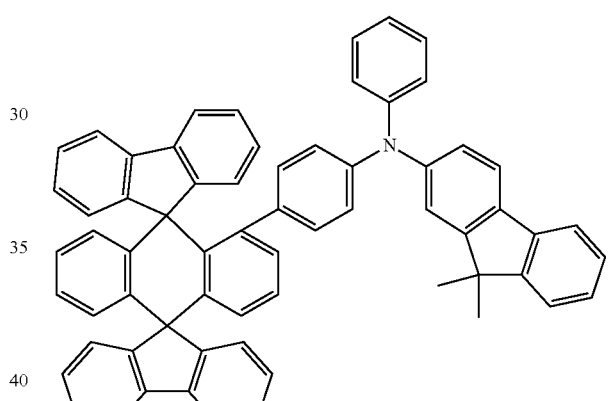
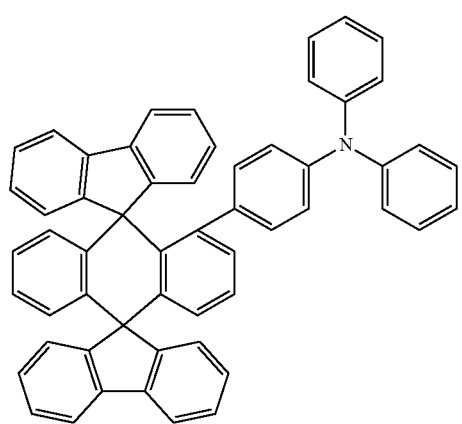
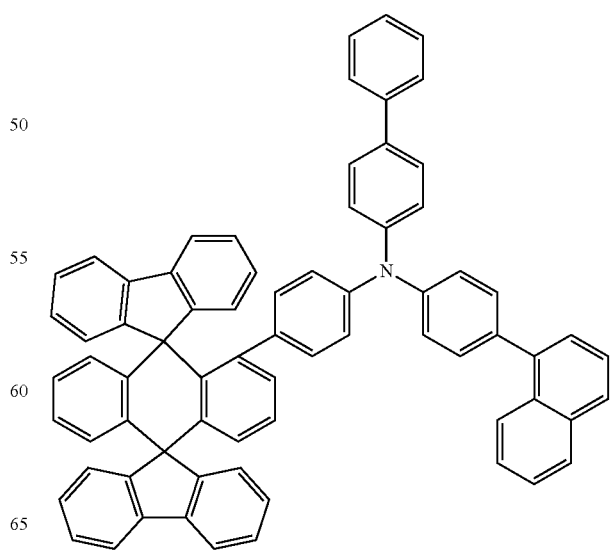

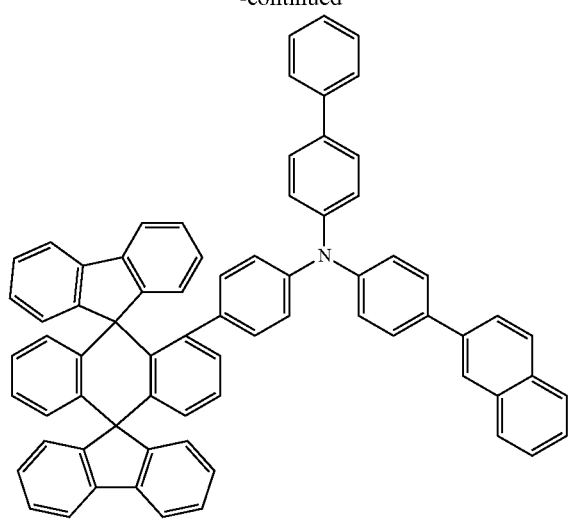
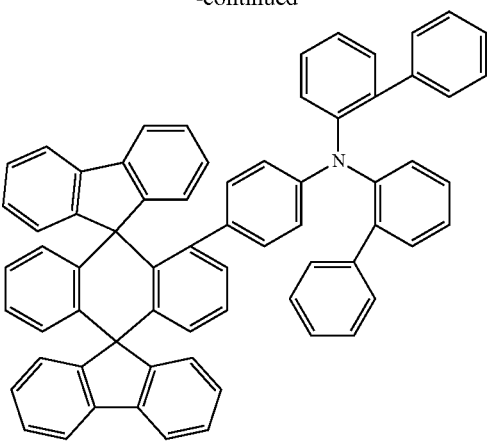
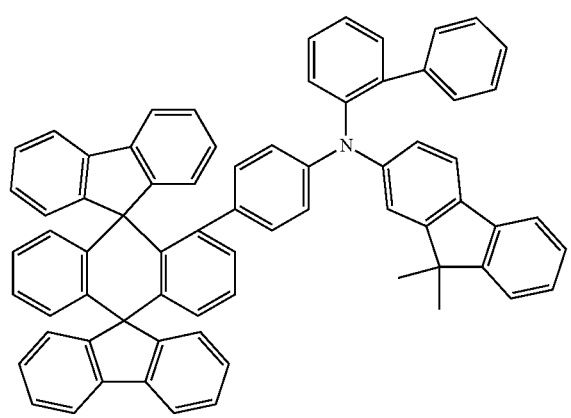
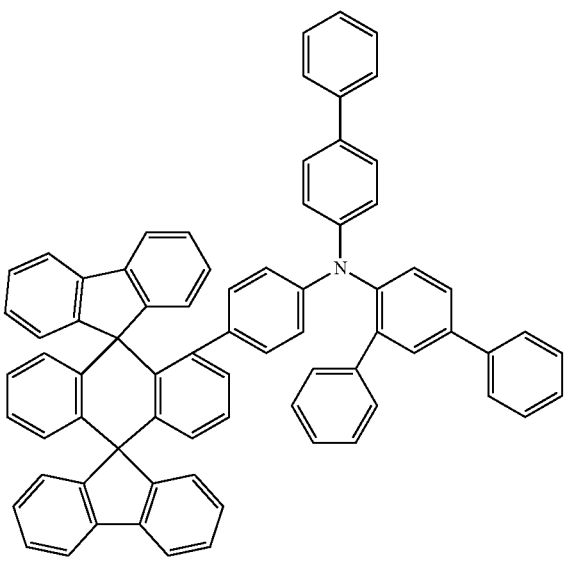
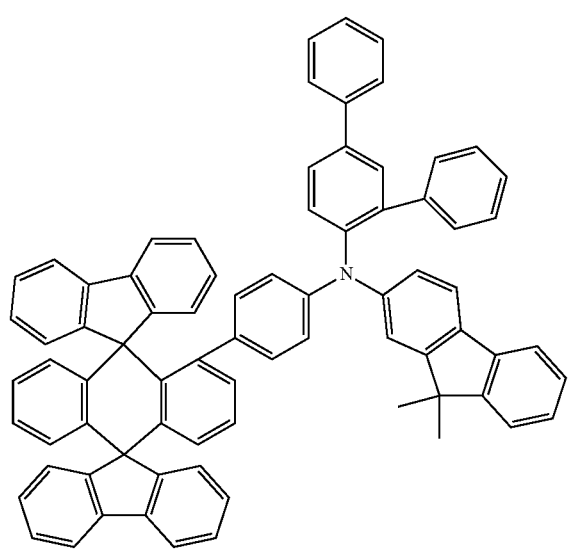
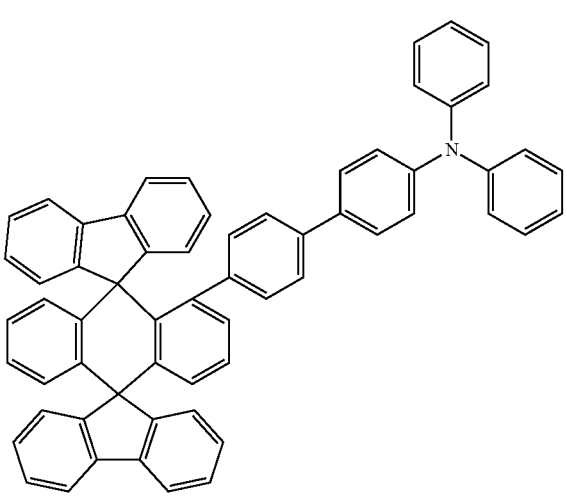

-continued
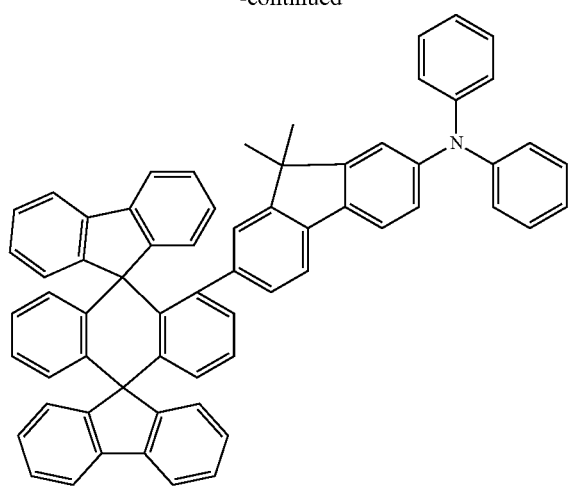
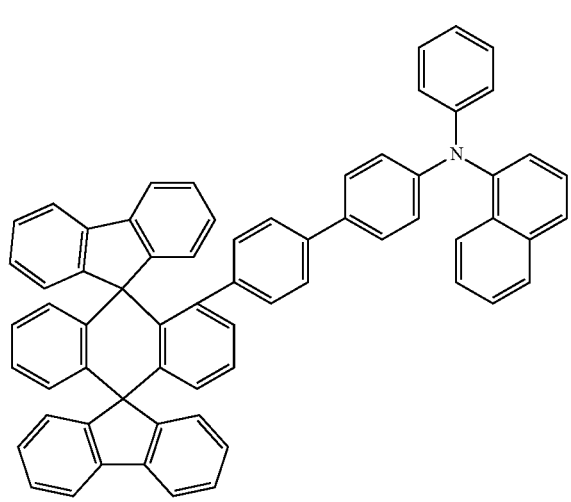
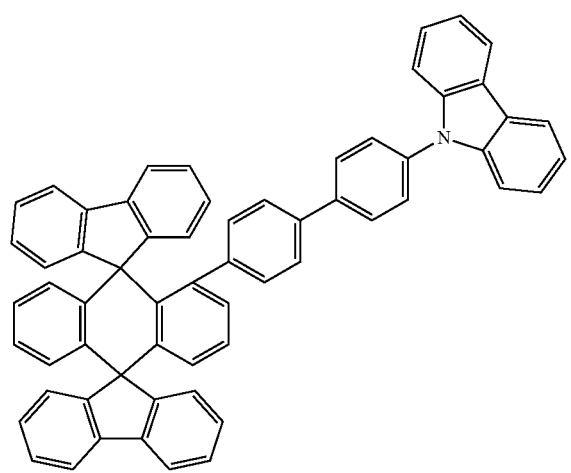
-continued
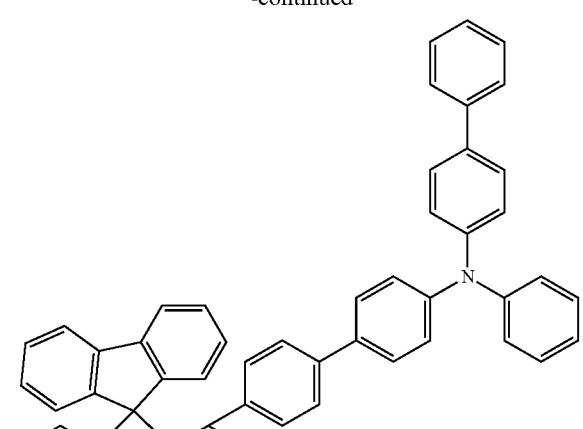
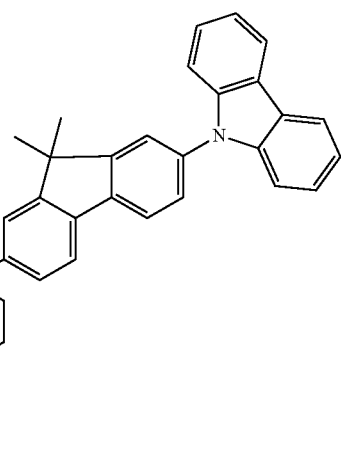
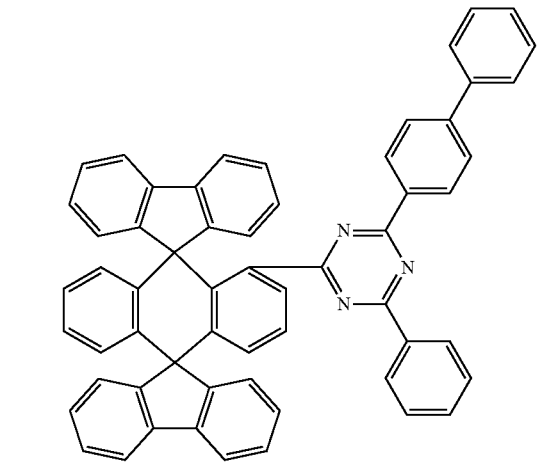

91
-continued
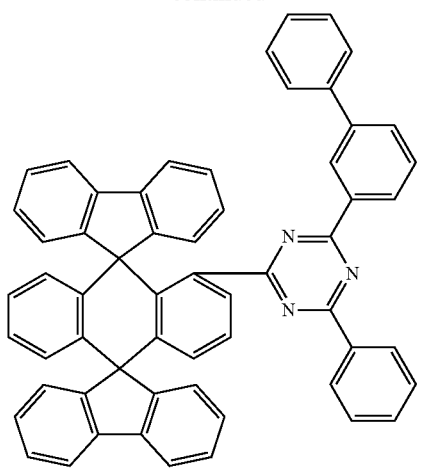
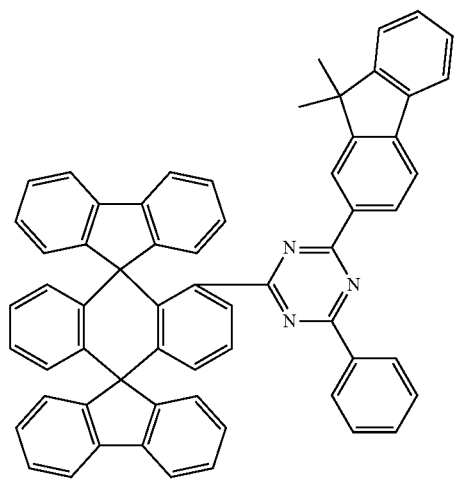
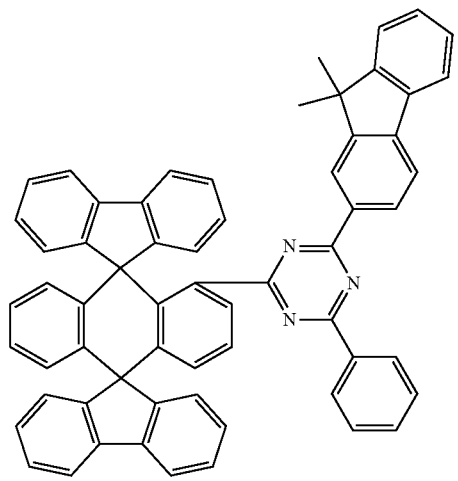
92
-continued
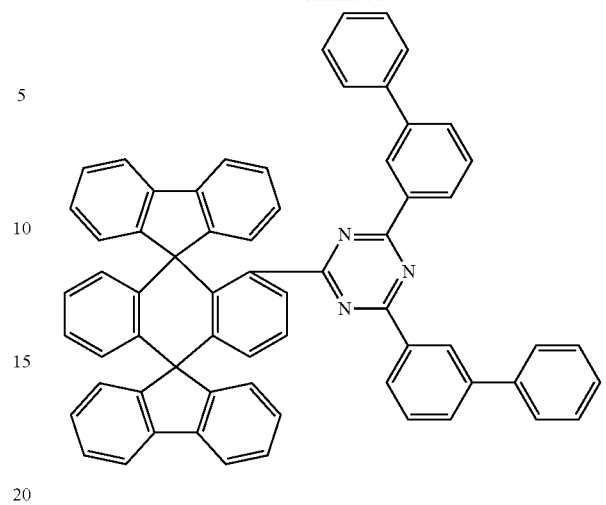
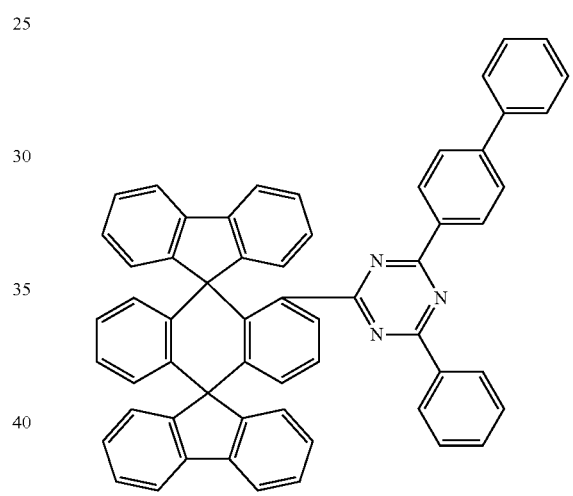
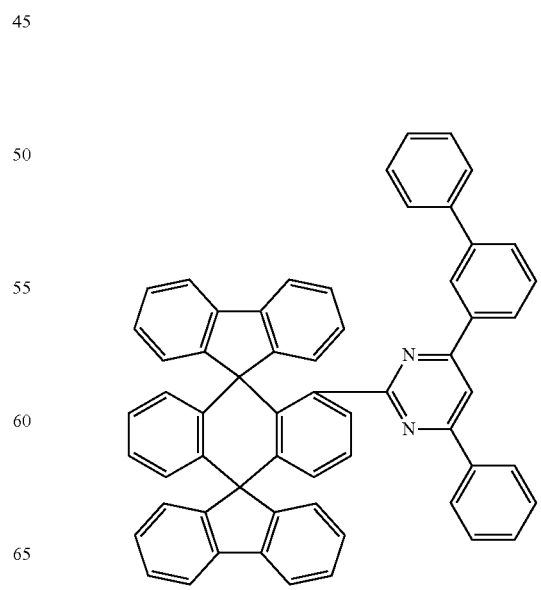

93
-continued
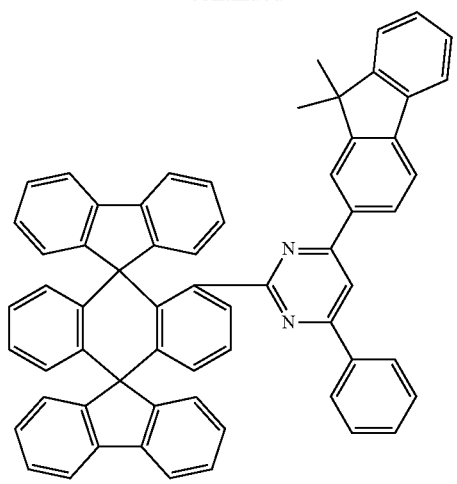
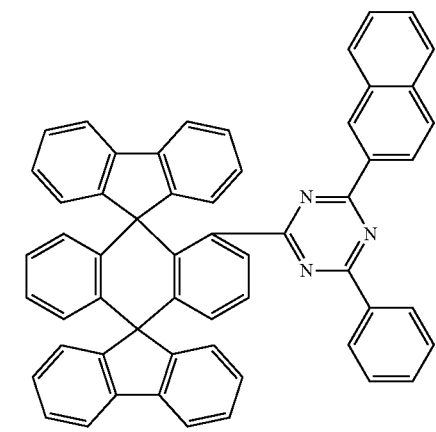
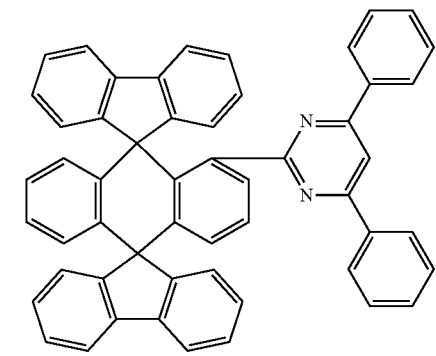
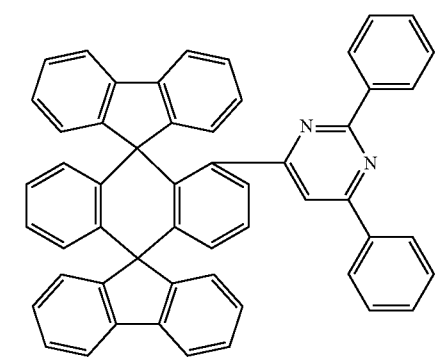
94
-continued
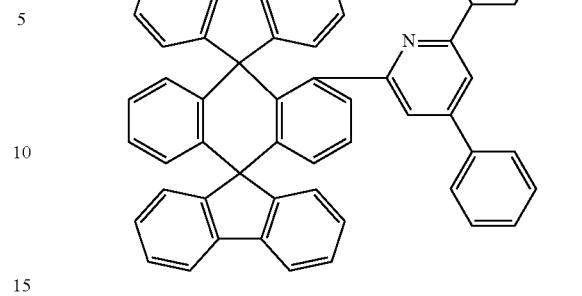
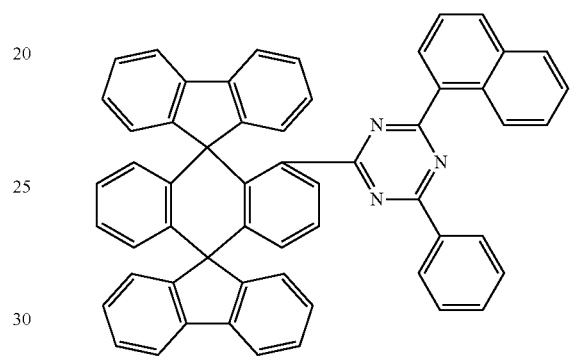
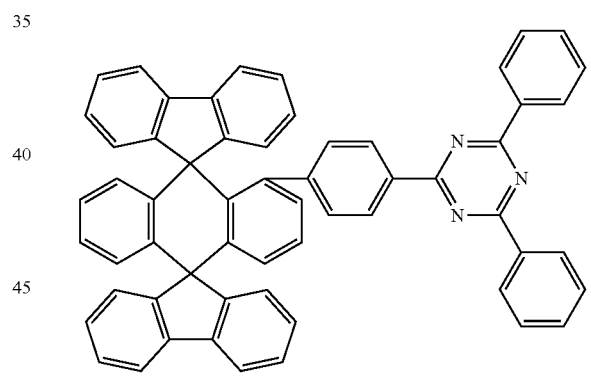
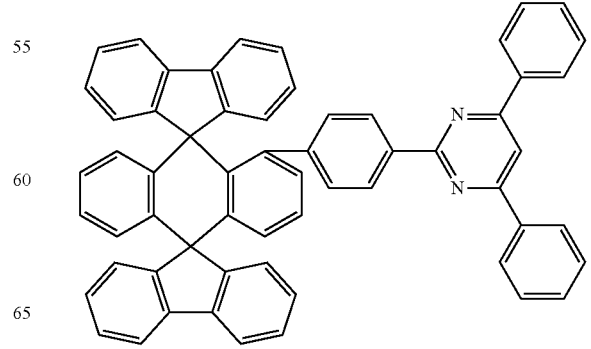

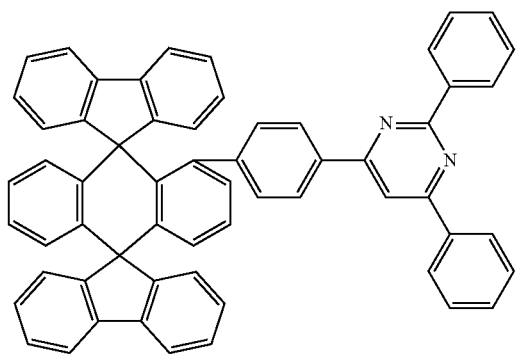
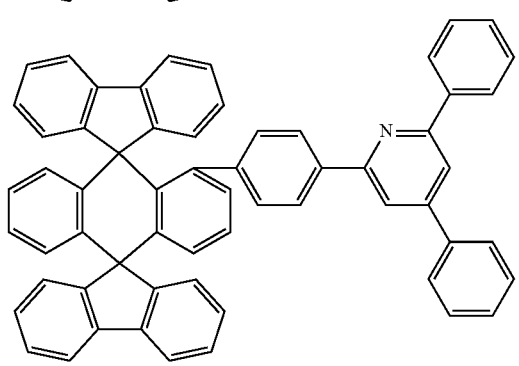
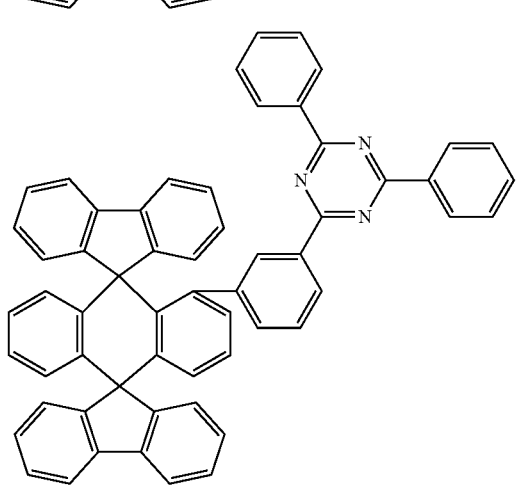
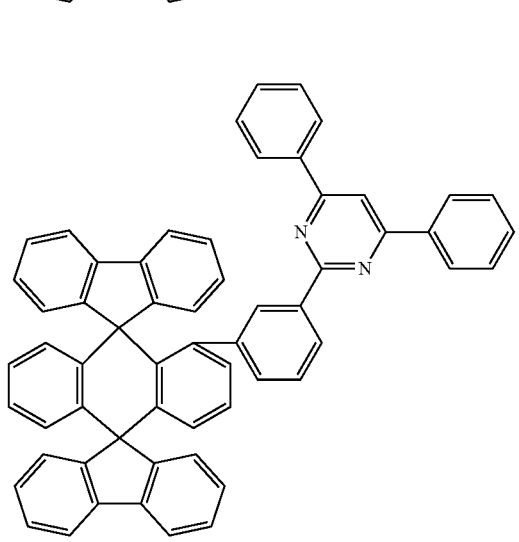
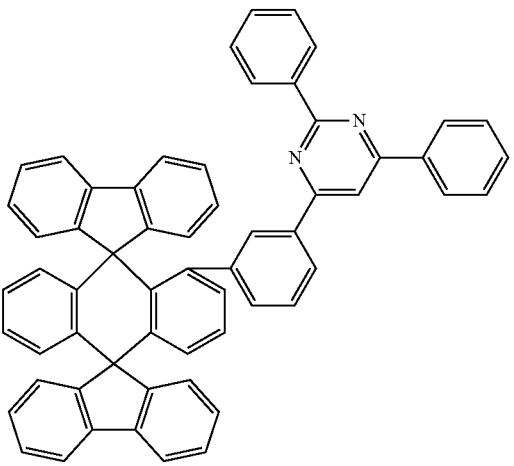
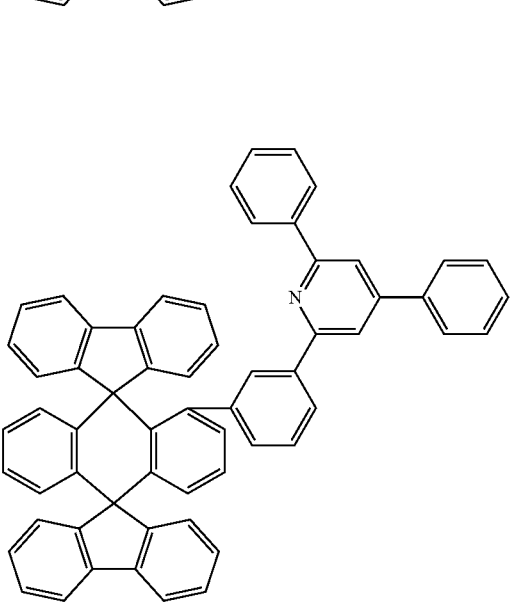
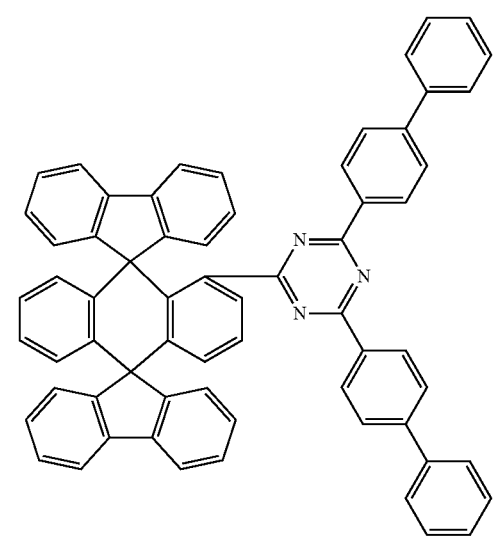

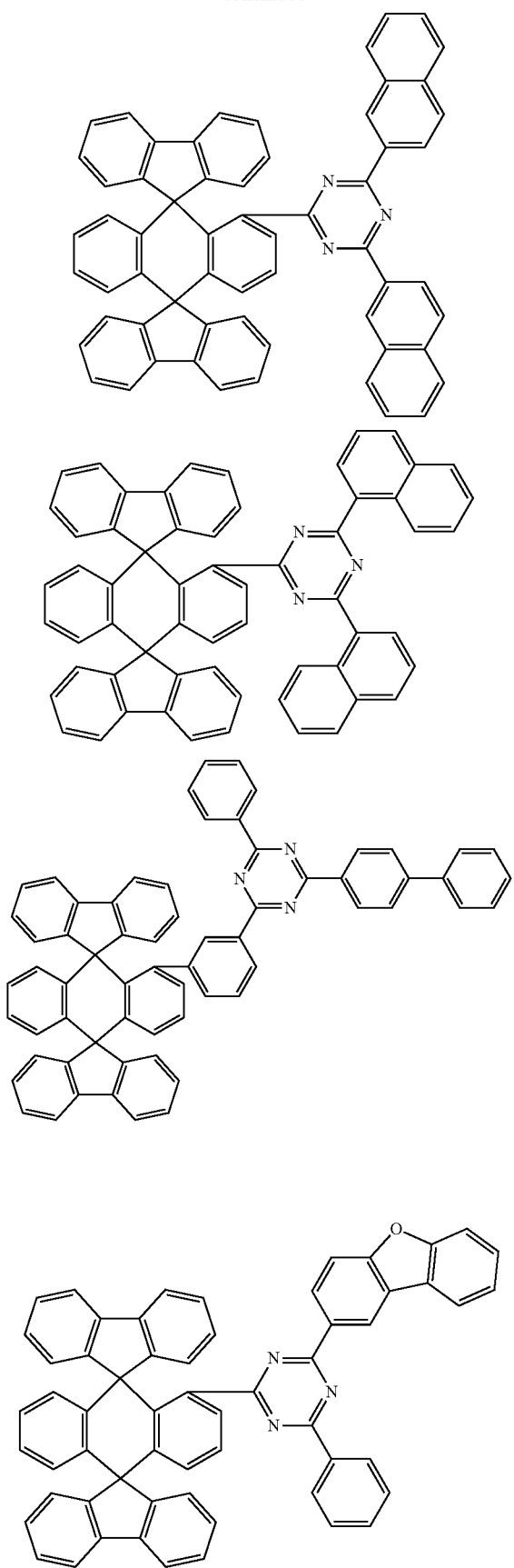
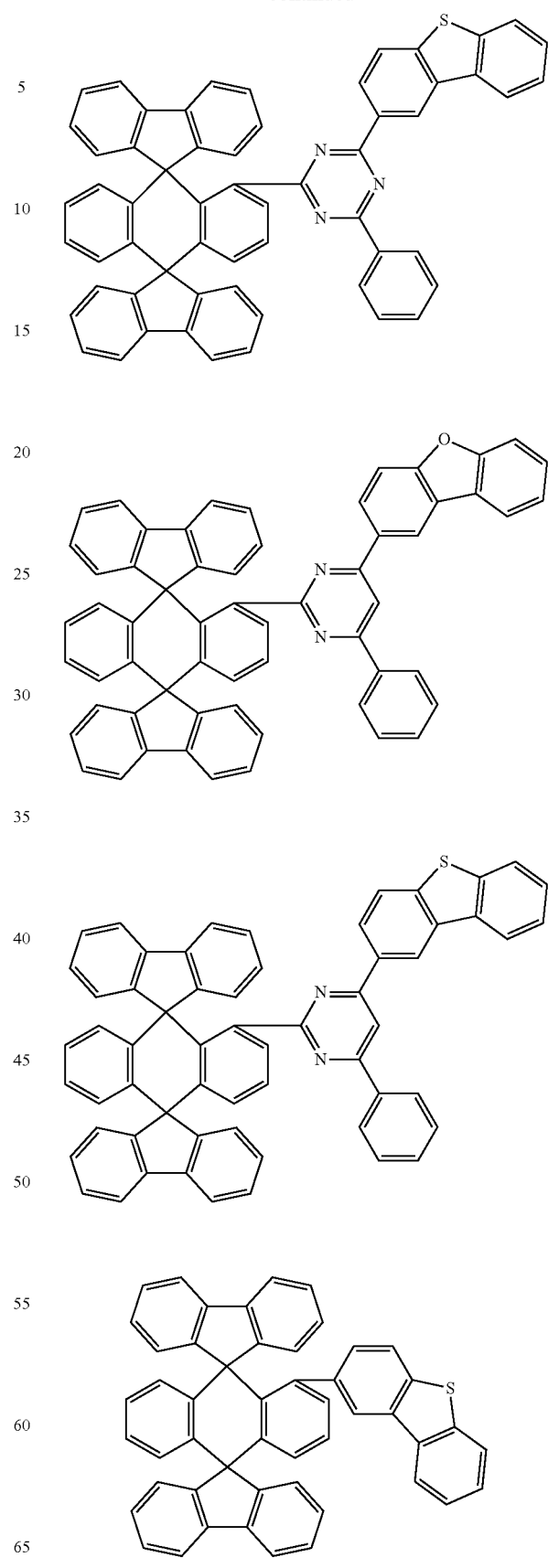

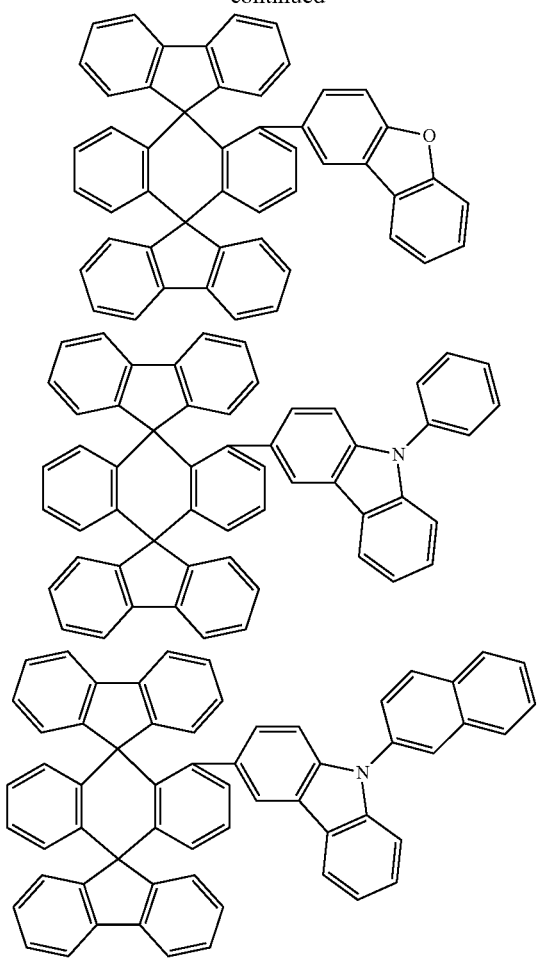
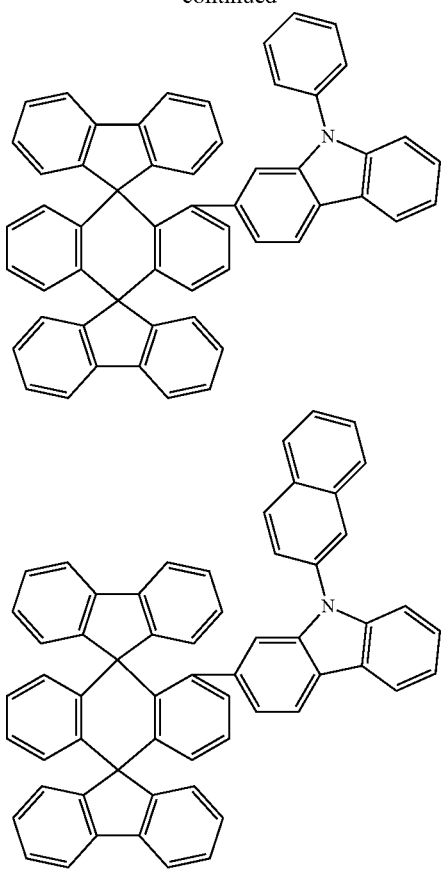
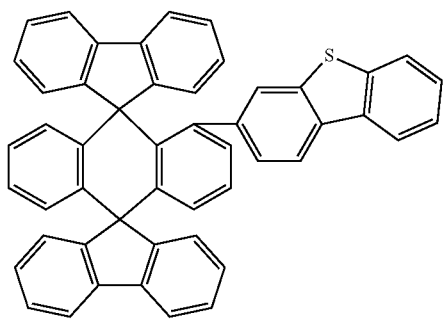
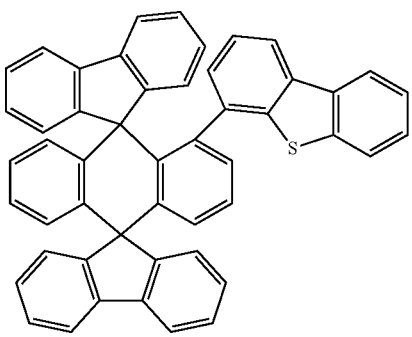
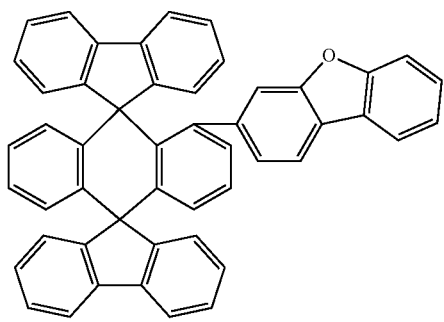
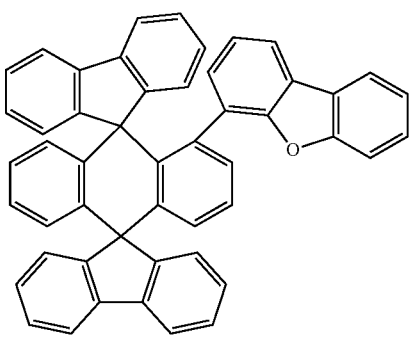

101
-continued
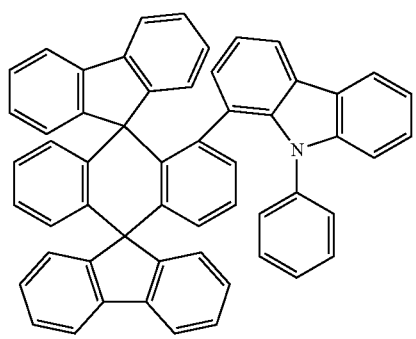
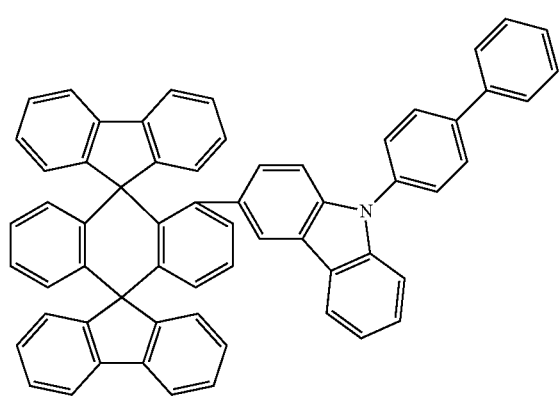
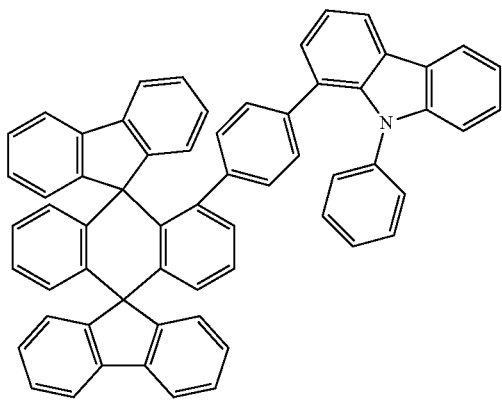
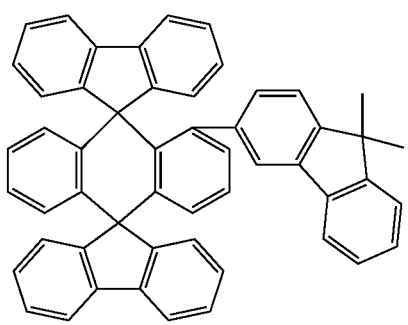
102
-continued
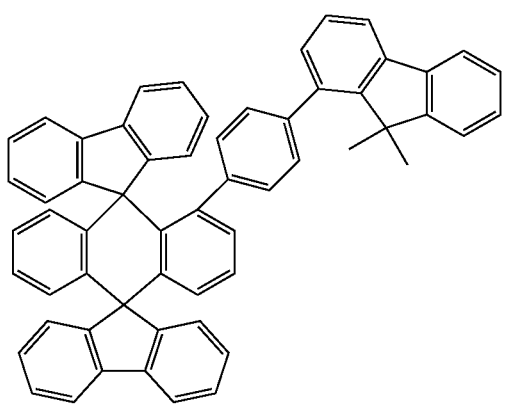
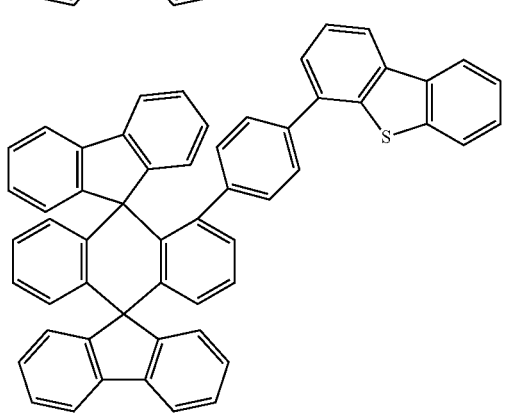
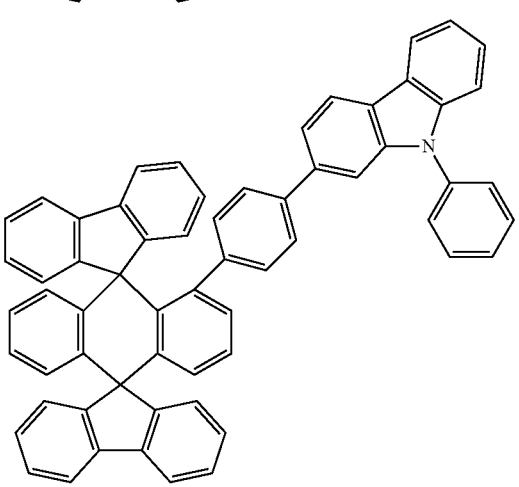
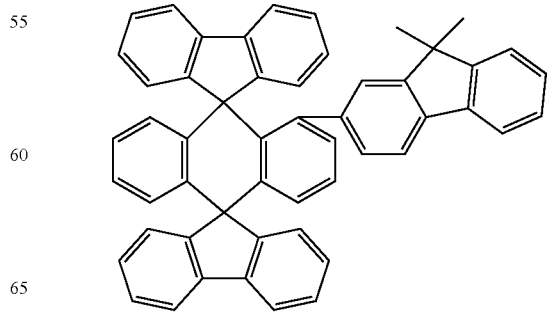

103
-continued
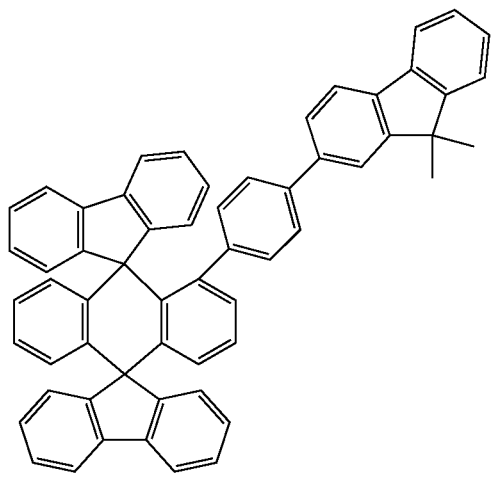
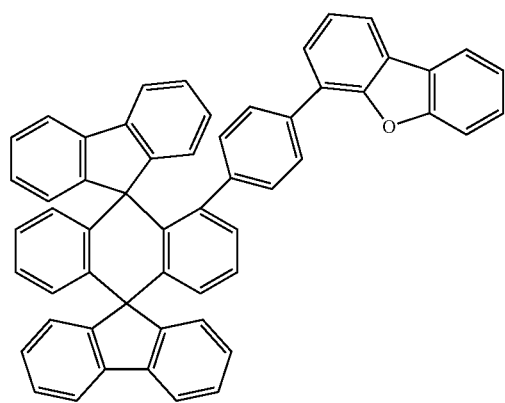
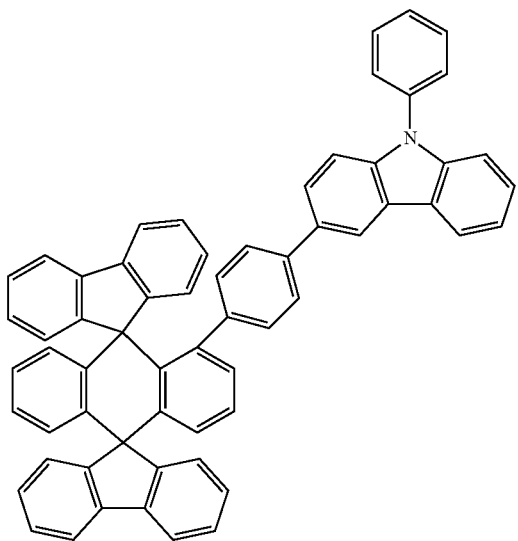
104
-continued
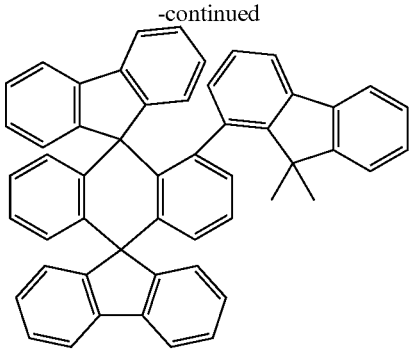
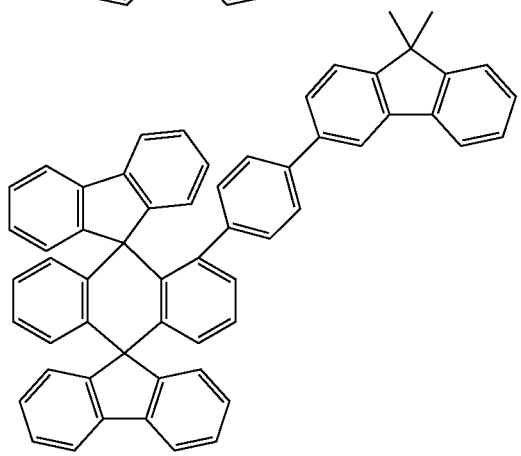
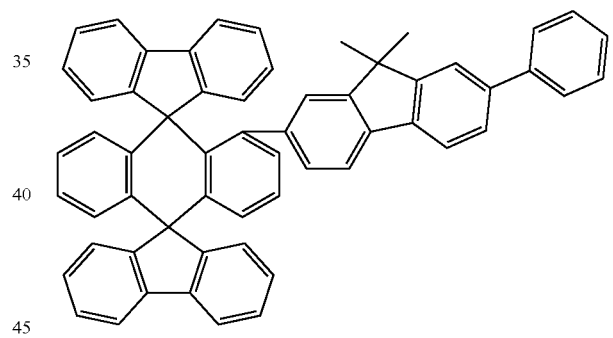
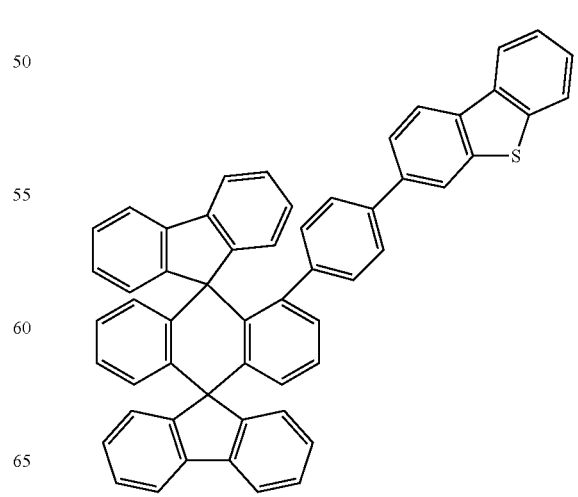

105
-continued
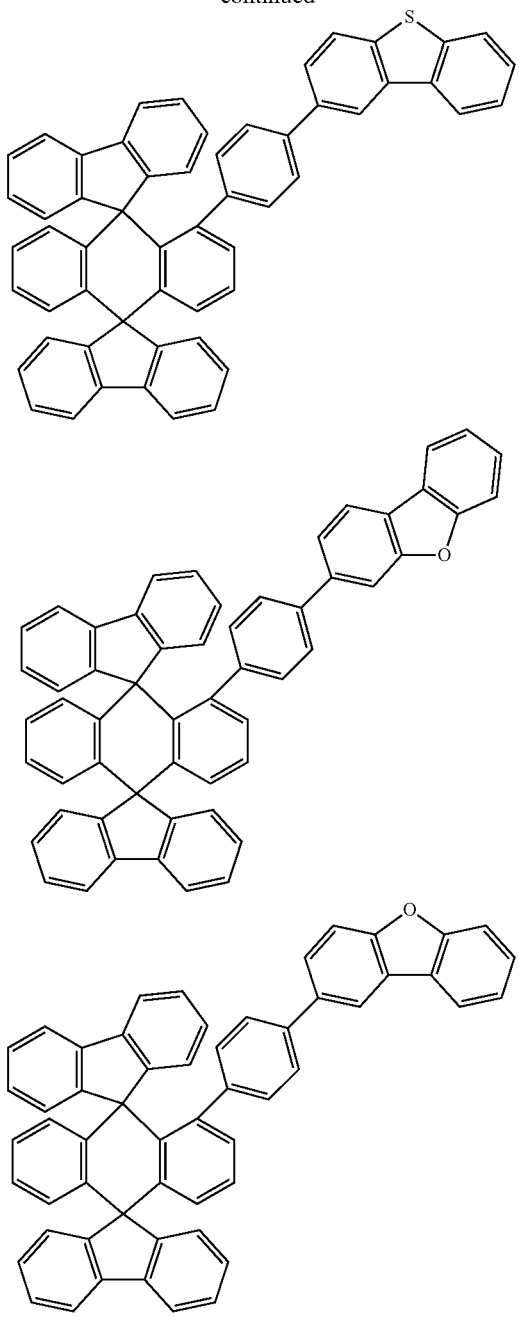
106
-continued
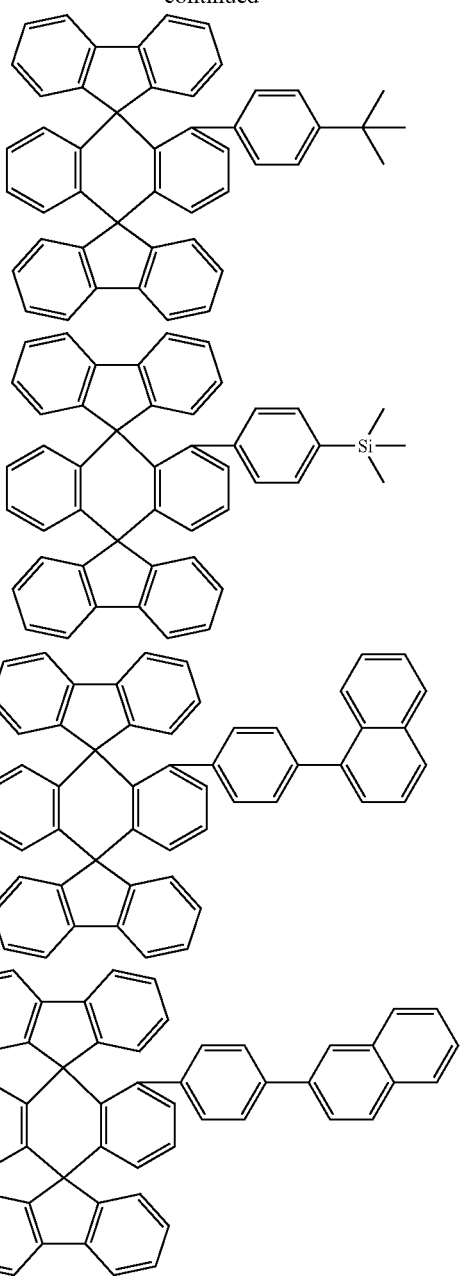
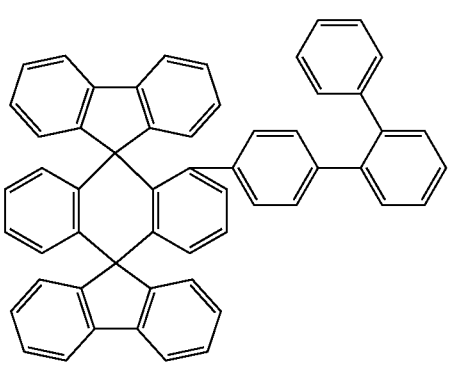

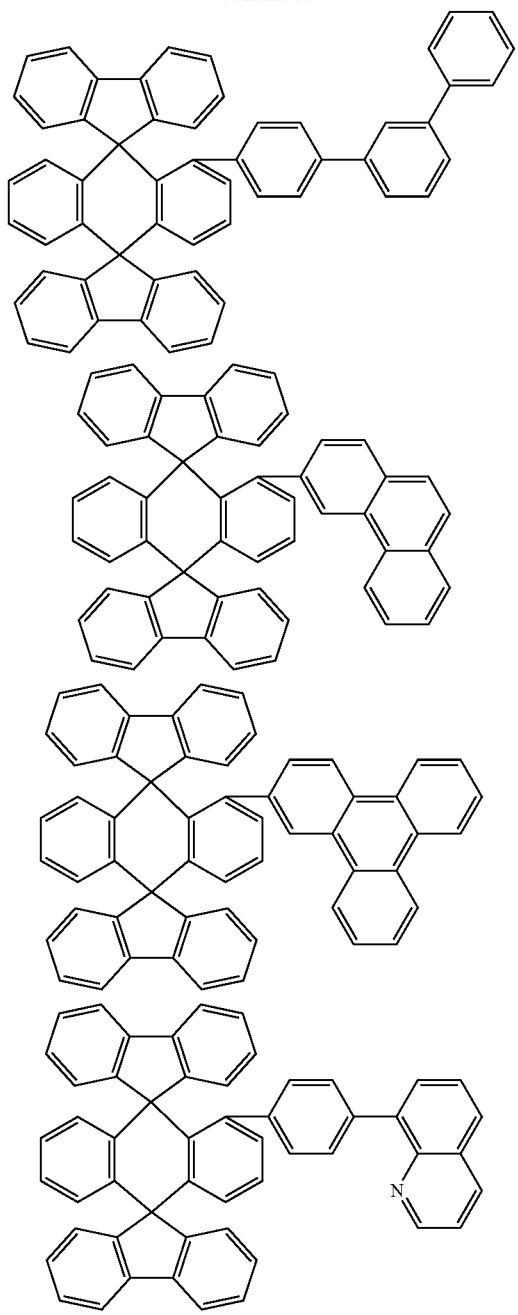
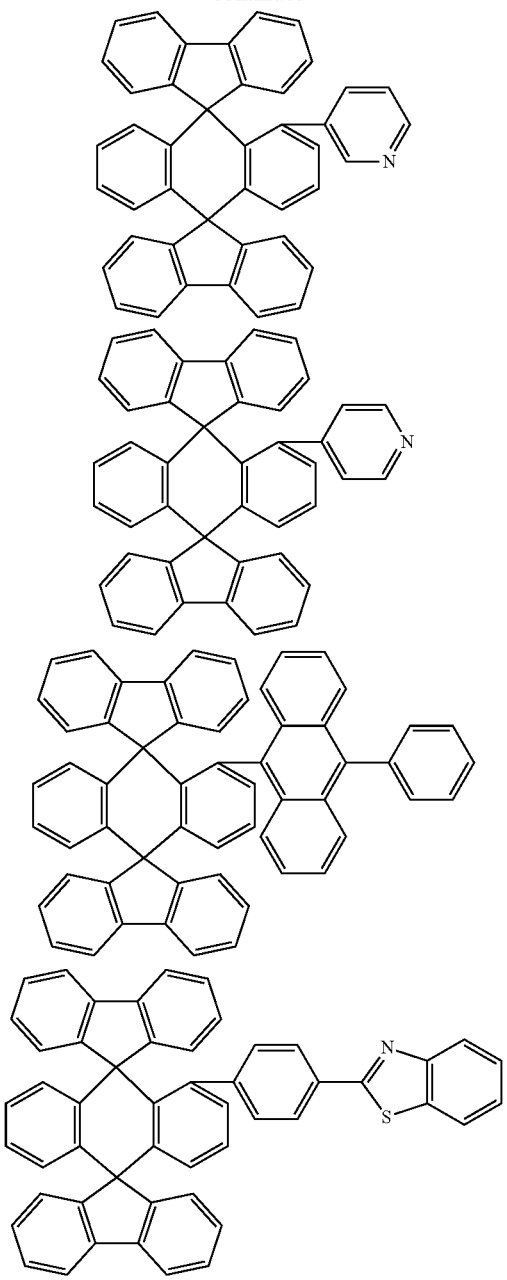
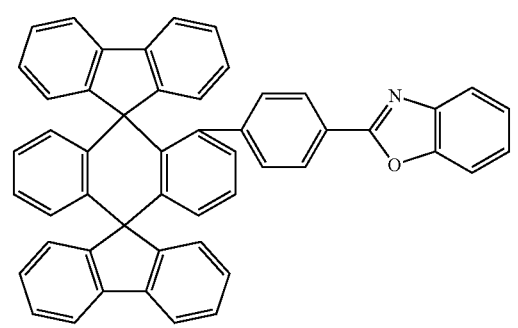
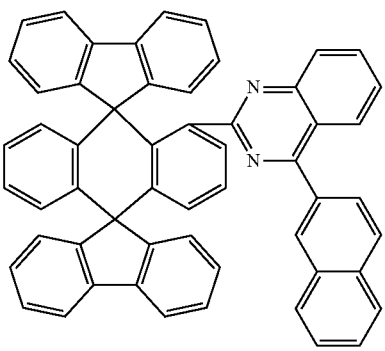

-continued
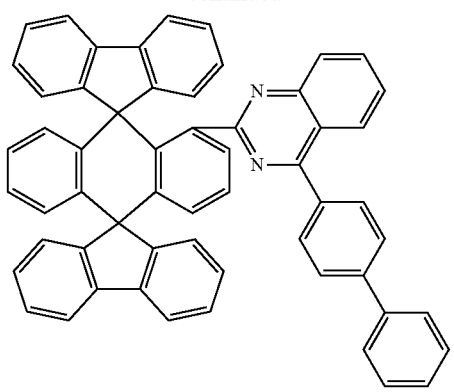
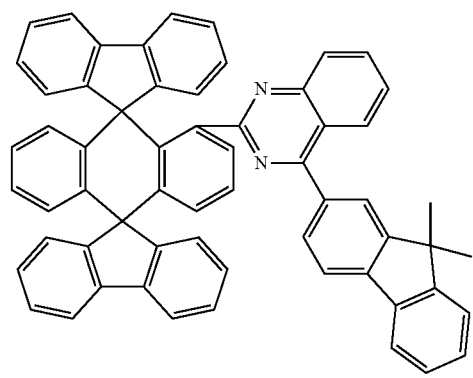
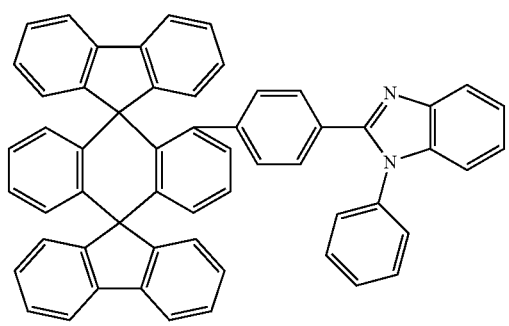
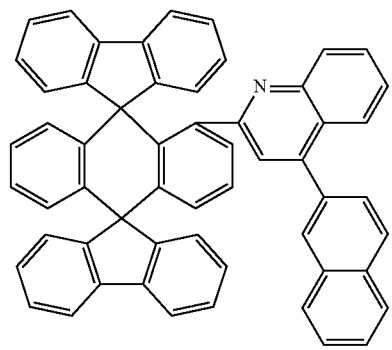
-continued
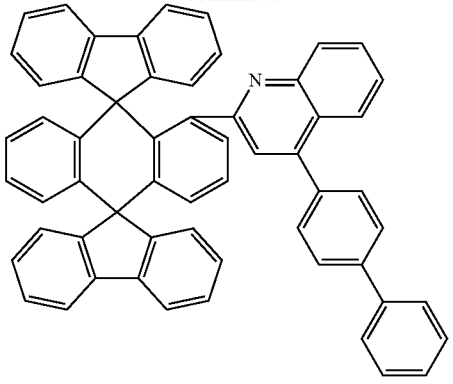
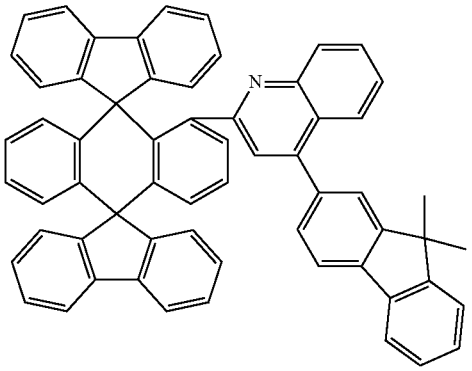
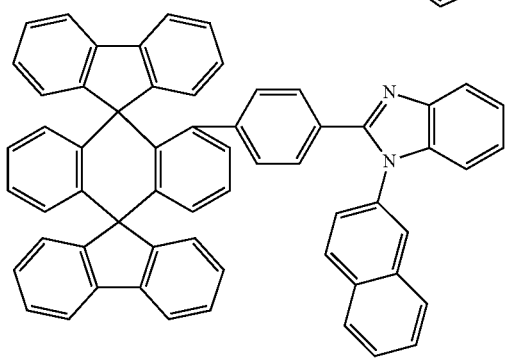
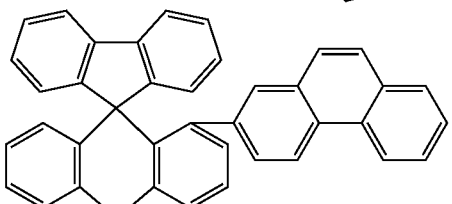
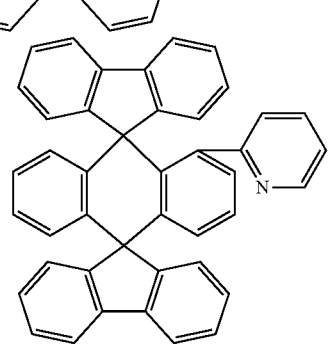

111
-continued
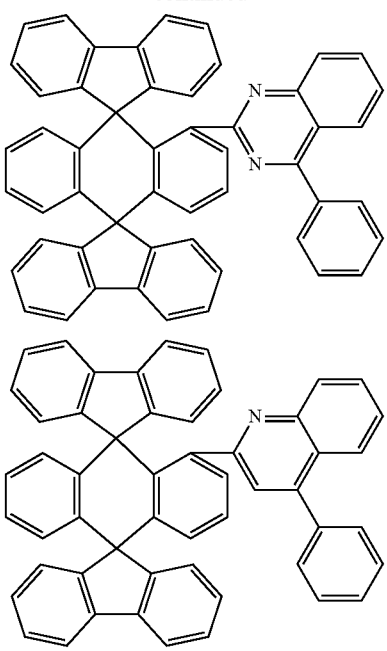
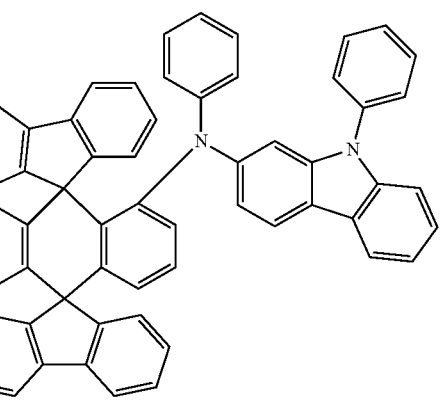
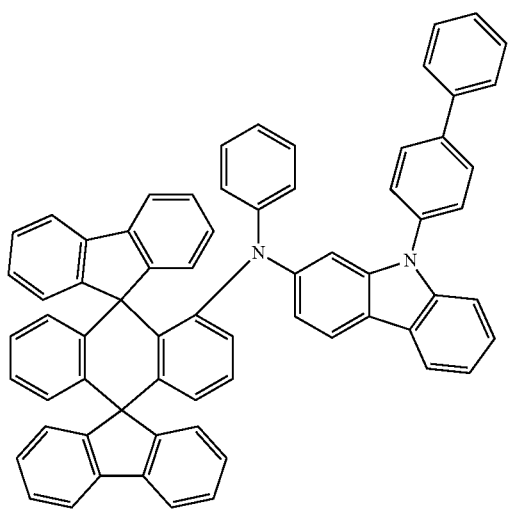
112
-continued
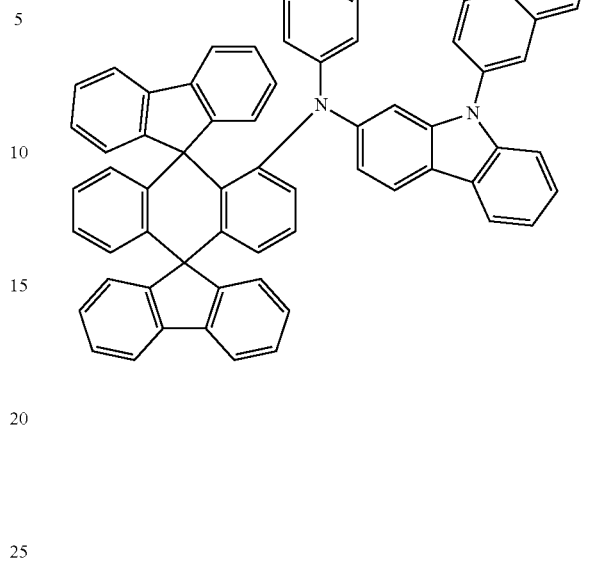
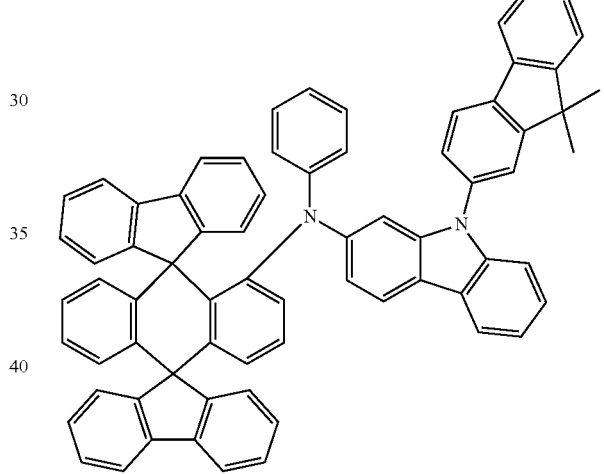
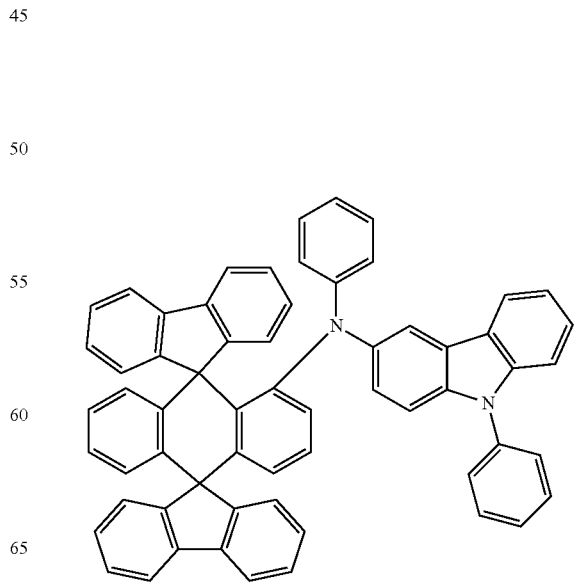

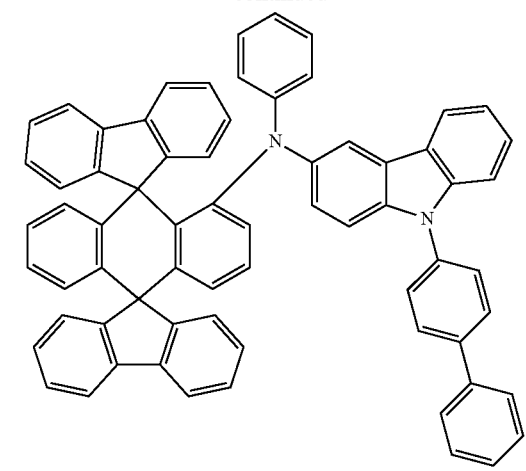
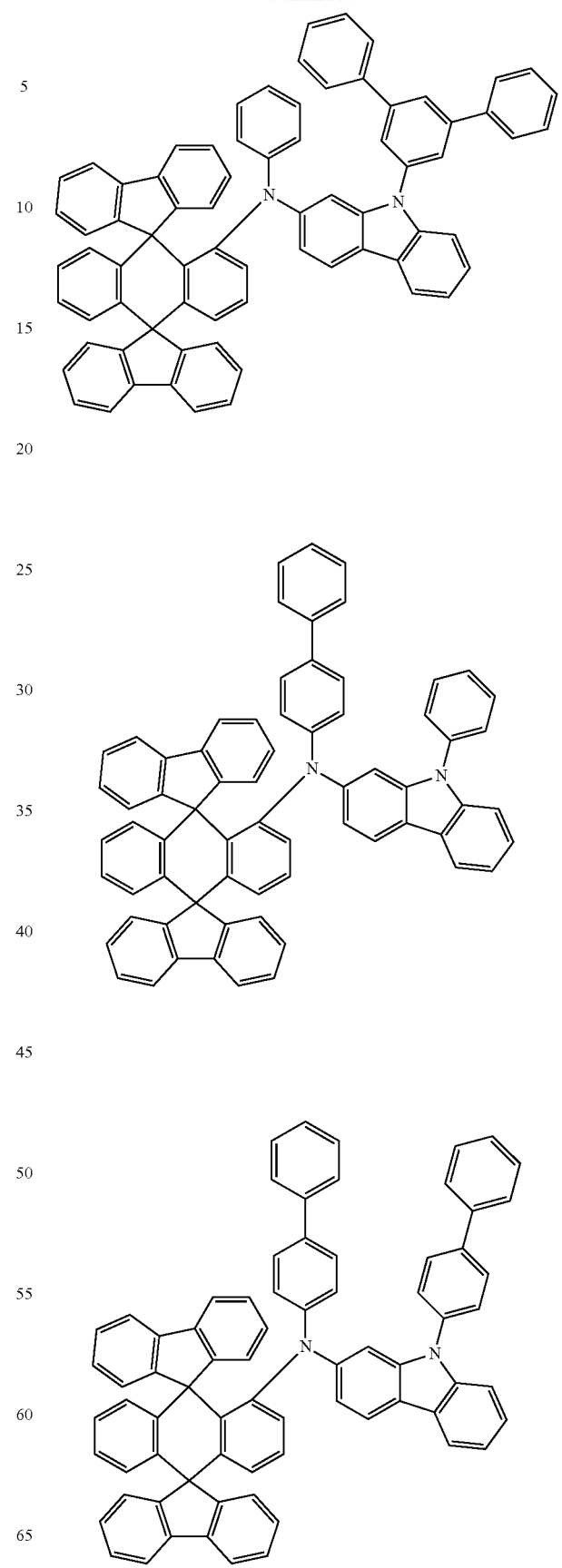

115
-continued
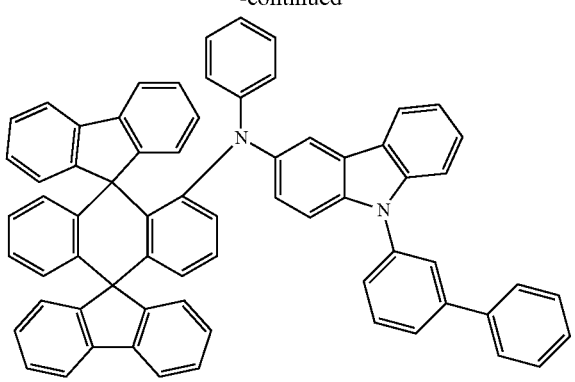
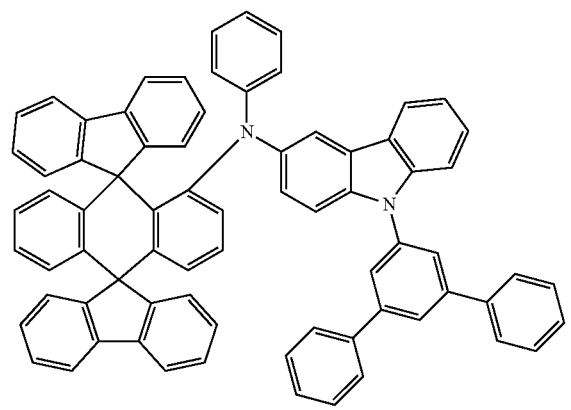
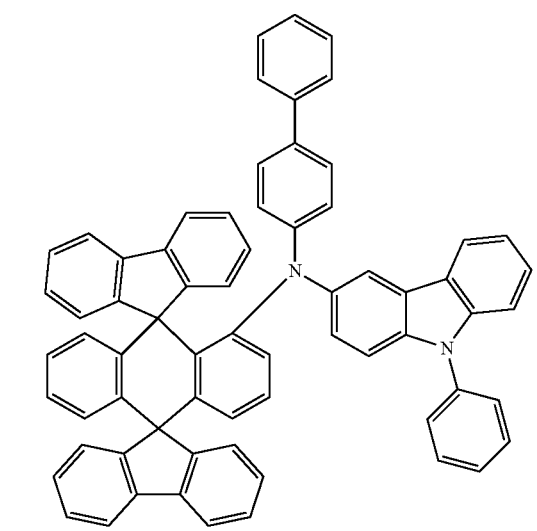
116
-continued
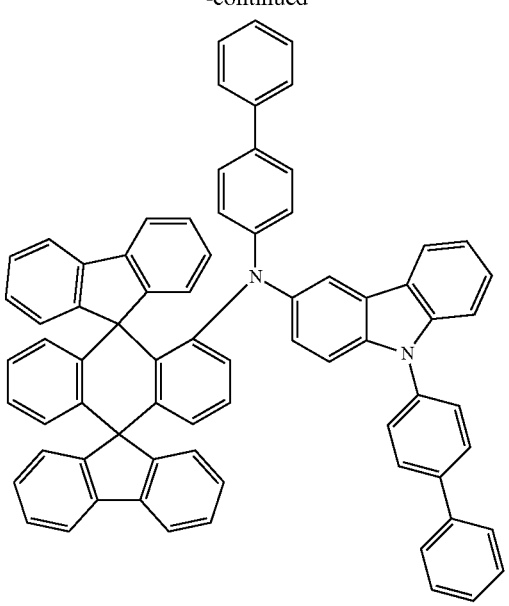
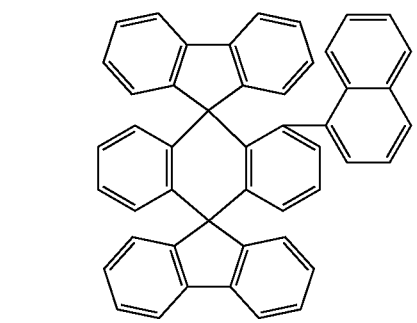
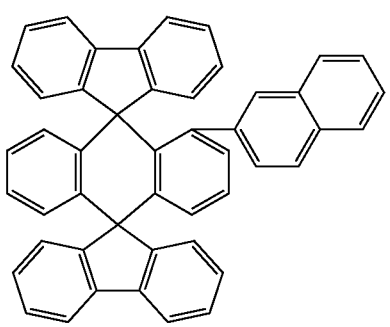

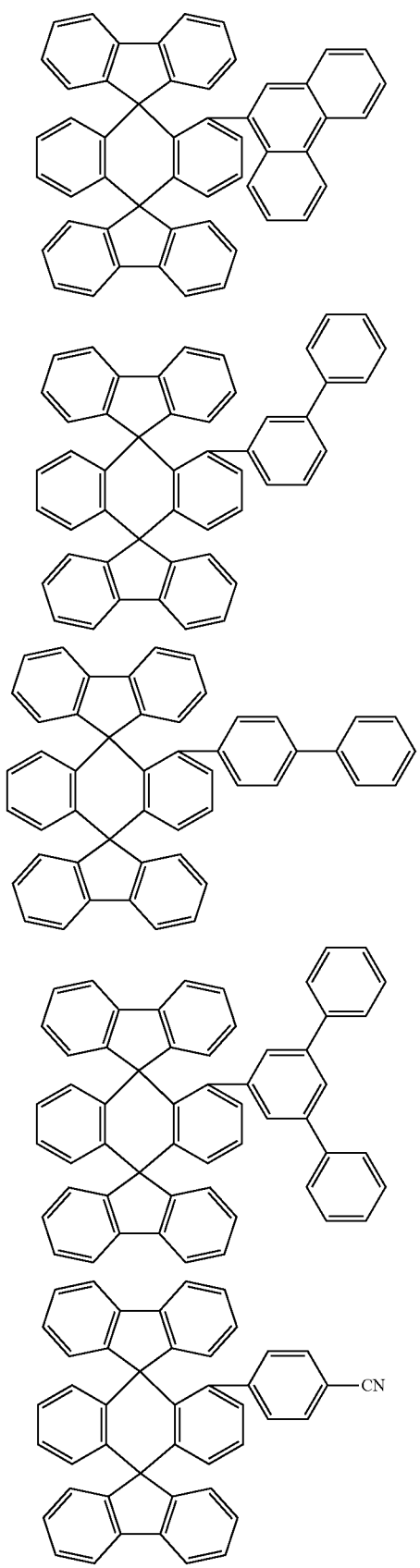
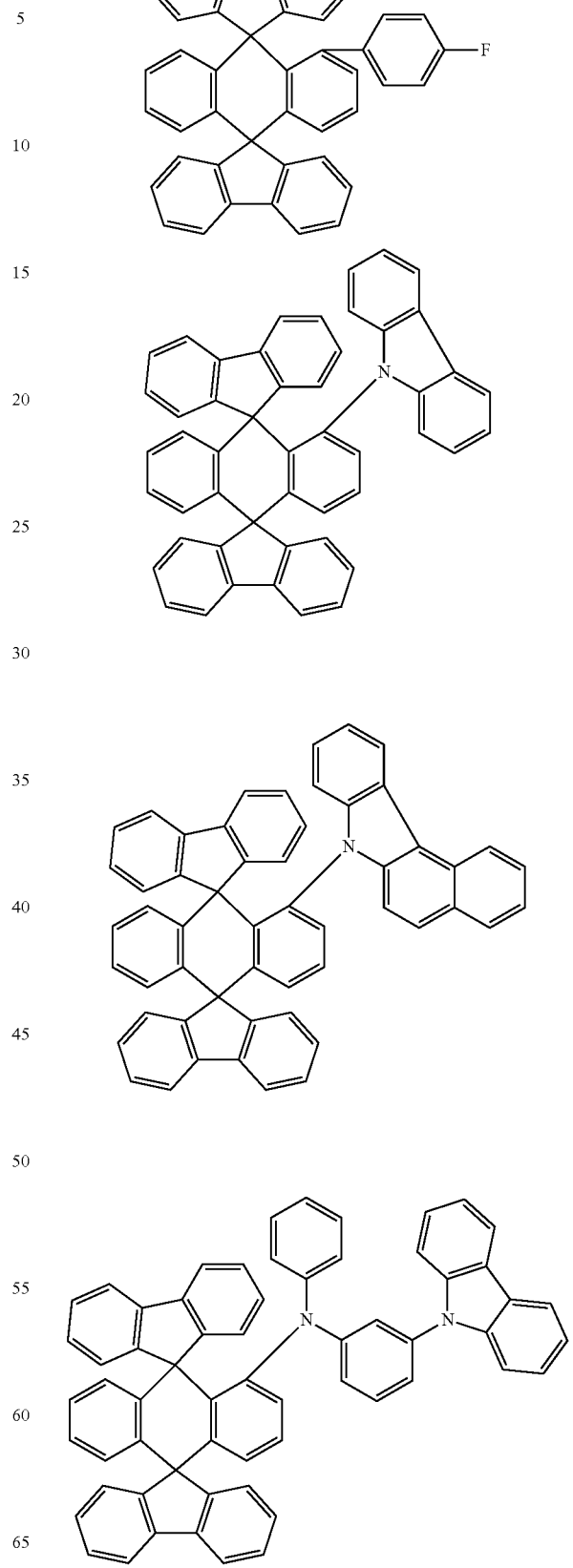

-continued
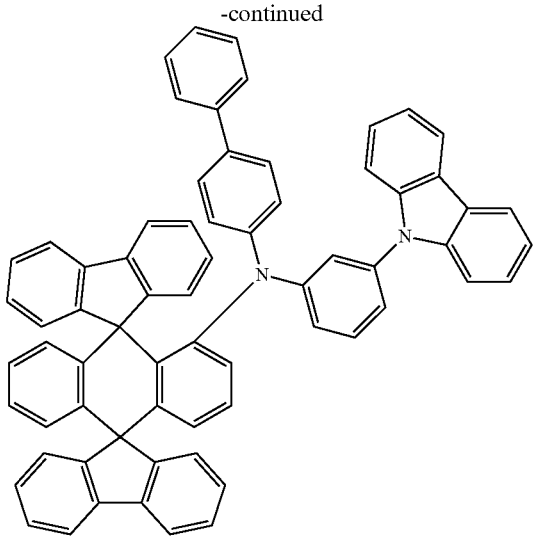
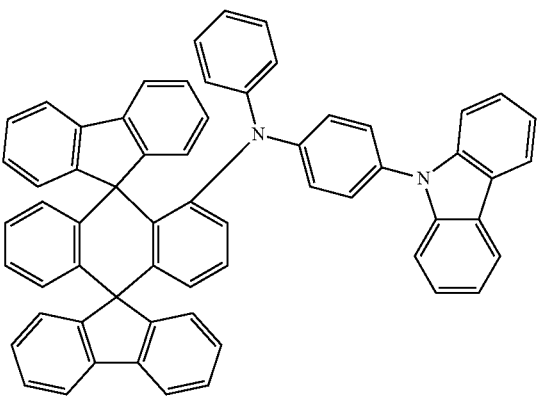
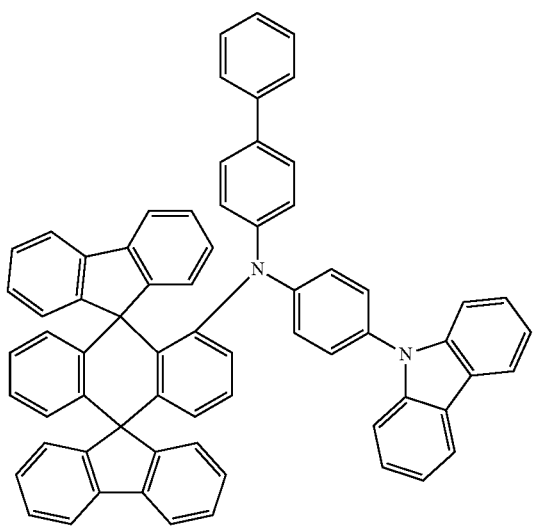
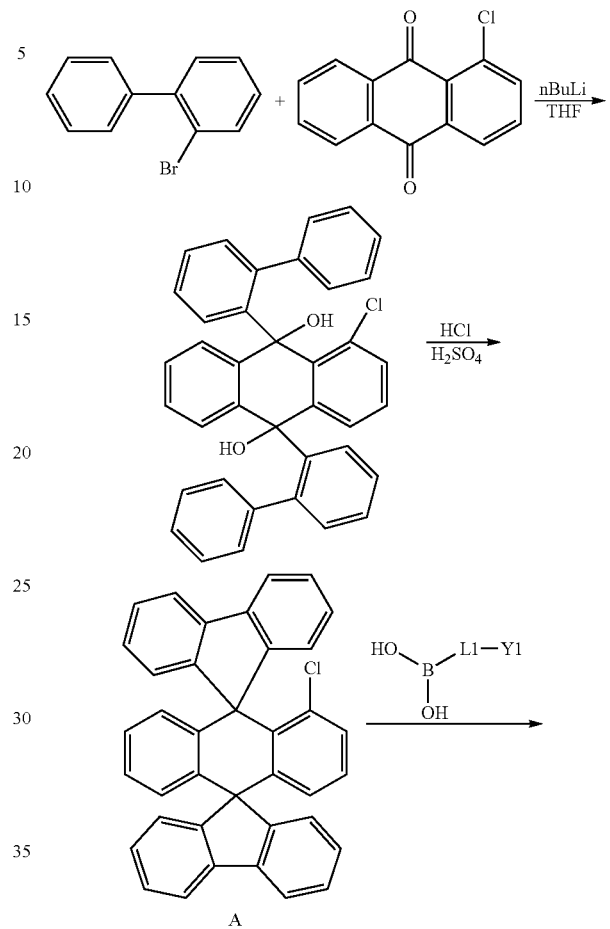
[General Formula 1]
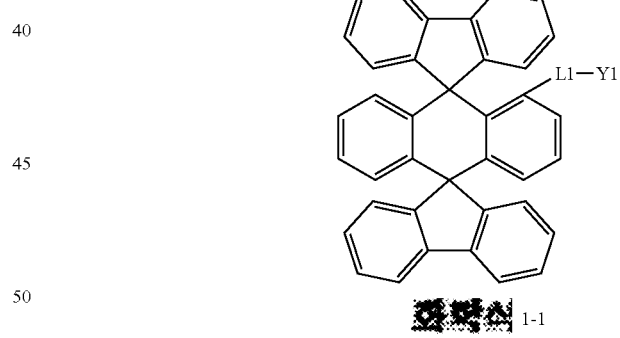
[General Formula 2]
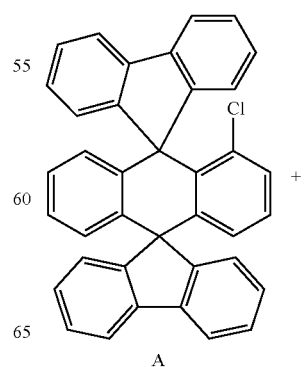
According to one embodiment of the present specification, Chemical Formula 1 may be represented by Chemical Formula 1-1, and the compound represented by Chemical Formula 1-1 may be prepared by the following General Formula 1 or General Formula 2, however, the preparation is not limited thereto.

-continued

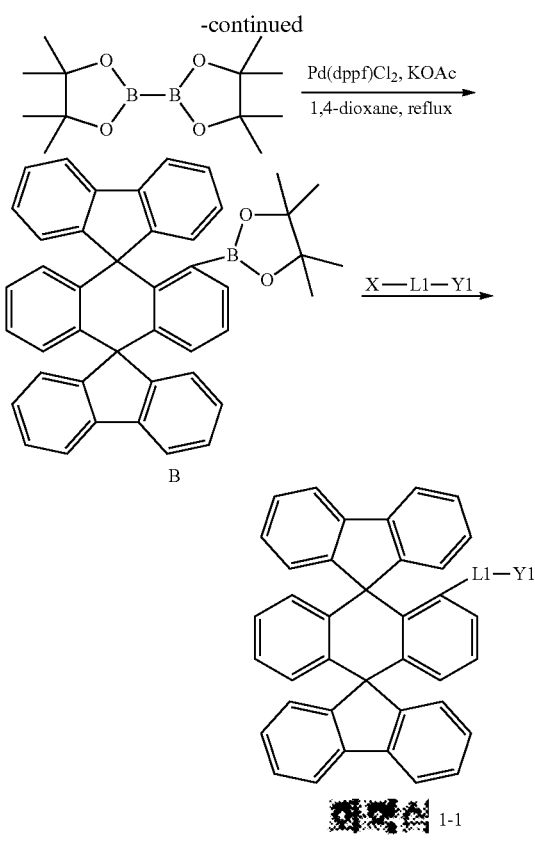

In General Formulae 1 and 2, definitions of L1 and Y1 are the same as in Chemical Formula 1, and X is hydrogen or a halogen group.

One embodiment of the present specification provides an organic light emitting device including a first electrode; a second electrode provided opposite to the first electrode; and one, two or more organic material layers provided between the first electrode and the second electrode, wherein one or more layers of the organic material layers include the double spiro structure compound represented by Chemical Formula 1.

The organic material layer of the organic light emitting device of the present specification may be formed in a single layer structure, but may be formed in a multilayer structure in which two or more organic material layers are laminated. For example, the organic light emitting device of the present disclosure may have a structure including a hole injection layer, a hole transfer layer, an electron blocking layer, a light emitting layer, a hole blocking layer, an electron transfer layer, an electron injection layer and the like as the organic material layer. However, the structure of the organic light emitting device is not limited thereto, and may include less numbers of organic material layers.

For example, the structure of the organic light emitting device of the present specification may be as shown in FIG. 1 and FIG. 2, but is not limited thereto.

FIG. 1 illustrates a structure of an organic light emitting device (10) in which a first electrode (30), a light emitting layer (40) and a second electrode (50) are consecutively laminated on a substrate (20). FIG. 1 is an illustrative structure of the organic light emitting device according to one embodiment of the present specification, and other organic material layers may be further included therein.

FIG. 2 illustrates a structure of an organic light emitting device in which a first electrode (30), a hole injection layer (60), a hole transfer layer (70), a light emitting layer (40), an electron transfer layer (80), an electron injection layer (90) and a second electrode (50) are consecutively laminated on a substrate (20). FIG. 2 is an illustrative structure of the organic light emitting device according to one embodiment of the present specification, and other organic material layers may be further included therein.

According to one embodiment of the present specification, the organic material layer includes a hole injection layer or a hole transfer layer, and the hole injection layer or the hole transfer layer includes the double spiro structure compound represented by Chemical Formula 1.

According to one embodiment of the present specification, the organic material layer includes an electron blocking layer, and the electron blocking layer includes the double spiro structure compound represented by Chemical Formula 1.

According to one embodiment of the present specification, the organic material layer includes a light emitting layer, and the light emitting layer includes the double spiro structure compound represented by Chemical Formula 1.

According to one embodiment of the present specification, the organic material layer includes a light emitting layer, and the light emitting layer includes the double Spiro structure compound represented by Chemical Formula 1 as a host of the light emitting layer.

According to one embodiment of the present specification, the organic material layer includes a light emitting layer, and the light emitting layer includes the double spiro structure compound represented by Chemical Formula 1 as a phosphorescent host or a fluorescent host of the light emitting layer.

According to one embodiment of the present specification, the organic material layer includes the double spiro structure compound represented by Chemical Formula 1 as a host of a light emitting layer, and includes other organic compounds, metals or metal compounds as a dopant.

According to one embodiment of the present specification, the organic material layer includes a hole blocking layer, and the hole blocking layer includes the double spiro structure compound represented by Chemical Formula 1.

According to one embodiment of the present specification, the organic material layer includes an electron transfer layer, an electron injection layer or a layer carrying out electron transfer and electron injection at the same time, and the electron transfer layer, the electron injection layer or the layer carrying out electron transfer and electron injection at the same time includes the double spiro structure compound.

According to one embodiment of the present specification, the organic material layer further includes a hole injection layer or a hole transfer layer including an arylamino group, a carbazole group or a benzocarbazole group in addition to an organic material layer including the double spiro structure compound represented by Chemical Formula 1.

According to one embodiment of the present specification, the organic material layer includes a light emitting layer, and the light emitting layer includes a compound represented by the following Chemical Formula 1-A.

[Chemical Formula 1-A]

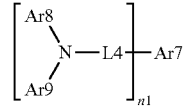

In Chemical Formula 1-A, n1 is an integer of 1 or more,

Ar7 is a substituted or unsubstituted monovalent or more benzofluorene group; a substituted or unsubstituted monovalent or more fluoranthen group; a substituted or unsubstituted monovalent or more pyrene group; or a substituted or unsubstituted monovalent or more crycene group, L4 is a direct bond; a substituted or unsubstituted arylene group; or a substituted or unsubstituted heteroarylene group, Ar8 and Ar9 are the same as or different from each other, and each independently a substituted or unsubstituted aryl group; a substituted or unsubstituted silyl group; a substituted or unsubstituted germanium group; a substituted or unsubstituted alkyl group; a substituted or unsubstituted arylalkyl group; or a substituted or unsubstituted heteroaryl group, or may bond to each other to form a substituted or unsubstituted ring, and When n1 is 2 or more, the structures in the two or more parentheses are the same as or different from each other.

According to one embodiment of the present specification, the organic material layer includes a light emitting layer, and the light emitting layer includes the compound represented by Chemical Formula 1-A as a dopant of the light emitting layer.

According to one embodiment of the present specification, L4 is a direct bond.

According to one embodiment of the present specification, n1 is 2.

In one embodiment of the present specification, Ar7 is a divalent pyrene group unsubstituted or substituted with deuterium, a methyl group, an ethyl group or a tert-butyl group.

According to one embodiment of the present specification, Ar8 and Ar9 are the same as or different from each other, and each independently a substituted or unsubstituted aryl group having 6 to 30 carbon atoms.

According to one embodiment of the present specification, Ar8 and Ar9 are the same as or different from each other, and each independently an aryl group unsubstituted or substituted with a germanium group substituted with an alkyl group.

According to one embodiment of the present specification, Ar8 and Ar9 are the same as or different from each other, and each independently an aryl group unsubstituted or substituted with a trimethyl germanium group.

According to one embodiment of the present specification, Ar8 and Ar9 are the same as or different from each other, and each independently a substituted or unsubstituted phenyl group.

According to one embodiment of the present specification, Ar8 and Ar9 are a phenyl group unsubstituted or substituted with a trimethyl germanium group.

According to one embodiment of the present specification, Chemical Formula 1-A is represented by the following compound.

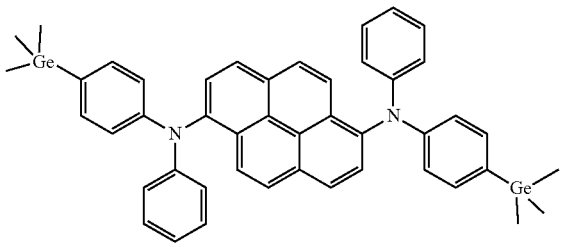

According to one embodiment of the present specification, the organic material layer includes a light emitting layer, and the light emitting layer includes a compound represented by the following Chemical Formula 2-A.

[Chemical Formula 2-A]

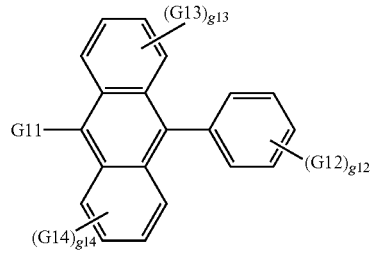

In Chemical Formula 2-A,

G11 is a phenyl group, a 1-naphthyl group, a 2-naphthyl group, a 1-anthryl group, a 2-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 3-methyl-2-naphthyl group, a 4-methyl-1-naphthyl group, or the following Chemical Formula

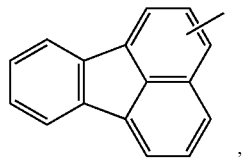

G12 is a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, an o-tolyl group, a m-tolyl group, a p-tolyl group, a p-t-butylphenyl group, a p-(2-phenylpropyl) phenyl group, a 3-methyl-2-naphthyl group, a 4-methyl-1-naphthyl group, a 4-methyl-1-anthryl group, a 4'-methylbiphenylyl group, a 4"-t-butyl-p-terphenyl-4-yl group, or a 3-fluoranthenyl group, G13 and G14 are the same as or different from each other, and each independently hydrogen; a substituted or unsubstituted alkyl group; a substituted or unsubstituted alkoxy group; a substituted or unsubstituted aryl group; or a substituted or unsubstituted heteroaryl group, g12 is an integer of 1 to 5, g13 and g14 are each an integer of 1 to 4, and when g12 to g14 are each 2 or more, the structures in the two or more parentheses are the same as or different from each other.

According to one embodiment of the present specification, the organic material layer includes a light emitting layer, the light emitting layer includes the compound represented by Chemical Formula 2-A as a host of the light emitting layer.

According to one embodiment of the present specification, G11 is a phenyl group.

According to one embodiment of the present specification, G11 is a 1-naphthyl group.

According to one embodiment of the present specification, G12 is a 2-naphthyl group.

According to one embodiment of the present specification, G13 and G14 are hydrogen.

According to one embodiment of the present specification, Chemical Formula 2-A is represented by any one of the following compounds.

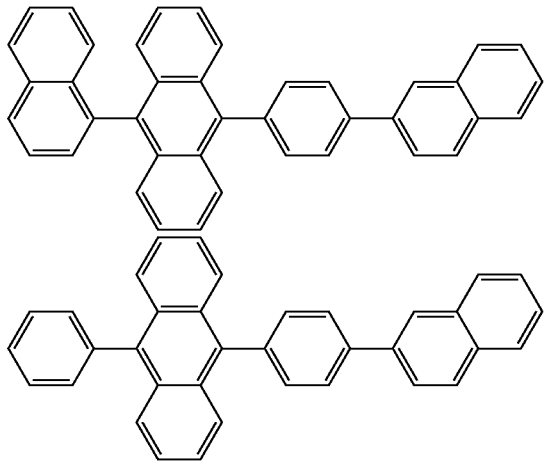

The organic light emitting device of the present specification may be manufactured using materials and methods known in the art, except that one or more layers of organic material layers include the double spiro structure compound of the present specification, that is, the double spiro structure compound represented by Chemical Formula 1.

When the organic light emitting device includes a plurality of organic material layers, the organic material layers may be formed with the same material or with different materials.

For example, the organic light emitting device of the present specification may be manufactured by consecutively laminating a first electrode, an organic material layer and a second electrode on a substrate. Herein, the organic light emitting device may be manufactured by forming the first electrode on the substrate by depositing a metal, a metal oxide having conductivity, or an alloy thereof using a physical vapor deposition (PVD) method such as a sputtering method or an e-beam evaporation method, forming the organic material layer including a hole injection layer, a hole transfer layer, a light emitting layer and an electron transfer layer thereon, then depositing a material capable of being used as the second electrode thereon. In addition to such a method, the organic light emitting device may be manufactured by consecutively depositing a cathode material, an organic material layer, and a first electrode material on a substrate. Furthermore, when manufacturing the organic light emitting device, the double spiro structure compound represented by Chemical Formula 1 may be formed as the organic material layer using a solution coating method as well as a vacuum deposition method. Herein, the solution coating method means spin coating, dip coating, doctor blading, ink jet printing, screen printing, a spray method, roll coating and the like, but is not limited thereto. In addition to such a method, the organic light emitting device may be also manufactured by consecutively depositing a cathode material, an organic material layer, and an anode material on a substrate (International Patent Application Laid-Open Publication No. 2003/012890). However, the manufacturing method is not limited thereto.

According to one embodiment of the present specification, the first electrode is an anode, and the second electrode is a cathode.

According to another embodiment of the present specification, the first electrode is a cathode, and the second electrode is an anode.

As the anode material, a material having large work function is normally preferable so that hole injection to an organic material layer is smooth. Specific examples of the anode material capable of being used in the present disclosure include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as $ZnO:Al$ or $SnO_2:Sb$; conductive polymers such as poly(3-methylthiophene), poly[3,4-(ethylen-1,2-dioxy)thiophene] (PEDOT), polypyrrole and polyaniline, and the like, but are not limited thereto.

As the cathode material, a material having small work function is normally preferable so that electron injection to an organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as $LiF/Al$, $LiO_2/Al$ or $Mg/Ag$, and the like, but are not limited thereto.

The hole injection layer is a layer that injects holes from an electrode, and the hole injection material is preferably a compound that has an ability to transfer holes, therefore, has a hole injection effect in an anode, has an excellent hole injection effect for a light emitting layer or a light emitting material, prevents excitons generated in the light emitting layer from moving to an electron injection layer or an electron injection material, and in addition, has an excellent thin film forming ability. The highest occupied molecular orbital (HOMO) of the hole injection material is preferably in between the work function of an anode material and the HOMO of surrounding organic material layers. Specific examples of the hole injection material include a metal porphyrin, oligothiophene, an arylamine-based organic material, a hexanitrile hexaazatriphenylene-based organic material, a quinacridone-based organic material, a perylene-based organic material, anthraquinone, and a polyaniline- and a polythiophene-based conductive polymer, and the like, but are not limited thereto.

The hole transfer layer is a layer that receives holes from a hole injection layer and transfers the holes to a light emitting layer, and as the hole transfer material, a material capable of receiving holes from an anode or a hole injection layer, moving the holes to a light emitting layer, and having high mobility for the holes, is suitable. Specific examples thereof include an arylamine-based organic material, a conductive polymer, a block copolymer having conjugated parts and non-conjugated parts together, and the like, but are not limited thereto.

The electron blocking layer is a layer capable of enhancing a lifespan and efficiency of a device by preventing electrons injected from an electron injection layer from passing through a light emitting layer and entering to a hole injection layer, and as necessary, may be formed in an appropriate place between the light emitting layer and the hole injection layer using materials known in the art.

A light emitting material of the light emitting layer is a material capable of emitting light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof include a 8-hydroxy-quinoline aluminum complex ($Alq_3$); a carbazole-based compound; a dimerized styryl compound; BAlq; a 10-hydroxybenzo quinoline-metal compound; a benzoxazole-, a benzthiazole- and a benzimidazole-based compound; a poly (p-phenylenevinylene) (PPV)-based polymer; a spiro compound; polyfluorene, rubrene, and the like, but are not limited thereto.

The light emitting layer may include a host material and a dopant material. The host material includes a fused aromatic ring derivative, a heteroring-containing compound or the like. Specifically, the fused aromatic ring derivative includes an anthracene derivative, a pyrene derivative, a naphthalene derivative, a pentacene derivative, a phenanthrene compound, a fluoranthene compound and the like, and the heteroring-containing compound includes a carbazole derivative, a dibenzofuran derivative, a ladder-type furan compound, a pyrimidine derivative and the like, but the material is not limited thereto.

The dopant material includes an aromatic amine derivative, a styrylamine compound, a boron complex, a fluoranthene compound, a metal complex and the like. Specifically, the aromatic amine derivative is a fused aromatic ring derivative having a substituted or unsubstituted arylamino group and includes arylamino group-included pyrene, anthracene, crycene, peryflanthene and the like, and the styrylamine compound is a compound in which substituted or unsubstituted arylamine is substituted with at least one arylvinyl group, and one, two or more substituents selected from the group consisting of an aryl group, a silyl group, an alkyl group, a cycloalkyl group and an arylamino group are substituted or unsubstituted. Specifically, styrylamine, styryldiamine, styryltriamine, styryltetramine or the like is included, but the styrylamine compound is not limited thereto. In addition, the metal complex includes an iridium complex, a platinum complex or the like, but is not limited thereto.

The electron transfer layer is a layer that receives electrons from an electron injection layer and transfers the electrons to a light emitting layer, and as the electron transfer material, a material capable of favorably receiving electrons from a cathode, moving the electrons to a light emitting layer, and having high mobility for the electrons, is suitable. Specific examples thereof include an Al complex of 8-hydroxyquinoline; a complex including $Alq_3$; an organic radical compound; a hydroxyflavon-metal complex and the like, but are not limited thereto. The electron transfer layer may be used together with any desired cathode material as used according to existing technologies. Particularly, examples of the suitable cathode material include common materials that have small work function, and in which an aluminum layer or a silver layer follows. Specifically, the cathode material includes cesium, barium, calcium, ytterbium and samarium, and in each case, an aluminum layer or a silver layer follows.

The electron injection layer is a layer that injects electrons from an electrode, and the electron injection material is preferably a compound that has an ability to transfer electrons, has an electron injection effect from a cathode, has an excellent electron injection effect for a light emitting layer or a light emitting material, prevents excitons generated in the light emitting layer from moving to a hole injection layer, and in addition, has an excellent thin film forming ability. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, a metal complex compound, a nitrogen-containing 5-membered ring derivative, and the like, but are not limited thereto.

The metal complex compound includes 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)berylium, bis(10-hydroxybenzo[h]quinolinato)zinc, bis(2-methyl-8-quinolinato)chlorogallium, bis(2-methyl-8-quinolinato)(0-cresolato)gallium, bis(2-methyl-8-quinolinato) (1-naphtholato)aluminum, bis(2-methyl-8-quinolinato) (2-naphtholato)gallium and the like, but is not limited thereto.

The hole blocking layer is a layer blocking holes from reaching a cathode, and may be generally formed under the same condition as the hole injection layer. Specifically, oxadiazole derivatives or triazole derivatives, phenanthroline derivatives, BCP, aluminum complexes and the like may be included, however, the hole blocking layer is not limited thereto.

The organic light emitting device according to the present specification may be a top-emission type, a bottom-emission type or a dual-emission type depending on the materials used.

According to one embodiment of the present specification, the double spiro structure compound represented by Chemical Formula 1 may be included in an organic solar cell or an organic transistor in addition to an organic light emitting device.

Hereinafter, the present specification will be described in detail with reference to examples. However, the examples of the present specification may be modified to various other forms and the scope of the present specification is not to be construed as being limited to the examples described below. The examples of the present specification are provided in order to more completely describe the present specification to those having average knowledge in the art.

<Preparation Example 1> Preparation of Compound 1

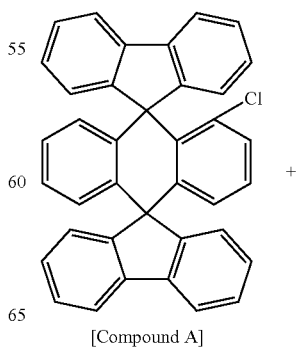

[Compound A]

-continued

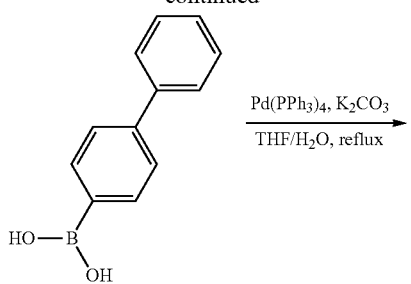

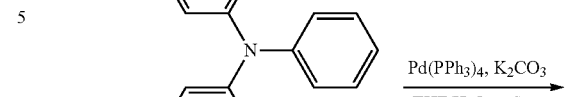

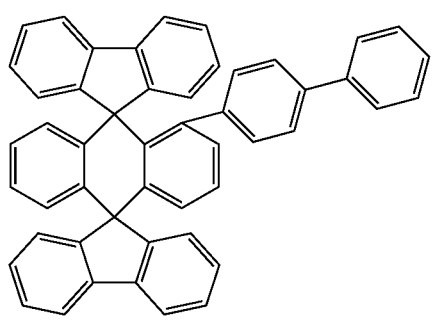

[Compound 1]

After completely dissolving Compound A (10.0 g, 17.92 mmol) and [1,1'-biphenyl]-4-ylboronic acid (4.08 g, 20.61 mmol) in 300 ml of tetrahydrofuran in a 500 ml round bottom flask under nitrogen atmosphere, a 2 M aqueous potassium carbonate solution (150 ml) and then tetrakis-(triphenylphosphine)palladium (0.62 g, 0.54 mmol) were added thereto, and the result was heated and stirred for 2 hours. After lowering the temperature to room temperature, the water layer was removed, and the result was dried with anhydrous magnesium sulfate, vacuum concentrated, and then recrystallized with 250 ml of ethyl acetate to prepare Compound 1 (9.42 g, yield: 83%).

MS[M+H]$^+$=633

<Preparation Example 2> Preparation of Compound 2

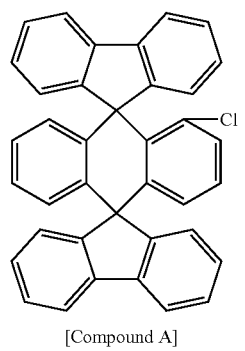

[Compound A]

-continued

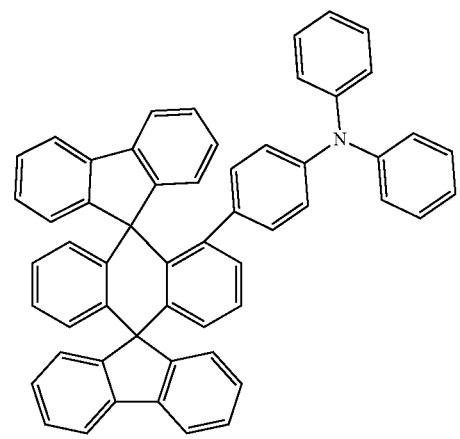

[Compound 2]

After completely dissolving Compound A (10.0 g, 17.92 mmol) and (4-(diphenylamino)phenyl)boronic acid (5.95 g, 20.61 mmol) in 280 ml of tetrahydrofuran in a 500 ml round bottom flask under nitrogen atmosphere, a 2 M aqueous potassium carbonate solution (140 ml) and then tetrakis-(triphenylphosphine)palladium (0.62 g, 0.54 mmol) were added thereto, and the result was heated and stirred for 5 hours. After lowering the temperature to room temperature, the water layer was removed, and the result was dried with anhydrous magnesium sulfate, vacuum concentrated, and then recrystallized with 200 ml of ethyl acetate to prepare Compound 2 (10.11 g, yield: 78%).

MS[M+H]$^+$=724

<Preparation Example 3> Preparation of Compound 3

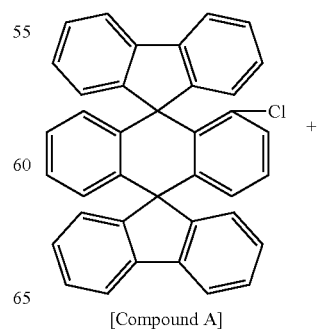

[Compound A]

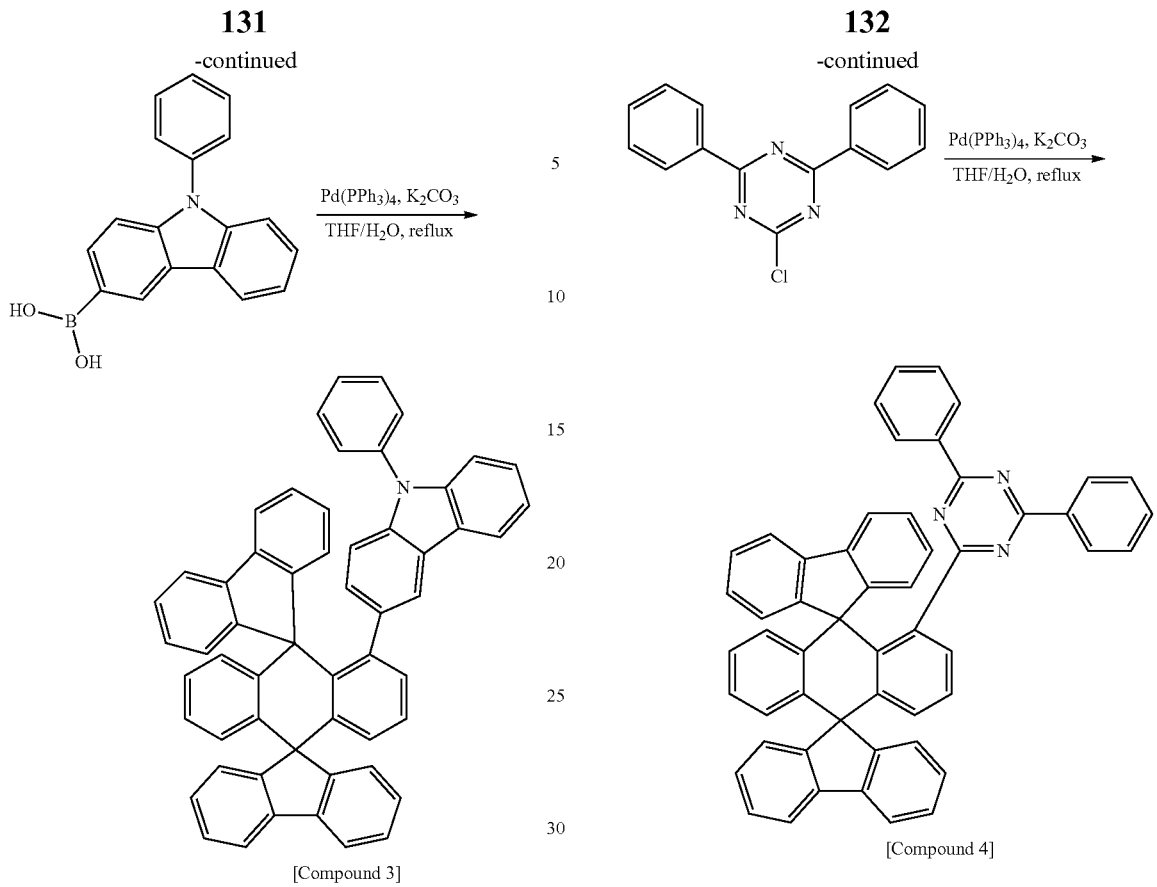

After completely dissolving Compound A (10.0 g, 17.92 mmol) and (9-phenyl-9H-carbazol-3-yl)boronic acid (5.95 g, 20.61 mmol) in 280 ml of tetrahydrofuran in a 500 ml round bottom flask under nitrogen atmosphere, a 2 M aqueous potassium carbonate solution (140 ml) and then tetrakis-(triphenylphosphine)palladium (0.62 g, 0.54 mmol) were added thereto, and the result was heated and stirred for 5 hours. After lowering the temperature to room temperature, the water layer was removed, and the result was dried with anhydrous magnesium sulfate, vacuum concentrated, and then recrystallized with 200 ml of ethyl acetate to prepare Compound 3 (11.23 g, yield: 85%).

MS[M+H]$^+$=722

After completely dissolving Compound B (10.0 g, 16.49 mmol) and 2-chloro-4,6-diphenyl-1,3,5-triazine (4.01 g, 14.99 mmol) in 320 ml of tetrahydrofuran in a 500 ml round bottom flask under nitrogen atmosphere, a 2 M aqueous potassium carbonate solution (160 ml) and then tetrakis-(triphenylphosphine)palladium (0.52 g, 0.45 mmol) were added thereto, and the result was heated and stirred for 4 hours. After lowering the temperature to room temperature, the water layer was removed, and the result was dried with anhydrous magnesium sulfate, vacuum concentrated, and then recrystallized with 370 ml of ethyl acetate to prepare Compound 4 (8.98 g, yield: 76%).

MS[M+H]$^+$=712

<Preparation Example 4> Preparation of Compound 4

<Preparation Example 5> Preparation of Compound 5

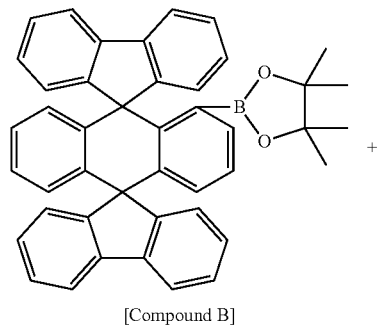

[Compound B]

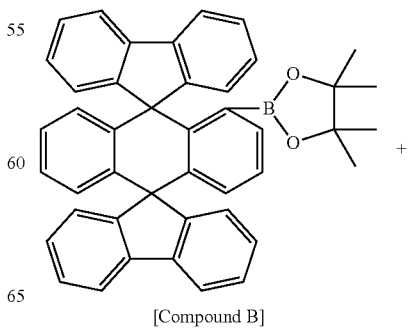

[Compound B]

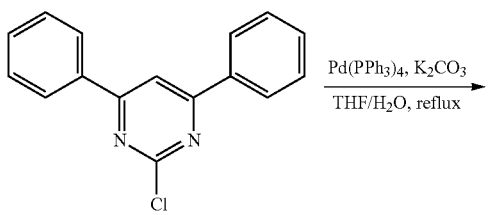

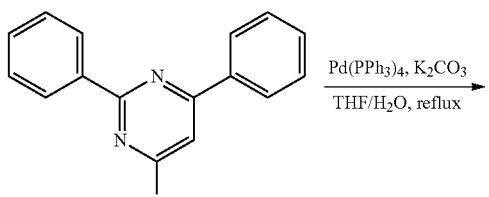

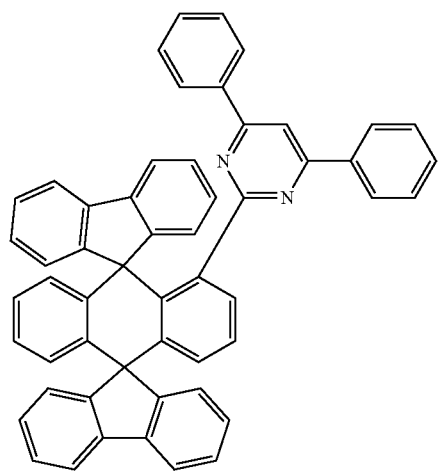

[Compound 5]

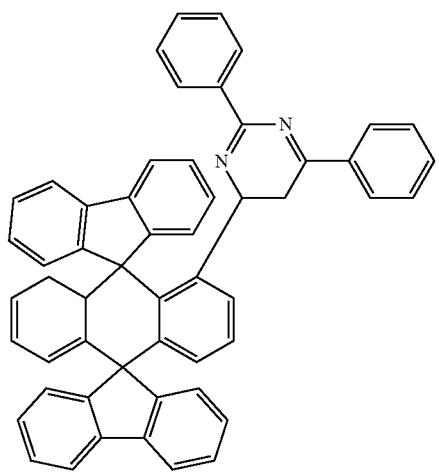

[Compound 6]

After completely dissolving Compound B (10.0 g, 16.49 mmol) and 2-chloro-4,6-diphenylpyrimidine (4.01 g, 14.99 mmol) in 380 ml of tetrahydrofuran in a 500 ml round bottom flask under nitrogen atmosphere, a 2 M aqueous potassium carbonate solution (190 ml) and then tetrakis-(triphenylphosphine)palladium (0.52 g, 0.45 mmol) were added thereto, and the result was heated and stirred for 6 hours. After lowering the temperature to room temperature, the water layer was removed, and the result was dried with anhydrous magnesium sulfate, vacuum concentrated, and then recrystallized with 350 ml of ethyl acetate to prepare Compound 5 (9.88 g, yield: 84%).

MS[M+H]$^+$=711

<Preparation Example 6> Preparation of Compound 6

After completely dissolving Compound B (10.0 g, 16.49 mmol) and 4-chloro-2,6-diphenylpyrimidine (4.01 g, 14.99 mmol) in 320 ml of tetrahydrofuran in a 500 ml round bottom flask under nitrogen atmosphere, a 2 M aqueous potassium carbonate solution (160 ml) and then tetrakis-(triphenylphosphine)palladium (0.52 g, 0.45 mmol) were added thereto, and the result was heated and stirred for 5 hours. After lowering the temperature to room temperature, the water layer was removed, and the result was dried with anhydrous magnesium sulfate, vacuum concentrated, and then recrystallized with 260 ml of ethyl acetate to prepare Compound 6 (10.84 g, yield: 92%).

MS[M+H]$^+$=711

<Preparation Example 7> Preparation of Compound 7

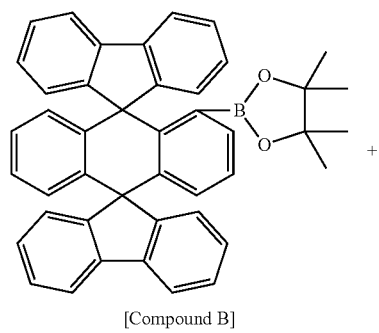

[Compound B]

+

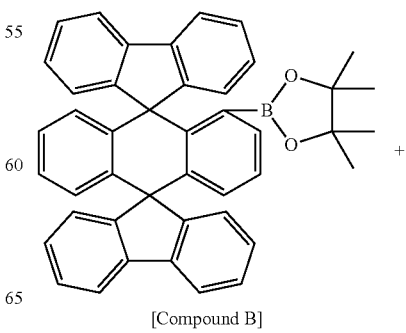

[Compound B]

+

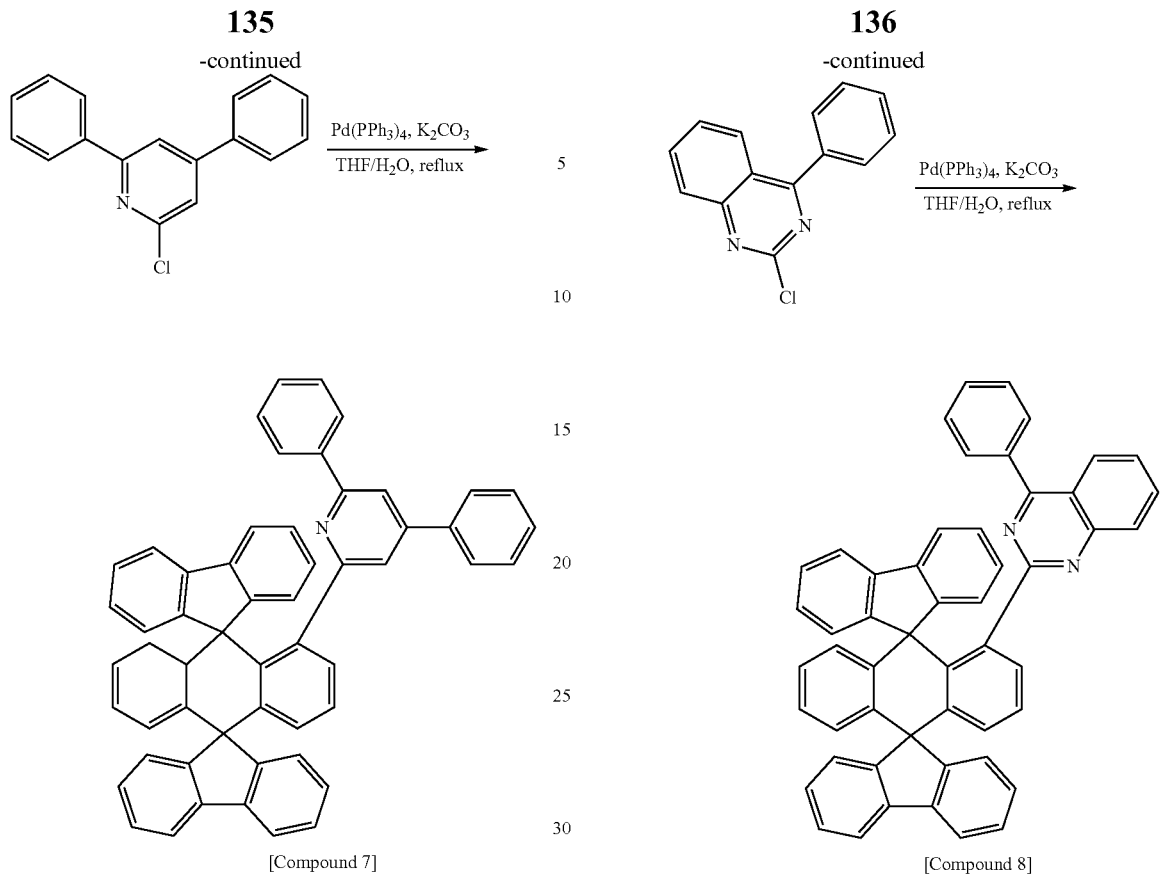

After completely dissolving Compound B (10.0 g, 16.49 mmol) and 2-chloro-4,6-diphenylpyridine (4.01 g, 14.99 mmol) in 340 ml of tetrahydrofuran in a 500 ml round bottom flask under nitrogen atmosphere, a 2 M aqueous potassium carbonate solution (170 ml) and then tetrakis-(triphenylphosphine)palladium (0.52 g, 0.45 mmol) were added thereto, and the result was heated and stirred for 3 hours. After lowering the temperature to room temperature, the water layer was removed, and the result was dried with anhydrous magnesium sulfate, vacuum concentrated, and then recrystallized with 240 ml of ethyl acetate to prepare Compound 7 (10.22 g, yield: 86%).

MS[M+H]$^+$=709

After completely dissolving Compound B (10.0 g, 16.49 mmol) and 2-chloro-4-phenylquinazoline (3.91 g, 14.99 mmol) in 320 ml of tetrahydrofuran in a 500 ml round bottom flask under nitrogen atmosphere, a 2 M aqueous potassium carbonate solution (160 ml) and then tetrakis-(triphenylphosphine)palladium (0.52 g, 0.45 mmol) were added thereto, and the result was heated and stirred for 8 hours. After lowering the temperature to room temperature, the water layer was removed, and the result was dried with anhydrous magnesium sulfate, vacuum concentrated, and then recrystallized with 330 ml of ethyl acetate to prepare Compound 8 (9.54 g, yield: 77%).

MS[M+H]$^+$=685

<Preparation Example 8> Preparation of Compound 8

<Preparation Example 9> Preparation of Compound 9

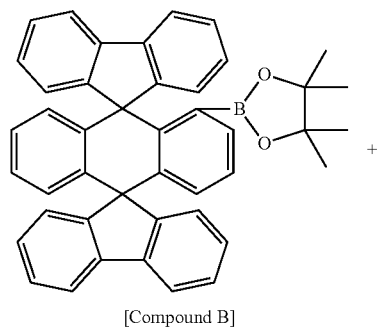 +

[Compound B]

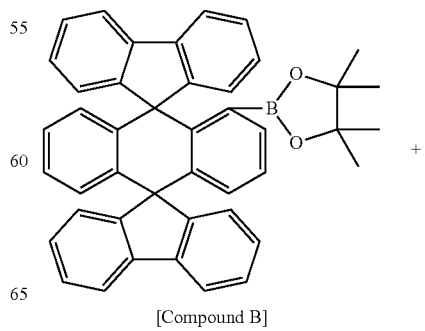 +

[Compound B]

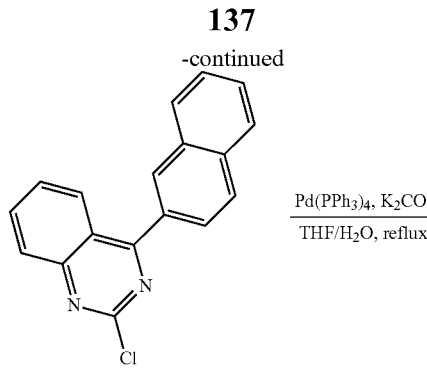

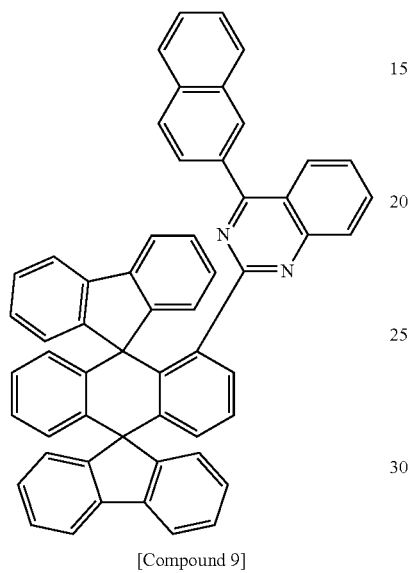

[Compound 9]

After completely dissolving Compound B (10.0 g, 16.49 mmol) and 2-chloro-4-(naphthalen-2-yl)quinazoline (4.51 g, 14.99 mmol) in 380 ml of tetrahydrofuran in a 500 ml round bottom flask under nitrogen atmosphere, a 2 M aqueous potassium carbonate solution (190 ml) and then tetrakis-(triphenylphosphine)palladium (0.52 g, 0.45 mmol) were added thereto, and the result was heated and stirred for 6 hours. After lowering the temperature to room temperature, the water layer was removed, and the result was dried with anhydrous magnesium sulfate, vacuum concentrated, and then recrystallized with 270 ml of ethyl acetate to prepare Compound 9 (11.25 g, yield: 85%).

MS[M+H]$^+$=735

<Preparation Example 10> Preparation of Compound 10

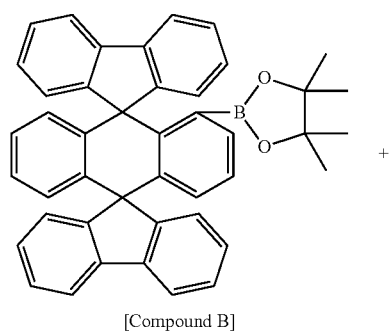

[Compound B]

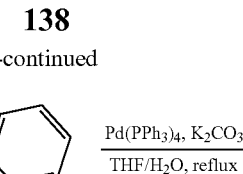

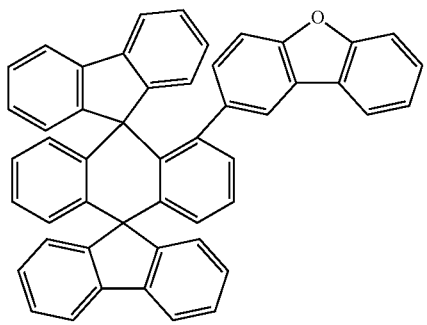

[Compound 10]

After completely dissolving Compound B (10.0 g, 16.49 mmol) and 2-bromodibenzo[b,d]furan (3.61 g, 14.99 mmol) in 260 ml of tetrahydrofuran in a 500 ml round bottom flask under nitrogen atmosphere, a 2 M aqueous potassium carbonate solution (130 ml) and then tetrakis-(triphenylphosphine)palladium (0.52 g, 0.45 mmol) were added thereto, and the result was heated and stirred for 3 hours. After lowering the temperature to room temperature, the water layer was removed, and the result was dried with anhydrous magnesium sulfate, vacuum concentrated, and then recrystallized with 330 ml of ethyl acetate to prepare Compound 10 (9.92 g, yield: 86%).

MS[M+H]$^+$=647

<Preparation Example 11> Preparation of Compound 11

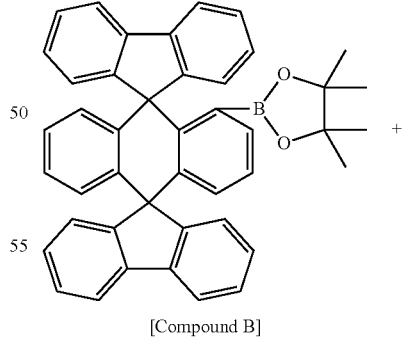

[Compound B]

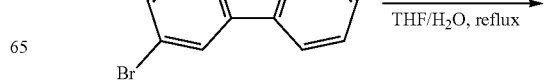

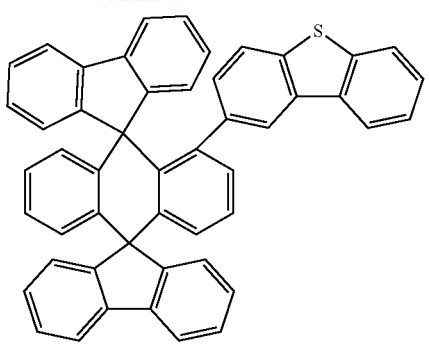

[Compound 11]

After completely dissolving Compound B (10.0 g, 16.49 mmol) and 2-bromodibenzo[b,d]thiophene (3.93 g, 14.99 mmol) in 240 ml of tetrahydrofuran in a 500 ml round bottom flask under nitrogen atmosphere, a 2 M aqueous potassium carbonate solution (120 ml) and then tetrakis-(triphenylphosphine)palladium (0.52 g, 0.45 mmol) were added thereto, and the result was heated and stirred for 4 hours. After lowering the temperature to room temperature, the water layer was removed, and the result was dried with anhydrous magnesium sulfate, vacuum concentrated, and then recrystallized with 330 ml of ethyl acetate to prepare Compound 11 (8.52 g, yield: 81%).

MS[M+H]$^+$=663

<Preparation Example 12> Preparation of Compound 12

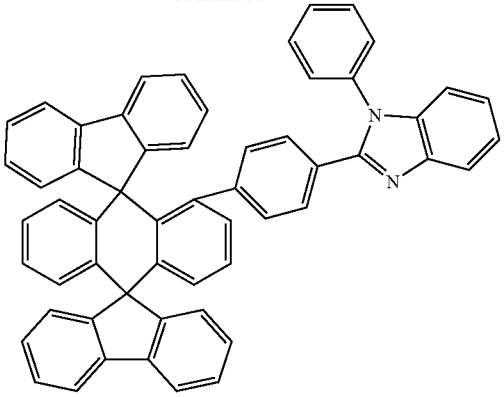

[Compound 12]

After completely dissolving Compound B (10.0 g, 16.49 mmol) and 2-2-(4-bromophenyl)-1-phenyl-1H-benzo[d]imidazole (5.21 g, 14.99 mmol) in 240 ml of tetrahydrofuran in a 500 ml round bottom flask under nitrogen atmosphere, a 2 M aqueous potassium carbonate solution (120 ml) and then tetrakis-(triphenylphosphine)palladium (0.62 g, 0.54 mmol) were added thereto, and the result was heated and stirred for 4 hours. After lowering the temperature to room temperature, the water layer was removed, and the result was dried with anhydrous magnesium sulfate, vacuum concentrated, and then recrystallized with 330 ml of ethyl acetate to prepare Compound 12 (8.98 g, yield: 76%).

MS[M+H]$^+$=749

<Preparation Example 13> Preparation of Compound 13

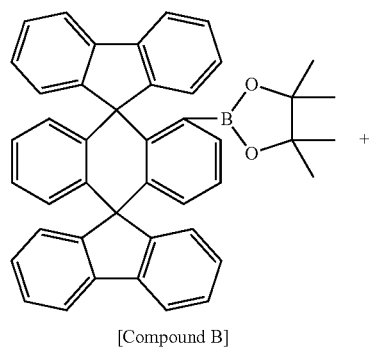

[Compound B]

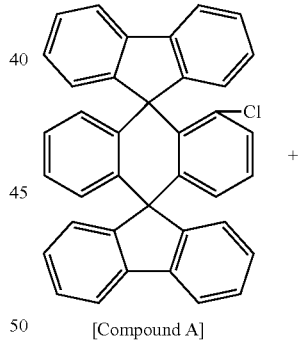

[Compound A]

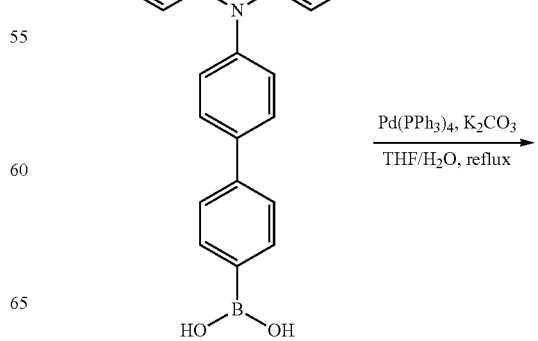

-continued

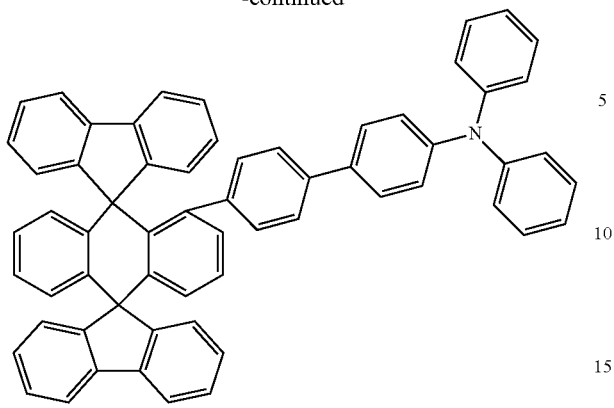

[Compound 13]

After completely dissolving Compound A (10.0 g, 17.92 mmol) and (4'-(diphenylamino)-[1,1'-biphenyl]-4-yl)boronic acid (7.54 g, 20.61 mmol) in 280 ml of tetrahydrofuran in a 500 ml round bottom flask under nitrogen atmosphere, a 2 M aqueous potassium carbonate solution (140 ml) and then tetrakis-(triphenylphosphine)palladium (0.62 g, 0.54 mmol) were added thereto, and the result was heated and stirred for 5 hours.

After lowering the temperature to room temperature, the water layer was removed, and the result was dried with anhydrous magnesium sulfate, vacuum concentrated, and then recrystallized with 200 ml of ethyl acetate to prepare Compound 13 (11.25 g, yield: 78%).

MS[M+H]$^+$=800

<Preparation Example 14> Preparation of Compound 14

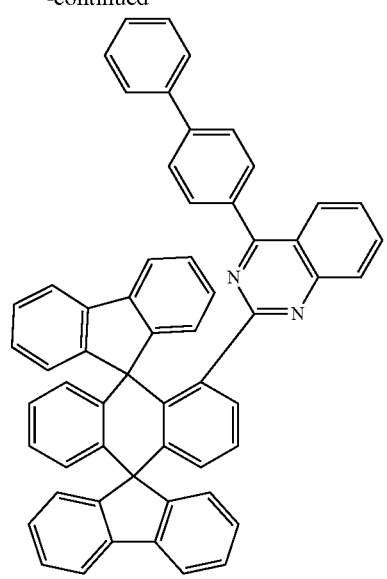

[Compound 14]

After completely dissolving Compound B (10.0 g, 16.49 mmol) and 4-([1,1'-biphenyl]-4-yl)-2-chloroquinazoline (5.41 g, 14.99 mmol) in 380 ml of tetrahydrofuran in a 500 ml round bottom flask under nitrogen atmosphere, a 2 M aqueous potassium carbonate solution (190 ml) and then tetrakis-(triphenylphosphine)palladium (0.52 g, 0.45 mmol) were added thereto, and the result was heated and stirred for 6 hours. After lowering the temperature to room temperature, the water layer was removed, and the result was dried with anhydrous magnesium sulfate, vacuum concentrated, and then recrystallized with 270 ml of ethyl acetate to prepare Compound 14 (11.25 g, yield: 85%).

MS[M+H]$^+$=761

<Preparation Example 15> Preparation of Compound 15

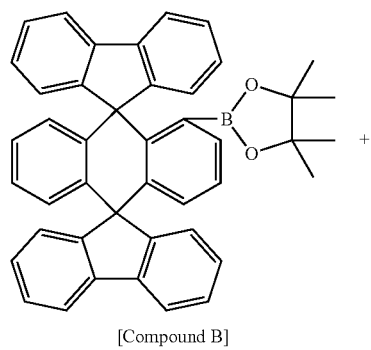

[Compound B]

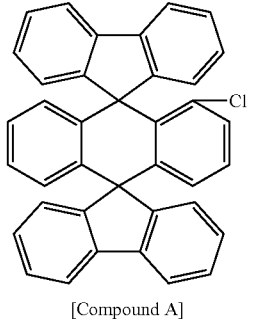

[Compound A]

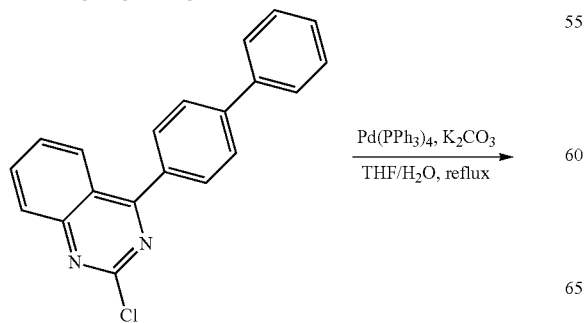

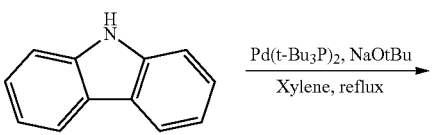

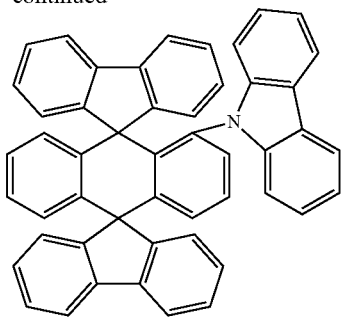

[Compound 15]

After completely dissolving Compound A (10.0 g, 17.92 mmol) and carbazole (2.82 g, 20.61 mmol) in 320 ml of xylene in a 500 ml round bottom flask under nitrogen atmosphere, sodium tert-butoxide (2.24 g, 23.29 mol) and then bis(tri-tert-butylphosphine) palladium(0) (0.09 g, 0.19 mmol) were added thereto, and the result was heated and stirred for 3 hours. After lowering the temperature to room temperature, the result was filtered to remove the base, the xylene was vacuum concentrated, and the result was columned using tetrahydrofuran:hexane=1:18 to prepare Compound 15 (8.65 g, yield: 75%).

MS[M+H]$^+$=646

<Preparation Example 16> Preparation of Compound 16

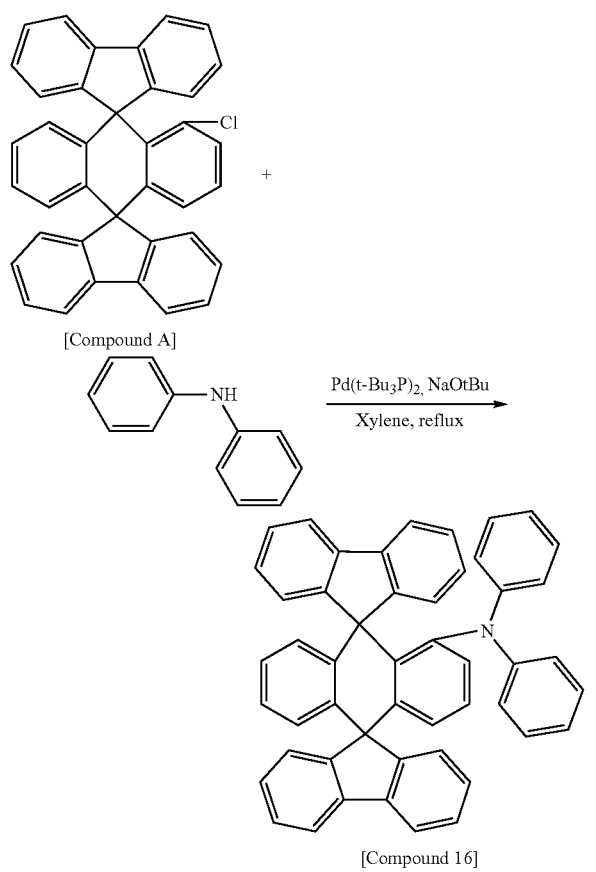

[Compound 16]

After completely dissolving Compound A (10.0 g, 17.92 mmol) and diphenylamine (2.81 g, 20.61 mmol) in 320 ml of xylene in a 500 ml round bottom flask under nitrogen atmosphere, sodium tert-butoxide (2.24 g, 23.29 mol) and then bis(tri-tert-butylphosphine) palladium(0) (0.09 g, 0.19 mmol) were added thereto, and the result was heated and stirred for 3 hours. After lowering the temperature to room temperature, the result was filtered to remove the base, the xylene was vacuum concentrated, and the result was columned using tetrahydrofuran:hexane=1:18 to prepare Compound 16 (9.92 g, yield: 86%).

MS[M+H]$^+$=646

<Preparation Example 17> Preparation of Compound 17

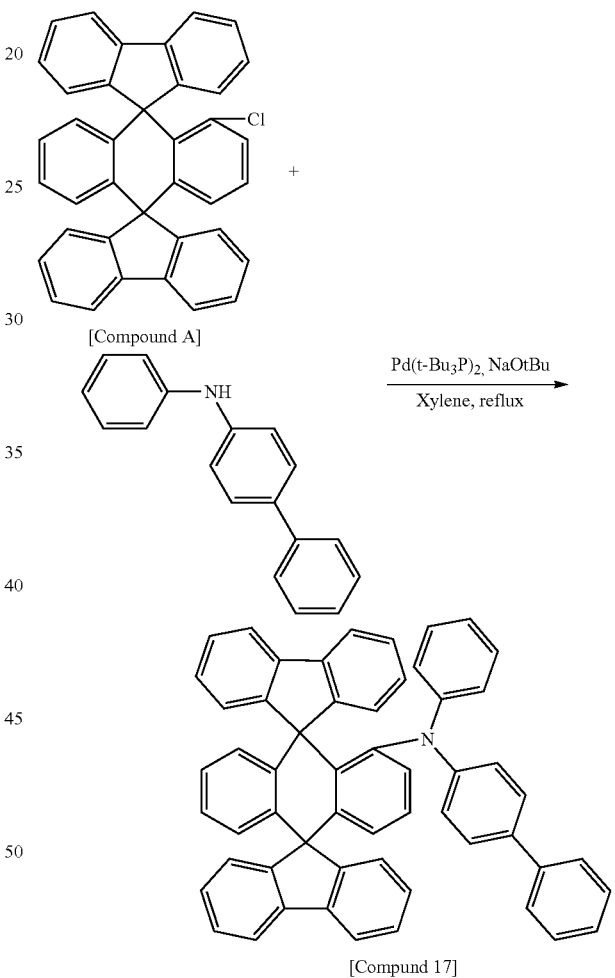

[Compund 17]

After completely dissolving Compound A (10.0 g, 17.92 mmol) and N-phenyl-[1,1'-biphenyl]-4-amine (5.05 g, 20.61 mmol) in 320 ml of xylene in a 500 ml round bottom flask under nitrogen atmosphere, sodium tert-butoxide (2.24 g, 23.29 mol) and then bis(tri-tert-butylphosphine) palladium (0) (0.09 g, 0.19 mmol) were added thereto, and the result was heated and stirred for 3 hours. After lowering the temperature to room temperature, the result was filtered to remove the base, the xylene was vacuum concentrated, and the result was columned using tetrahydrofuran:hexane=1:18 to prepare Compound 17 (10.33 g, yield: 79%).

MS[M+H]⁺=724

<Preparation Example 18> Preparation of Compound 18

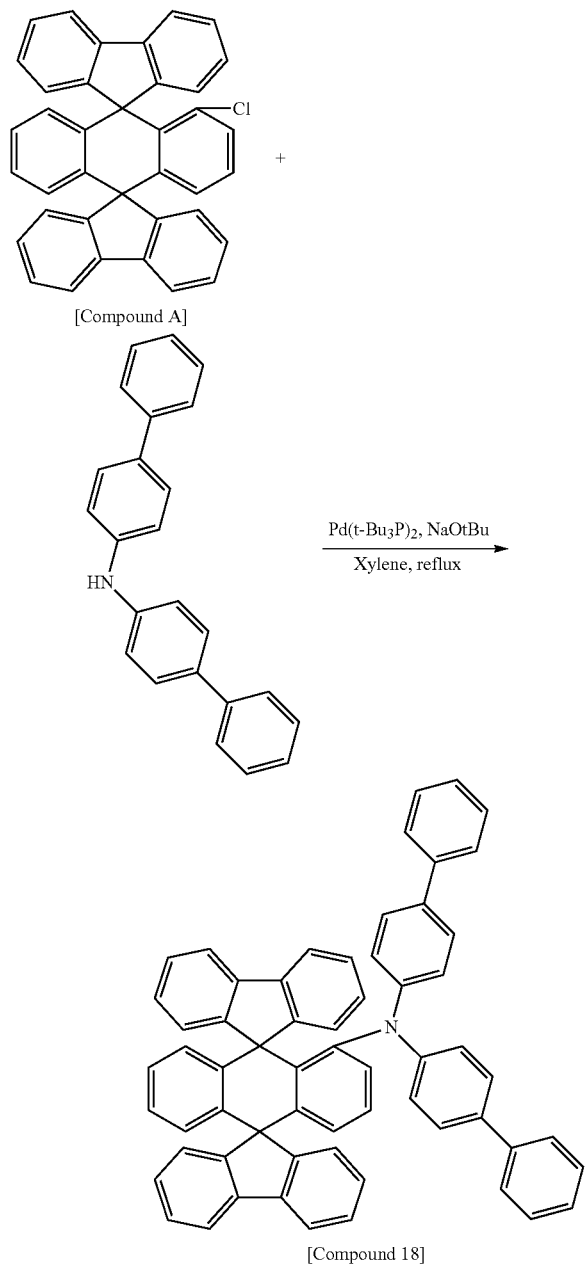 [SMILES: Clc1cccc2c1C1(c3ccccc3-c3ccccc31)c1ccccc1C21c2ccccc2-c2ccccc21 ; c1ccc(-c2ccc(Nc3ccc(-c4ccccc4)cc3)cc2)cc1 ; c1ccc(-c2ccc(N(c3ccc(-c4ccccc4)cc3)c3cccc4c3C3(c5ccccc5-c5ccccc53)c3ccccc3C43c4ccccc4-c4ccccc43)cc2)cc1]

<Preparation Example 19> Preparation of Compound 19

MS[M+H]⁺=800

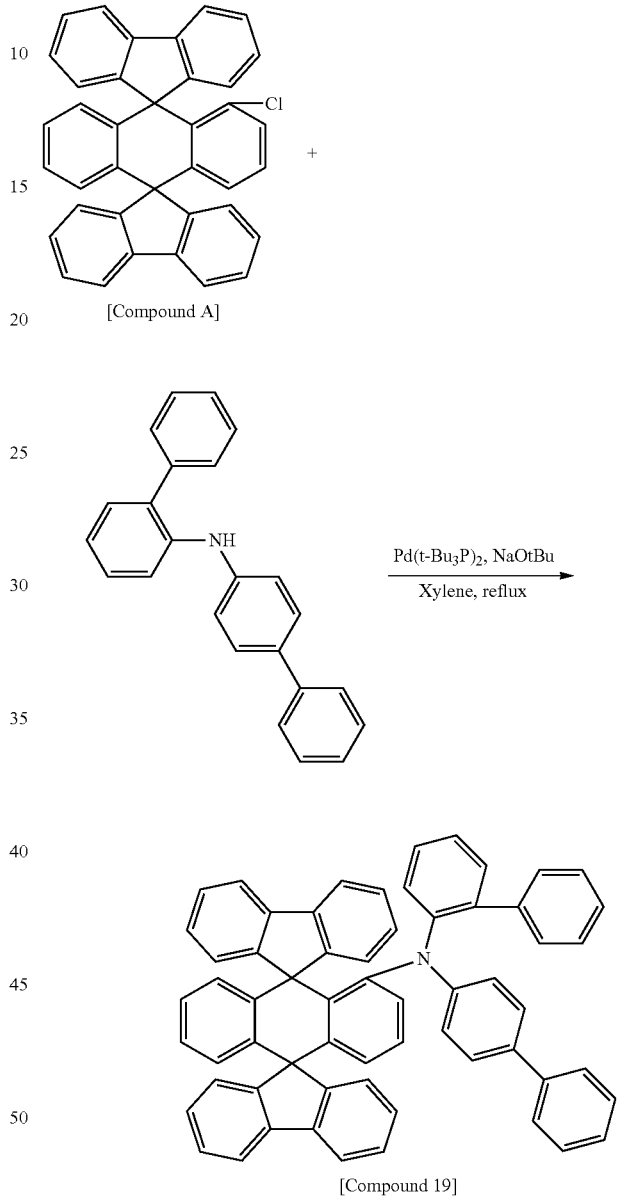

After completely dissolving Compound A (10.0 g, 17.92 mmol) and di([1,1'-biphenyl]-4-yl)amine (6.61 g, 20.61 mmol) in 320 ml of xylene in a 500 ml round bottom flask under nitrogen atmosphere, sodium tert-butoxide (2.24 g, 23.29 mol) and then bis(tri-tert-butylphosphine) palladium (0) (0.09 g, 0.19 mmol) were added thereto, and the result was heated and stirred for 3 hours. After lowering the temperature to room temperature, the result was filtered to remove the base, the xylene was vacuum concentrated, and the result was columned using tetrahydrofuran:hexane=1:18 to prepare Compound 18 (12.14 g, yield: 85%).

After completely dissolving Compound A (10.0 g, 17.92 mmol) and N-([1,1'-biphenyl]-4-yl)-[1,1'-biphenyl]-2-amine (6.61 g, 20.61 mmol) in 320 ml of xylene in a 500 ml round bottom flask under nitrogen atmosphere, sodium tert-butoxide (2.24 g, 23.29 mol) and then bis(tri-tert-butylphosphine) palladium(0) (0.09 g, 0.19 mmol) were added thereto, and the result was heated and stirred for 3 hours. After lowering the temperature to room temperature, the result was filtered to remove the base, the xylene was vacuum concentrated, and the result was columned using tetrahydrofuran:hexane=1:18 to prepare Compound 19 (10.92 g, yield: 77%).

MS[M+H]⁺=724

MS[M+H]⁺=840

<Preparation Example 20> Preparation of Compound 20

<Preparation Example 21> Preparation of Compound 21

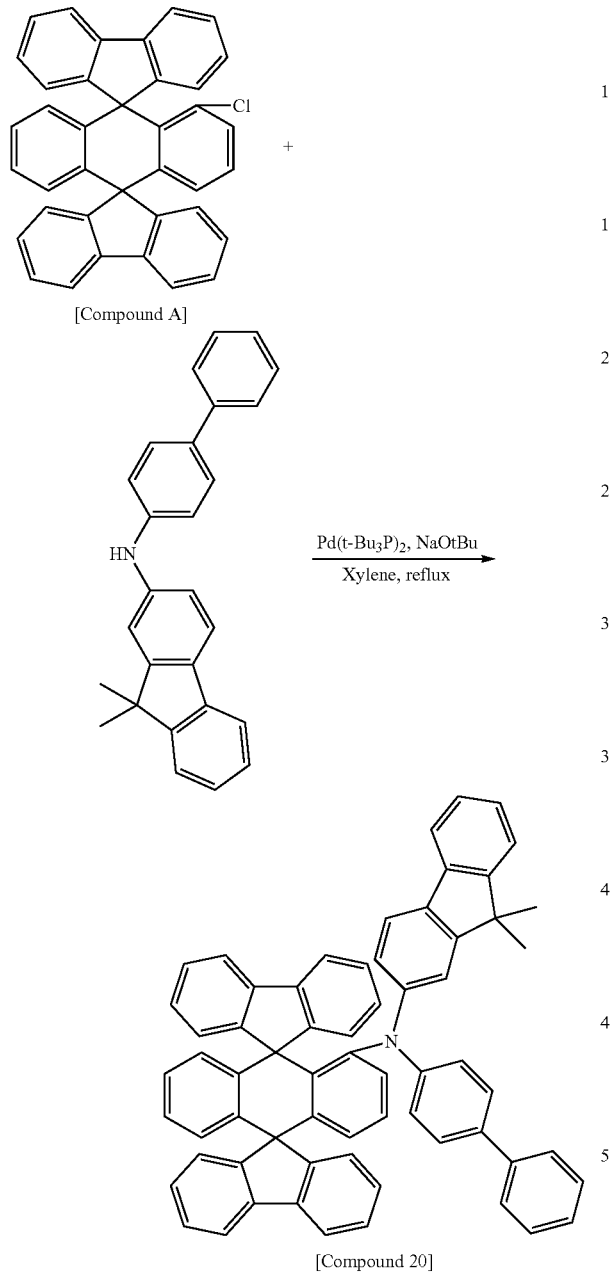

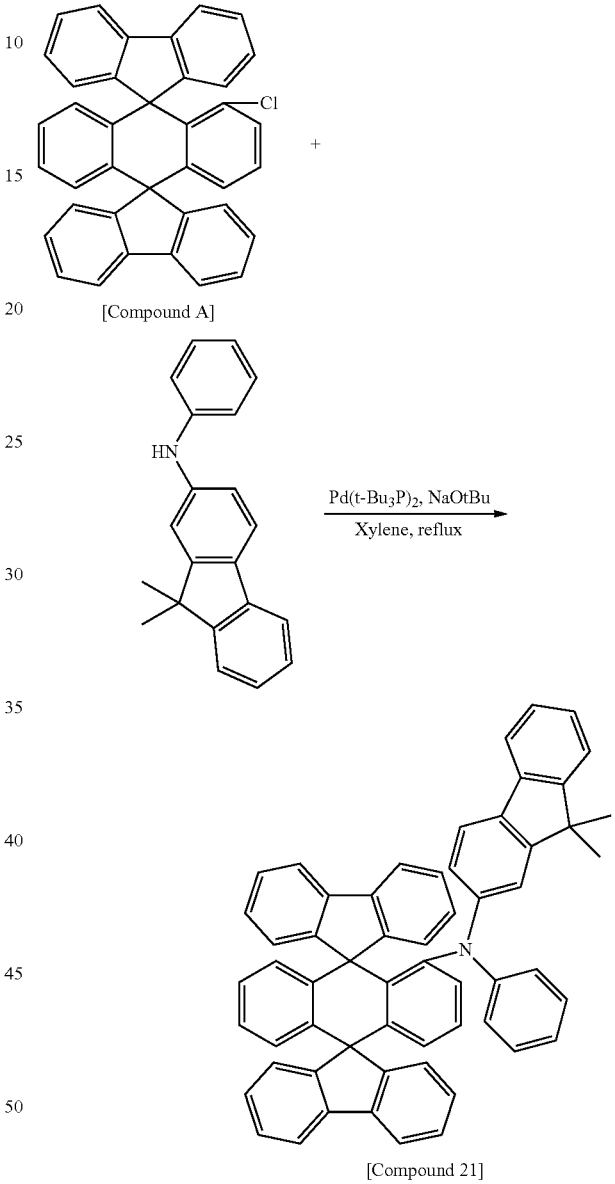

After completely dissolving Compound A (10.0 g, 17.92 mmol) and N-([1,1'-biphenyl]-4-yl)-9,9-dimethyl-9H-fluoren-2-amine (7.44 g, 20.61 mmol) in 320 ml of xylene in a 500 ml round bottom flask under nitrogen atmosphere, sodium tert-butoxide (2.24 g, 23.29 mol) and then bis(tri-tert-butylphosphine) palladium(0) (0.09 g, 0.19 mmol) were added thereto, and the result was heated and stirred for 3 hours. After lowering the temperature to room temperature, the result was filtered to remove the base, the xylene was vacuum concentrated, and the result was columned using tetrahydrofuran:hexane=1:18 to prepare Compound 20 (13.16 g, yield: 87%).

After completely dissolving Compound A (10.0 g, 17.92 mmol) and 9,9-dimethyl-N-phenyl-9H-fluoren-2-amine (5.87 g, 20.61 mmol) in 320 ml of xylene in a 500 ml round bottom flask under nitrogen atmosphere, sodium tert-butoxide (2.24 g, 23.29 mol) and then bis(tri-tert-butylphosphine) palladium(0) (0.09 g, 0.19 mmol) were added thereto, and the result was heated and stirred for 3 hours. After lowering the temperature to room temperature, the result was filtered to remove the base, the xylene was vacuum concentrated, and the result was columned using tetrahydrofuran:hexane=1:18 to prepare Compound 21 (10.92 g, yield: 80%).

MS[M+H]+=764 MS[M+H]+=840

<Preparation Example 22> Preparation of Compound 22

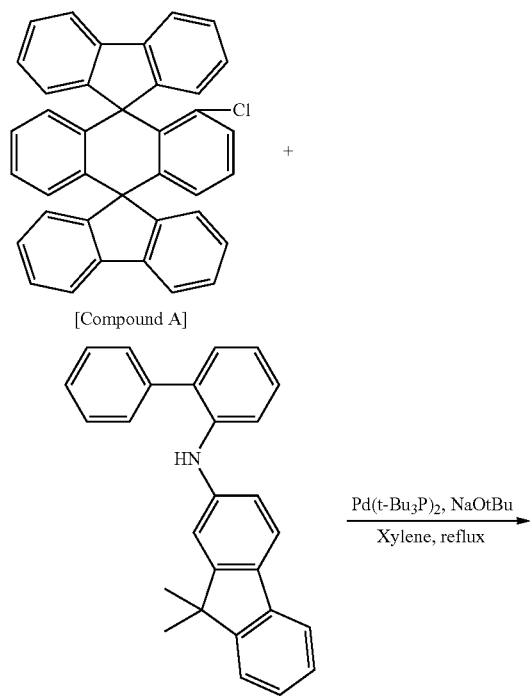

<Preparation Example 23> Preparation of Compound 23

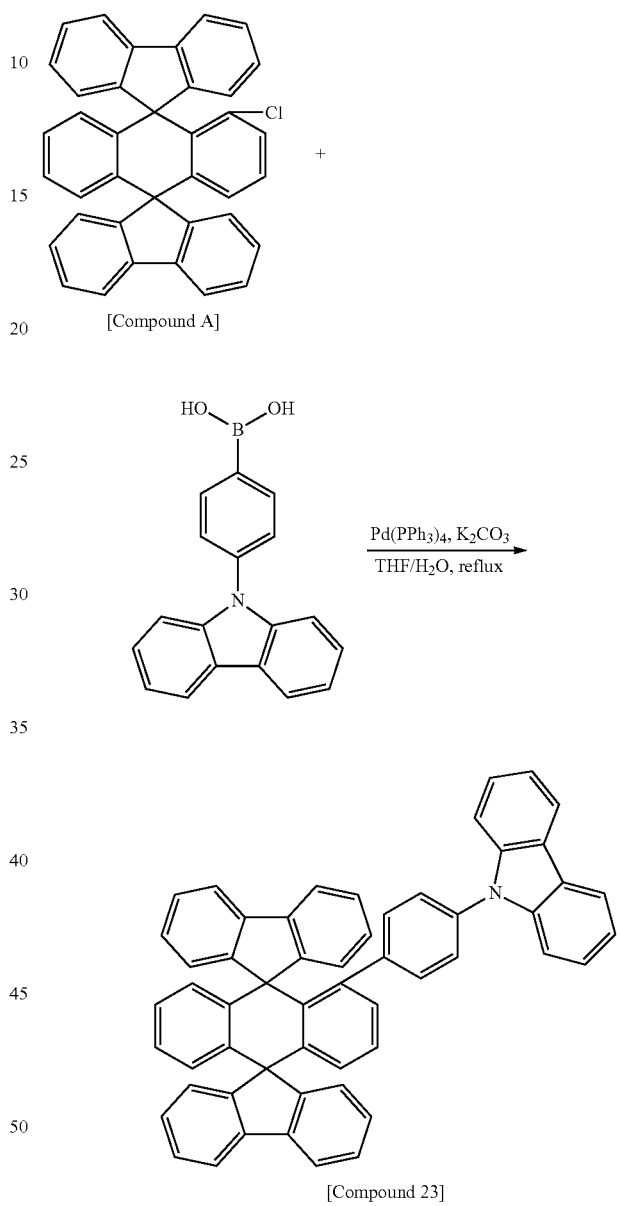

After completely dissolving Compound A (10.0 g, 17.92 mmol) and N-([1,1'-biphenyl]-2-yl)-9,9-dimethyl-9H-fluoren-2-amine (7.44 g, 20.61 mmol) in 320 ml of xylene in a 500 ml round bottom flask under nitrogen atmosphere, sodium tert-butoxide (2.24 g, 23.29 mol) and then bis(tri-tert-butylphosphine) palladium(0) (0.09 g, 0.19 mmol) were added thereto, and the result was heated and stirred for 3 hours. After lowering the temperature to room temperature, the result was filtered to remove the base, the xylene was vacuum concentrated, and the result was columned using tetrahydrofuran:hexane=1:18 to prepare Compound 22 (10.40 g, yield: 86%).

After completely dissolving Compound A (10.0 g, 17.92 mmol) and (4-(9H-carbazol-9-yl)phenyl)boronic acid (5.95 g, 20.61 mmol) in 280 ml of tetrahydrofuran in a 500 ml round bottom flask under nitrogen atmosphere, a 2 M aqueous potassium carbonate solution (140 ml) and then tetrakis-(triphenylphosphine)palladium (0.62 g, 0.54 mmol) were added thereto, and the result was heated and stirred for 5 hours. After lowering the temperature to room temperature, the water layer was removed, and the result was dried with anhydrous magnesium sulfate, vacuum concentrated, and then recrystallized with 200 ml of ethyl acetate to prepare Compound 23 (12.34 g, yield: 93%).

151

MS[M+H]⁺=722

<Preparation Example 24> Preparation of Compound 24

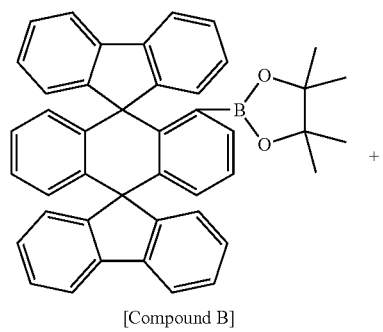

[Compound B]

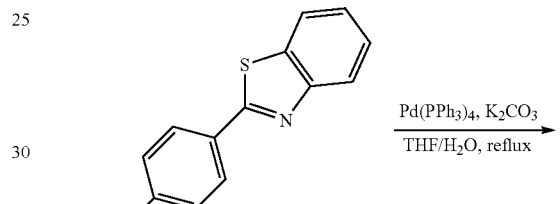

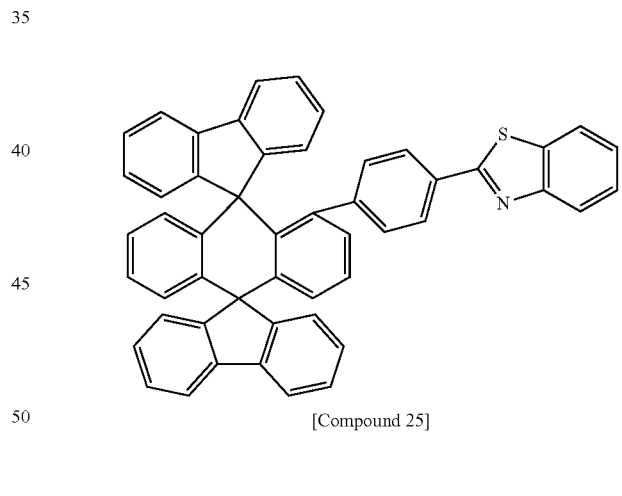

[Compound 24]

After completely dissolving Compound B (10.0 g, 16.49 mmol) and 2-(4-bromophenyl)benzo[d]oxazole (4.11 g, 14.99 mmol) in 240 ml of tetrahydrofuran in a 500 ml round bottom flask under nitrogen atmosphere, a 2 M aqueous potassium carbonate solution (120 ml) and then tetrakis-(triphenylphosphine)palladium (0.62 g, 0.54 mmol) were added thereto, and the result was heated and stirred for 4 hours. After lowering the temperature to room temperature, the water layer was removed, and the result was dried with anhydrous magnesium sulfate, vacuum concentrated, and then recrystallized with 330 ml of ethyl acetate to prepare Compound 24 (8.98 g, yield: 76%).

152

MS[M+H]⁺=674

<Preparation Example 25> Preparation of Compound 25

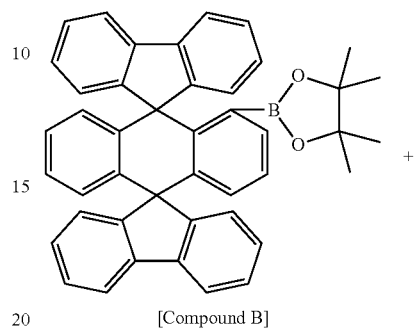

[Compound B]

[Compound 25]

After completely dissolving Compound B (10.0 g, 16.49 mmol) and 2-(4-bromophenyl)benzo[d]thiazole (4.33 g, 14.99 mmol) in 240 ml of tetrahydrofuran in a 500 ml round bottom flask under nitrogen atmosphere, a 2 M aqueous potassium carbonate solution (120 ml) and then tetrakis-(triphenylphosphine)palladium (0.62 g, 0.54 mmol) were added thereto, and the result was heated and stirred for 5 hours. After lowering the temperature to room temperature, the water layer was removed, and the result was dried with anhydrous magnesium sulfate, vacuum concentrated, and then recrystallized with 290 ml of ethyl acetate to prepare Compound 25 (8.41 g, yield: 72%).

MS[M+H]⁺=690

<Preparation Example 26> Preparation of Compound 26

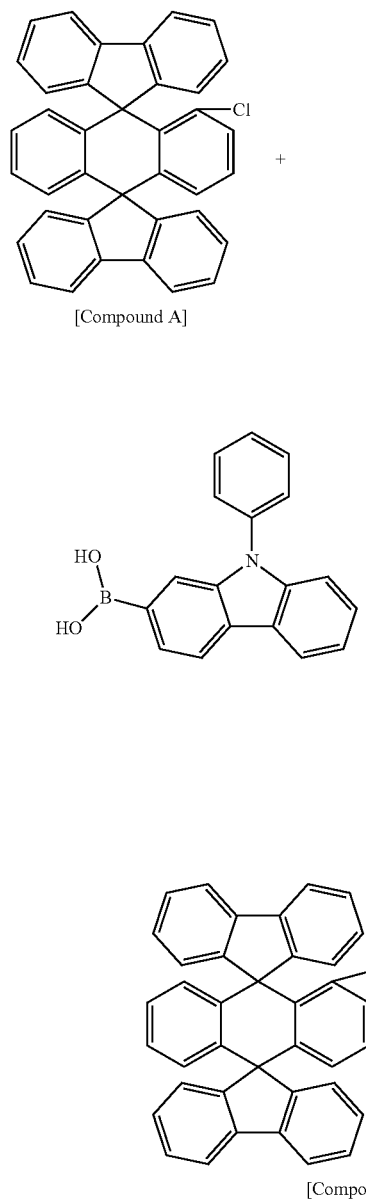

[Compound A]

[Compound 26]

After completely dissolving Compound A (10.0 g, 17.92 mmol) and (9-phenyl-9H-carbazol-2-yl)boronic acid (5.95 g, 20.61 mmol) in 280 ml of tetrahydrofuran in a 500 ml round bottom flask under nitrogen atmosphere, a 2 M aqueous potassium carbonate solution (140 ml) and then tetrakis-(triphenylphosphine)palladium (0.62 g, 0.54 mmol) were added thereto, and the result was heated and stirred for 9 hours. After lowering the temperature to room temperature, the water layer was removed, and the result was dried with anhydrous magnesium sulfate, vacuum concentrated, and then recrystallized with 260 ml of ethyl acetate to prepare Compound 26 (10.11 g, yield: 77%).

MS[M+H]⁺=722

<Preparation Example 27> Preparation of Compound 27

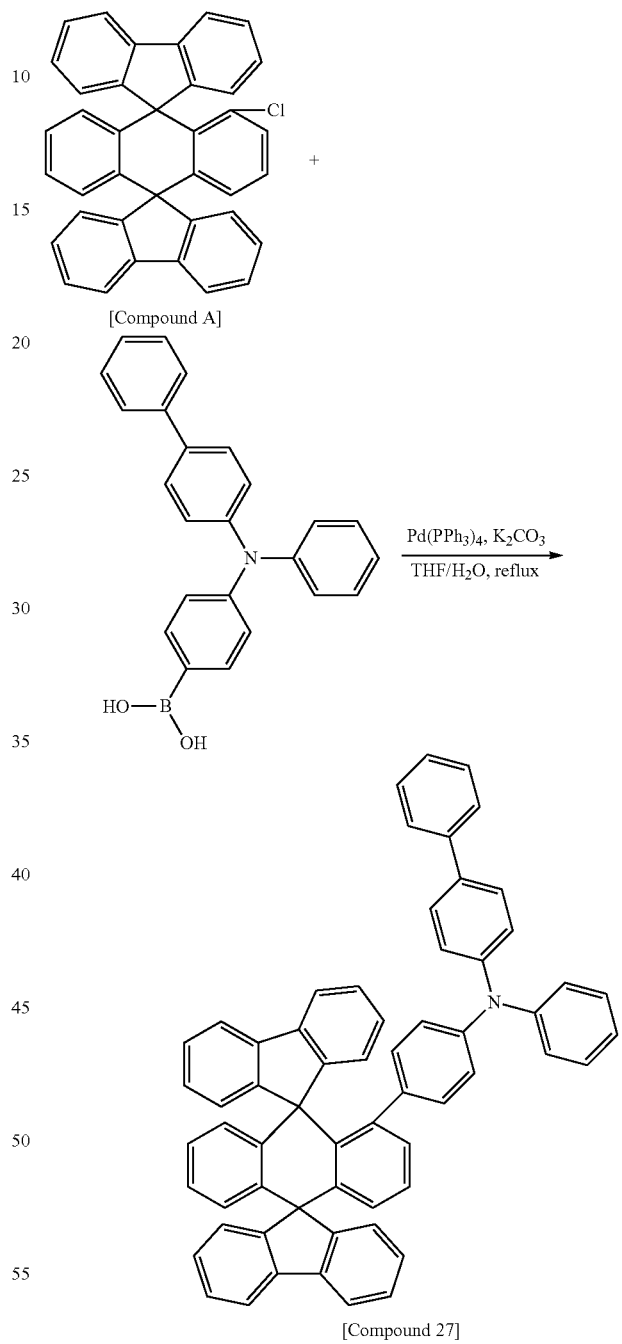

[Compound A]

[Compound 27]

After completely dissolving Compound A (10.0 g, 17.92 mmol) and (4-([1,1'-biphenyl]-4-yl(phenyl)amino)phenyl) boronic acid (7.41 g, 20.61 mmol) in 280 ml of tetrahydrofuran in a 500 ml round bottom flask under nitrogen atmosphere, a 2 M aqueous potassium carbonate solution (140 ml) and then tetrakis-(triphenylphosphine)palladium (0.62 g, 0.54 mmol) were added thereto, and the result was heated and stirred for 3 hours. After lowering the temperature to room temperature, the water layer was removed, and the result was dried with anhydrous magnesium sulfate, vacuum concentrated, and then recrystallized with 200 ml of ethyl acetate to prepare Compound 27 (10.11 g, yield: 78%).
MS[M+H]$^+$=800

<Preparation Example 28> Preparation of Compound 28

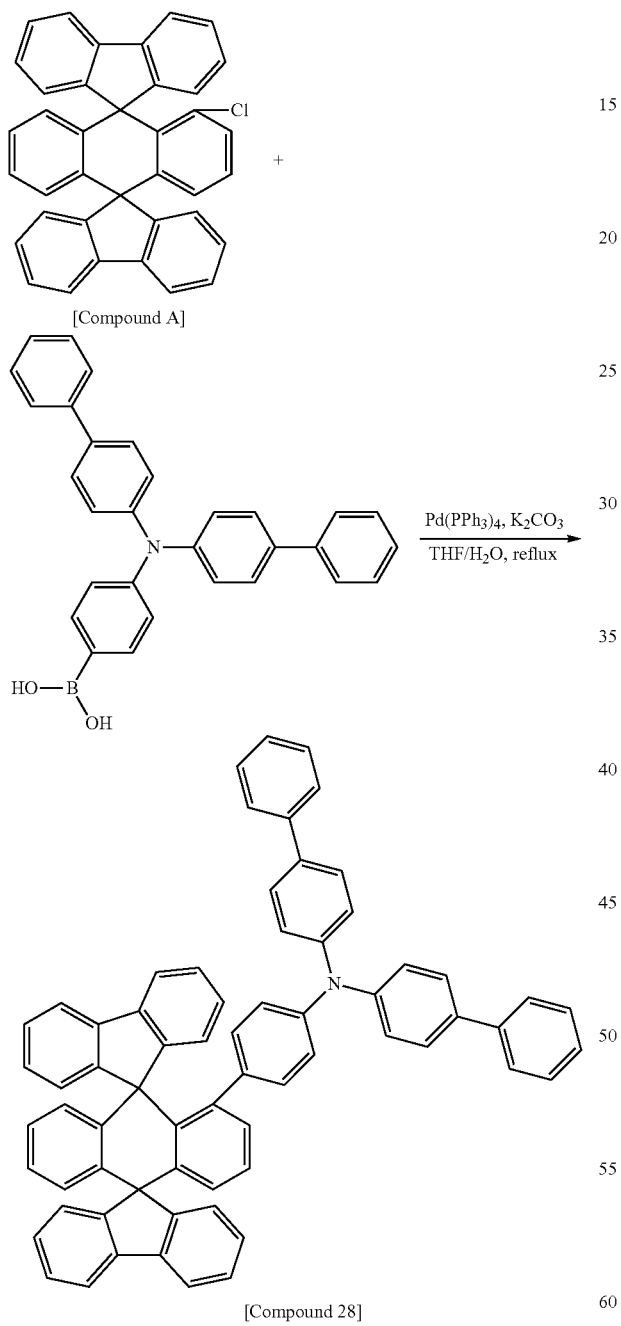

[Compound 28]

After completely dissolving Compound A (10.0 g, 17.92 mmol) and (4-(di([1,1'-biphenyl]-4-yl)amino)phenyl)boronic acid (7.41 g, 20.61 mmol) in 280 ml of tetrahydrofuran in a 500 ml round bottom flask under nitrogen atmosphere, a 2 M aqueous potassium carbonate solution (140 ml) and then tetrakis-(triphenylphosphine)palladium (0.62 g, 0.54 mmol) were added thereto, and the result was heated and stirred for 3 hours. After lowering the temperature to room temperature, the water layer was removed, and the result was dried with anhydrous magnesium sulfate, vacuum concentrated, and then recrystallized with 200 ml of ethyl acetate to prepare Compound 28 (10.11 g, yield: 78%).
MS[M+H]$^+$=876

<Preparation Example 29> Preparation of Compound 29

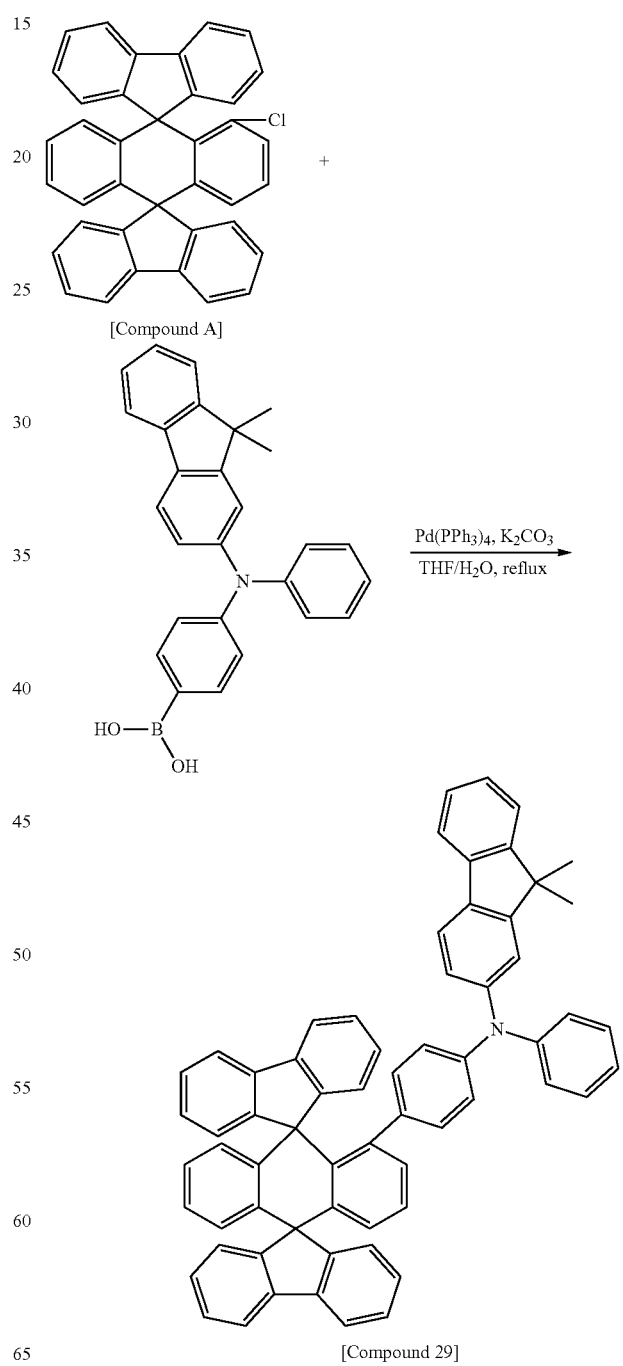

[Compound 29]

After completely dissolving Compound A (10.0 g, 17.92 mmol) and (4-((9,9-dimethyl-9H-fluoren-2-yl)(phenyl)amino)phenyl)boronic acid (7.41 g, 20.61 mmol) in 280 ml of tetrahydrofuran in a 500 ml round bottom flask under nitrogen atmosphere, a 2 M aqueous potassium carbonate solution (140 ml) and then tetrakis-(triphenylphosphine)palladium (0.62 g, 0.54 mmol) were added thereto, and the result was heated and stirred for 3 hours. After lowering the temperature to room temperature, the water layer was removed, and the result was dried with anhydrous magnesium sulfate, vacuum concentrated, and then recrystallized with 200 ml of ethyl acetate to prepare Compound 29 (10.11 g, yield: 78%).

MS[M+H]$^+$=840

<Preparation Example 30> Preparation of Compound 30

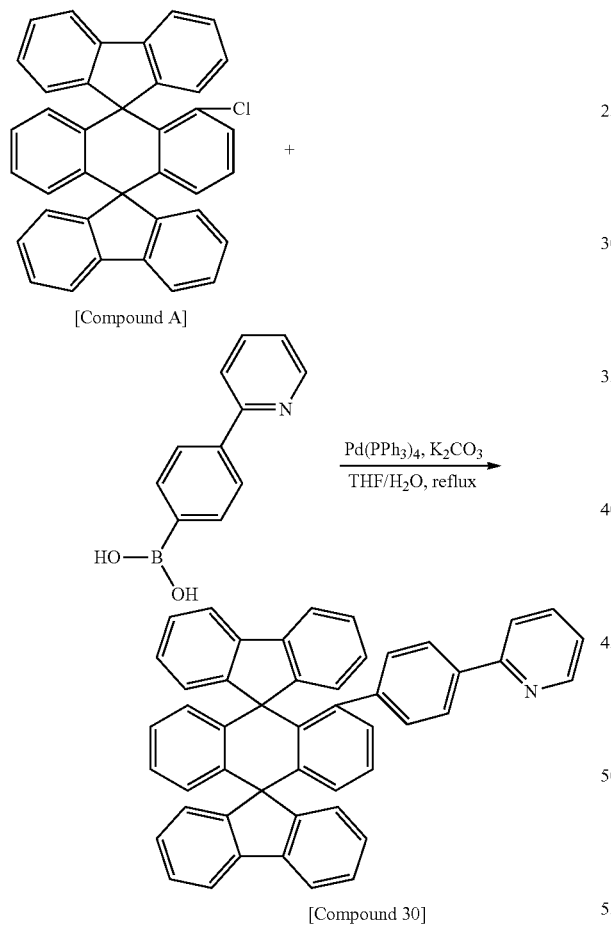

After completely dissolving Compound A (10.0 g, 17.92 mmol) and (4-(pyridin-2-yl)phenyl)boronic acid (4.09 g, 20.61 mmol) in 300 ml of tetrahydrofuran in a 500 ml round bottom flask under nitrogen atmosphere, a 2 M aqueous potassium carbonate solution (150 ml) and then tetrakis-(triphenylphosphine)palladium (0.62 g, 0.54 mmol) were added thereto, and the result was heated and stirred for 6 hours. After lowering the temperature to room temperature, the water layer was removed, and the result was dried with anhydrous magnesium sulfate, vacuum concentrated, and then recrystallized with 220 ml of ethyl acetate to prepare Compound 30 (8.82 g, yield: 79%).

MS[M+H]$^+$=634

<Preparation Example 31> Preparation of Compound 31

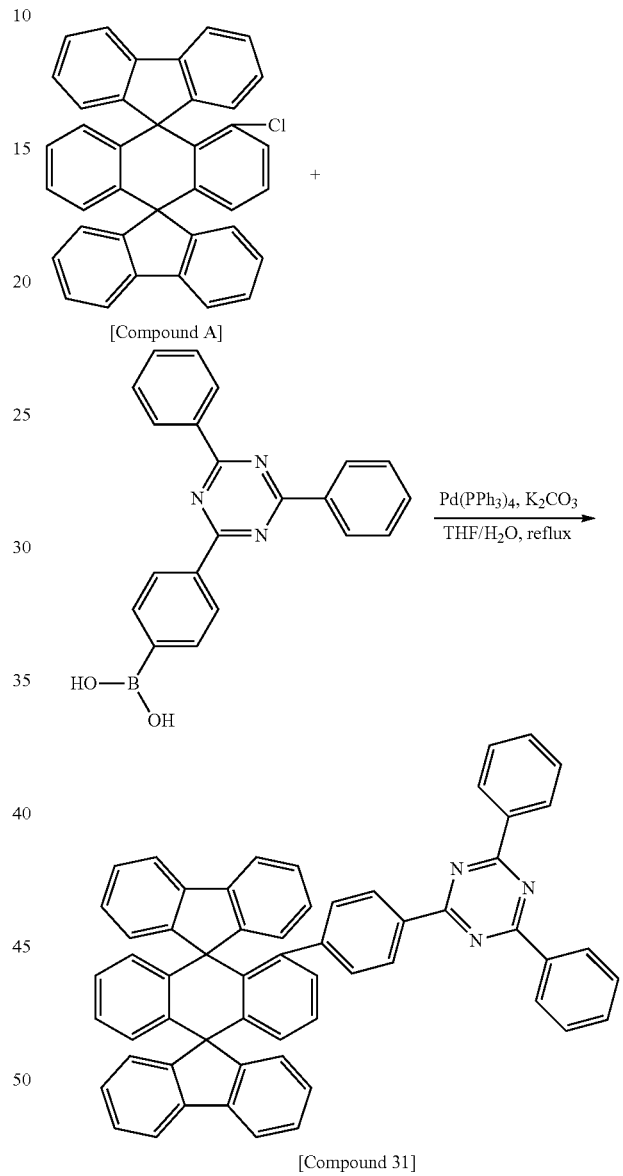

After completely dissolving Compound A (10.0 g, 17.92 mmol) and (4-(4,6-diphenyl-1,3,5-triazin-2-yl)phenyl)boronic acid (7.28 g, 20.61 mmol) in 400 ml of tetrahydrofuran in a 500 ml round bottom flask under nitrogen atmosphere, a 2 M aqueous potassium carbonate solution (200 ml) and then tetrakis-(triphenylphosphine)palladium (0.62 g, 0.54 mmol) were added thereto, and the result was heated and stirred for 9 hours. After lowering the temperature to room temperature, the water layer was removed, and the result was dried with anhydrous magnesium sulfate, vacuum concentrated, and then recrystallized with 350 ml of ethyl acetate to prepare Compound 31 (12.85 g, yield: 91%).

MS[M+H]⁺=788

MS[M+H]⁺=787

<Preparation Example 32> Preparation of Compound 32

<Preparation Example 33> Preparation of Compound 33

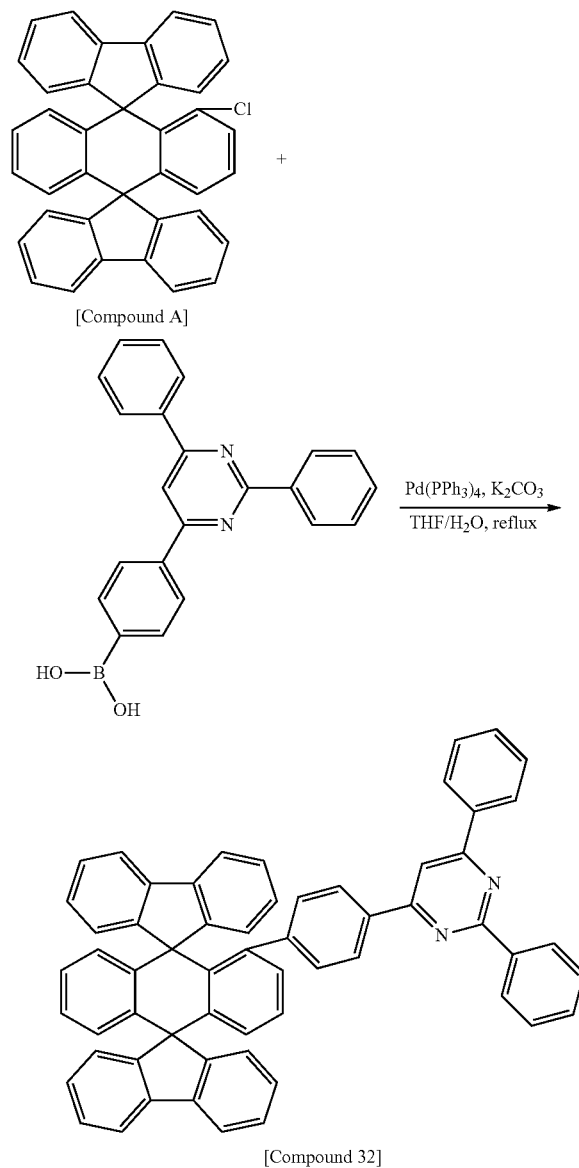

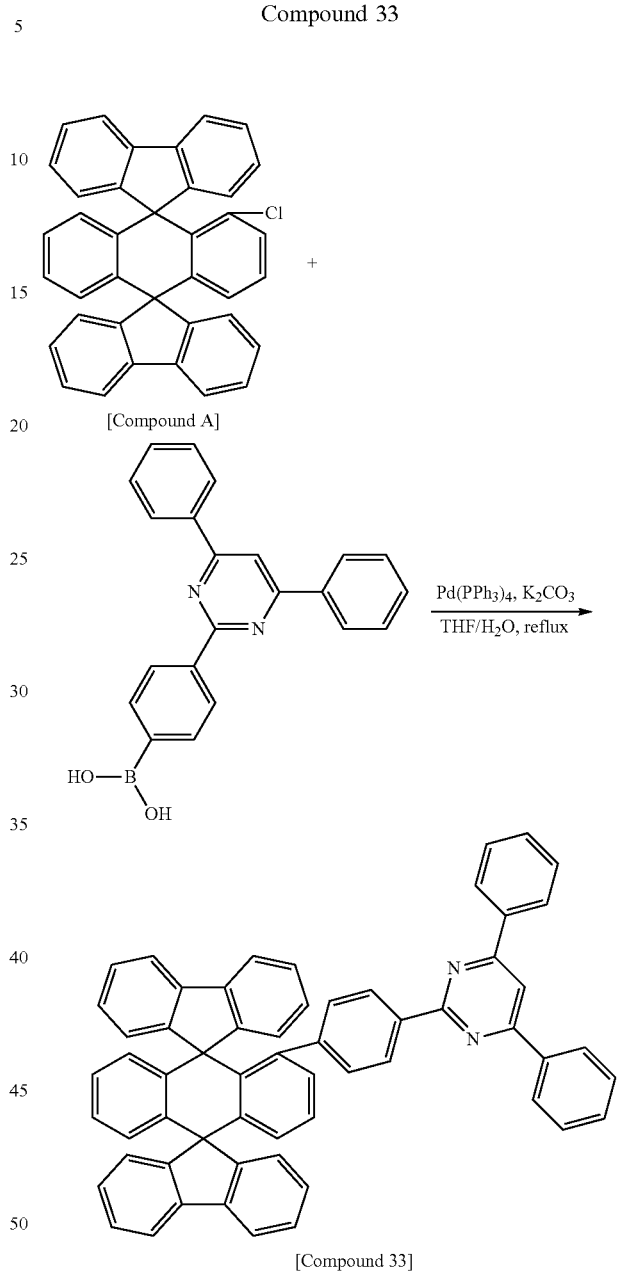

After completely dissolving Compound A (10.0 g, 17.92 mmol) and (4-(2,6-diphenylpyrimidin-4-yl)phenyl)boronic acid (7.28 g, 20.61 mmol) in 400 ml of tetrahydrofuran in a 500 ml round bottom flask under nitrogen atmosphere, a 2 M aqueous potassium carbonate solution (200 ml) and then tetrakis-(triphenylphosphine)palladium (0.62 g, 0.54 mmol) were added thereto, and the result was heated and stirred for 9 hours. After lowering the temperature to room temperature, the water layer was removed, and the result was dried with anhydrous magnesium sulfate, vacuum concentrated, and then recrystallized with 350 ml of ethyl acetate to prepare Compound 32 (12.85 g, yield: 91%).

After completely dissolving Compound A (10.0 g, 17.92 mmol) and (4-(4,6-diphenylpyrimidin-2-yl)phenyl)boronic acid (7.28 g, 20.61 mmol) in 400 ml of tetrahydrofuran in a 500 ml round bottom flask under nitrogen atmosphere, a 2 M aqueous potassium carbonate solution (200 ml) and then tetrakis-(triphenylphosphine)palladium (0.62 g, 0.54 mmol) were added thereto, and the result was heated and stirred for 5 hours. After lowering the temperature to room temperature, the water layer was removed, and the result was dried with anhydrous magnesium sulfate, vacuum concentrated, and then recrystallized with 310 ml of ethyl acetate to prepare Compound 33 (11.73 g, yield: 82%).

MS[M+H]⁺=787

<Preparation Example 34> Preparation of Compound 34

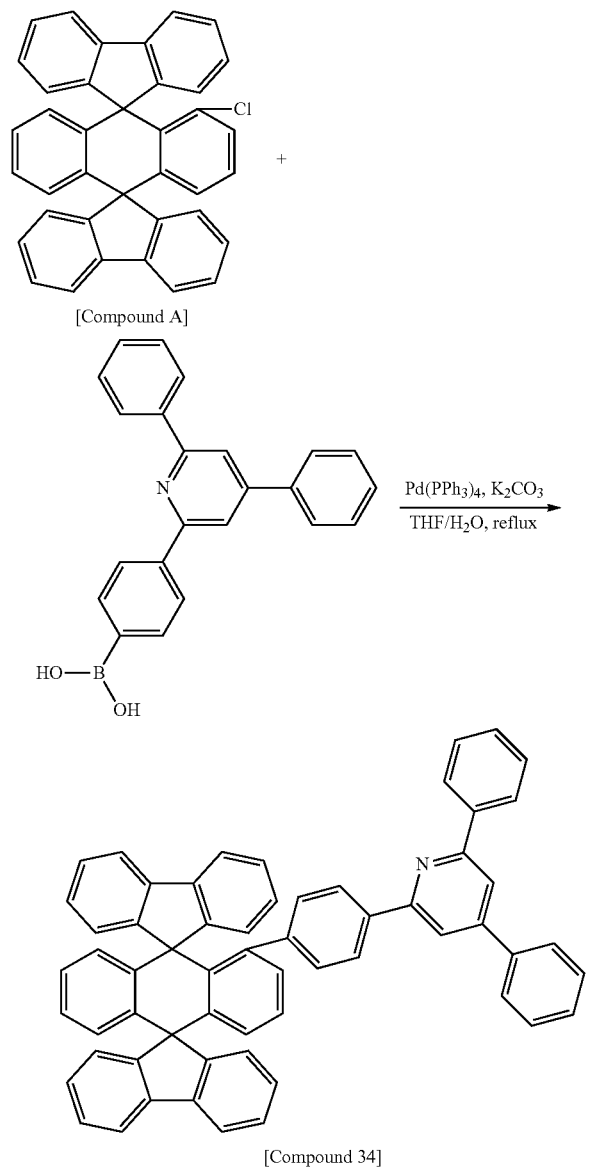 [SMILES: Clc1cccc2c1C1(c3ccccc3-c3ccccc31)c1ccccc1C21c2ccccc2-c2ccccc21 ; OB(O)c1ccc(-c2cc(-c3ccccc3)cc(-c3ccccc3)n2)cc1 ; c1ccc(-c2cc(-c3ccccc3)nc(-c3ccc(-c4cccc5c4C4(c6ccccc6-c6ccccc64)c4ccccc4C54c5ccccc5-c5ccccc54)cc3)c2)cc1]

MS[M+H]⁺=786

<Preparation Example 35> Preparation of Compound 35

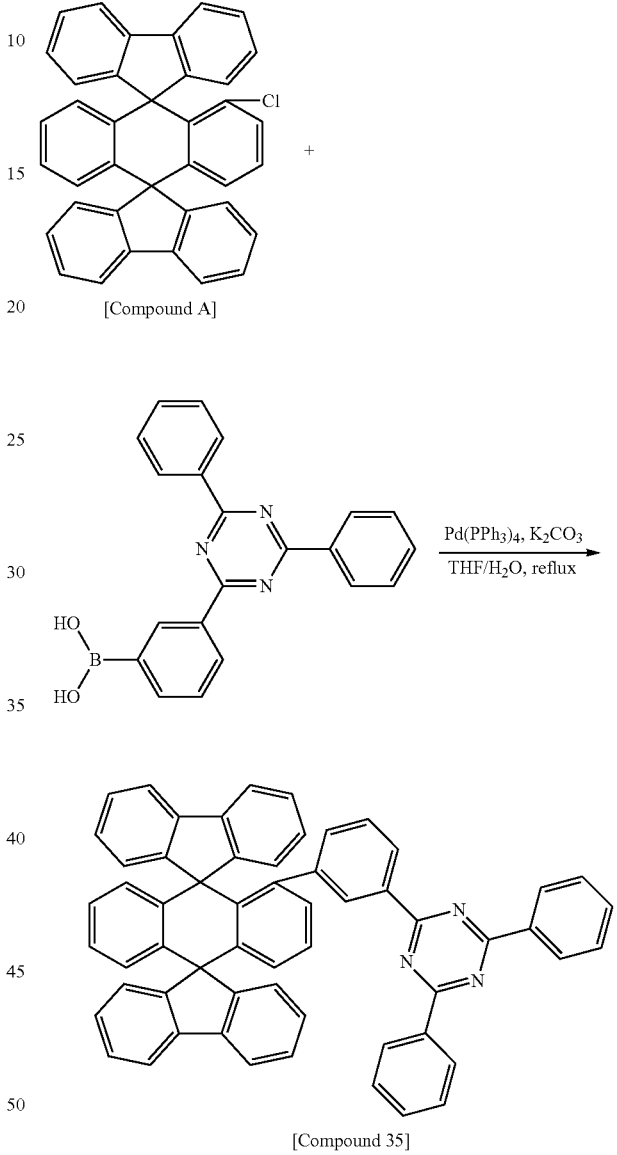

After completely dissolving Compound A (10.0 g, 17.92 mmol) and (4-(4,6-diphenylpyridin-2-yl)phenyl)boronic acid (7.29 g, 20.61 mmol) in 400 ml of tetrahydrofuran in a 500 ml round bottom flask under nitrogen atmosphere, a 2 M aqueous potassium carbonate solution (200 ml) and then tetrakis-(triphenylphosphine)palladium (0.62 g, 0.54 mmol) were added thereto, and the result was heated and stirred for 4 hours. After lowering the temperature to room temperature, the water layer was removed, and the result was dried with anhydrous magnesium sulfate, vacuum concentrated, and then recrystallized with 370 ml of ethyl acetate to prepare Compound 34 (10.54 g, yield: 75%).

After completely dissolving Compound A (10.0 g, 17.92 mmol) and (3-(4,6-diphenyl-1,3,5-triazin-2-yl)phenyl)boronic acid (7.28 g, 20.61 mmol) in 400 ml of tetrahydrofuran in a 500 ml round bottom flask under nitrogen atmosphere, a 2 M aqueous potassium carbonate solution (200 ml) and then tetrakis-(triphenylphosphine)palladium (0.62 g, 0.54 mmol) were added thereto, and the result was heated and stirred for 9 hours. After lowering the temperature to room temperature, the water layer was removed, and the result was dried with anhydrous magnesium sulfate, vacuum concentrated, and then recrystallized with 350 ml of ethyl acetate to prepare Compound 35 (11.78 g, yield: 88%).

MS[M+H]⁺=788

<Preparation Example 36> Preparation of Compound 36

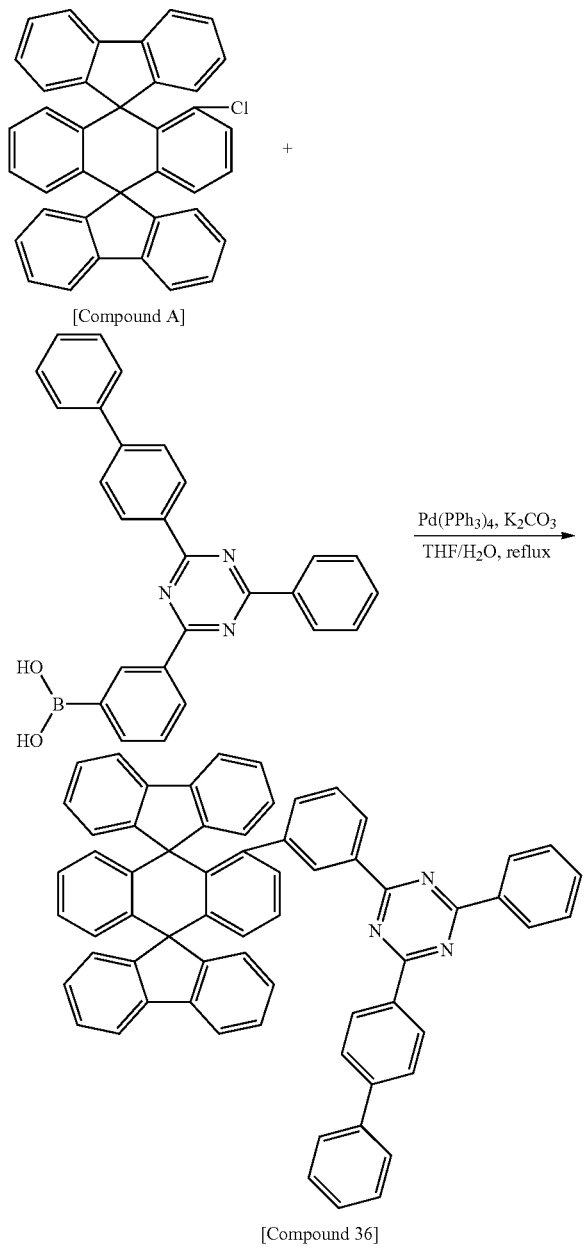

[Compound 36]

MS[M+H]⁺=788

<Preparation Example 37> Preparation of Compound 37

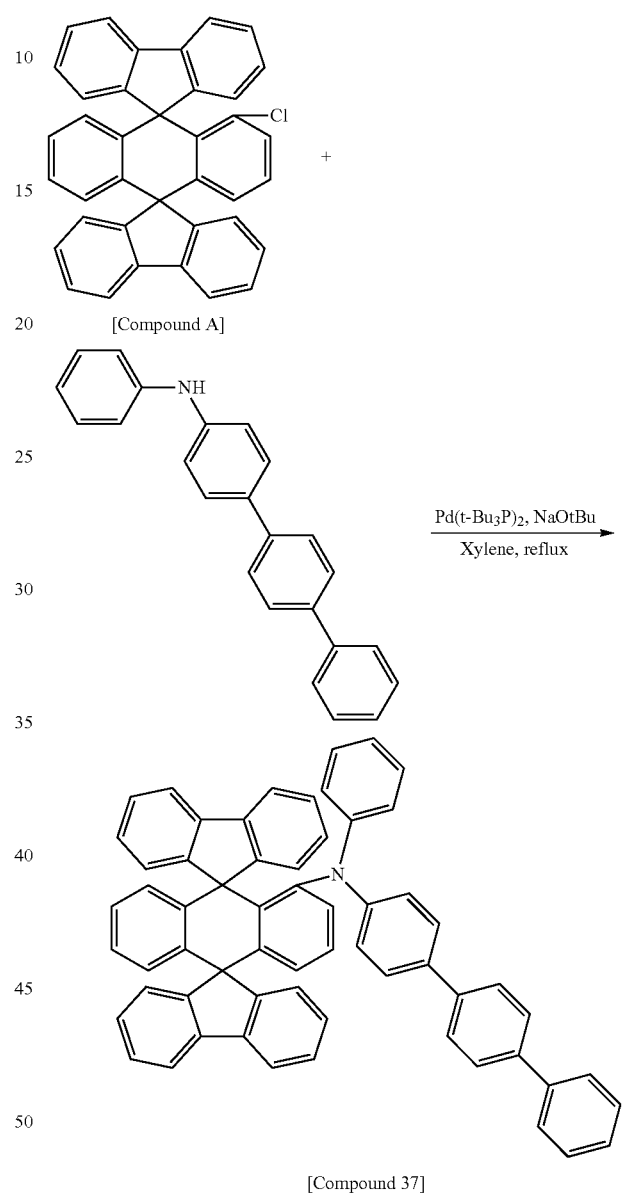

[Compound 37]

After completely dissolving Compound A (10.0 g, 17.92 mmol) and (3-(4-([1,1'-biphenyl]-4-yl)-6-phenyl-1,3,5-triazin-2-yl)phenyl)boronic acid (8.84 g, 20.61 mmol) in 400 ml of tetrahydrofuran in a 500 ml round bottom flask under nitrogen atmosphere, a 2 M aqueous potassium carbonate solution (200 ml) and then tetrakis-(triphenylphosphine) palladium (0.62 g, 0.54 mmol) were added thereto, and the result was heated and stirred for 9 hours. After lowering the temperature to room temperature, the water layer was removed, and the result was dried with anhydrous magnesium sulfate, vacuum concentrated, and then recrystallized with 350 ml of ethyl acetate to prepare Compound 36 (11.78 g, yield: 88%).

After completely dissolving Compound A (10.0 g, 17.92 mmol) and N-phenyl-[1,1'-biphenyl]-4-amine (6.61 g, 20.61 mmol) in 320 ml of xylene in a 500 ml round bottom flask under nitrogen atmosphere, sodium tert-butoxide (2.24 g, 23.29 mol) and then bis(tri-tert-butylphosphine) palladium (0) (0.09 g, 0.19 mmol) were added thereto, and the result was heated and stirred for 5 hours. After lowering the temperature to room temperature, the result was filtered to remove the base, the xylene was vacuum concentrated, and the result was columned using tetrahydrofuran:hexane=1:18 to prepare Compound 37 (10.33 g, yield: 79%).

MS[M+H]⁺=800

MS[M+H]⁺=696

<Preparation Example 38> Preparation of Compound 38

<Preparation Example 39> Preparation of Compound 39

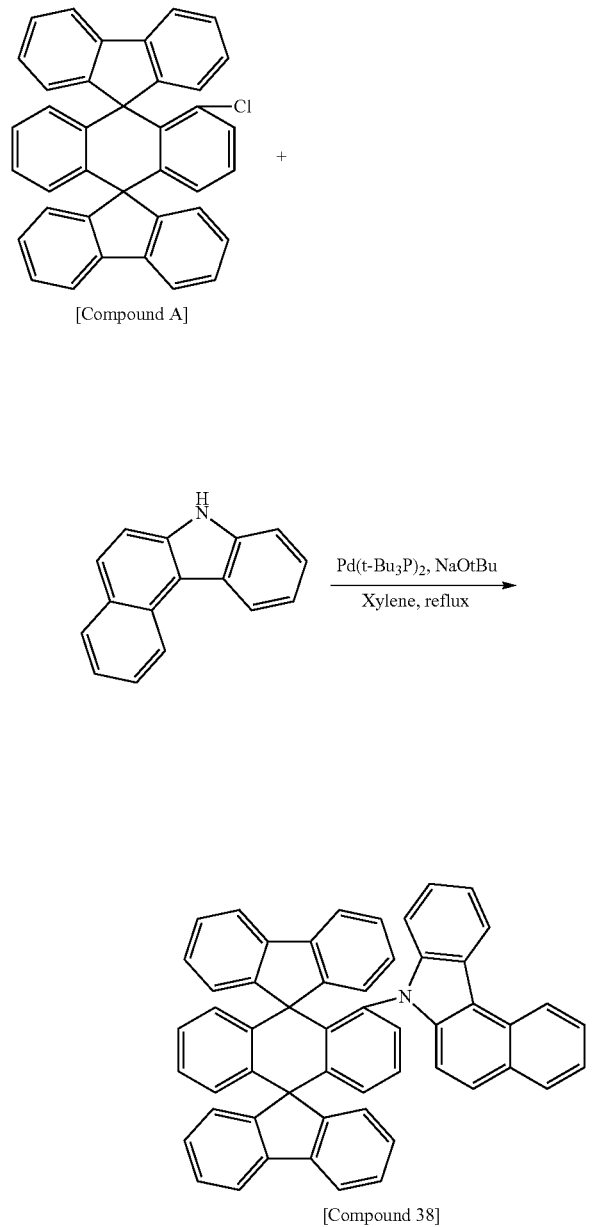

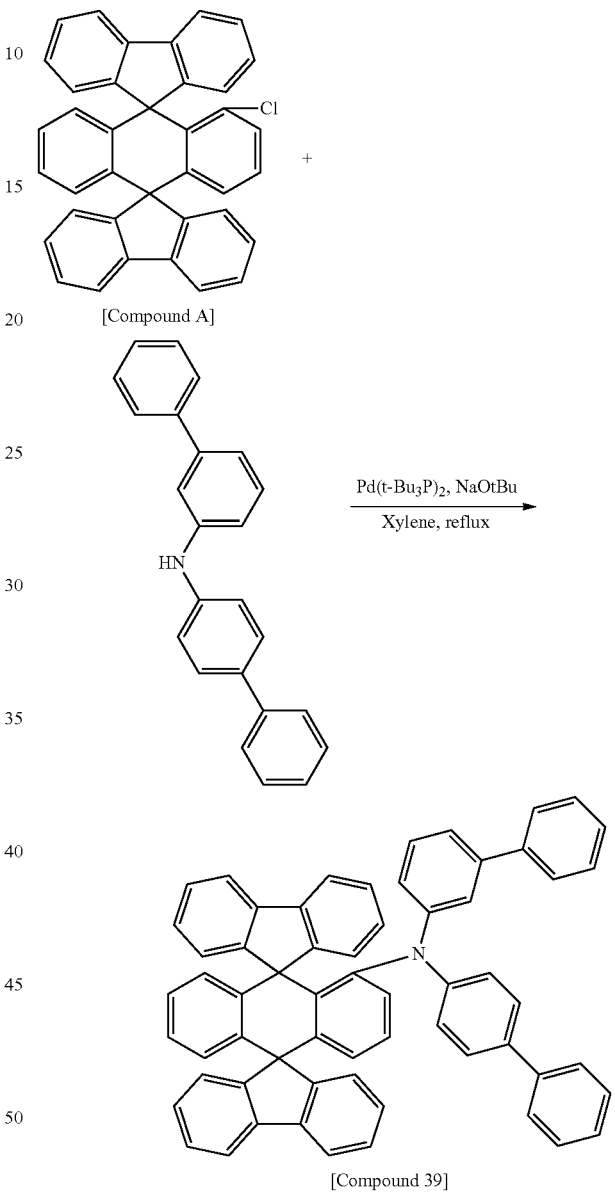

After completely dissolving Compound A (10.0 g, 17.92 mmol) and 7H-benzo[c]carbazole (5.61 g, 20.61 mmol) in 320 ml of xylene in a 500 ml round bottom flask under nitrogen atmosphere, sodium tert-butoxide (2.24 g, 23.29 mol) and then bis(tri-tert-butylphosphine) palladium(0) (0.09 g, 0.19 mmol) were added thereto, and the result was heated and stirred for 3 hours. After lowering the temperature to room temperature, the result was filtered to remove the base, the xylene was vacuum concentrated, and the result was columned using tetrahydrofuran:hexane=1:18 to prepare Compound 38 (8.65 g, yield: 69%).

After completely dissolving Compound A (10.0 g, 17.92 mmol) and N-([1,1'-biphenyl]-4-yl)-[1,1'-biphenyl]-3-amine (6.61 g, 20.61 mmol) in 320 ml of xylene in a 500 ml round bottom flask under nitrogen atmosphere, sodium tert-butoxide (2.24 g, 23.29 mol) and then bis(tri-tert-butylphosphine) palladium(0) (0.09 g, 0.19 mmol) were added thereto, and the result was heated and stirred for 7 hours. After lowering the temperature to room temperature, the result was filtered to remove the base, the xylene was vacuum concentrated, and the result was columned using tetrahydrofuran:hexane=1:10 to prepare Compound 39 (11.56 g, yield: 81%).

MS[M+H]⁺=800

<Preparation Example 40> Preparation of Compound 40

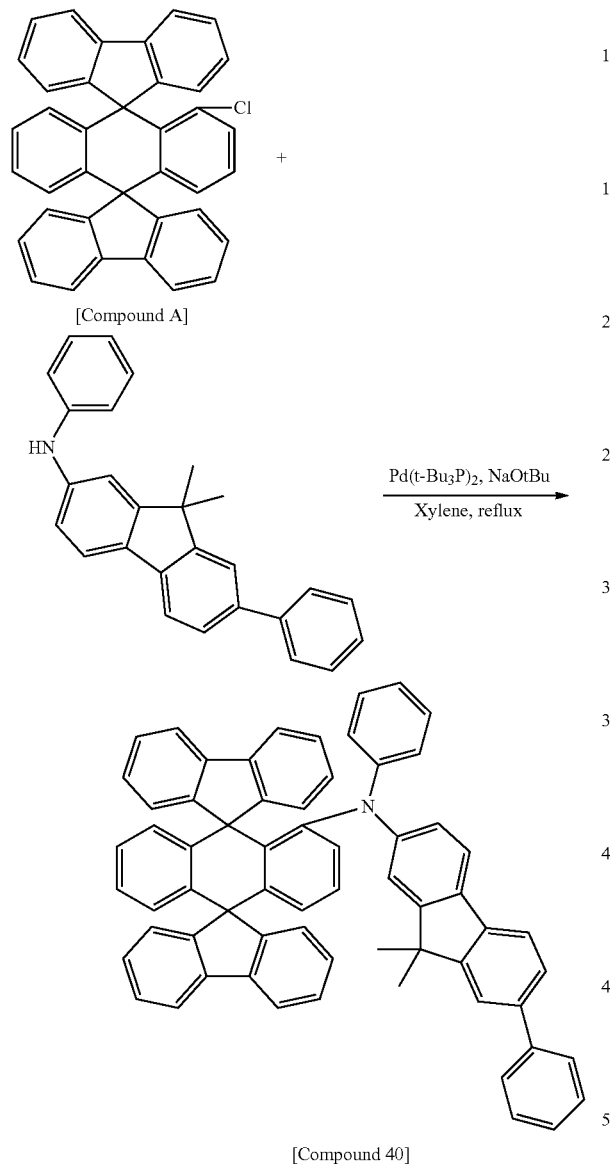

After completely dissolving Compound A (10.0 g, 17.92 mmol) and 9,9-dimethyl-N,7-diphenyl-9H-fluoren-2-amine (7.44 g, 20.61 mmol) in 320 ml of xylene in a 500 ml round bottom flask under nitrogen atmosphere, sodium tert-butoxide (2.24 g, 23.29 mol) and then bis(tri-tert-butylphosphine) palladium(0) (0.09 g, 0.19 mmol) were added thereto, and the result was heated and stirred for 5 hours. After lowering the temperature to room temperature, the result was filtered to remove the base, the xylene was vacuum concentrated, and the result was columned using tetrahydrofuran: hexane=1:21 to prepare Compound 40 (12.08 g, yield: 80%).

MS[M+H]⁺=840

Example 1-1

A glass substrate on which indium tin oxide (ITO) was coated as a thin film to a thickness of 1,000 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 5 minutes using oxygen plasma, and then transferred to a vacuum depositor.

On the transparent ITO electrode prepared as above, a hole injection layer was formed by thermal vacuum depositing hexanitrile hexaazatriphenylene (HAT) of the following chemical formula to a thickness of 500 Å.

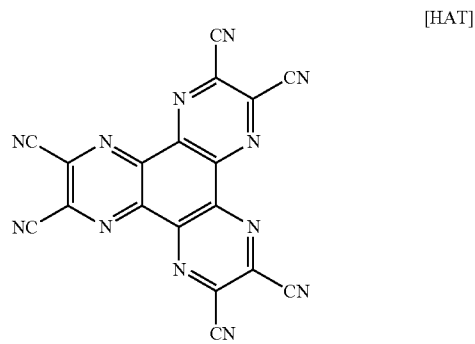 [SMILES: N#Cc1nc2c3nc(C#N)c(C#N)nc3c3nc(C#N)c(C#N)nc3c2nc1C#N]

[HAT]

A hole transfer layer was formed on the hole injection layer by vacuum depositing the following compound 4-4'-bis[N-(1-naphthyl)-N-phenylamino]biphenyl (NPB) (300 Å), a material transferring holes.

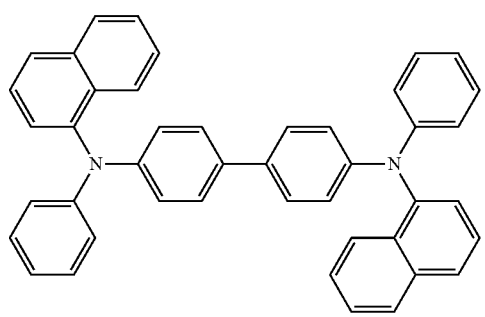

[NPB]

Subsequently, an electron blocking layer was formed on the hole transfer layer to a film thickness of 100 Å by vacuum depositing the following Compound 2.

[Compound 2]

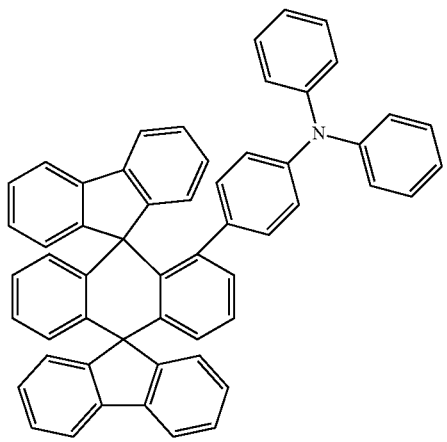

Next, a light emitting layer was formed on the electron blocking layer to a film thickness of 300 Å by vacuum depositing BH and BD shown below in a weight ratio of 25:1.

[BH]

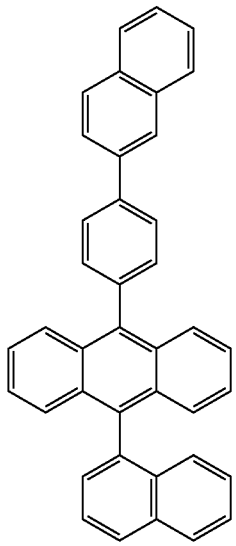

-continued

[BD]

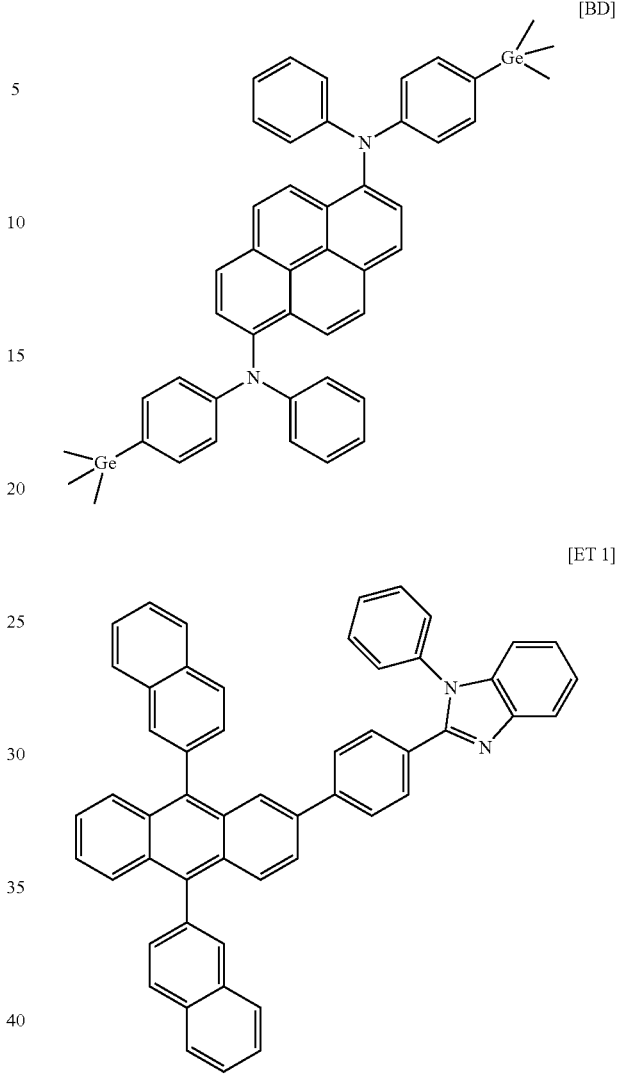

[ET 1]

[LiQ]

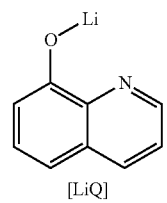

An electron injection and transfer layer was formed on the light emitting layer to a thickness of 300 Å by vacuum depositing the compound ET1 and the compound lithium quinolate (LiQ) in a weight ratio of 1:1. A cathode was formed on the electron injection and transfer layer by depositing lithium fluoride (LiF) to a thickness of 12 Å and aluminum to a thickness of 2,000 Å in consecutive order.

An organic light emitting device was manufactured by maintaining, in the above-mentioned processes, the deposition rates of the organic materials at 0.4 Å/sec to 0.7 Å/sec, the deposition rates of the lithium fluoride and the aluminum of the cathode at 0.3 Å/sec and 2 Å/sec, respectively, and the degree of vacuum during the deposition at $2 \times 10^{-7}$ torr to $5 \times 10^{-6}$ torr.

Example 1-2

An organic light emitting device was manufactured in the same manner as in Example 1-1 except that Compound 3 was used instead of Compound 2.

Example 1-3

An organic light emitting device was manufactured in the same manner as in Example 1-1 except that Compound 13 was used instead of Compound 2.

Example 1-4

An organic light emitting device was manufactured in the same manner as in Example 1-1 except that Compound 15 was used instead of Compound 2.

Example 1-5

An organic light emitting device was manufactured in the same manner as in Example 1-1 except that Compound 16 was used instead of Compound 2.

Example 1-6

An organic light emitting device was manufactured in the same manner as in Example 1-1 except that Compound 17 was used instead of Compound 2.

Example 1-7

An organic light emitting device was manufactured in the same manner as in Example 1-1 except that Compound 18 was used instead of Compound 2.

Example 1-8

An organic light emitting device was manufactured in the same manner as in Example 1-1 except that Compound 19 was used instead of Compound 2.

Example 1-9

An organic light emitting device was manufactured in the same manner as in Example 1-1 except that Compound 20 was used instead of Compound 2.

Example 1-10

An organic light emitting device was manufactured in the same manner as in Example 1-1 except that Compound 21 was used instead of Compound 2.

Example 1-11

An organic light emitting device was manufactured in the same manner as in Example 1-1 except that Compound 22 was used instead of Compound 2.

Example 1-12

An organic light emitting device was manufactured in the same manner as in Example 1-1 except that Compound 23 was used instead of Compound 2.

Example 1-13

An organic light emitting device was manufactured in the same manner as in Example 1-1 except that Compound 26 was used instead of Compound 2.

Example 1-14

An organic light emitting device was manufactured in the same manner as in Example 1-1 except that Compound 27 was used instead of Compound 2.

Example 1-15

An organic light emitting device was manufactured in the same manner as in Example 1-1 except that Compound 28 was used instead of Compound 2.

Example 1-16

An organic light emitting device was manufactured in the same manner as in Example 1-1 except that Compound 29 was used instead of Compound 2.

Example 1-17

An organic light emitting device was manufactured in the same manner as in Example 1-1 except that Compound 39 was used instead of Compound 2.

Example 1-18

An organic light emitting device was manufactured in the same manner as in Example 1-1 except that Compound 40 was used instead of Compound 2.

Comparative Example 1-1

An organic light emitting device was manufactured in the same manner as in Example 1-1 except that the following EB 1 (TCTA) was used instead of Compound 2.

[EB 1]

Comparative Example 1-2

An organic light emitting device was manufactured in the same manner as in Example 1-1 except that the following EB 2 was used instead of Compound 2.

[EB 2]

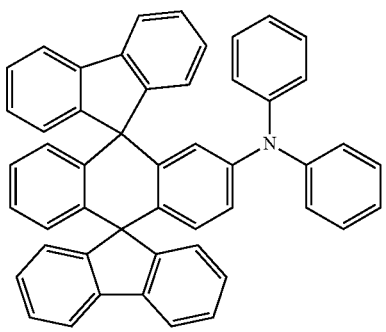

Comparative Example 1-3

An organic light emitting device was manufactured in the same manner as in Example 1-1 except that the following EB 3 was used instead of Compound 2.

[EB 3]

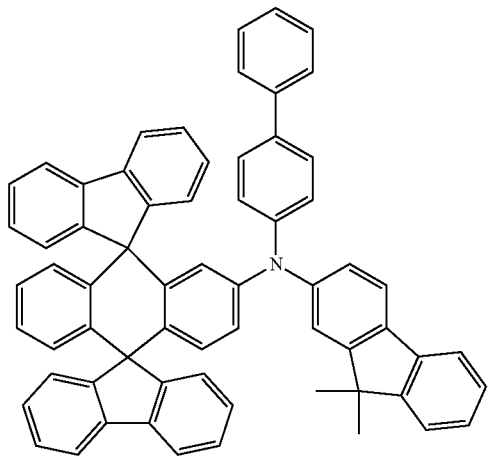

Comparative Example 1-4

An organic light emitting device was manufactured in the same manner as in Example 1-1 except that the following EB 4 was used instead of Compound 2.

[EB 4]

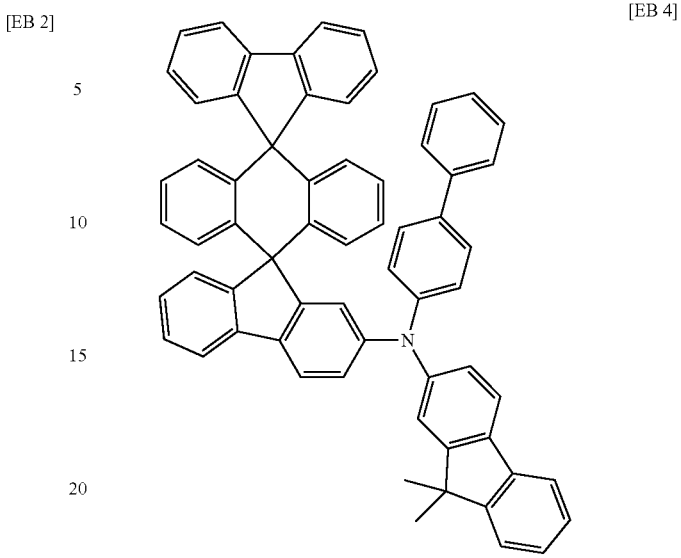

When a current was applied to the organic light emitting devices manufactured in Examples 1-1 to 1-18 and Comparative Examples 1-1 to 1-4, results of Table 1 were obtained.

TABLE 1

| | Compound (Electron Blocking Layer) | Voltage (V@10 mA/cm$^2$) | Efficiency (cd/A@10 mA/cm$^2$) | Color Coordinate (x, y) |
|---|---|---|---|---|
| Example 1-1 | Compound 2 | 3.95 | 5.35 | (0.139, 0.122) |
| Example 1-2 | Compound 3 | 3.82 | 5.38 | (0.138, 0.126) |
| Example 1-3 | Compound 13 | 3.67 | 5.51 | (0.138, 0.127) |
| Example 1-4 | Compound 15 | 3.68 | 5.62 | (0.137, 0.125) |
| Example 1-5 | Compound 16 | 3.69 | 5.73 | (0.136, 0.125) |
| Example 1-6 | Compound 17 | 3.64 | 5.67 | (0.136, 0.127) |
| Example 1-7 | Compound 18 | 3.63 | 5.78 | (0.136, 0.125) |
| Example 1-8 | Compound 19 | 3.64 | 5.61 | (0.137, 0.125) |
| Example 1-9 | Compound 20 | 3.73 | 5.58 | (0.138, 0.125) |
| Example 1-10 | Compound 21 | 3.78 | 5.42 | (0.136, 0.125) |
| Example 1-11 | Compound 22 | 3.73 | 5.57 | (0.137, 0.125) |
| Example 1-12 | Compound 23 | 3.75 | 5.45 | (0.136, 0.125) |
| Example 1-13 | Compound 26 | 3.82 | 5.58 | (0.138, 0.126) |
| Example 1-14 | Compound 27 | 3.87 | 5.51 | (0.137, 0.125) |
| Example 1-15 | Compound 28 | 3.80 | 5.42 | (0.136, 0.127) |
| Example 1-16 | Compound 29 | 3.81 | 5.53 | (0.135, 0.127) |
| Example 1-17 | Compound 39 | 3.64 | 5.67 | (0.138, 0.127) |
| Example 1-18 | Compound 40 | 3.73 | 5.58 | (0.137, 0.125) |
| Comparative Example 1-1 | EB 1 | 4.36 | 4.93 | (0.138, 0.127) |
| Comparative Example 1-2 | EB 2 | 4.31 | 4.95 | (0.139, 0.125) |
| Comparative Example 1-3 | EB 3 | 4.49 | 4.89 | (0.139, 0.126) |
| Comparative Example 1-4 | EB 4 | 4.56 | 5.05 | (0.139, 0.127) |

As shown in Table 1, it was seen that the organic light emitting devices using the compounds of Examples 1-1 to 1-18 exhibited low voltage and high efficiency properties compared to Comparative Examples 1-1 to 1-4 in which substituents bonded to sites different from Chemical Formula 1 according to the present specification.

It was identified that the compound represented by Chemical Formula 1 according to the present specification had an excellent electron inhibiting ability and thereby exhibited low voltage and high efficiency properties, and may be used in organic light emitting devices.

Examples 2-1 to 2-18

An experiment was carried out in the same manner as in Example 1-1 except that EB 1 was used instead of Compound 2 as the electron blocking layer, and the compounds of Examples 1-1 to 1-18 were used instead of NPB as the hole transfer layer.

Comparative Example 2-1

An experiment was carried out in the same manner as in Example 1-1 except that EB 1 was used instead of Compound 2 as the electron blocking layer, and HT 1 was used instead of NPB as the hole transfer layer.

[HT 1]

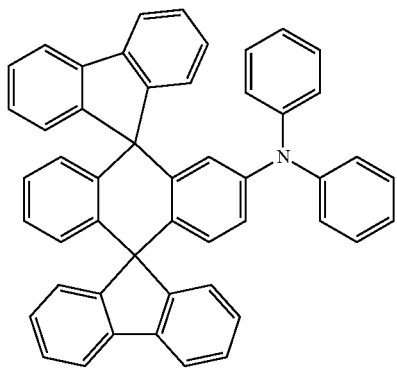

Comparative Example 2-2

An experiment was carried out in the same manner as in Example 1-1 except that EB 1 was used instead of Compound 2 as the electron blocking layer, and HT 2 was used instead of NPB as the hole transfer layer.

[HT 2]

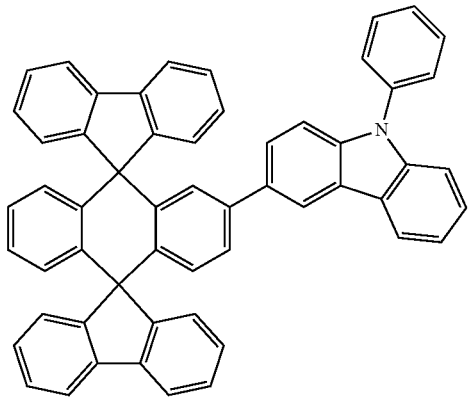

Comparative Example 2-3

An experiment was carried out in the same manner as in Example 1-1 except that EB 1 was used instead of Compound 2 as the electron blocking layer, and HT 3 was used instead of NPB as the hole transfer layer.

[HT 3]

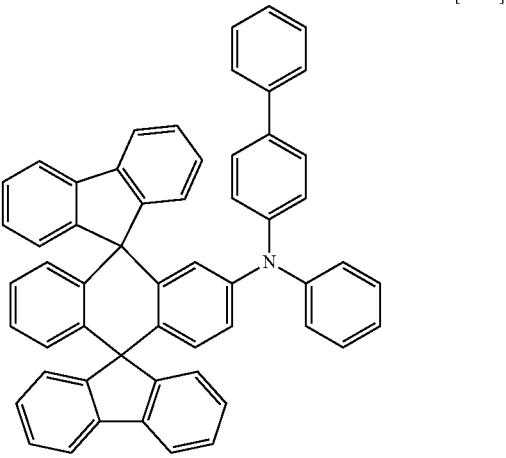

Comparative Example 2-4

An experiment was carried out in the same manner as in Example 1-1 except that EB 1 was used instead of Compound 2 as the electron blocking layer, and HT 4 was used instead of NPB as the hole transfer layer.

[HT 4]

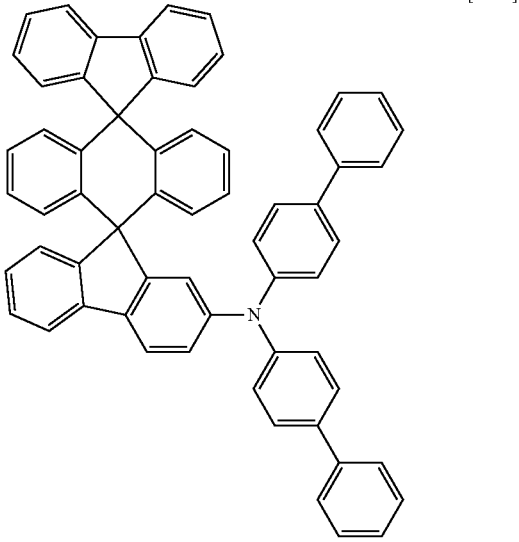

When a current was applied to the organic light emitting devices manufactured in Examples 2-1 to 2-18 and Comparative Examples 2-1 to 2-4, results of Table 2 were obtained.

TABLE 2

| | Compound (Hole Transfer Layer) | Voltage (V@10 mA/cm$^2$) | Efficiency (cd/A@10 mA/cm$^2$) | Color Coordinate (x, y) |
|---|---|---|---|---|
| Example 2-1 | Compound 2 | 4.15 | 5.75 | (0.139, 0.122) |
| Example 2-2 | Compound 3 | 4.02 | 5.88 | (0.138, 0.126) |
| Example 2-3 | Compound 13 | 3.87 | 6.25 | (0.138, 0.127) |
| Example 2-4 | Compound 15 | 3.88 | 6.24 | (0.137, 0.125) |
| Example 2-5 | Compound 16 | 3.89 | 6.22 | (0.136, 0.125) |
| Example 2-6 | Compound 17 | 3.84 | 6.13 | (0.136, 0.127) |
| Example 2-7 | Compound 18 | 3.83 | 6.20 | (0.136, 0.125) |
| Example 2-8 | Compound 19 | 3.84 | 6.10 | (0.137, 0.125) |
| Example 2-9 | Compound 20 | 3.93 | 6.01 | (0.138, 0.125) |
| Example 2-10 | Compound 21 | 3.98 | 5.92 | (0.136, 0.125) |
| Example 2-11 | Compound 22 | 3.93 | 6.05 | (0.137, 0.125) |
| Example 2-12 | Compound 23 | 3.95 | 5.95 | (0.136, 0.125) |
| Example 2-13 | Compound 26 | 4.02 | 6.08 | (0.138, 0.126) |
| Example 2-14 | Compound 27 | 3.97 | 6.01 | (0.137, 0.125) |
| Example 2-15 | Compound 28 | 4.00 | 5.92 | (0.136, 0.127) |
| Example 2-16 | Compound 29 | 4.01 | 6.02 | (0.135, 0.127) |
| Example 2-17 | Compound 39 | 3.84 | 6.15 | (0.138, 0.125) |
| Example 2-18 | Compound 40 | 3.93 | 6.03 | (0.137, 0.125) |
| Comparative Example 2-1 | HT 1 | 4.75 | 5.23 | (0.138, 0.127) |
| Comparative Example 2-2 | HT 2 | 4.83 | 5.35 | (0.139, 0.125) |
| Comparative Example 2-3 | HT 3 | 4.64 | 5.54 | (0.139, 0.126) |
| Comparative Example 2-4 | HT 4 | 4.73 | 5.50 | (0.139, 0.127) |

As shown in Table 2, it was seen that the organic light emitting devices using the compounds of Examples 2-1 to 2-18 exhibited low voltage and high efficiency properties compared to Comparative Examples 2-1 to 2-4 in which substituents bonded to sites different from Chemical Formula 1 according to the present specification.

It was identified that the compound represented by Chemical Formula 1 according to the present specification also had an excellent hole transport ability, and therefore, exhibited low voltage and high efficiency properties, and may be used in organic light emitting devices.

Example 3-1

The compounds synthesized in Preparation Examples 1 to 40 were high-purity sublimation purified using commonly known methods, and then a green organic light emitting device was manufactured using a method as below.

A glass substrate on which indium tin oxide (ITO) was coated as a thin film to a thickness of 1,000 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 5 minutes using oxygen plasma, and then transferred to a vacuum depositor.

An organic EL device was manufactured by forming a light emitting device in the order of m-MTDATA (60 nm)/TCTA (80 nm)/Compound 4+10% Ir(ppy) 3 (300 nm)/BCP (10 nm)/Alq$_3$ (30 nm)/LiF (1 nm)/Al (200 nm) on the transparent ITO electrode prepared as above using Compound 4 as a host.

Structures of the m-MTDATA, the TCTA, the Ir(ppy)$_3$ and the BCP are as follows.

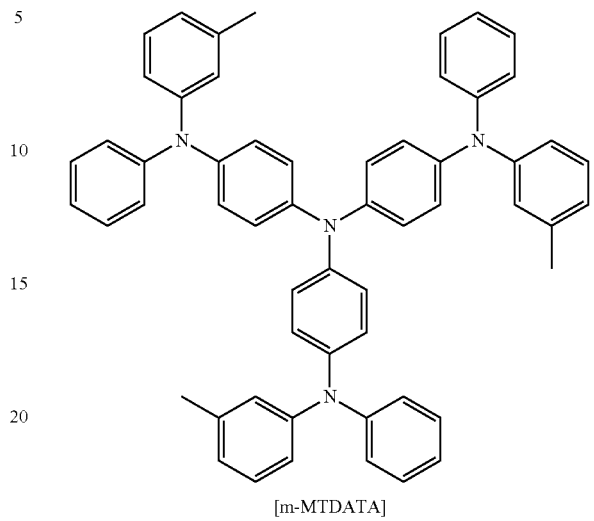

[m-MTDATA]

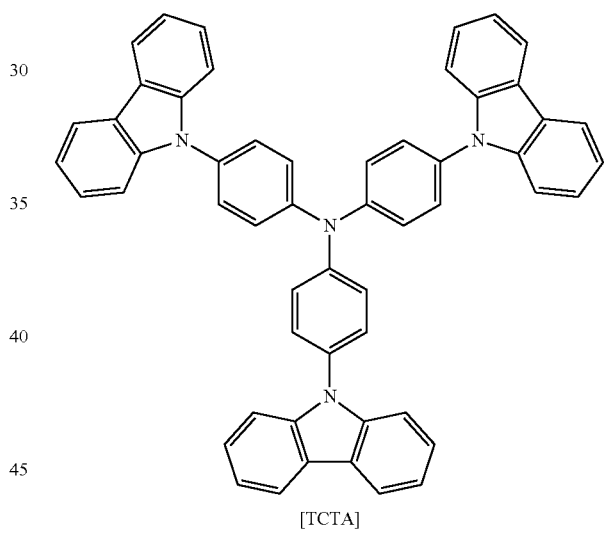

[TCTA]

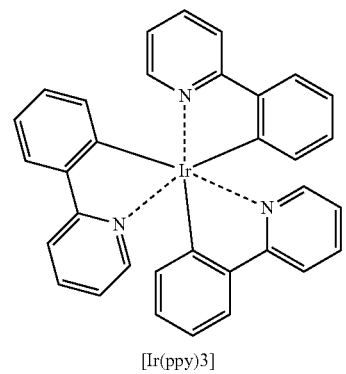

[Ir(ppy)3]

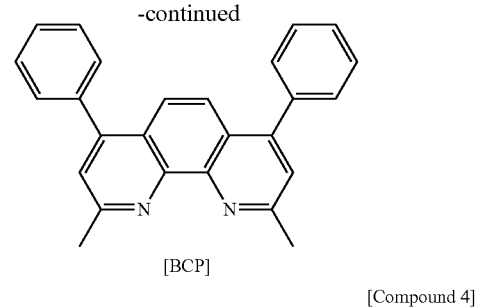

[BCP]

[Compound 4]

Example 3-2

An organic light emitting device was manufactured in the same manner as in Example 3-1 except that Compound 5 was used instead of Compound 4.

Example 3-3

An organic light emitting device was manufactured in the same manner as in Example 3-1 except that Compound 6 was used instead of Compound 4.

Example 3-4

An organic light emitting device was manufactured in the same manner as in Example 3-1 except that Compound 7 was used instead of Compound 4.

Example 3-5

An organic light emitting device was manufactured in the same manner as in Example 3-1 except that Compound 8 was used instead of Compound 4.

Example 3-6

An organic light emitting device was manufactured in the same manner as in Example 3-1 except that Compound 9 was used instead of Compound 4.

Example 3-7

An organic light emitting device was manufactured in the same manner as in Example 3-1 except that Compound 31 was used instead of Compound 4.

Example 3-8

An organic light emitting device was manufactured in the same manner as in Example 3-1 except that Compound 32 was used instead of Compound 4.

Example 3-9

An organic light emitting device was manufactured in the same manner as in Example 3-1 except that Compound 33 was used instead of Compound 4.

Example 3-10

An organic light emitting device was manufactured in the same manner as in Example 3-1 except that Compound 34 was used instead of Compound 4.

Example 3-11

An organic light emitting device was manufactured in the same manner as in Example 3-1 except that Compound 35 was used instead of Compound 4.

Example 3-12

An organic light emitting device was manufactured in the same manner as in Example 3-1 except that Compound 36 was used instead of Compound 4.

Comparative Example 3-1

An organic light emitting device was manufactured in the same manner as in Example 3-1 except that GH 1 was used instead of Compound 4.

[GH 1]

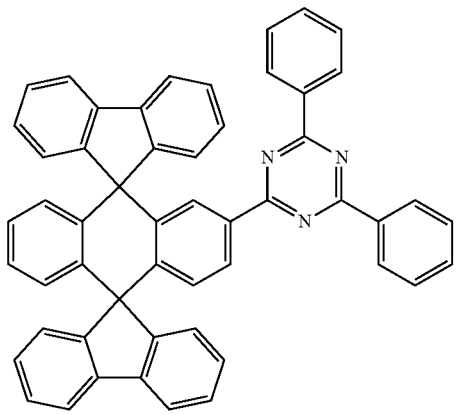

Comparative Example 3-2

An organic light emitting device was manufactured in the same manner as in Example 3-1 except that GH 2 was used instead of Compound 4.

[GH 2]

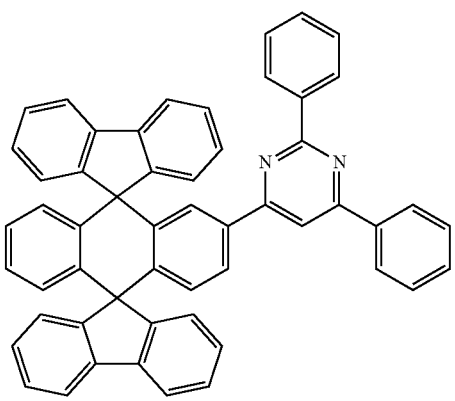

[GH 4]

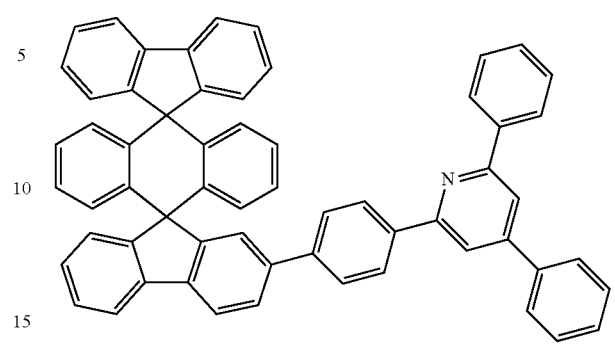

When a current was applied to the organic light emitting devices manufactured in Examples 3-1 to 3-12 and Comparative Examples 3-1 to 3-4, results of Table 3 were obtained.

TABLE 3

|  | Compound (Host) | Voltage (V@10 mA/cm$^2$) | Efficiency (cd/A@10 mA/cm$^2$) | Light Emission Peak (nm) |
| --- | --- | --- | --- | --- |
| Example 3-1 | Compound 4 | 6.18 | 43.93 | 517 |
| Example 3-2 | Compound 5 | 6.26 | 45.24 | 516 |
| Example 3-3 | Compound 6 | 6.15 | 44.79 | 518 |
| Example 3-4 | Compound 7 | 6.29 | 46.15 | 517 |
| Example 3-5 | Compound 8 | 6.28 | 44.31 | 515 |
| Example 3-6 | Compound 9 | 6.13 | 45.63 | 516 |
| Example 3-7 | Compound 31 | 6.29 | 45.62 | 516 |
| Example 3-8 | Compound 32 | 6.27 | 46.64 | 517 |
| Example 3-9 | Compound 33 | 6.24 | 46.68 | 518 |
| Example 3-10 | Compound 34 | 6.18 | 43.83 | 517 |
| Example 3-11 | Compound 35 | 6.26 | 45.24 | 516 |
| Example 3-12 | Compound 36 | 6.15 | 44.52 | 518 |
| Comparative Example 3-1 | GH 1 | 7.21 | 38.72 | 517 |
| Comparative Example 3-2 | GH 2 | 7.12 | 38.64 | 517 |
| Comparative Example 3-3 | GH 3 | 7.03 | 39.42 | 517 |
| Comparative Example 3-4 | GH 4 | 7.11 | 39.05 | 517 |

Comparative Example 3-3

An organic light emitting device was manufactured in the same manner as in Example 3-1 except that GH 3 was used instead of Compound 4.

[GH 3]

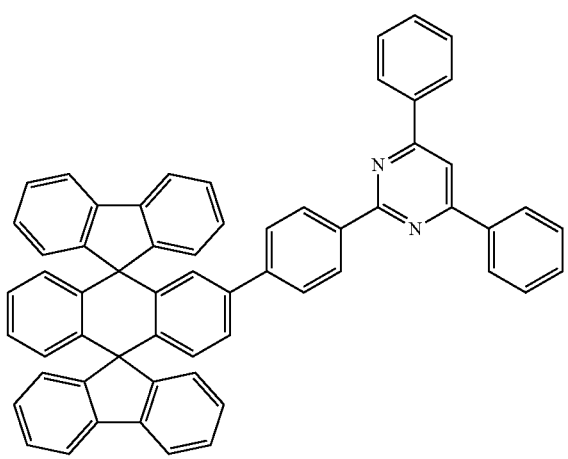

Comparative Example 3-4

An organic light emitting device was manufactured in the same manner as in Example 3-1 except that GH 4 was used instead of Compound 4.

As shown in Table 3, it was identified that the green organic light emitting devices of Examples 3-1 to 3-12 using the compound represented by Chemical Formula 1 according to the present specification as a host material of a green light emitting layer exhibited superior performance in current efficiency and a driving voltage compared to the green organic light emitting devices of Comparative Examples 3-1 to 3-4 in which substituents bonded to sites different from Chemical Formula 1 according to the present specification.

Example 4-1

The compounds synthesized in Preparation Examples 1 to 40 were high-purity sublimation purified using commonly known methods, and then a red organic light emitting device was manufactured using a method as below.

An ITO glass was patterned so that a light emitting area became a 2 mm×2 mm size, and then washed. After installing the substrate in a vacuum chamber, the base pressure was set at 1×10$^{-6}$ torr, and as organic materials on the ITO, DNTPD (700 Å), a-NPB (300 Å), Compound 4 as a host (90 wt %), and the following (piq)$_2$Ir(acac) (10 wt %) as a dopant (300 Å) were vacuum deposited, then Alga (350 Å), LiF (5 Å) and Al (1,000 Å) were layered in this order, and measurements were carried out at 0.4 mA.

The structures of the DNTPD, the α-NPB, the (piq)$_2$Ir(acac) and the Alga are as follows.

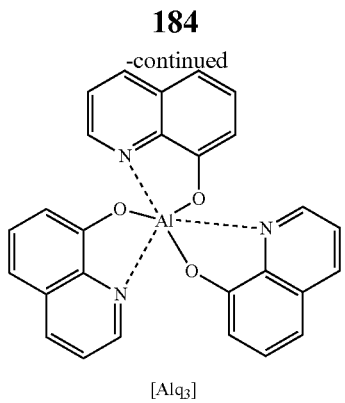

[Alq$_3$]

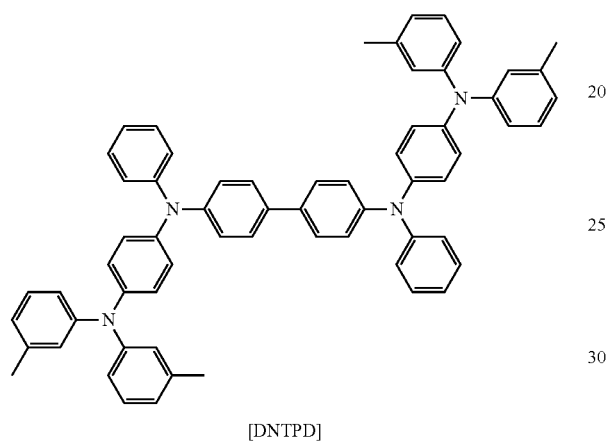

[DNTPD]

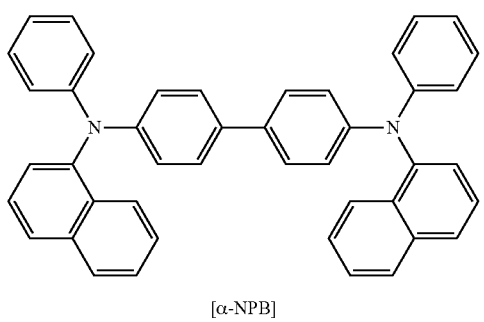

[α-NPB]

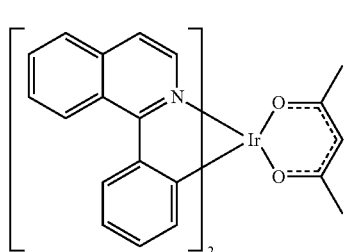

[(piq)$_2$Ir(acac)]

Example 4-2

An organic light emitting device was manufactured in the same manner as in Example 4-1 except that Compound 8 was used instead of Compound 4.

Example 4-3

An organic light emitting device was manufactured in the same manner as in Example 4-1 except that Compound 9 was used instead of Compound 4.

Example 4-4

An organic light emitting device was manufactured in the same manner as in Example 4-1 except that Compound 14 was used instead of Compound 4.

Example 4-5

An organic light emitting device was manufactured in the same manner as in Example 4-1 except that Compound 31 was used instead of Compound 4.

Example 4-6

An organic light emitting device was manufactured in the same manner as in Example 4-1 except that Compound 35 was used instead of Compound 4.

Example 4-7

An organic light emitting device was manufactured in the same manner as in Example 4-1 except that Compound 36 was used instead of Compound 4.

Comparative Example 4-1

An organic light emitting device was manufactured in the same manner as in Example 4-1 except that the following Compound RH 1 (CBP) was used instead of Compound 4.

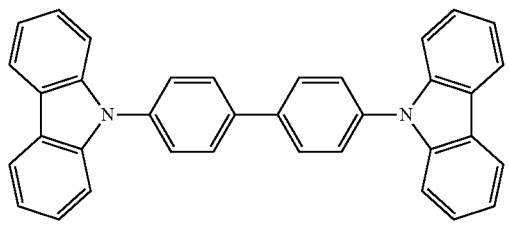

[RH 1 (CBP)]

Comparative Example 4-2

An organic light emitting device was manufactured in the same manner as in Example 4-1 except that the following Compound RH 2 was used instead of Compound 4.

[RH 2]

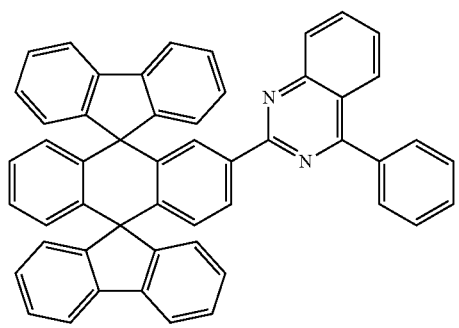

Comparative Example 4-3

An organic light emitting device was manufactured in the same manner as in Example 4-1 except that the following Compound RH 3 was used instead of Compound 4.

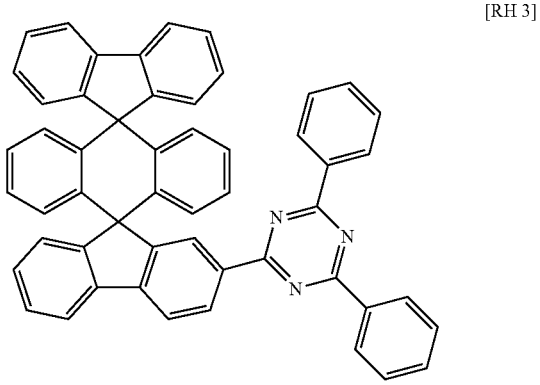 [SMILES: c1ccc(-c2nc(-c3ccccc3)nc(-c3ccc4c(c3)C3(c5ccccc5-4)c4ccccc4C4(c5ccccc5-c5ccccc54)c4ccccc43)n2)cc1]

[RH 3]

For the organic light emitting devices manufactured according to Examples 4-1 to 4-7 and Comparative Examples 4-1 to 4-3, a voltage, current density, luminance, a color coordinate and a lifespan were measured, and the results are shown in the following Table 4. T95 means time taken for the luminance decreasing to 95% of its initial luminance (5000 nit).

TABLE 4

| Category | Host | Dopant | Voltage (V) | Luminance (cd/m$^2$) | Color Coordinate (x, y) | T95 (hr) |
|---|---|---|---|---|---|---|
| Example4-1 | Compound 4 | (piq)$_2$Ir(acac) | 4.3 | 1860 | (0.670, 0.329) | 465 |
| Example4-2 | Compound 8 | (piq)$_2$Ir(acac) | 4.2 | 1850 | (0.674, 0.325) | 415 |
| Example4-3 | Compound 9 | (piq)$_2$Ir(acac) | 4.1 | 1900 | (0.672, 0.327) | 440 |
| Example4-4 | Compound 14 | (piq)$_2$Ir(acac) | 4.3 | 1840 | (0.673, 0.335) | 435 |
| Example4-5 | Compound 31 | (piq)$_2$Ir(acac) | 4.0 | 1790 | (0.675, 0.333) | 405 |
| Example4-6 | Compound 35 | (piq)$_2$Ir(acac) | 4.2 | 1810 | (0.670, 0.339) | 420 |
| Example4-7 | Compound 36 | (piq)$_2$Ir(acac) | 4.3 | 1970 | (0.671, 0.338) | 445 |
| Comparative Example 4-1 | RH 1 | (piq)$_2$Ir(acac) | 6.5 | 1050 | (0.673, 0.327) | 265 |
| Comparative Example 4-2 | RH 2 | (piq)$_2$Ir(acac) | 6.3 | 1100 | (0.672, 0.326) | 255 |
| Comparative Example 4-3 | RH 3 | (piq)$_2$Ir(acac) | 6.1 | 1200 | (0.671, 0.325) | 245 |

As shown in Table 4, it was identified that the red organic light emitting devices of Examples 4-1 to 4-7 using the compound represented by Chemical Formula 1 according to the present specification as a host material of a light emitting layer exhibited superior performance in current efficiency, a driving voltage and a lifespan compared to the red organic light emitting device of Comparative Example 4-1 using existing RH 1 (CBP) and the red organic light emitting devices of Comparative Examples 4-2 and 4-3 in which substituents bonded to sites different from Chemical Formula 1 according to the present specification.

Example 5-1

A glass substrate on which indium tin oxide (ITO) was coated as a thin film to a thickness of 1,000 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 5 minutes using oxygen plasma, and then transferred to a vacuum depositor.

On the transparent ITO electrode prepared as above, a hole injection layer was formed by thermal vacuum depositing hexanitrile hexaazatriphenylene (HAT) of the following chemical formula to a thickness of 500 Å.

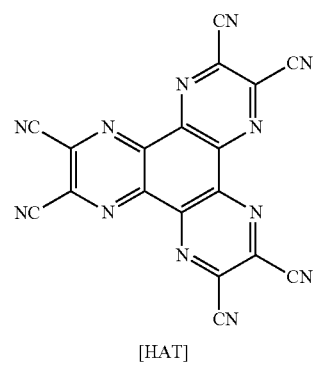

[HAT]

A hole transfer layer was formed on the hole injection layer by vacuum depositing the following compound 4-4'-bis[N-(1-naphthyl)-N-phenylamino]biphenyl (NPB) (400 Å), a material transferring holes.

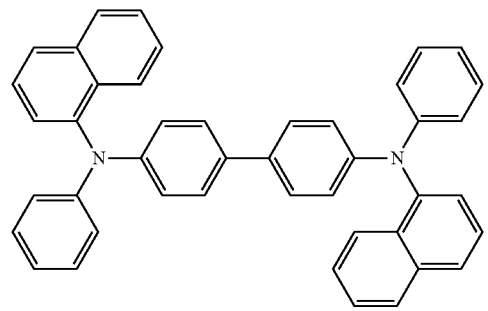

[NPB]

Subsequently, a light emitting layer was formed on the hole transfer layer to a film thickness of 300 Å by vacuum depositing BH and BD shown below in a weight ratio of 25:1.

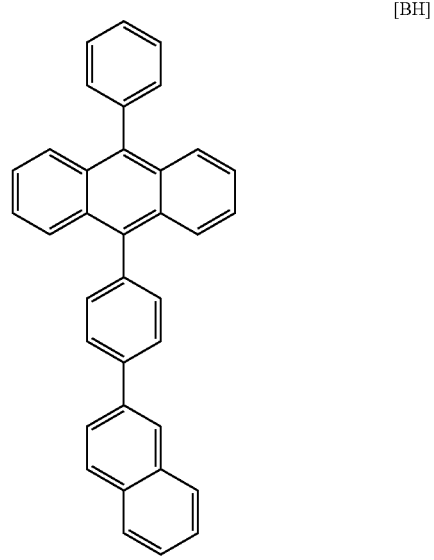

[BH]

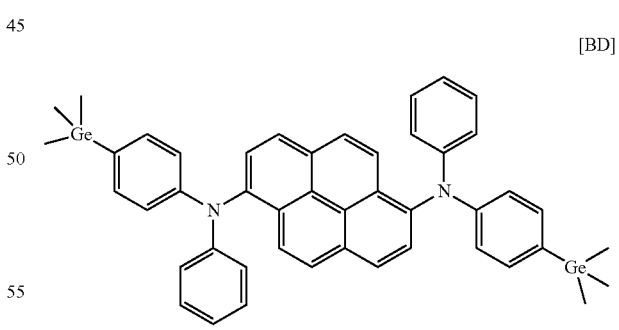

[BD]

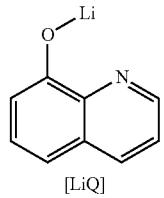

[LiQ]

[Compound 4]

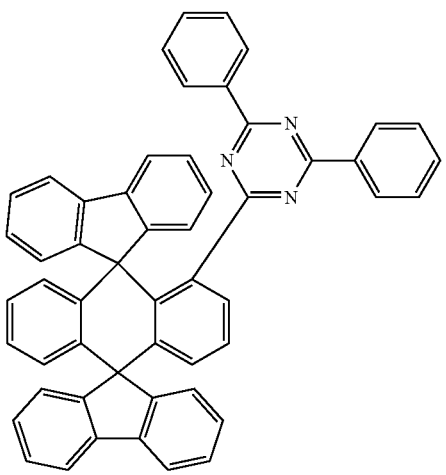

An electron injection and transfer layer was formed on the light emitting layer to a thickness of 300 Å by vacuum depositing Compound 4 prepared in Preparation Example 4 and the compound lithium quinolate (LiQ) in a weight ratio of 1:1. A cathode was formed on the electron injection and transfer layer by depositing lithium fluoride (LiF) to a thickness of 12 Å and aluminum to a thickness of 2,000 Å in consecutive order.

An organic light emitting device was manufactured by maintaining, in the above-mentioned processes, the deposition rates of the organic materials at 0.4 Å/sec to 0.7 Å/sec, the deposition rates of the lithium fluoride and the aluminum of the cathode at 0.3 Å/sec and 2 Å/sec, respectively, and the degree of vacuum during the deposition at $2 \times 10^{-7}$ torr to $5 \times 10^{-6}$ torr.

Example 5-2

An experiment was carried out in the same manner as in Example 5-1 except that Compound 5 was used instead of Compound 4 as the electron transfer layer.

Example 5-3

An experiment was carried out in the same manner as in Example 5-1 except that Compound 6 was used instead of Compound 4 as the electron transfer layer.

Example 5-4

An experiment was carried out in the same manner as in Example 5-1 except that Compound 7 was used instead of Compound 4 as the electron transfer layer.

Example 5-5

An experiment was carried out in the same manner as in Example 5-1 except that Compound 8 was used instead of Compound 4 as the electron transfer layer.

Example 5-6

An experiment was carried out in the same manner as in Example 5-1 except that Compound 9 was used instead of Compound 4 as the electron transfer layer.

Example 5-7

An experiment was carried out in the same manner as in Example 5-1 except that Compound 12 was used instead of Compound 4 as the electron transfer layer.

Example 5-8

An experiment was carried out in the same manner as in Example 5-1 except that Compound 14 was used instead of Compound 4 as the electron transfer layer.

Example 5-9

An experiment was carried out in the same manner as in Example 5-1 except that Compound 24 was used instead of Compound 4 as the electron transfer layer.

Example 5-10

An experiment was carried out in the same manner as in Example 5-1 except that Compound 25 was used instead of Compound 4 as the electron transfer layer.

Example 5-11

An experiment was carried out in the same manner as in Example 5-1 except that Compound 30 was used instead of Compound 4 as the electron transfer layer.

Example 5-12

An experiment was carried out in the same manner as in Example 5-1 except that Compound 31 was used instead of Compound 4 as the electron transfer layer.

Example 5-13

An experiment was carried out in the same manner as in Example 5-1 except that Compound 32 was used instead of Compound 4 as the electron transfer layer.

Example 5-14

An experiment was carried out in the same manner as in Example 5-1 except that Compound 33 was used instead of Compound 4 as the electron transfer layer.

Example 5-15

An experiment was carried out in the same manner as in Example 5-1 except that Compound 34 was used instead of Compound 4 as the electron transfer layer.

Example 5-16

An experiment was carried out in the same manner as in Example 5-1 except that Compound 35 was used instead of Compound 4 as the electron transfer layer.

Example 5-17

An experiment was carried out in the same manner as in Example 5-1 except that Compound 36 was used instead of Compound 4 as the electron transfer layer.

Comparative Example 5-1

An experiment was carried out in the same manner as in Example 5-1 except that the following Compound ET 1 was used instead of Compound 4 as the electron transfer layer.

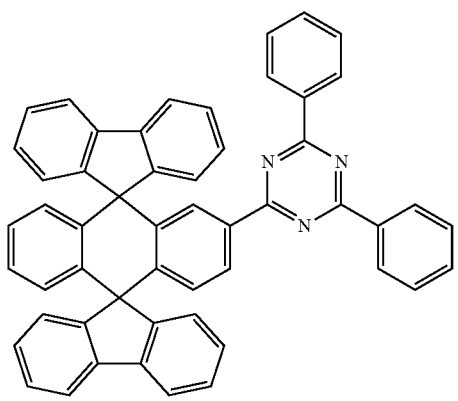

[ET 1]

Comparative Example 5-2

An experiment was carried out in the same manner as in Example 5-1 except that the following Compound ET 2 was used instead of Compound 4 as the electron transfer layer.

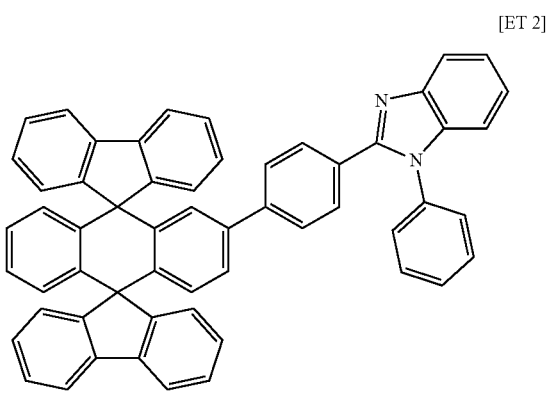 [SMILES: c1ccc(-n2c(-c3ccc(-c4ccc5c(c4)C4(c6ccccc6-c6ccccc64)c4ccccc4C54c5ccccc5-c5ccccc54)cc3)nc3ccccc32)cc1]

[ET 2]

When a current was applied to the organic light emitting devices manufactured in Examples 5-1 to 5-17, and Comparative Examples 5-1 and 5-2, results of Table 5 were obtained.

TABLE 5

| Compound (Host) | Voltage (V@10 mA/cm$^2$) | Efficiency (cd/A@10 mA/cm$^2$) | Light Emission Peak (nm) |
| --- | --- | --- | --- |
| Example 5-1 | Compound 4 | 6.38 | 44.93 | 517 |
| Example 5-2 | Compound 5 | 6.46 | 43.24 | 516 |
| Example 5-3 | Compound 6 | 6.55 | 41.79 | 518 |
| Example 5-4 | Compound 7 | 6.29 | 46.15 | 517 |
| Example 5-5 | Compound 8 | 6.28 | 46.31 | 515 |
| Example 5-6 | Compound 9 | 6.23 | 456.63 | 516 |
| Example 5-7 | Compound 12 | 6.29 | 45.62 | 516 |
| Example 5-8 | Compound 14 | 6.17 | 47.64 | 517 |
| Example 5-9 | Compound 24 | 6.34 | 46.68 | 518 |
| Example 5-10 | Compound 25 | 6.48 | 44.83 | 517 |
| Example 5-11 | Compound 30 | 6.46 | 45.24 | 516 |
| Example 5-12 | Compound 31 | 6.44 | 44.94 | 518 |
| Example 5-13 | Compound 32 | 6.35 | 43.22 | 517 |
| Example 5-14 | Compound 33 | 6.43 | 45.75 | 515 |
| Example 5-15 | Compound 34 | 6.35 | 46.16 | 516 |
| Example 5-16 | Compound 35 | 6.24 | 47.34 | 516 |
| Example 5-17 | Compound 36 | 6.25 | 47.62 | 517 |

TABLE 5-continued

| Compound (Host) | Voltage (V@10 mA/cm$^2$) | Efficiency (cd/A@10 mA/cm$^2$) | Light Emission Peak (nm) |
| --- | --- | --- | --- |
| Comparative Example 5-1 | ET 1 | 7.27 | 32.52 | 517 |
| Comparative Example 5-2 | ET 2 | 7.16 | 35.45 | 517 |

As shown in Table 5, when comparing the organic light emitting devices of Examples 5-1 to 5-17 manufactured using the compound represented by Chemical Formula 1 according to the present specification as an electron injection and electron transfer material with the organic light emitting devices manufactured in Comparative Examples 5-1 and 5-2, it was identified that electron transport and injection abilities of the organic light emitting devices of Examples 5-1 to 5-17 were more superior compared to Comparative Examples 5-1 and 5-2.

It can be that the compounds represented by Chemical Formula 1 having triazine, benzimidazole, arylphosphine, quinoline, benzothiazole, imidazoquinazoline and the like as a substituent of Chemical Formula 1 are suitable as a material of organic light emitting devices.

Hereinbefore, preferred embodiments of the present disclosure (electron blocking layer, hole transfer layer, green light emitting layer, red light emitting layer, electron transfer layer) have been described, however, the present disclosure is not limited thereto, and various modifications may be made within the scope of the claims and the detailed descriptions, and the modifications are also included in the scope of the present disclosure.

REFERENCE NUMERAL 10, 11: Organic Light Emitting Device
20: Substrate
30: First Electrode
40: Light Emitting Layer
50: Second Electrode
60: Hole Injection Layer
70: Hole Transfer Layer
80: Electron Transfer Layer
90: Electron Injection Layer

The invention claimed is:

1. A double Spiro structure compound represented by the following Chemical Formula 1-1:

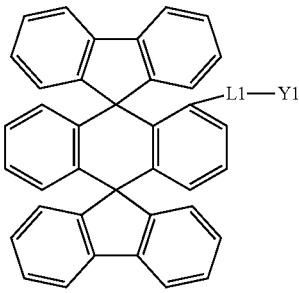

[Chemical Formula 1-1]

wherein, in Chemical Formula 1-1,
L1 is a direct bond; a substituted or unsubstituted arylene group; or a substituted or unsubstituted heteroarylene group; and Y1 is selected from the group consisting of a substituted or unsubstituted amine group; a substituted or unsubstituted silyl group; a substituted or unsubstituted aryl group; and a substituted or unsubstituted heteroaryl group,
wherein the term "the substituted or unsubstituted" means being substituted with one, two or more substituents selected from the group consisting of deuterium; a halogen group; a nitrile group; a nitro group; an imide group; an amide group; a carbonyl group; an ester group; a hydroxyl group; an alkyl group; a cycloalkyl group; an alkoxy group; an aryloxy group; an alkylthioxy group; an arylthioxy group; an alkylsulfoxy group; an arylsulfoxy group; an alkenyl group; a silyl group; a boron group; an amine group; an arylphosphine group; an aryl group; and a heterocyclic group, or being substituted linking two or more substituents among the substituents illustrated above, or having no substituents.

2. The double Spiro structure compound of claim 1, wherein Y1 is independently selected from the group consisting of a substituted or unsubstituted phenyl group; a substituted or unsubstituted biphenyl group; a substituted or unsubstituted phenanthrenyl group; a substituted or unsubstituted naphthyl group; a substituted or unsubstituted terphenyl group; a substituted or unsubstituted fluorenyl group; a substituted or unsubstituted anthracenyl group; a substituted or unsubstituted crycenyl group; a substituted or unsubstituted quaterphenyl group; a substituted or unsubstituted spirobifluorenyl group; a substituted or unsubstituted pyrenyl group; a substituted or unsubstituted triphenylenyl group; a substituted or unsubstituted perylenyl group; a substituted or unsubstituted triazinyl group; a substituted or unsubstituted pyrimidyl group; a substituted or unsubstituted pyridyl group; a substituted or unsubstituted quinolinyl group; a substituted or unsubstituted quinazolinyl group; a substituted or unsubstituted benzoquinolinyl group; a substituted or unsubstituted phenanthrolinyl group; a substituted or unsubstituted quinoxalinyl group; a substituted or unsubstituted dibenzofuranyl group; a substituted or unsubstituted dibenzothiophene group; a substituted or unsubstituted benzonaphthofuranyl group; a substituted or unsubstituted benzonaphthothiophene group; a substituted or unsubstituted benzoxazolyl group; a substituted or unsubstituted benzothiazolyl group; a substituted or unsubstituted benzimidazolyl group; a substituted or unsubstituted triphenylsilyl group; a substituted or unsubstituted phenothiazinyl group; a substituted or unsubstituted phenoxazinyl group; a substituted or unsubstituted thiophene group; a substituted or unsubstituted diphenylamine group; a substituted or unsubstituted N-phenylnaphthylamine group; a substituted or unsubstituted N-phenylbiphenylamine group; a substituted or unsubstituted N-phenylphenanthrenylamine group; a substituted or unsubstituted N-biphenylnaphthylamine group; a substituted or unsubstituted dibiphenylamine group; a substituted or unsubstituted N-biphenylphenanthrenylamine group; a substituted or unsubstituted dinaphthylamine group; a substituted or unsubstituted N-quaterphenylfluorenylamine group; a substituted or unsubstituted N-terphenylfluorenylamine group; a substituted or unsubstituted N-biphenylterphenylamine group; a substituted or unsubstituted N-biphenylfluorenylamine group; a substituted or unsubstituted N-phenylfluorenylamine group; a substituted or unsubstituted N-naphthylfluorenylamine group; a substituted or unsubstituted N-phenanthrenylfluorenylamine group; a substituted or unsubstituted difluorenylamine group; a substituted or unsubstituted N-phenylterphenylamine group; a substituted or unsubstituted N-phenylcarbazolylamine group; a substituted or unsubstituted N-biphenylcarbazolylamine group; a substituted or unsubstituted N-phenylbenzocarbazolylamine group; a substituted or unsubstituted N-biphenylbenzocarbazolylamine group; a substituted or unsubstituted N-fluorenylcarbazolylamine group; a substituted or unsubstituted benzocarbazolyl group; a substituted or unsubstituted dibenzocarbazolyl group; a substituted or unsubstituted carbazolyl group; a substituted or unsubstituted

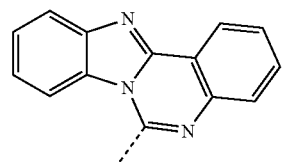
;

a substituted or unsubstituted

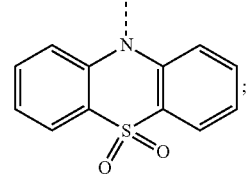
;

and structures represented by the following Chemical Formula a; and
---- is a site bonding to L1 of Chemical Formula 1-1:

[Chemical Formula a]

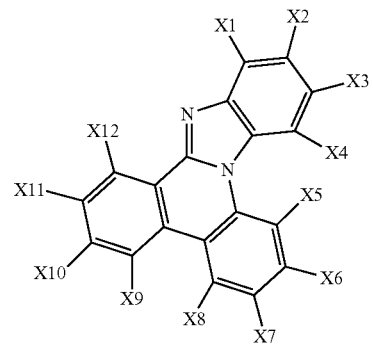

wherein, in Chemical Formula a,
any one of X1 to X12 is a site bonding to Chemical Formula 1-1, and the remaining atoms are the same as or different from each other, and each independently hydrogen; a substituted or unsubstituted alkyl group; a substituted or unsubstituted aryl group; or a substituted or unsubstituted heteroaryl group, or adjacent groups bond to each other to form a substituted or unsubstituted ring,
wherein the term "the substituted or unsubstituted" means being substituted with one, two or more substituents selected from the group consisting of deuterium; a halogen group; a nitrile group; a nitro group; an imide group; an amide group; a carbonyl group; an ester group; a hydroxyl group; an alkyl group; a cycloalkyl group; an alkoxy group; an aryloxy group; an alkylthioxy group; an arylthioxy group; an alkylsulfoxy group; an arylsulfoxy group; an alkenyl group; a silyl group; a boron group; an amine group; an arylphosphine group; an aryl group; and a heterocyclic group, or being substituted linking two or more substituents among the substituents illustrated above, or having no substituents.

3. The double spiro structure compound of claim 1, wherein Y1 is represented by any one of the following Structural Formulae [A-1] to [A-5]:

[A-1]

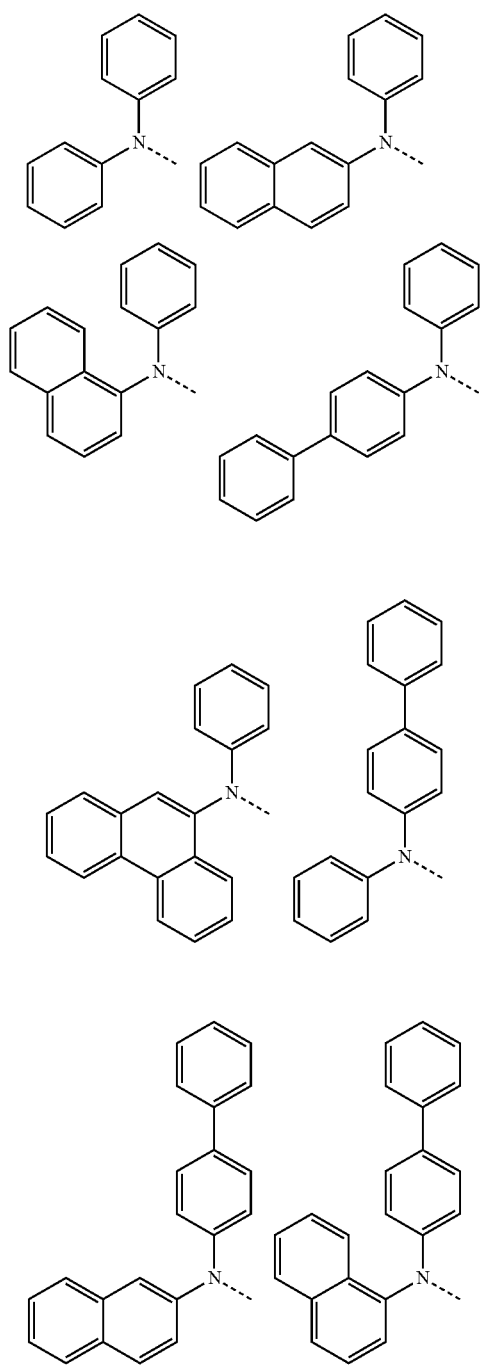

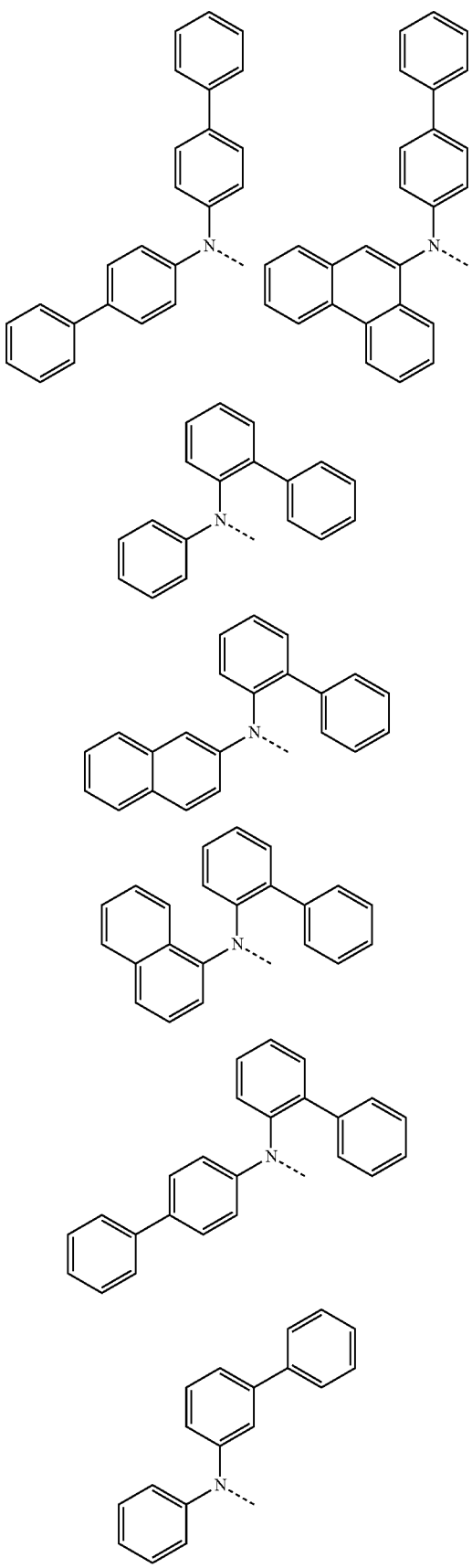

197
-continued
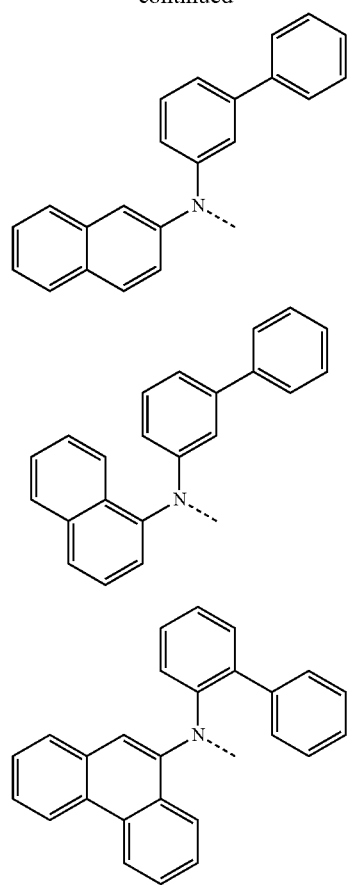
198
-continued
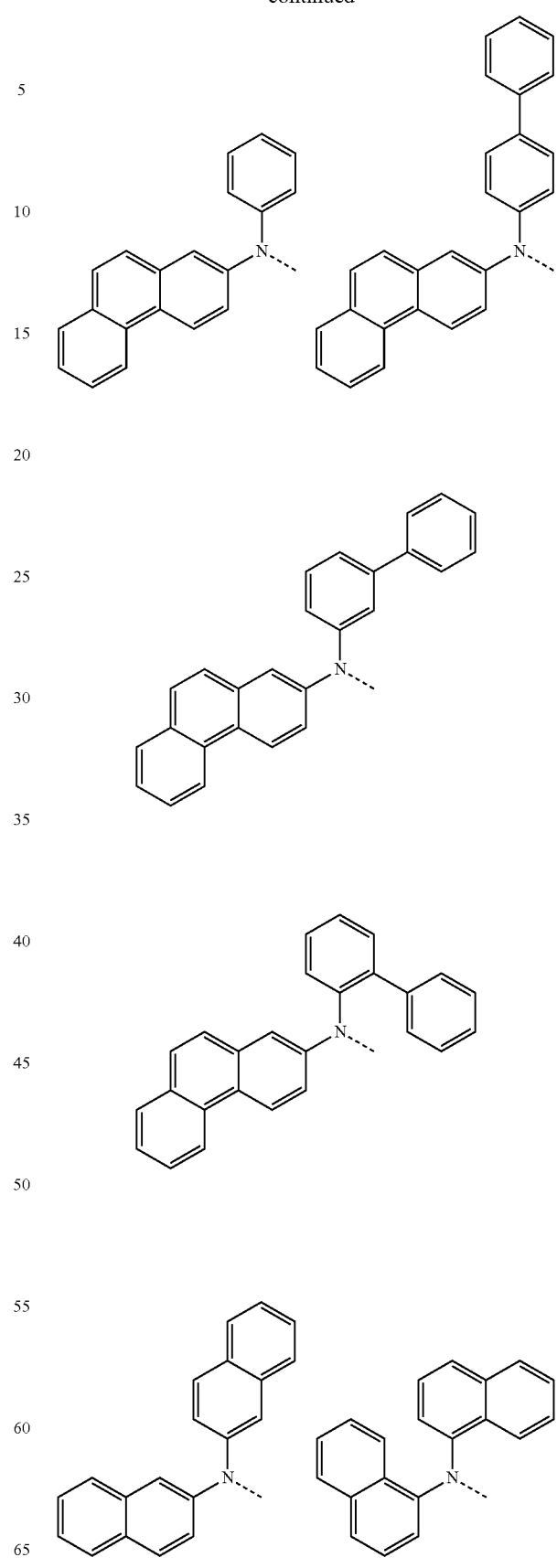

199
-continued
200
-continued
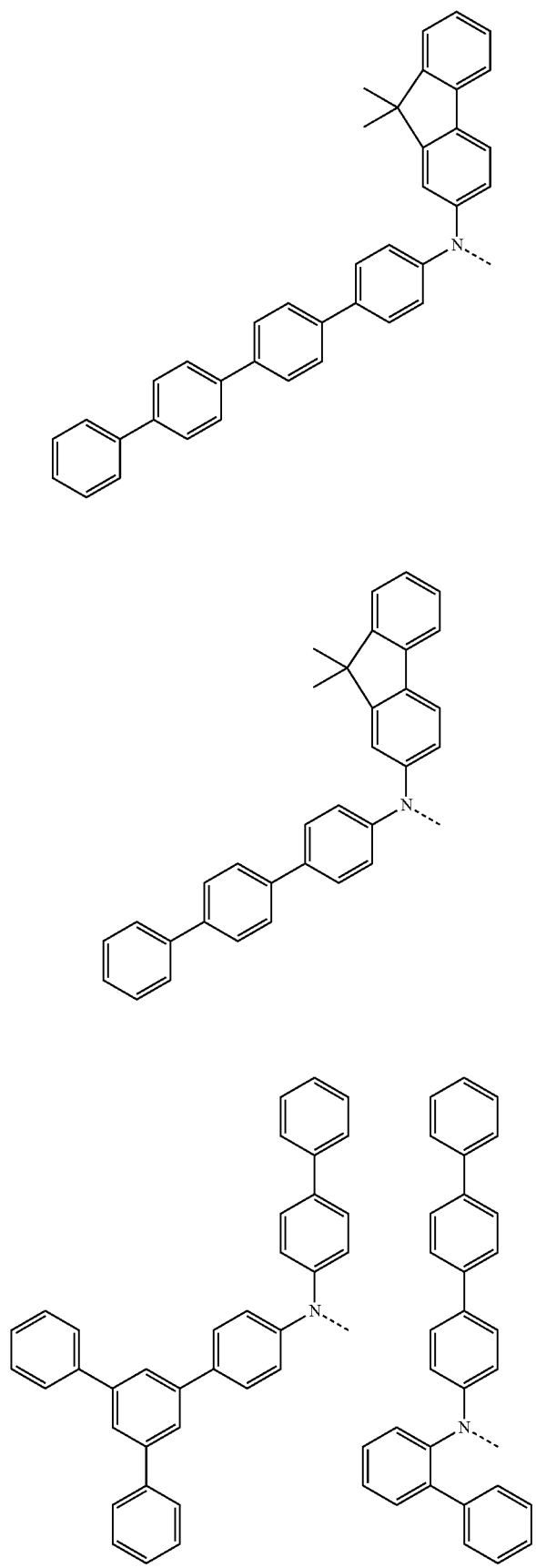
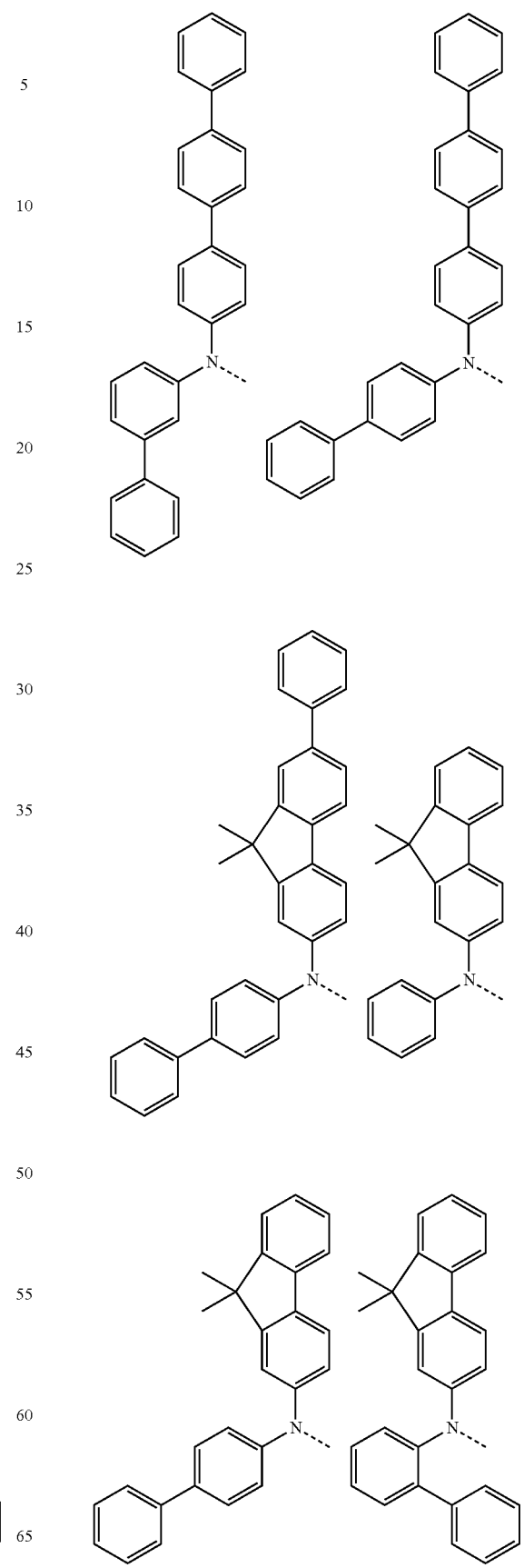

201 202
-continued -continued
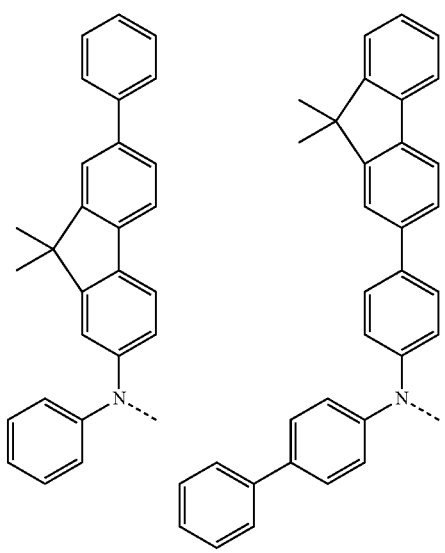
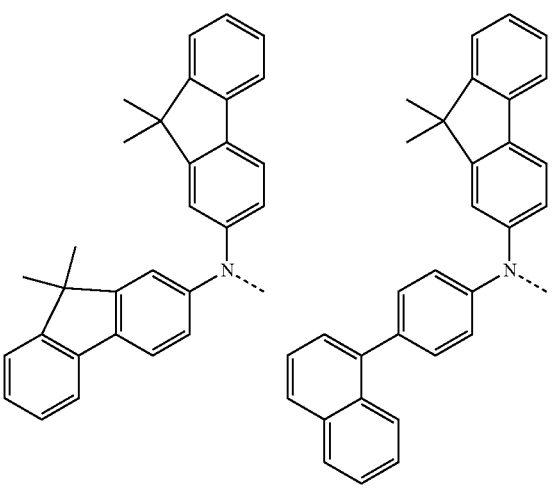
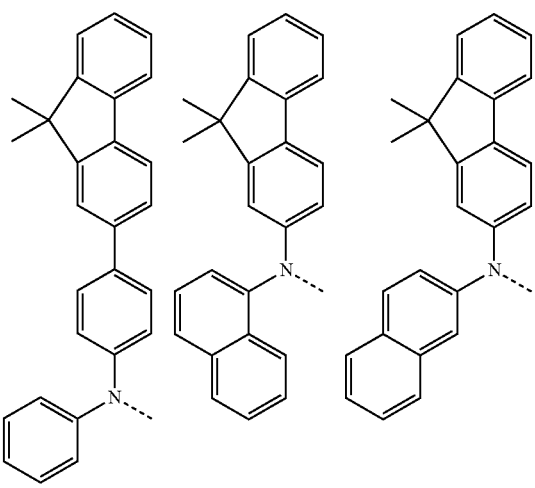
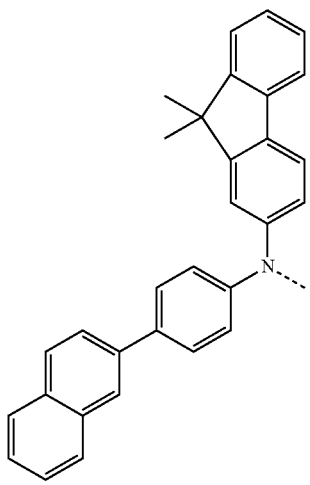
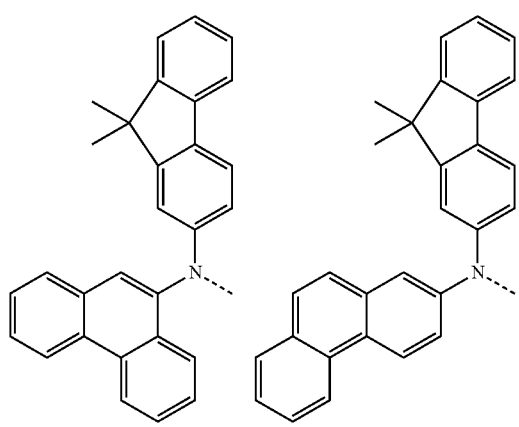
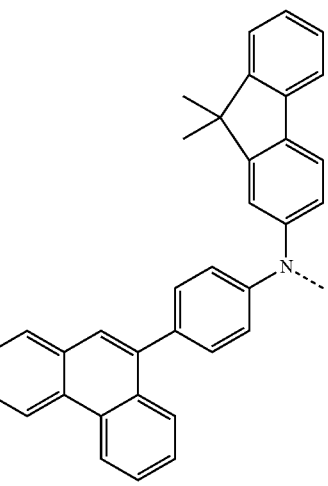

203
-continued
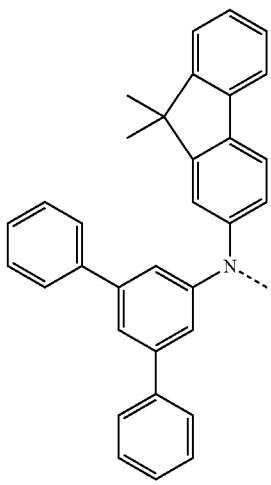
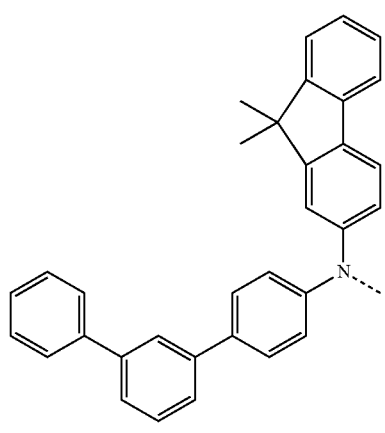
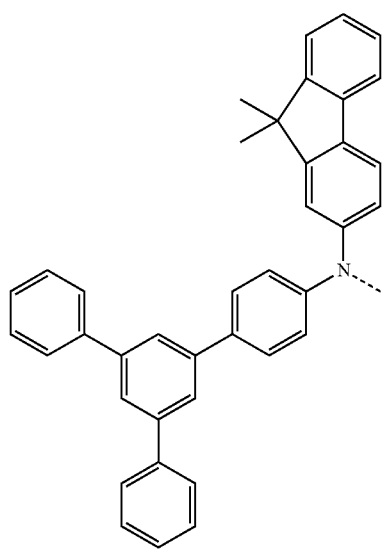
204
-continued
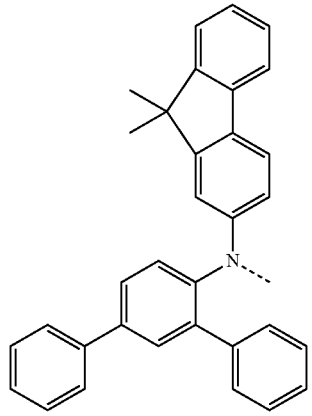
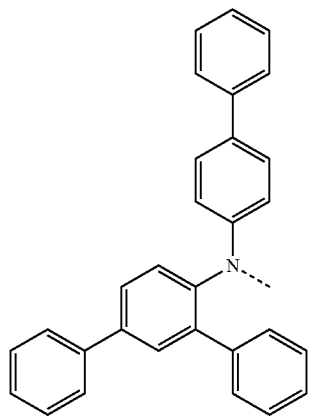
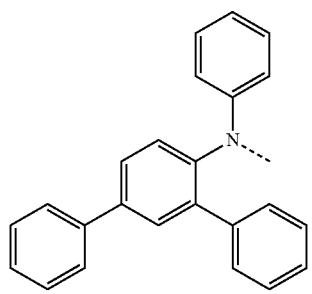
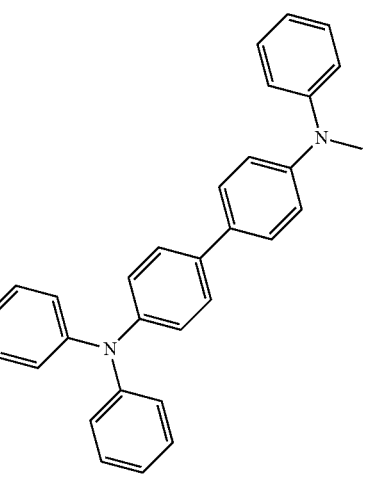

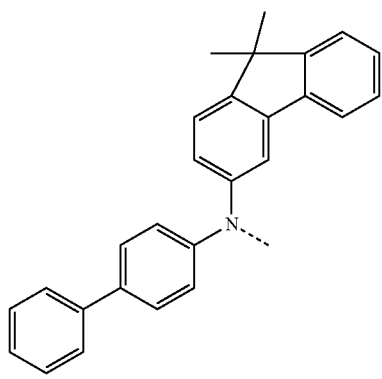
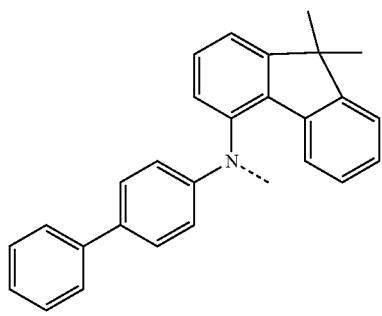
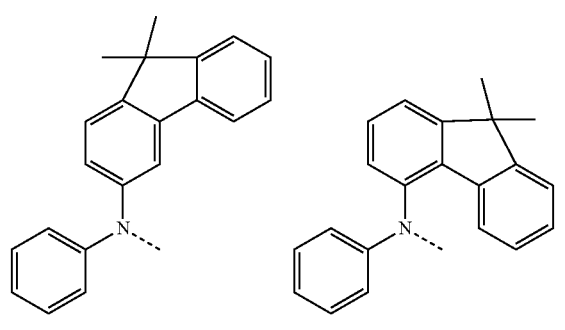
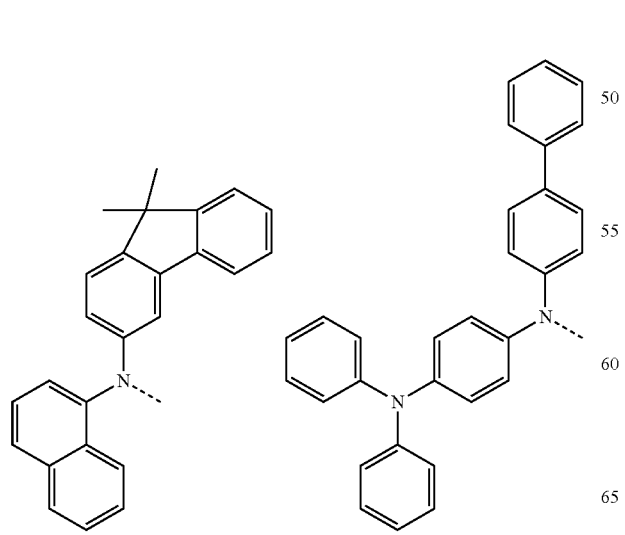
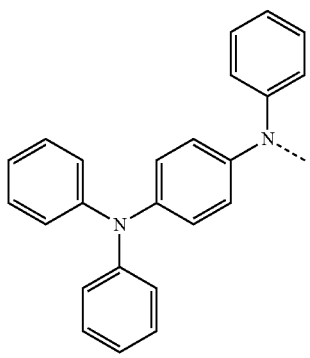
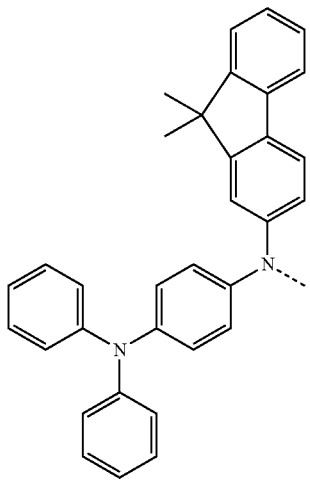
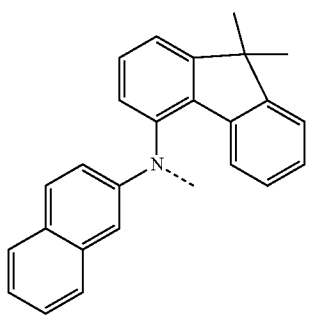
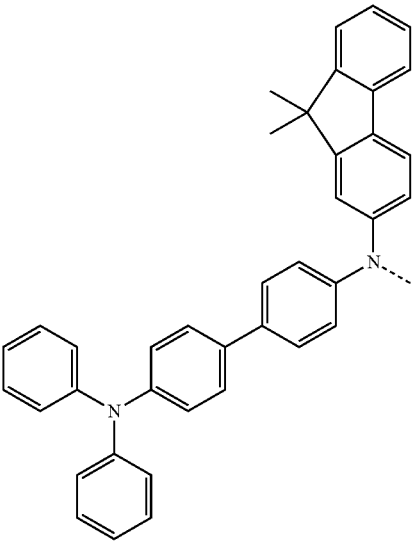

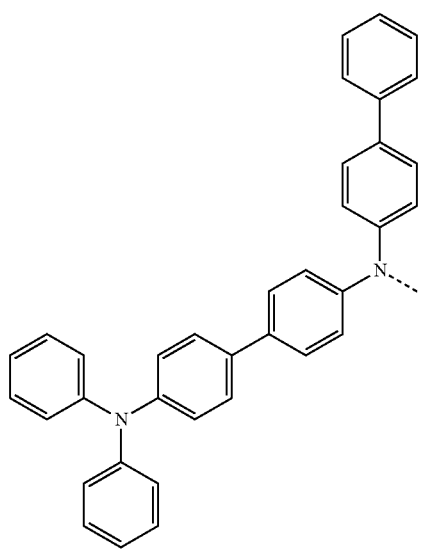
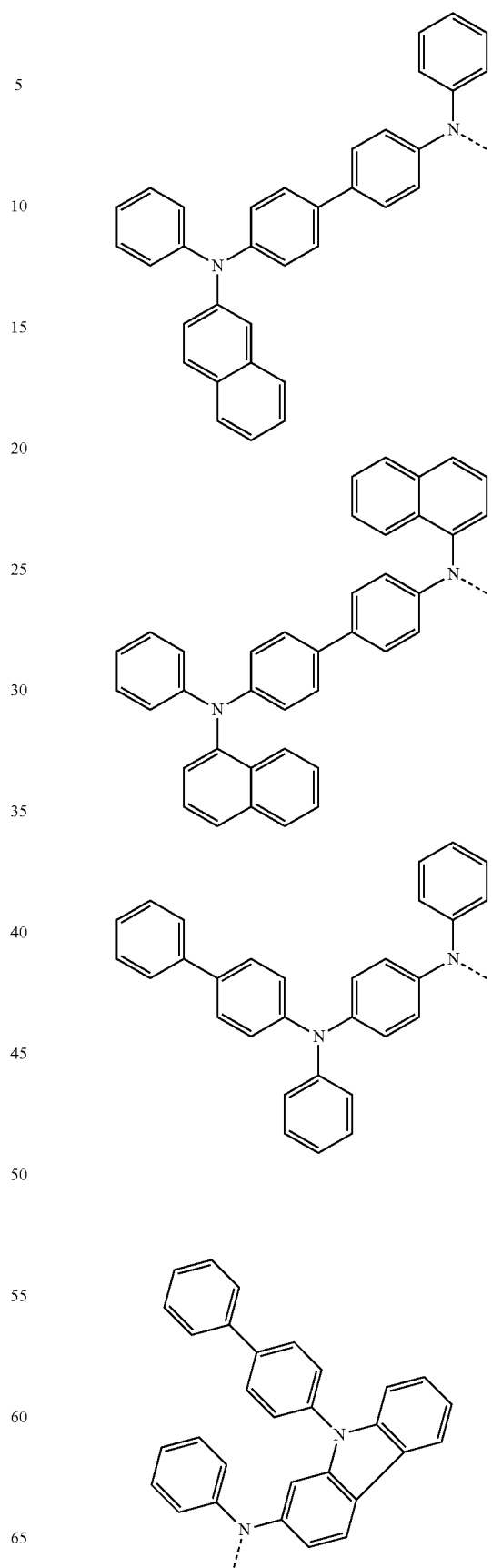

-continued
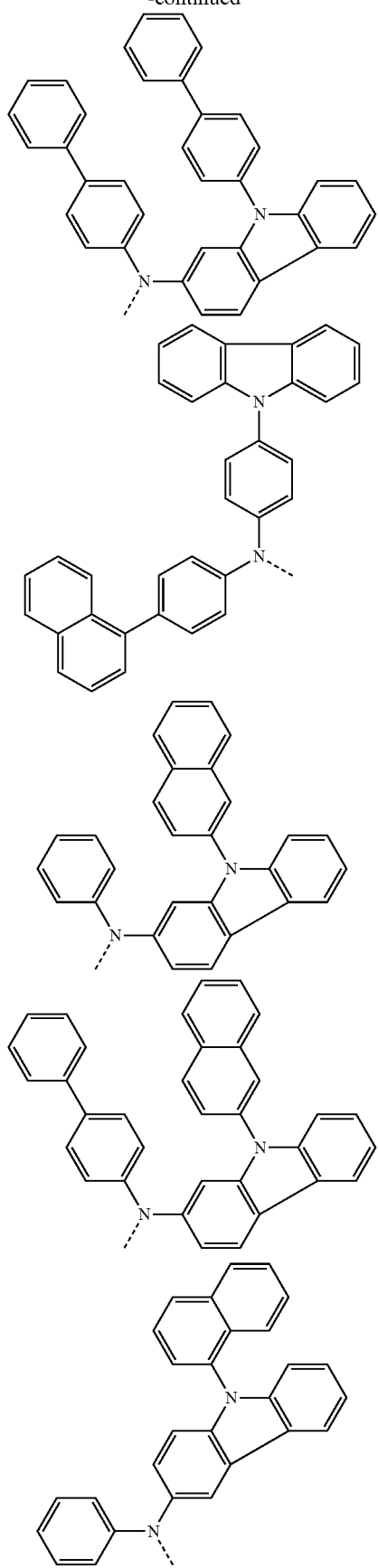
-continued
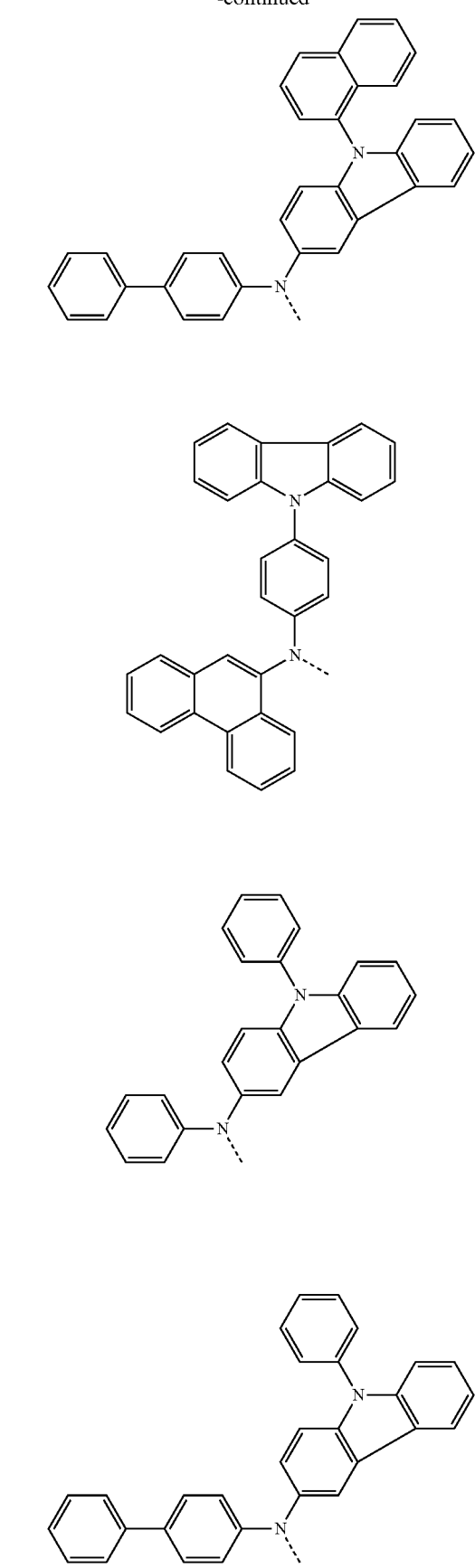

211
-continued
212
-continued
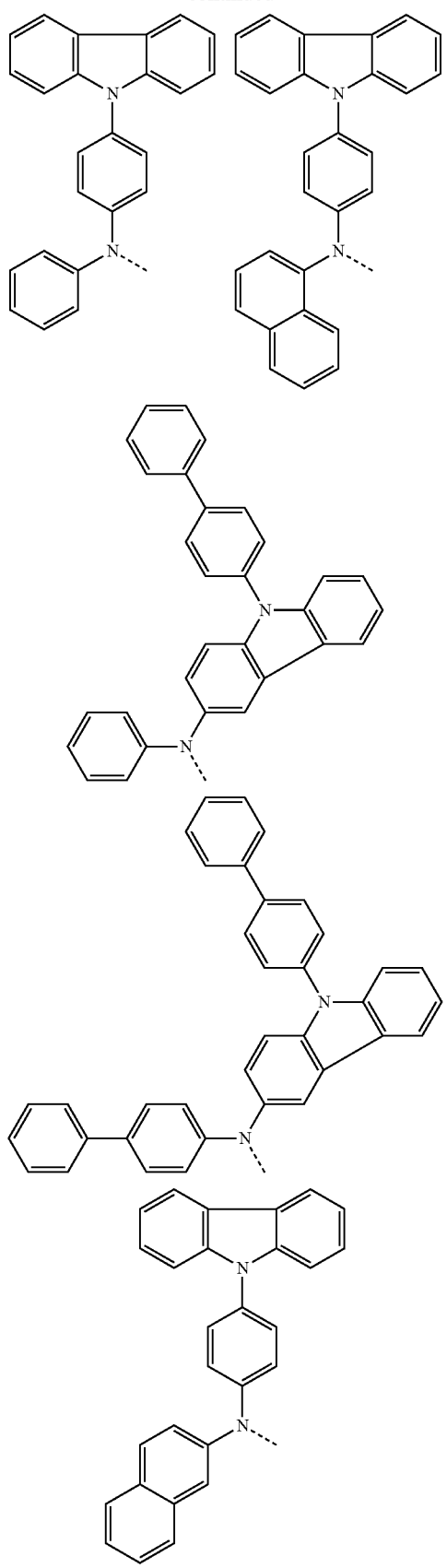
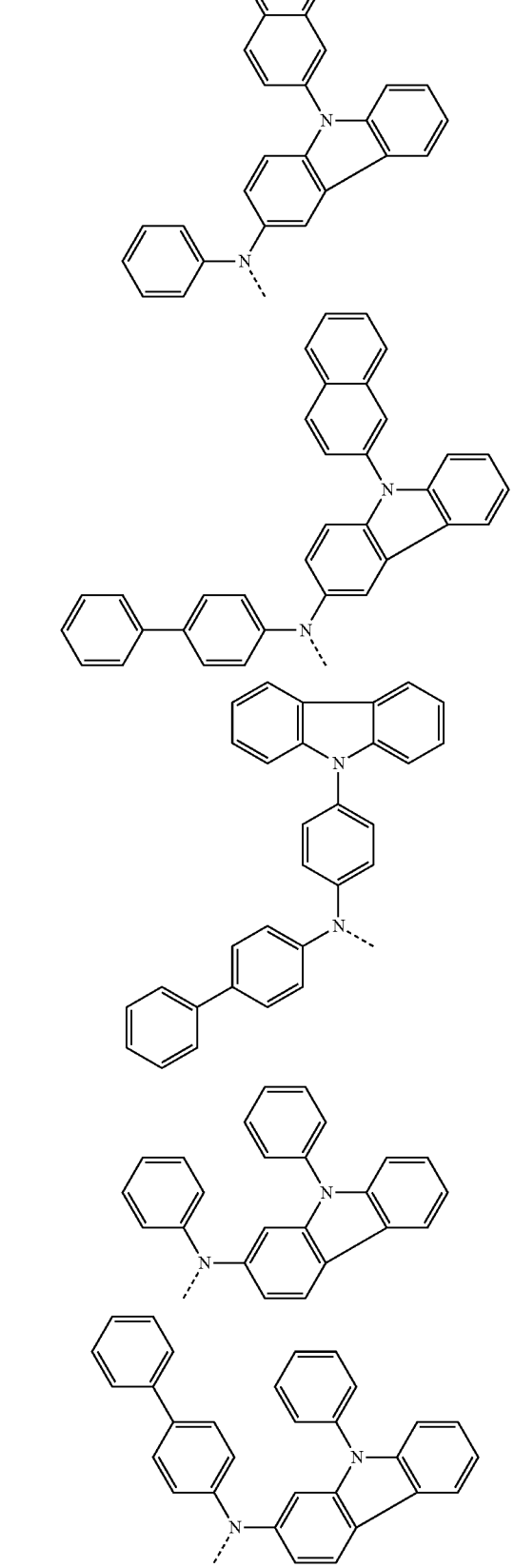

213
-continued
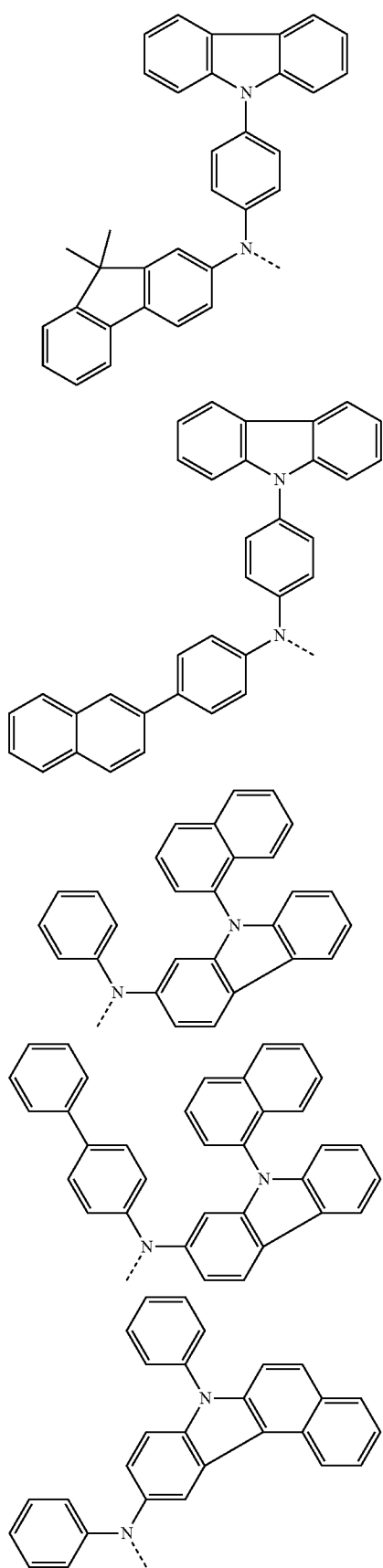
214
-continued
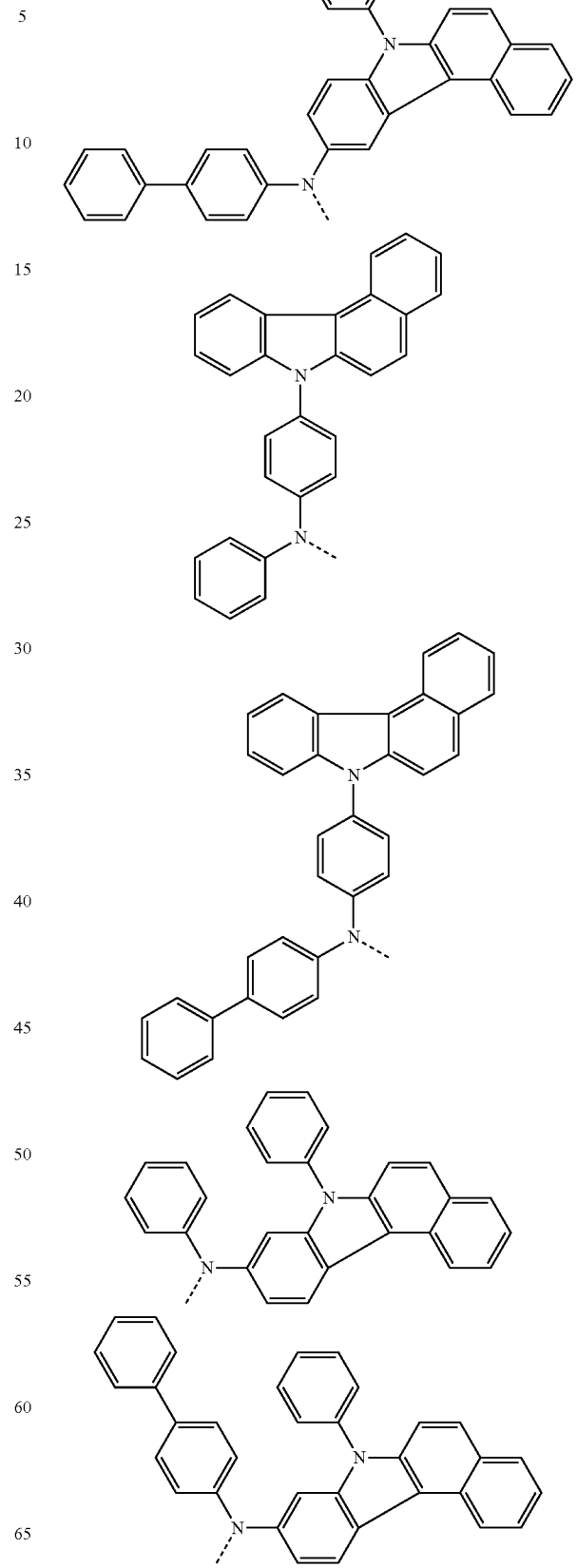

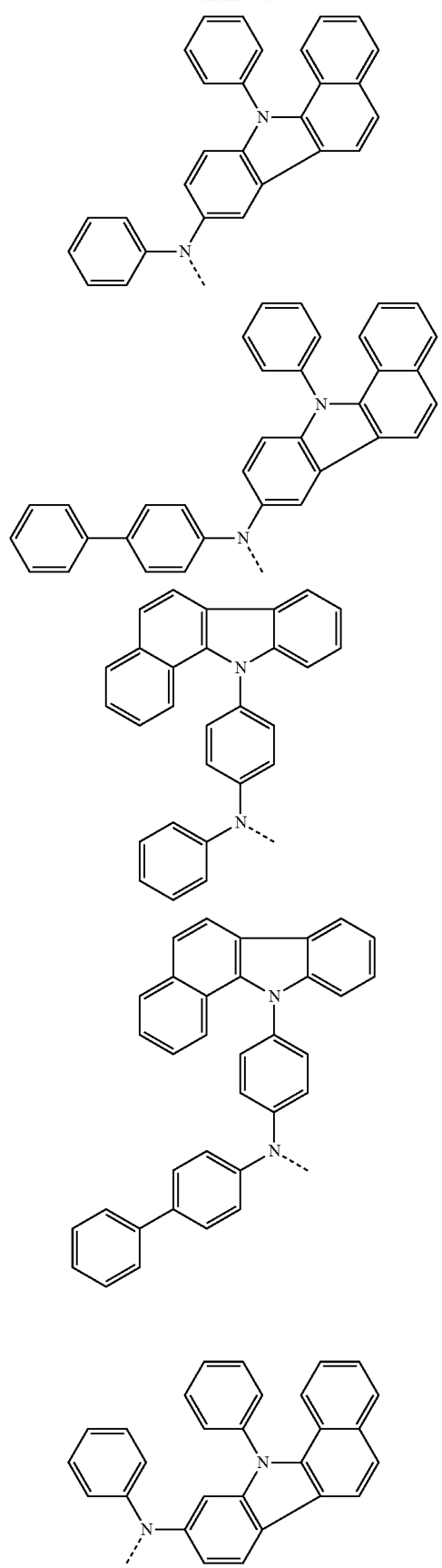
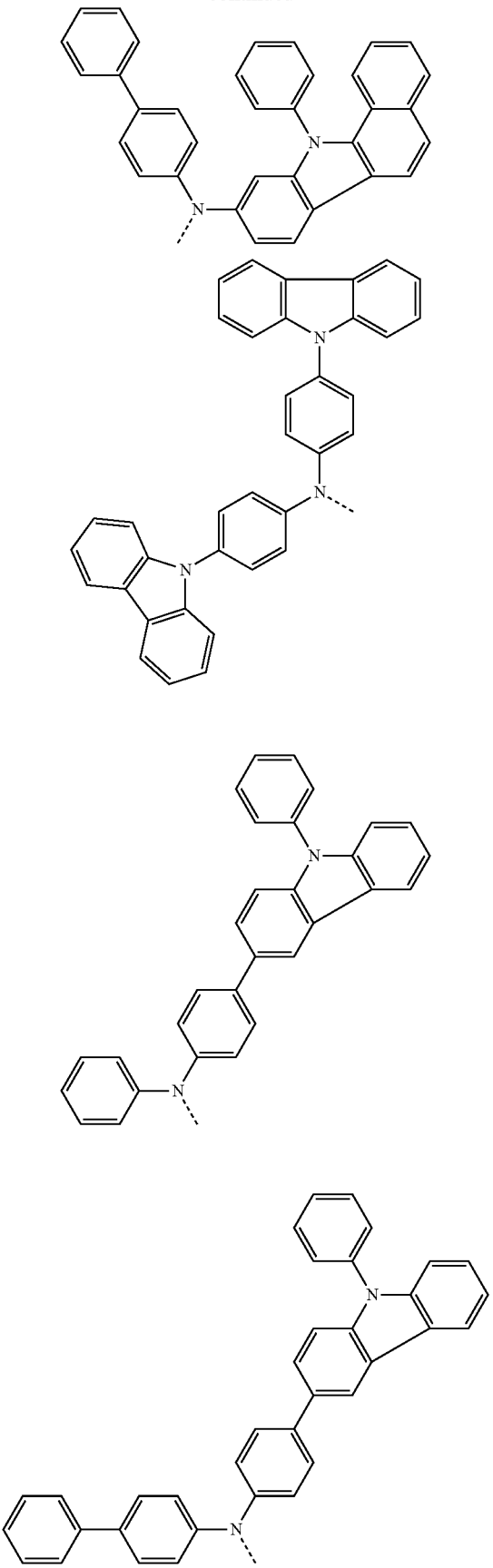

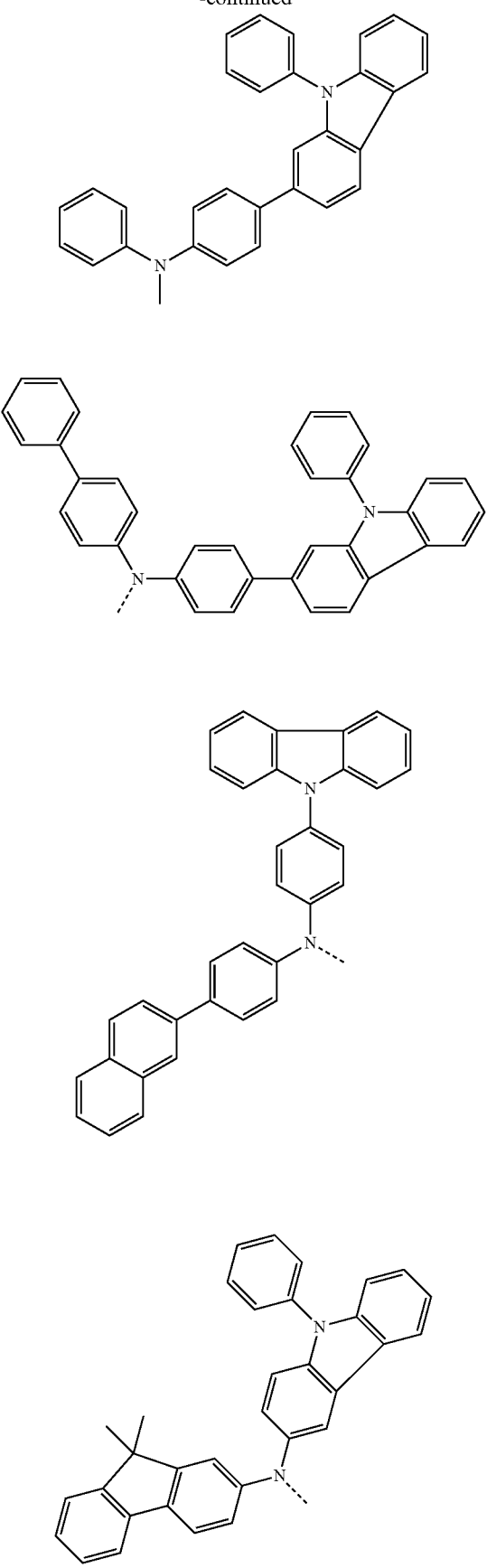
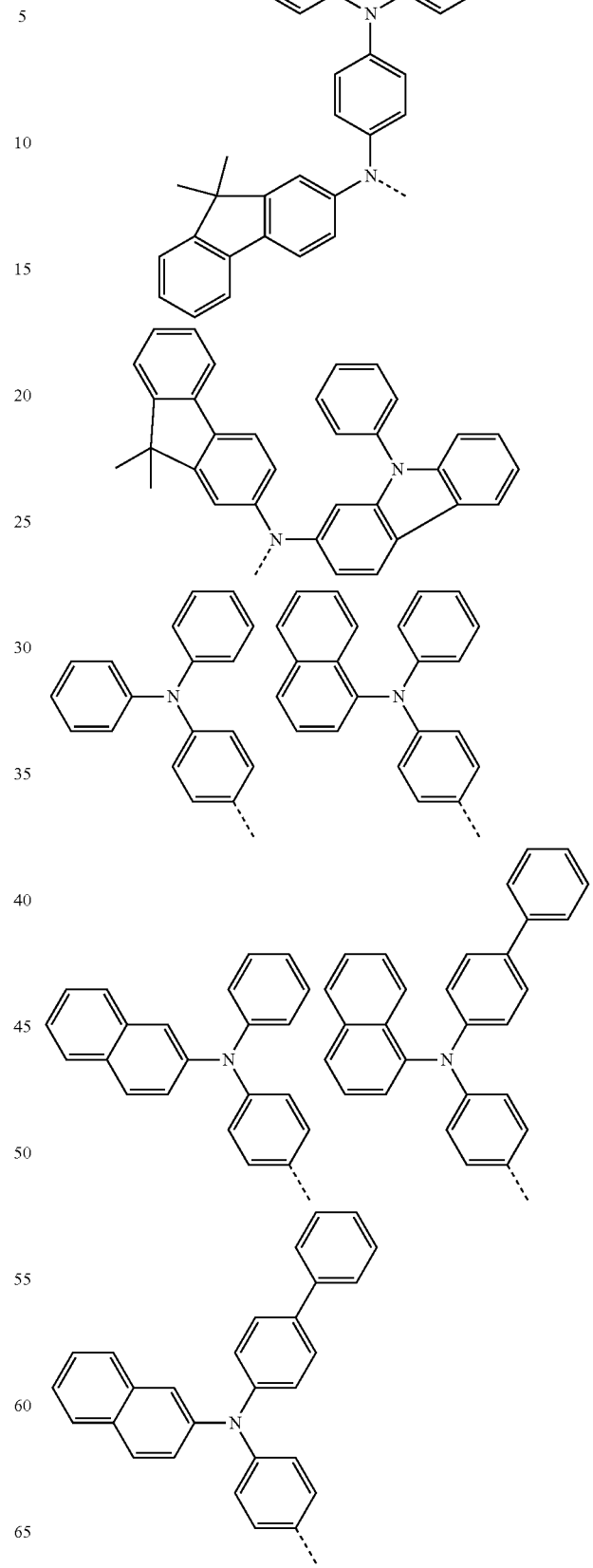

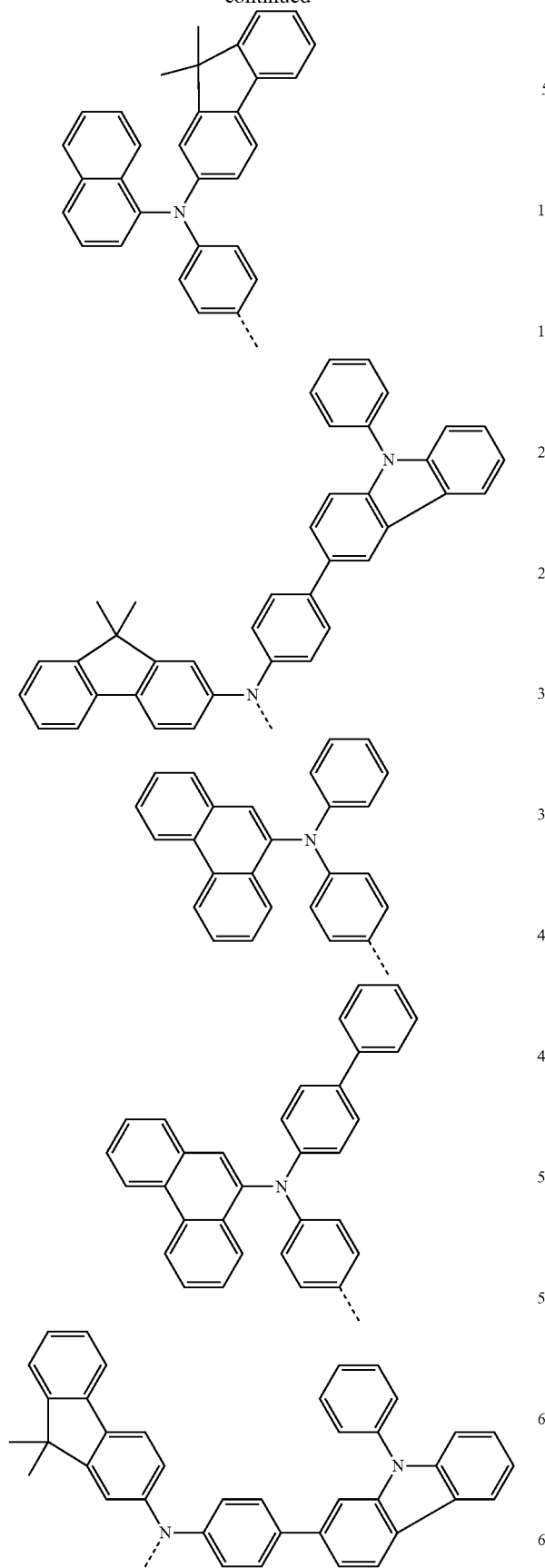

221
-continued
222
-continued
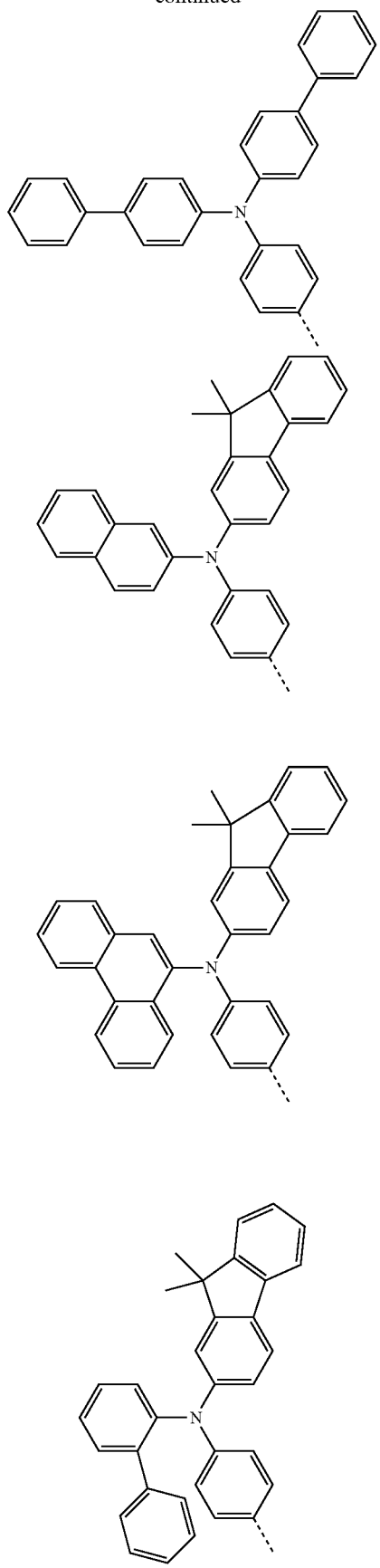
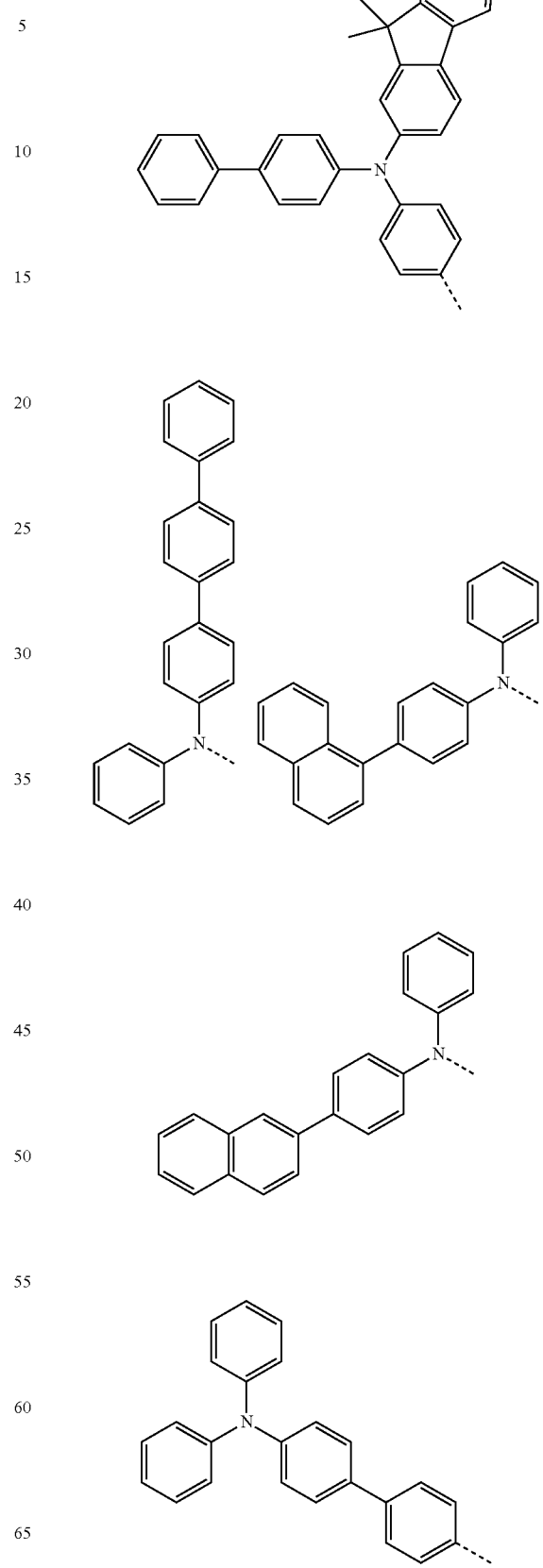

223
-continued
224
-continued
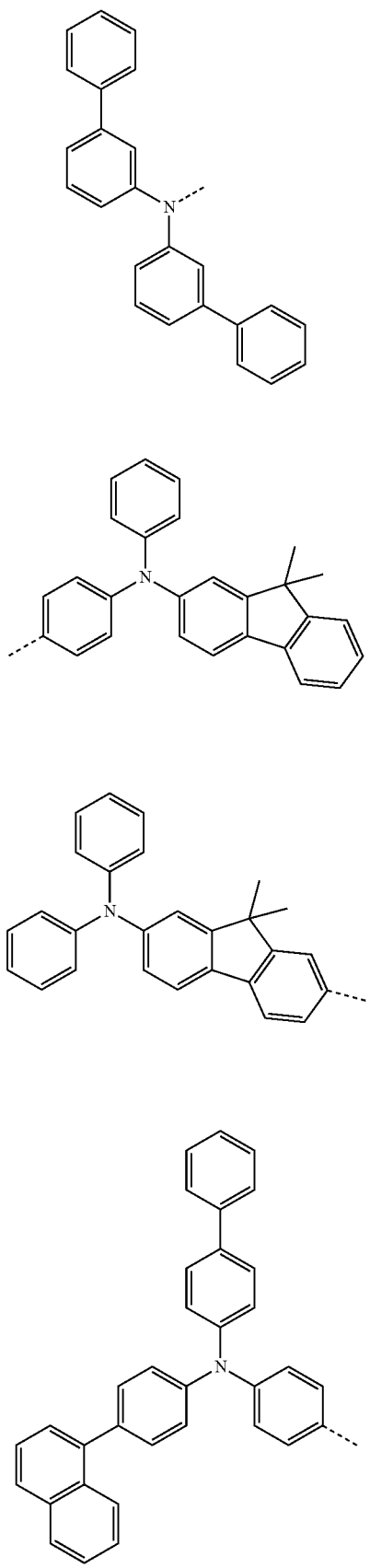
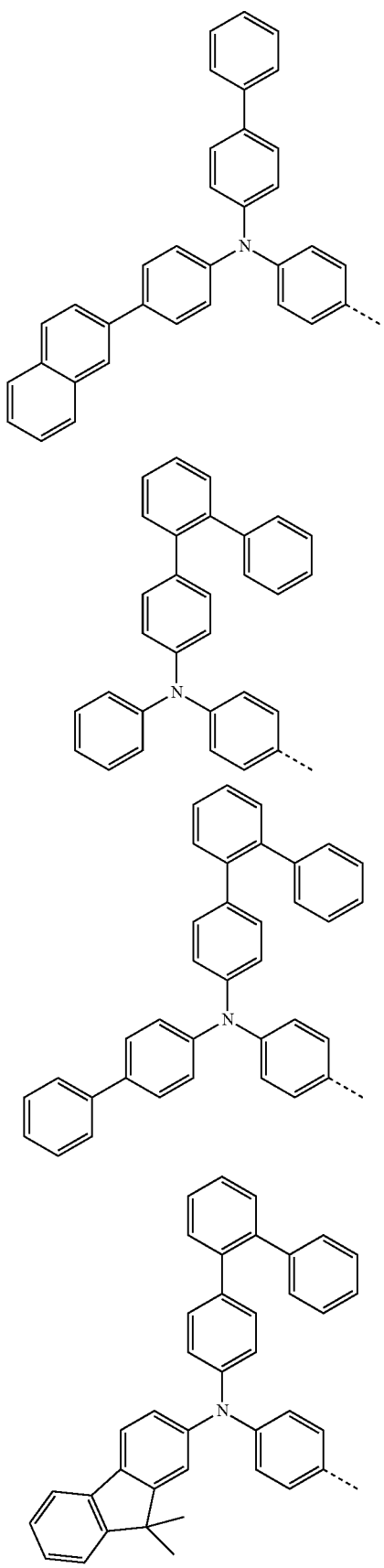

225
-continued
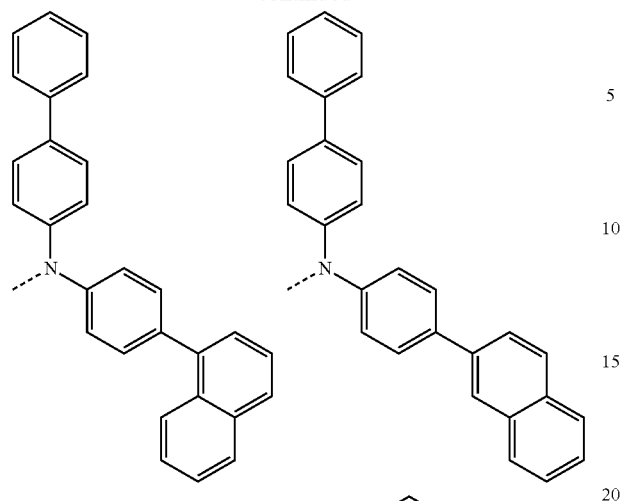
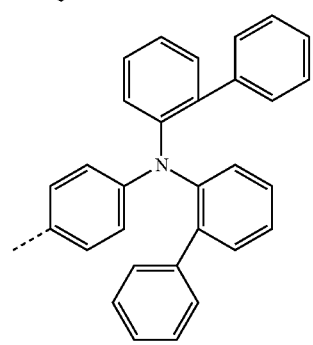
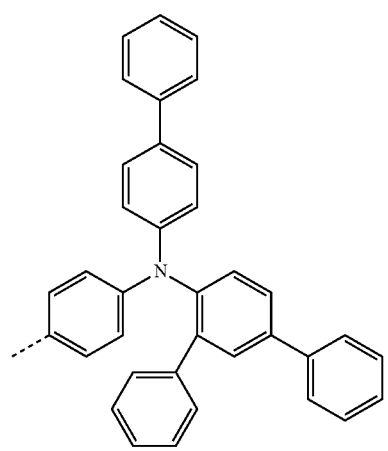
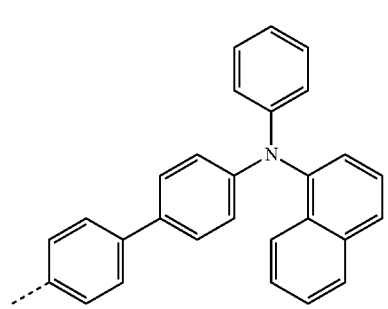
226
-continued
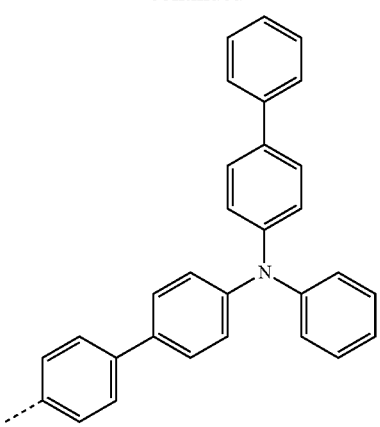
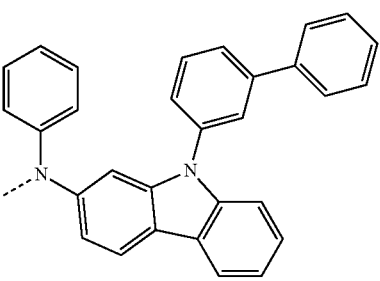
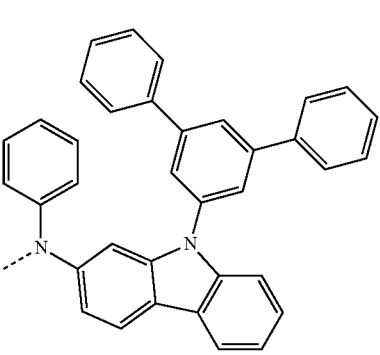
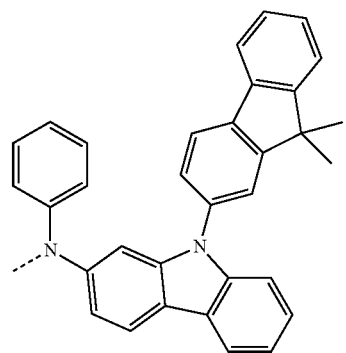

227
-continued
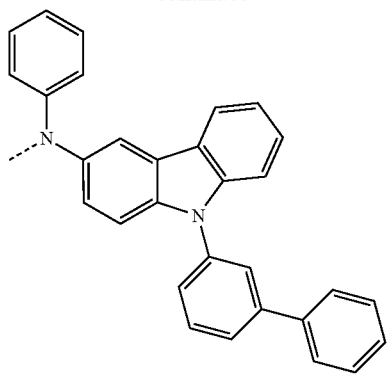
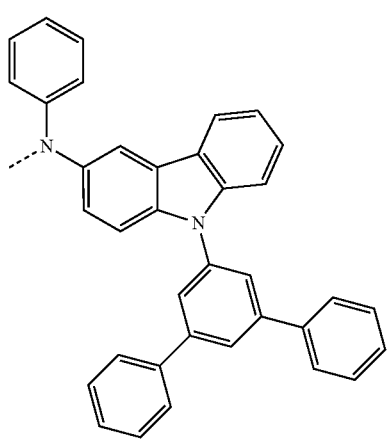
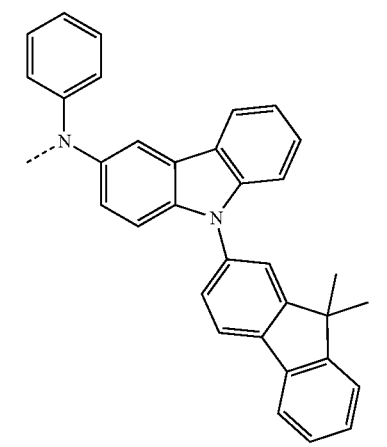
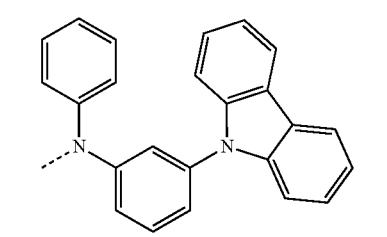
228
-continued
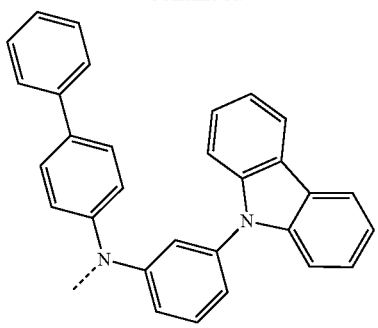
[A-2]
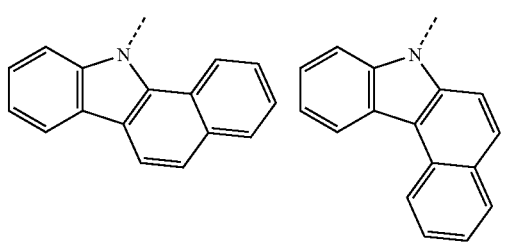
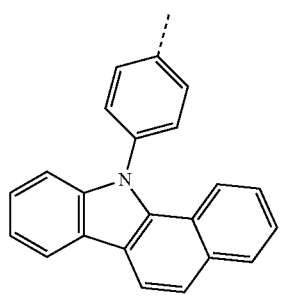
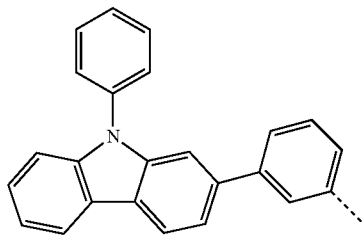
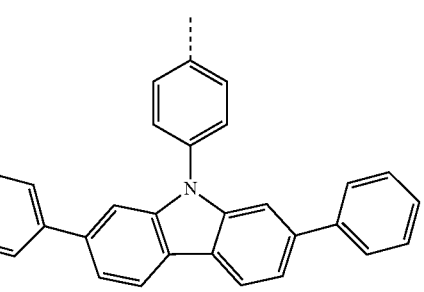

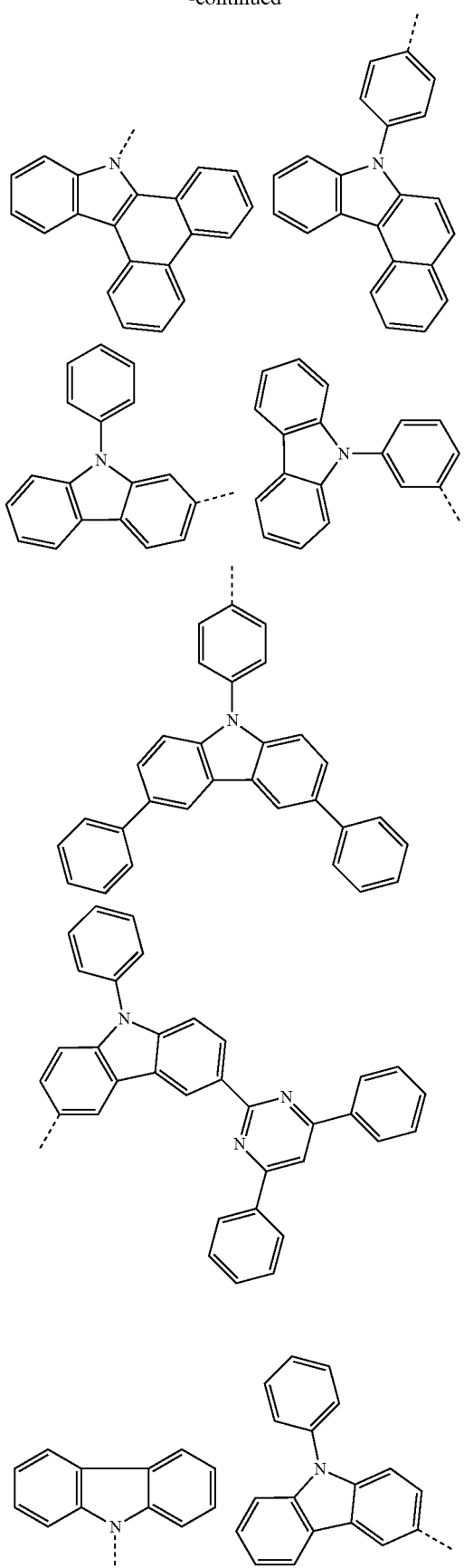
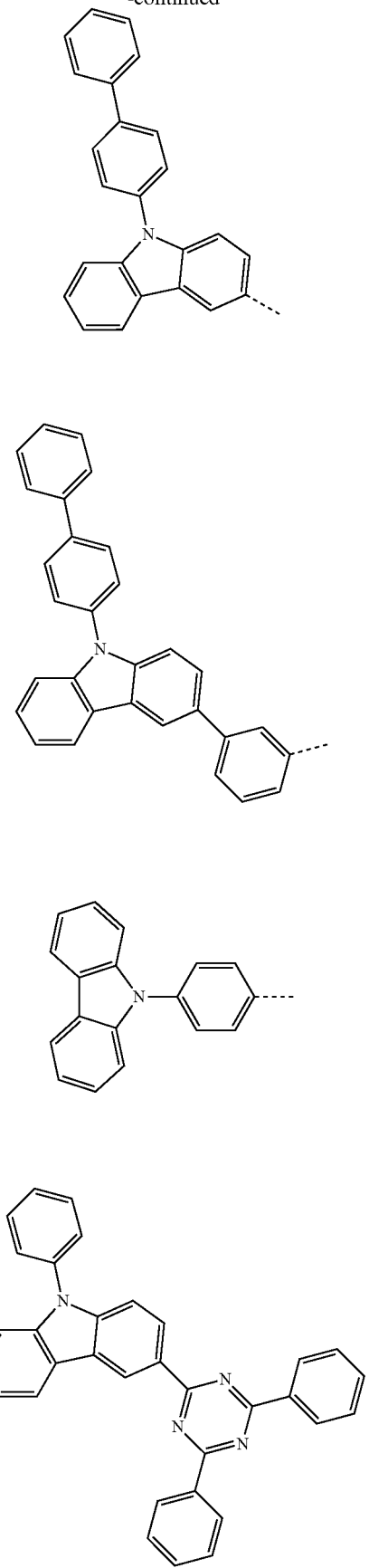

231
-continued
232
-continued
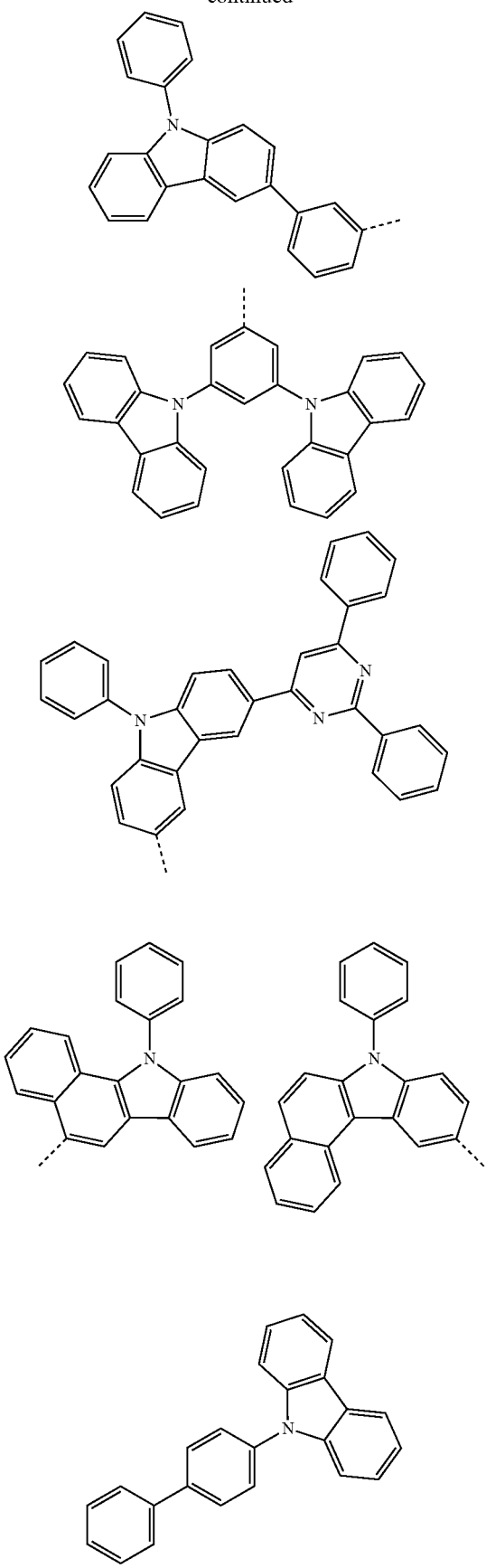
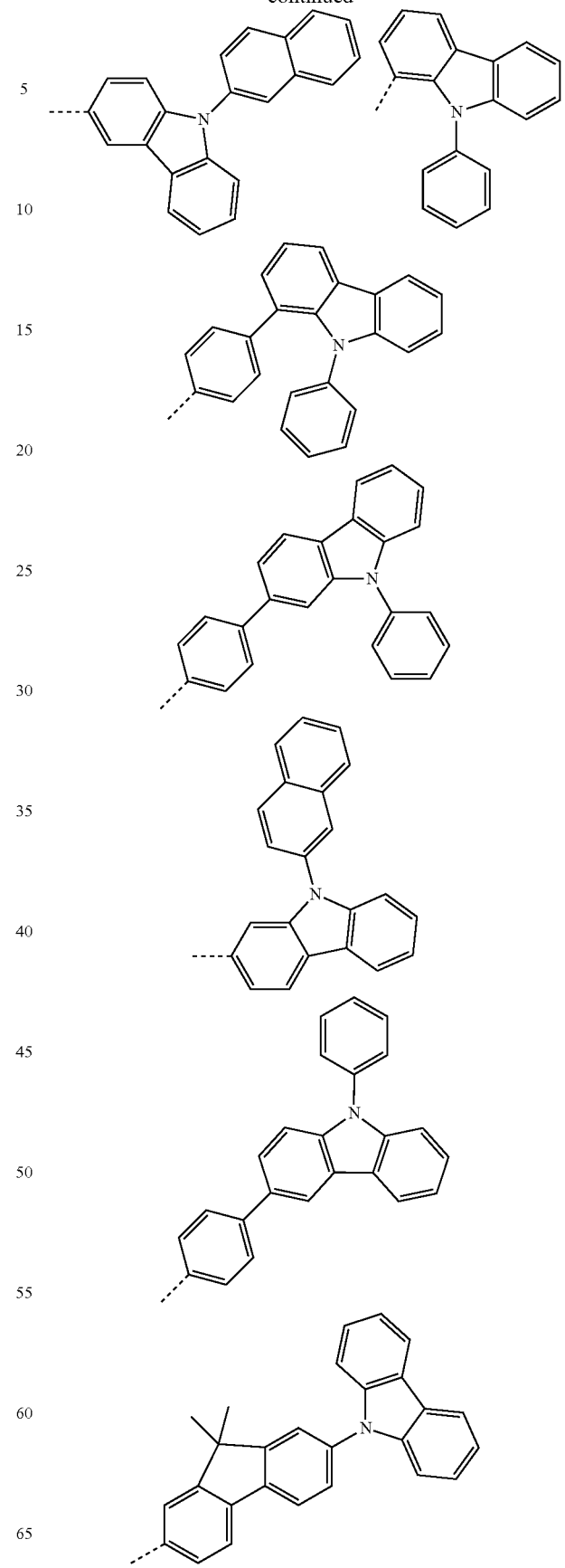

233
-continued
[A-3]
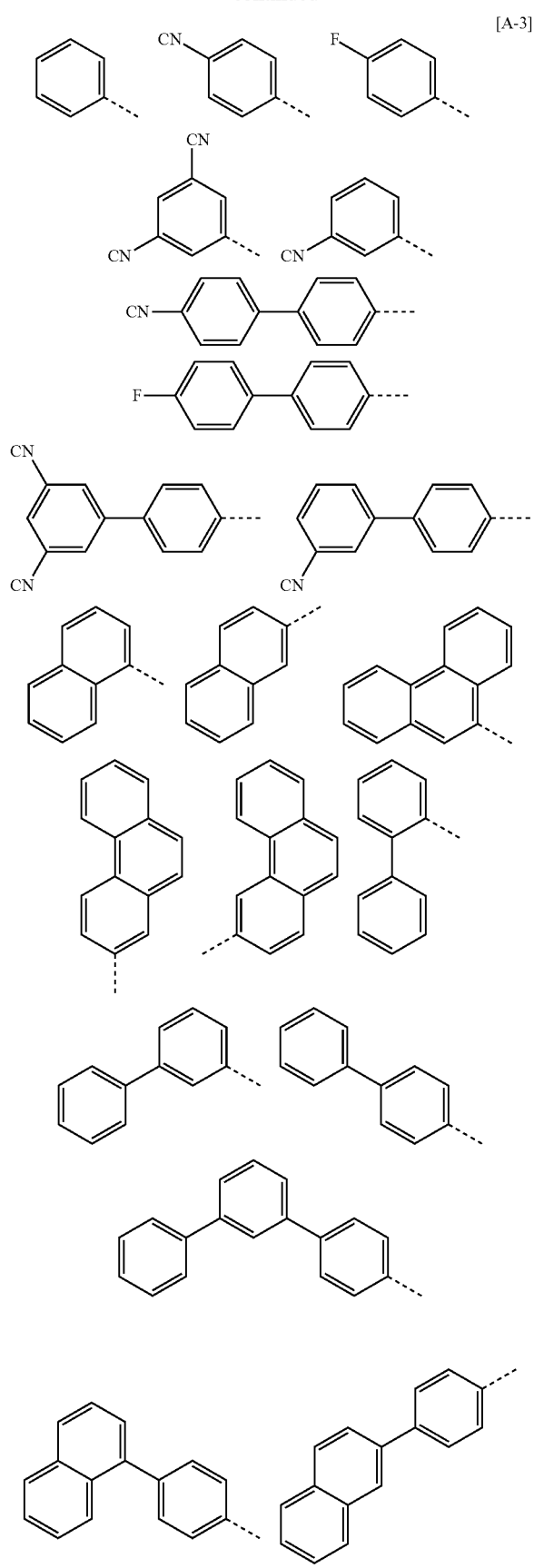
234
-continued
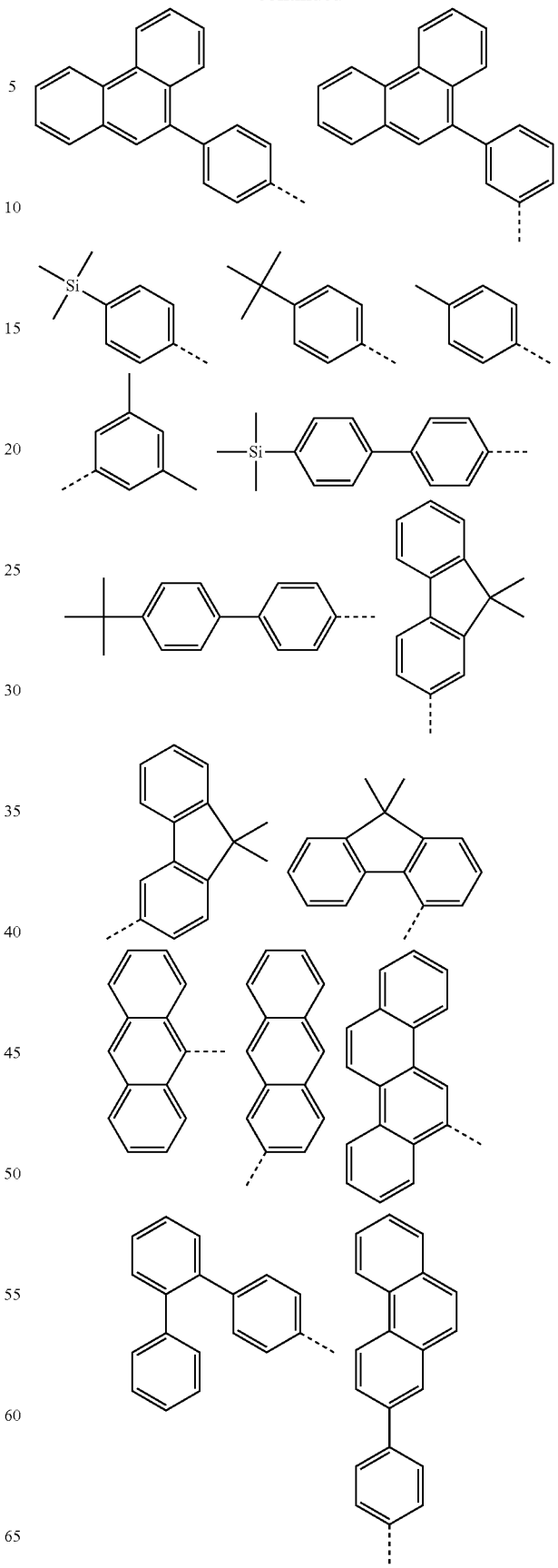

235
-continued
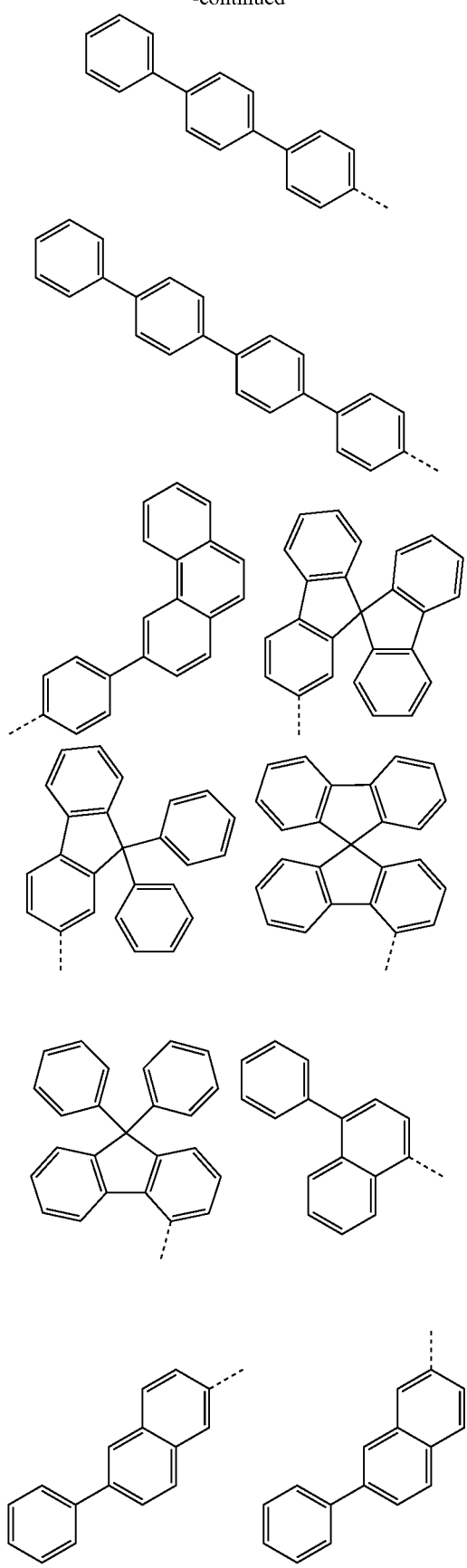
236
-continued
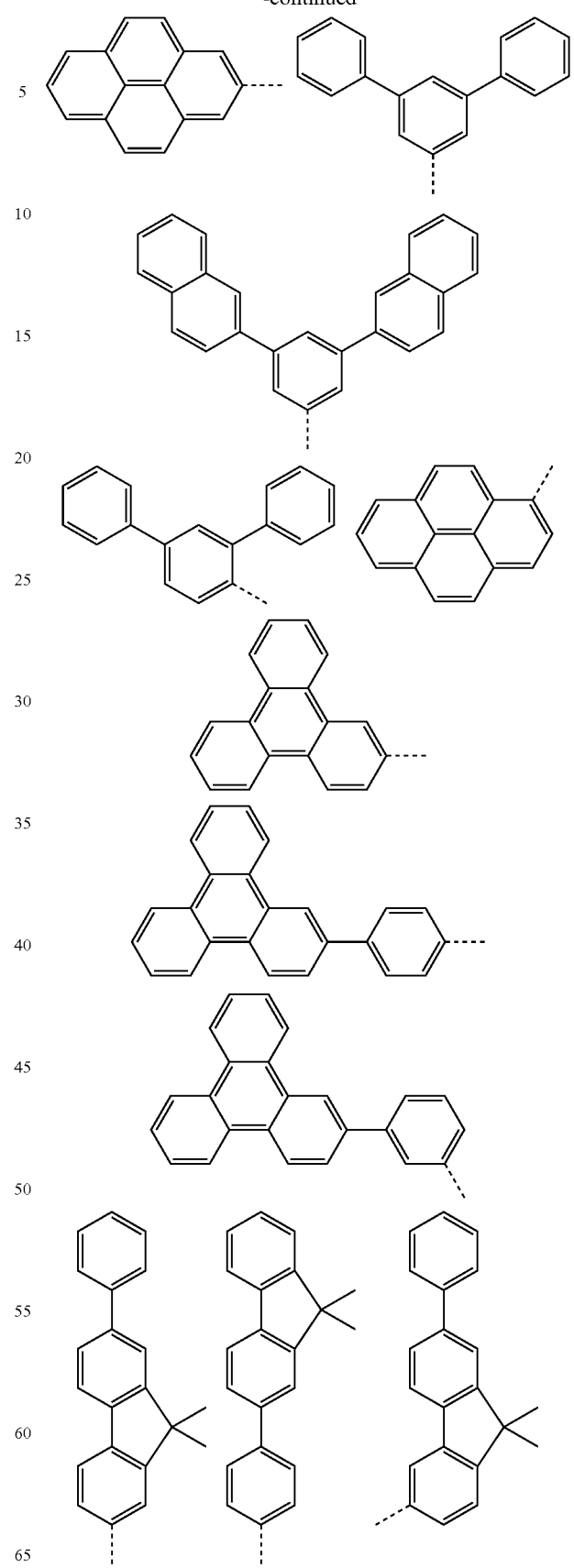

237
-continued
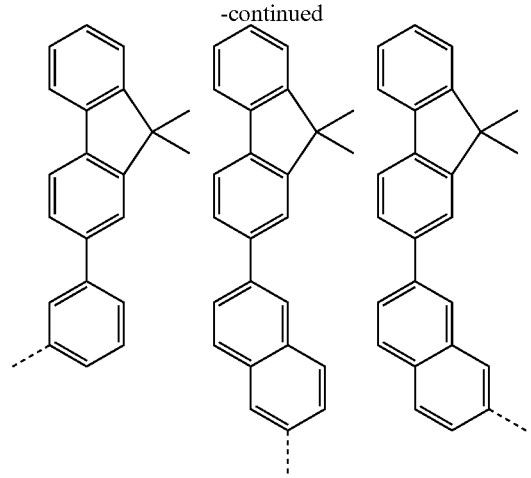
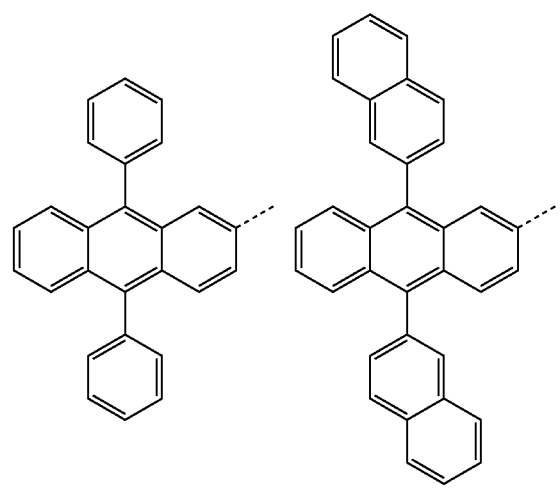
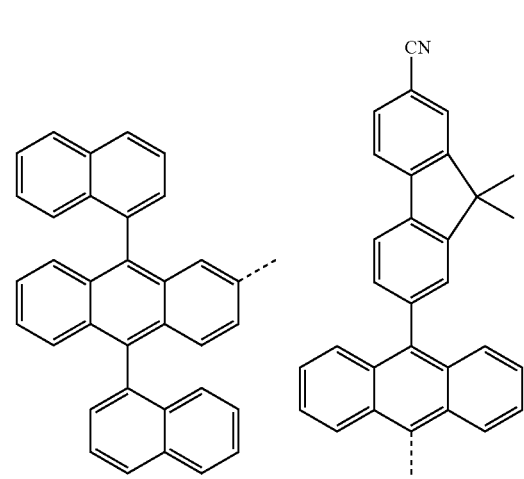
238
-continued
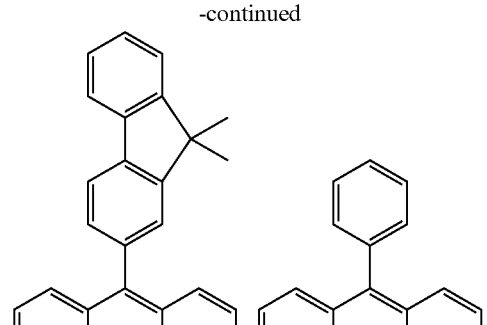
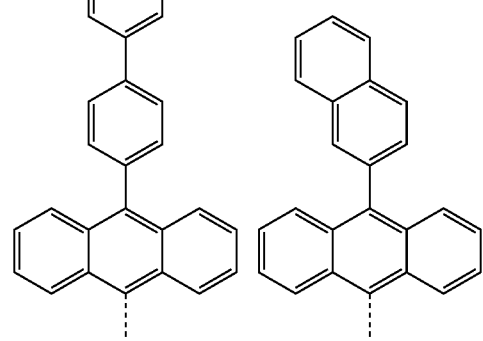
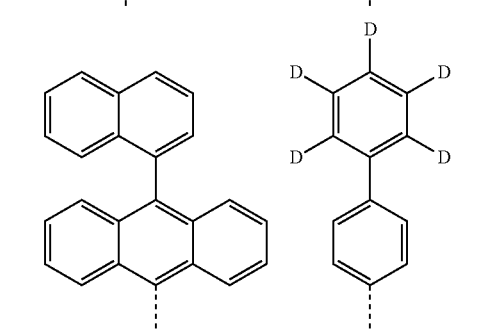
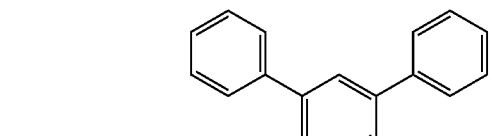
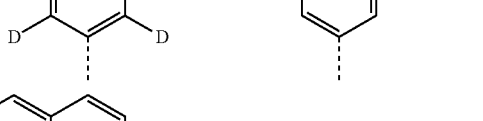
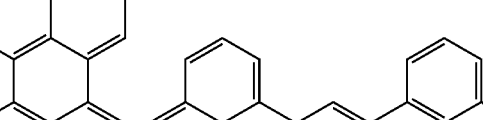
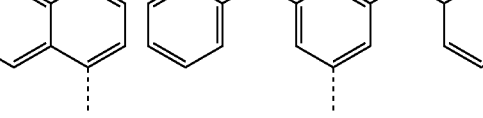

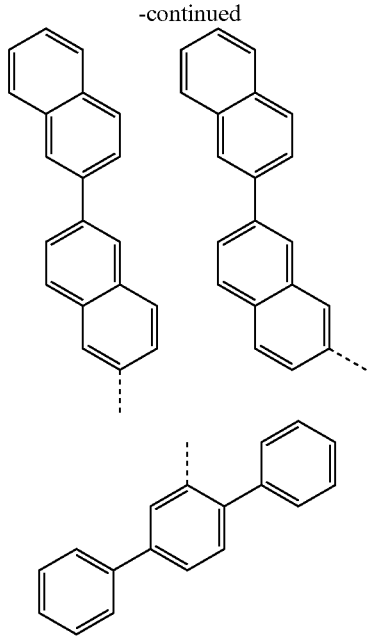
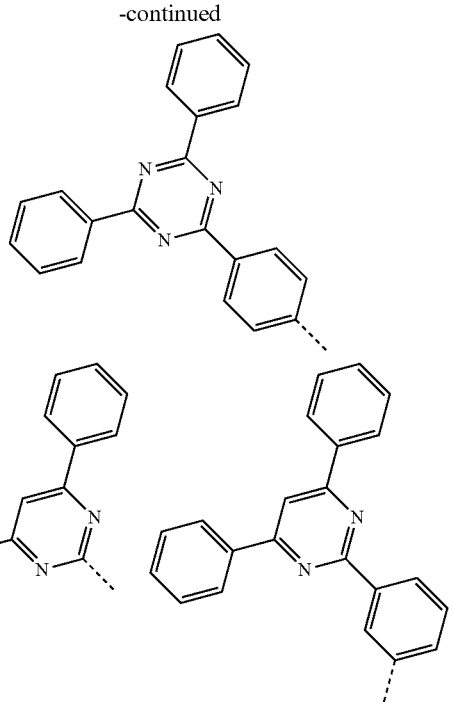
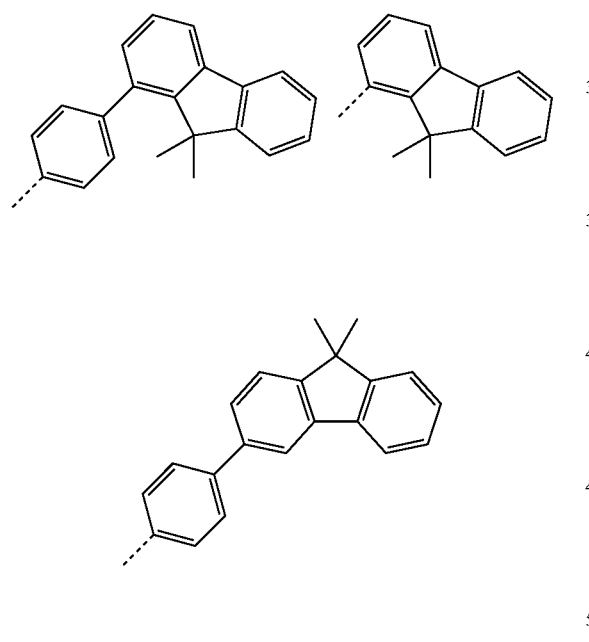
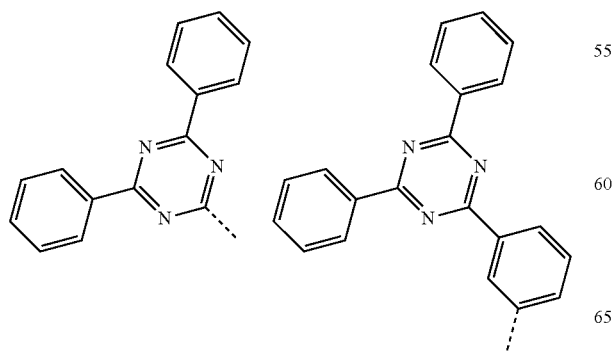
[A-4]
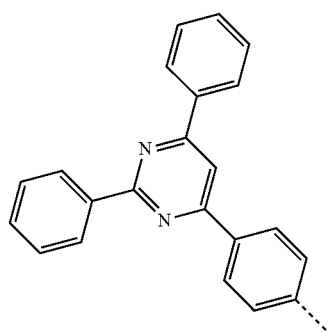

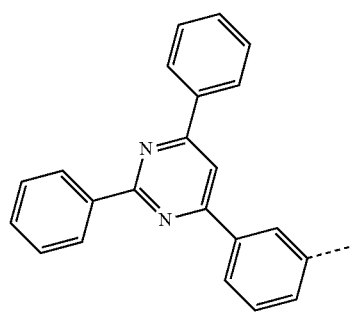
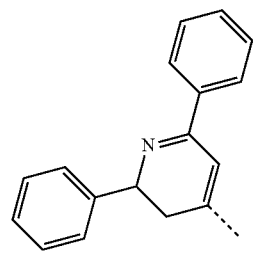
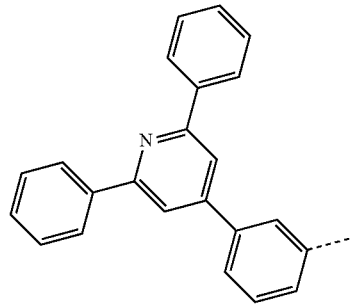
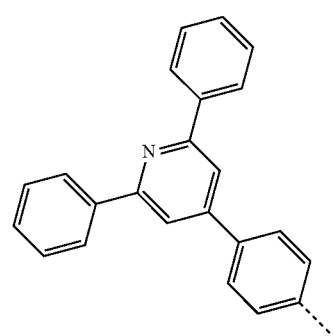
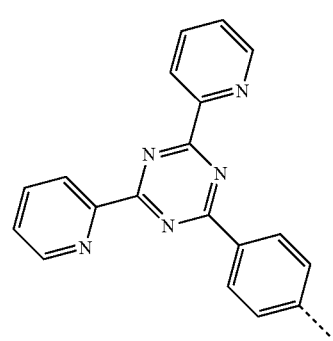
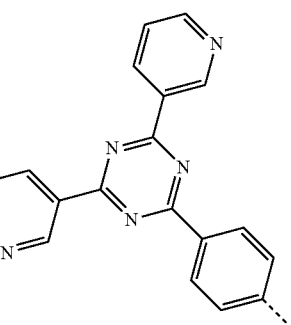
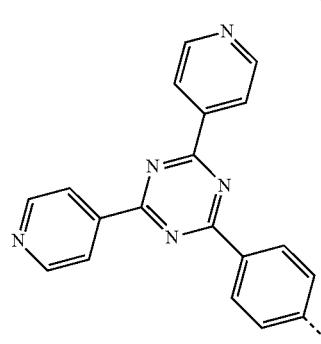
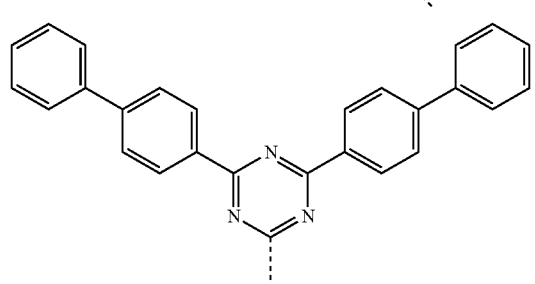
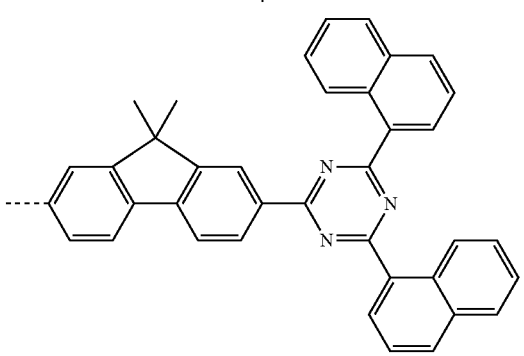
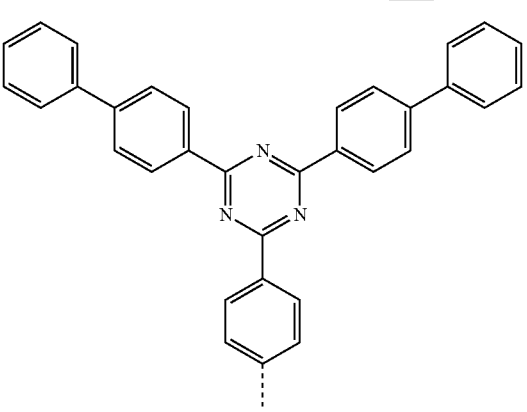

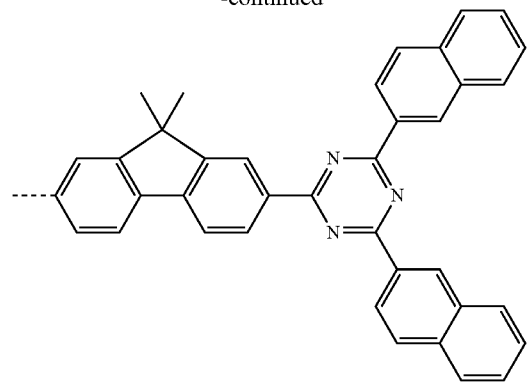
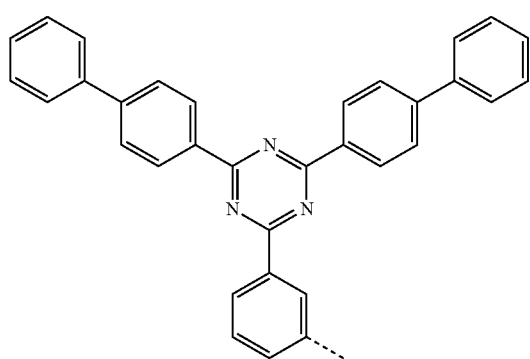
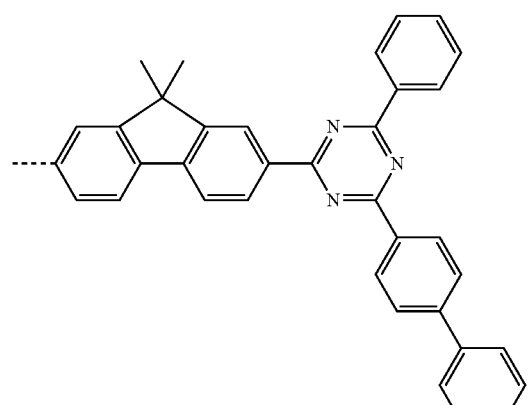
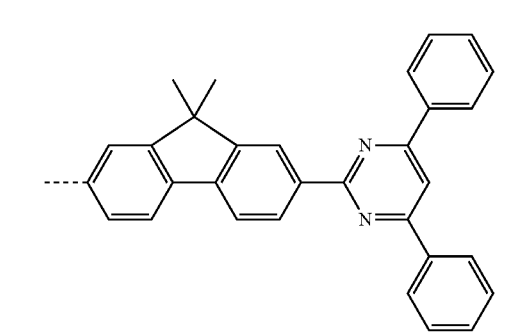
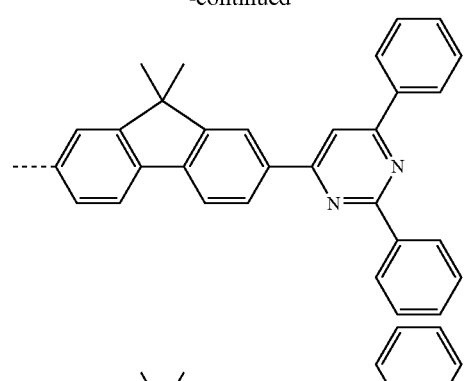
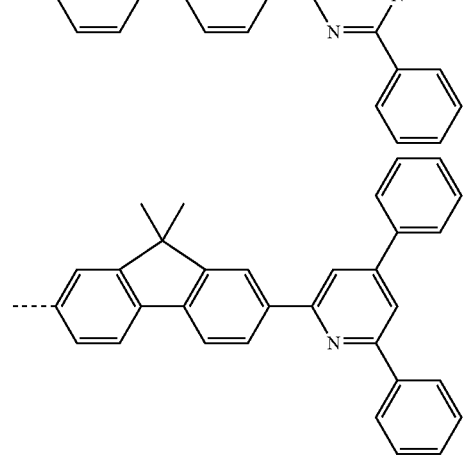
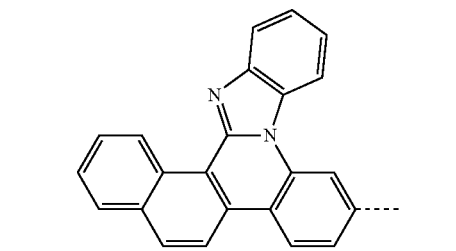
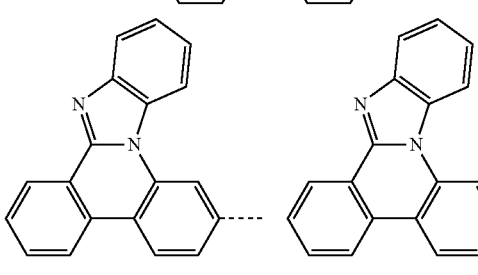
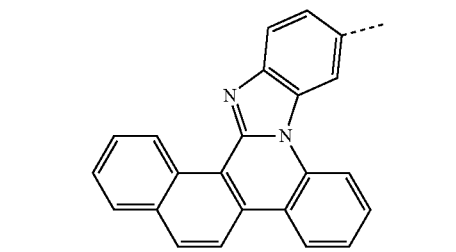

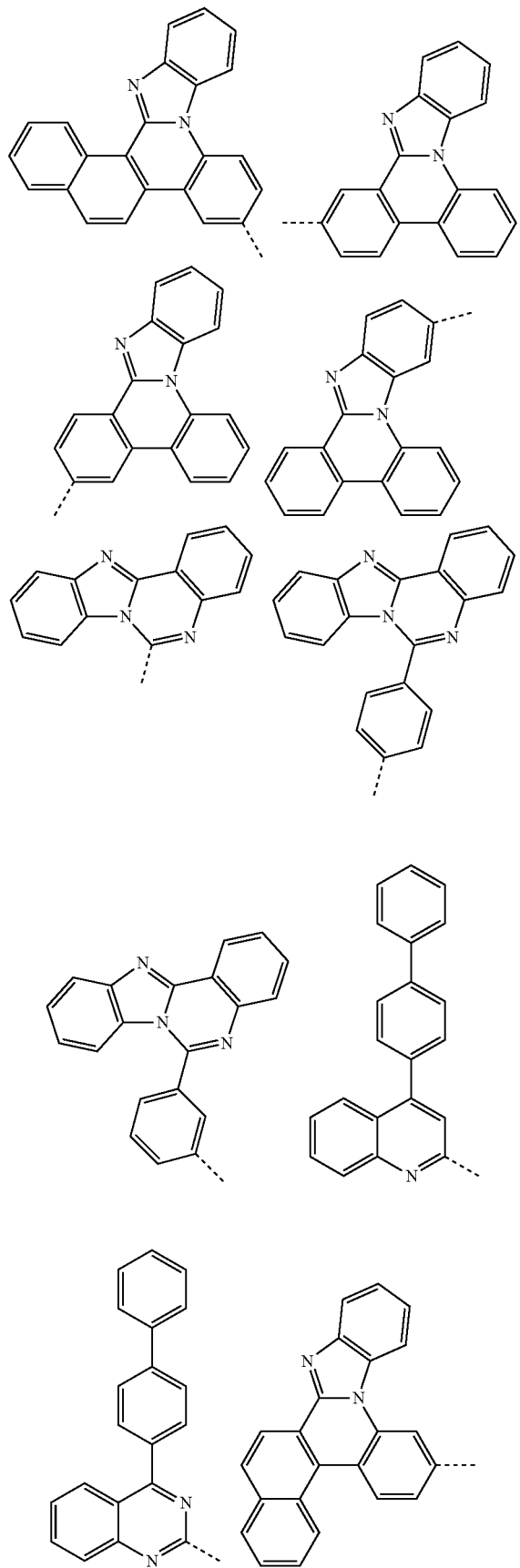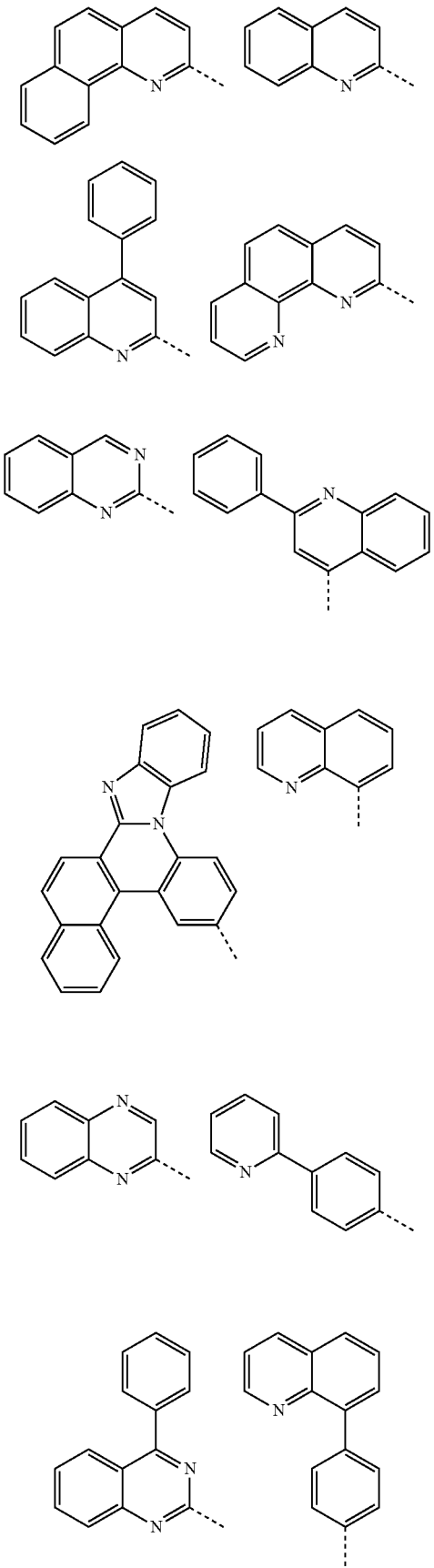

247
-continued
248
-continued
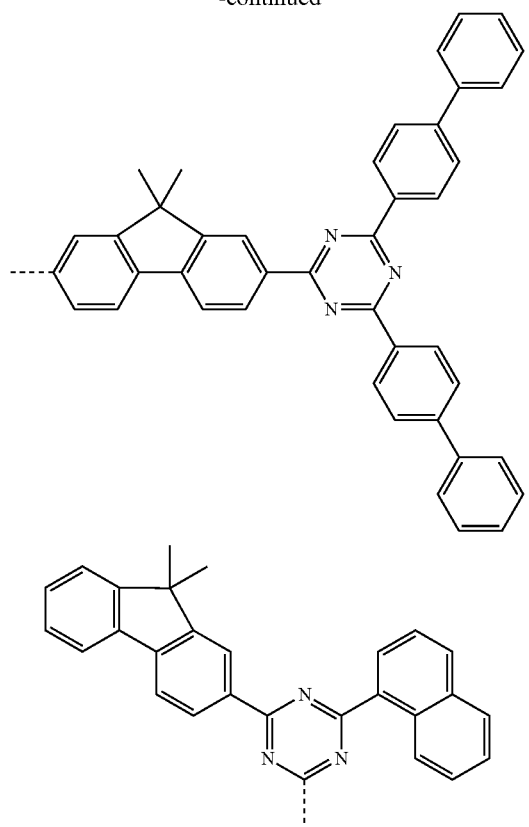
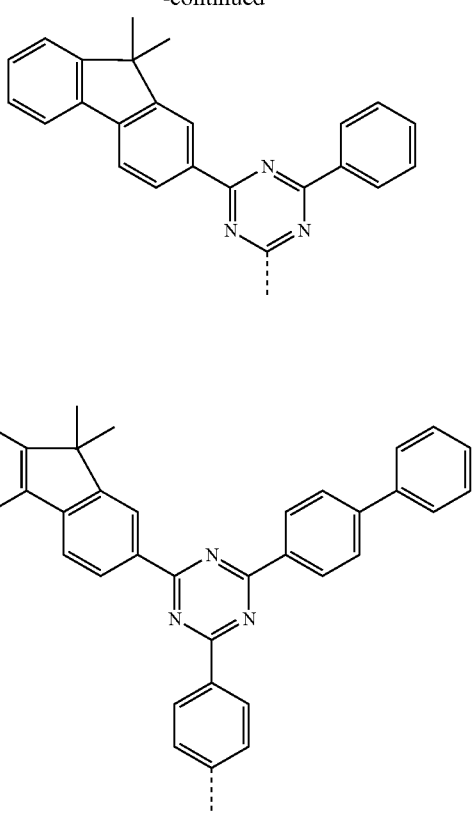
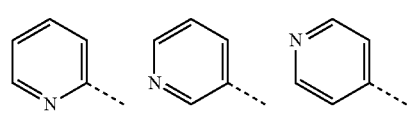
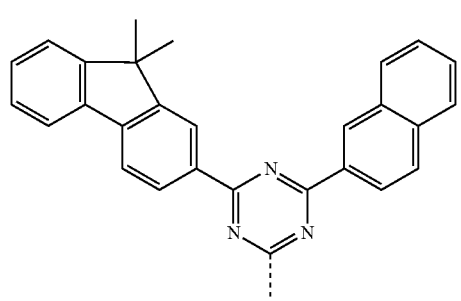
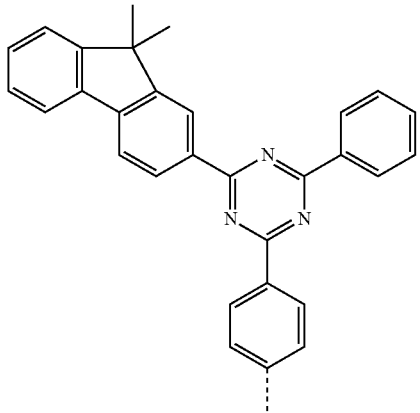
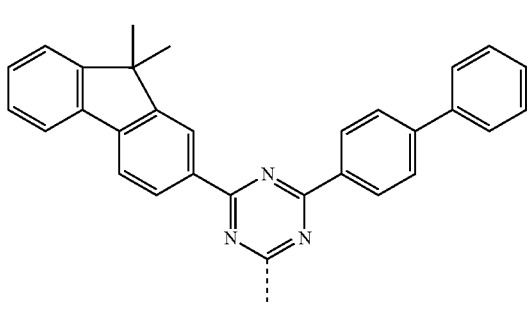
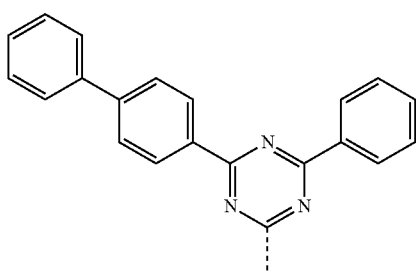

249
-continued
250
-continued
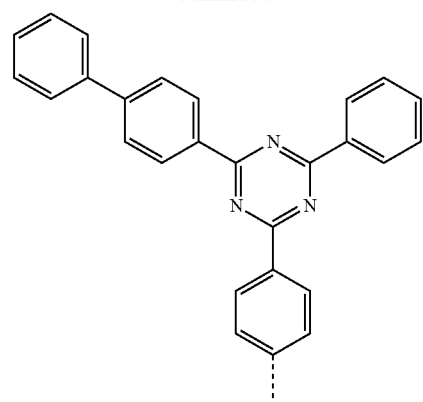
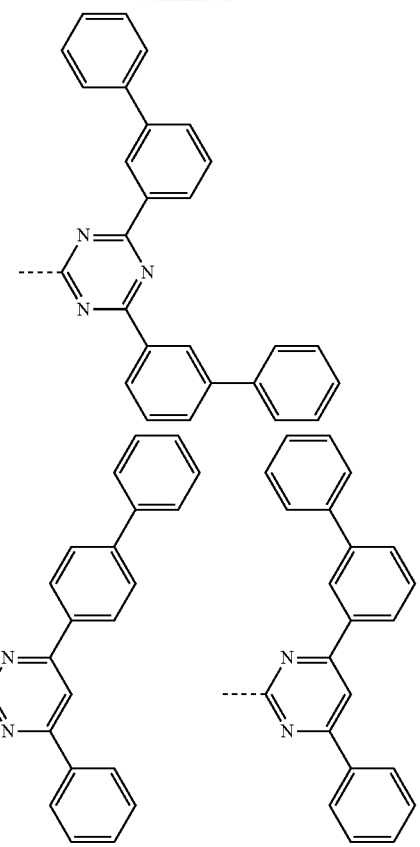
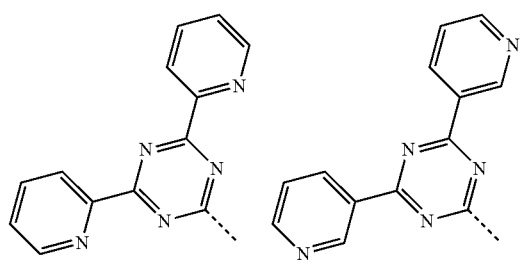
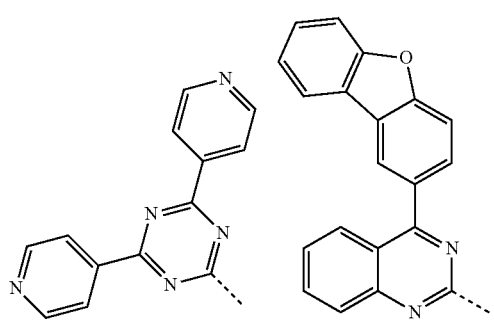
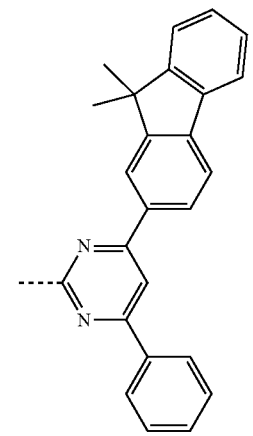
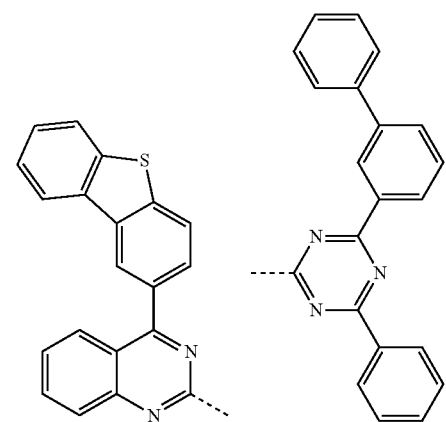
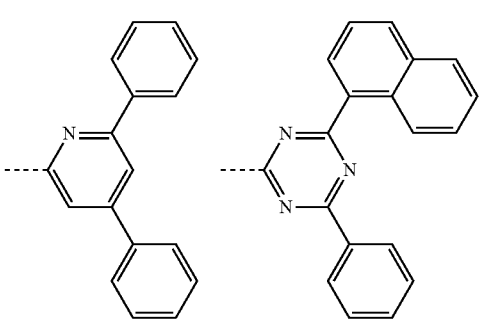

251
-continued
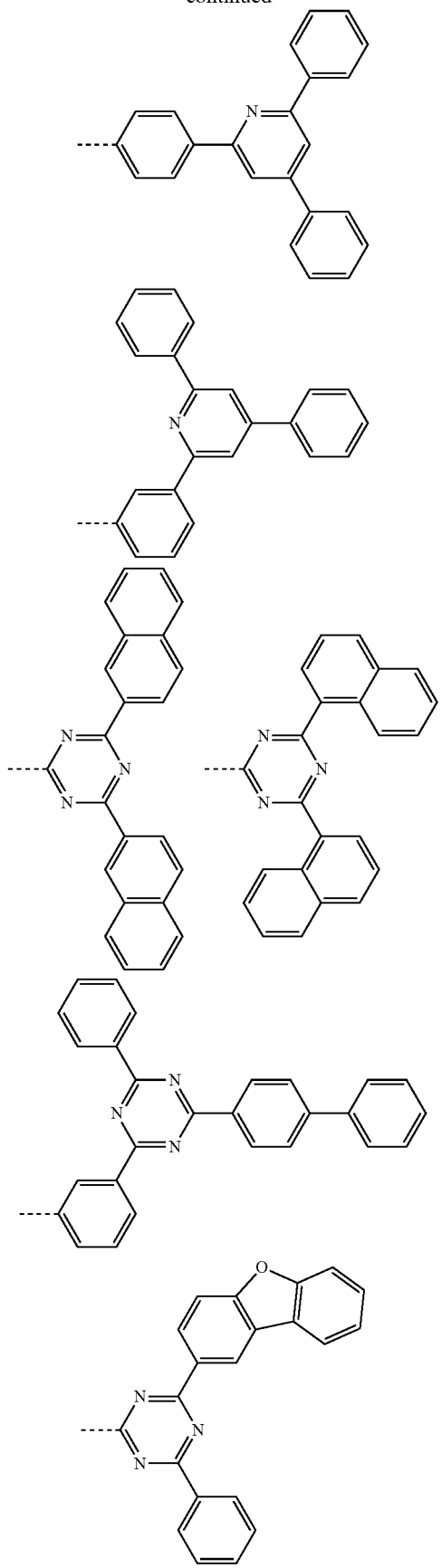
252
-continued
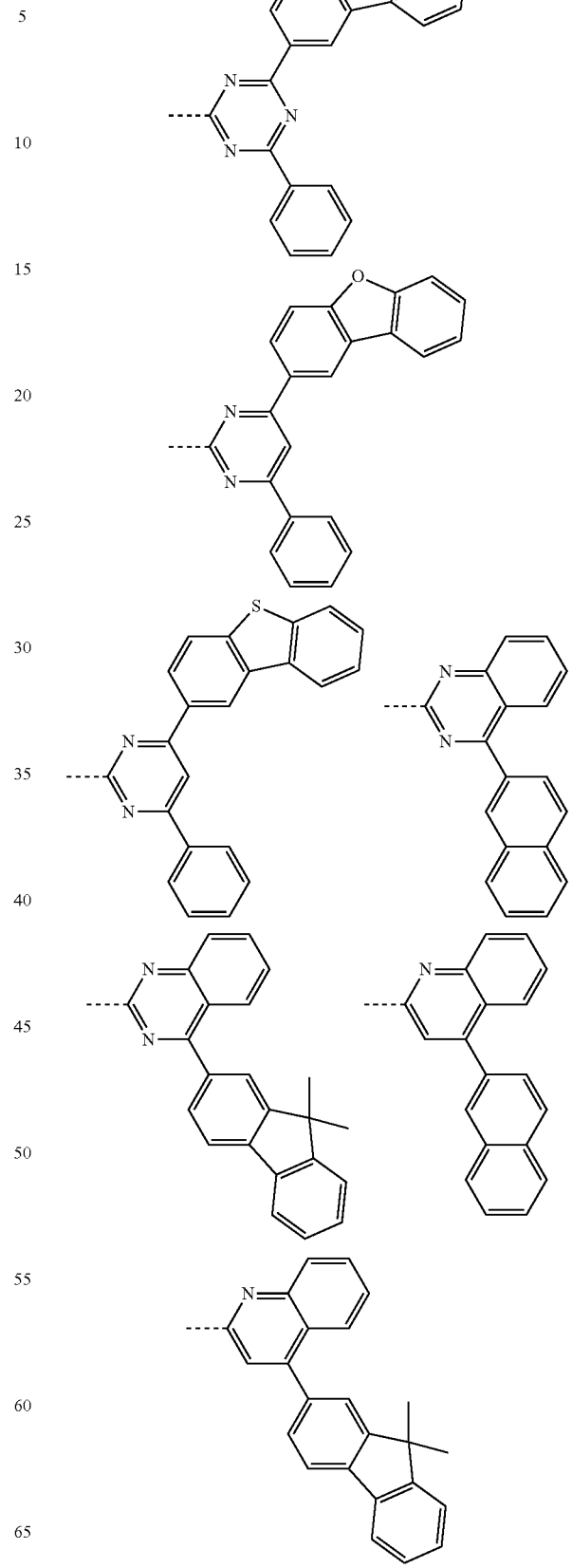

[A-5]
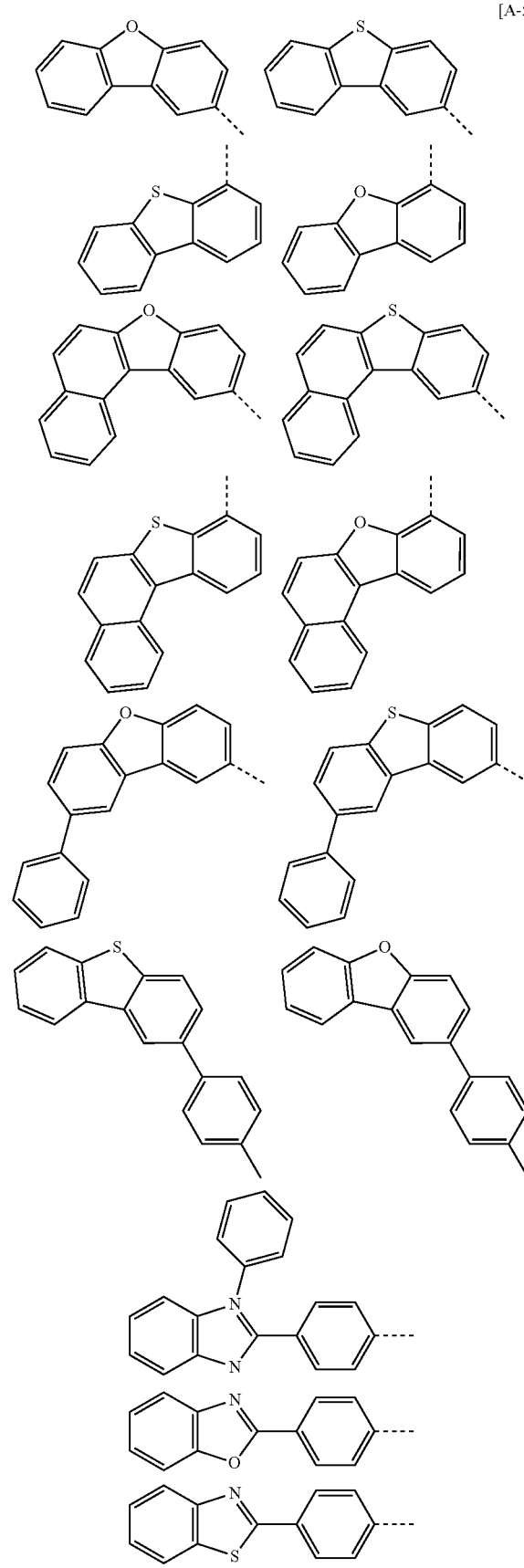
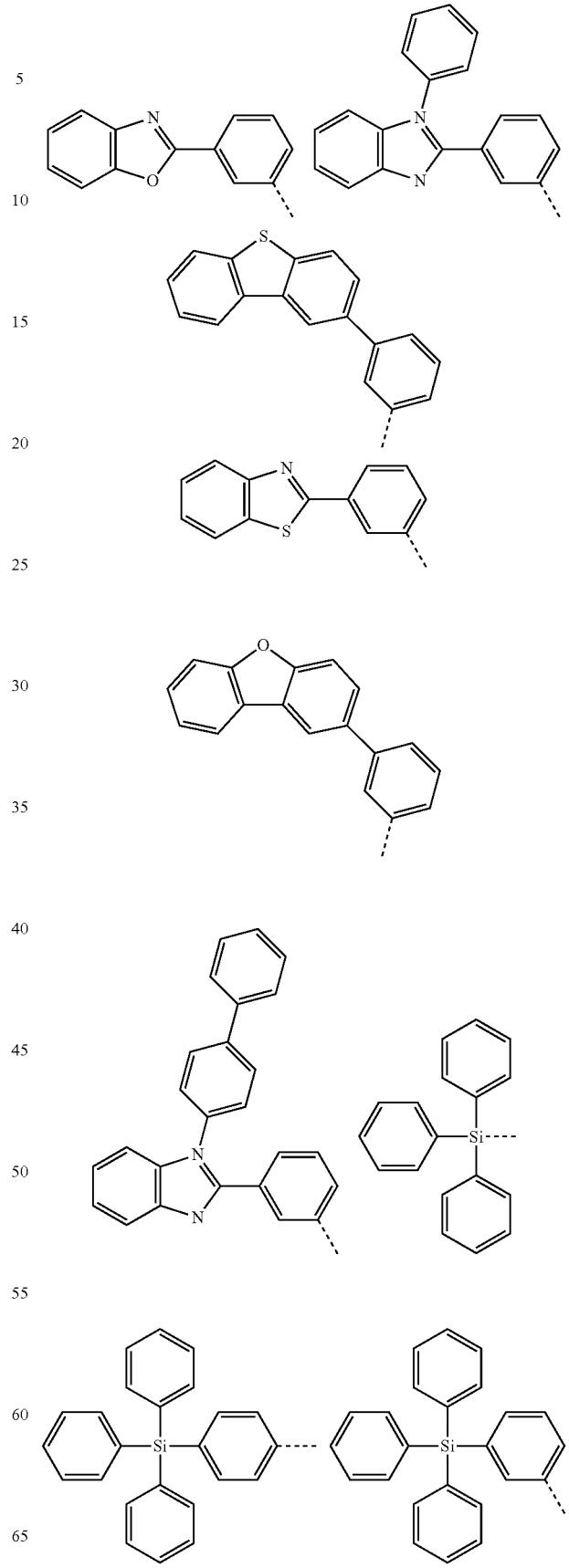

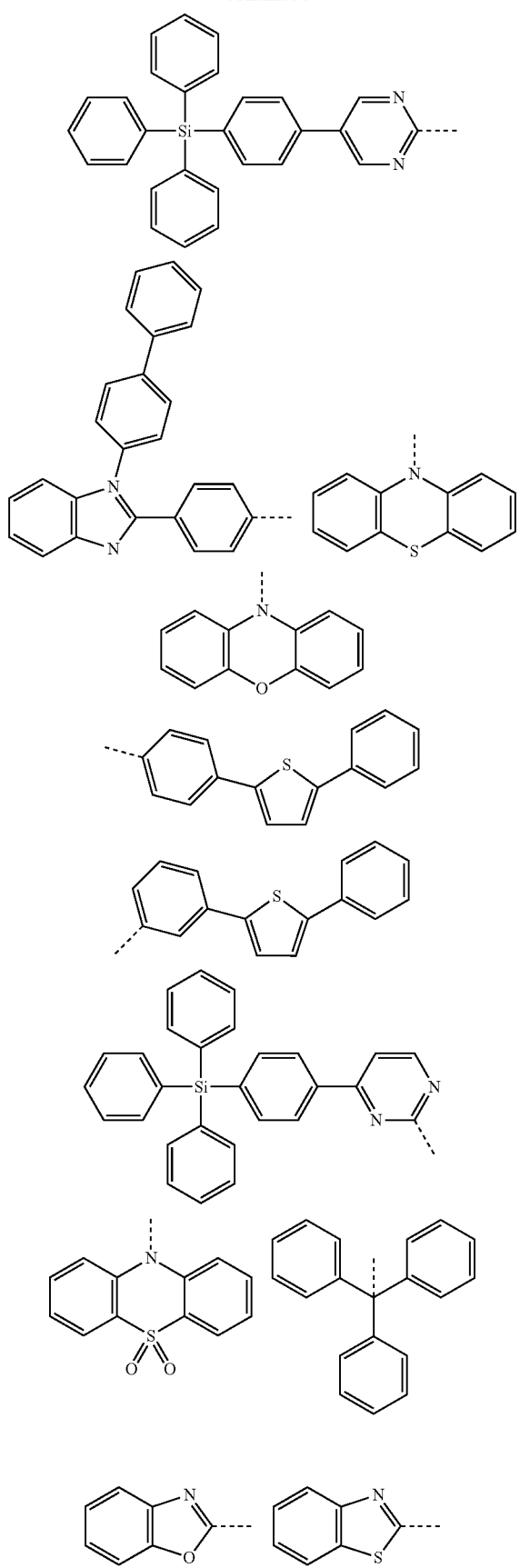
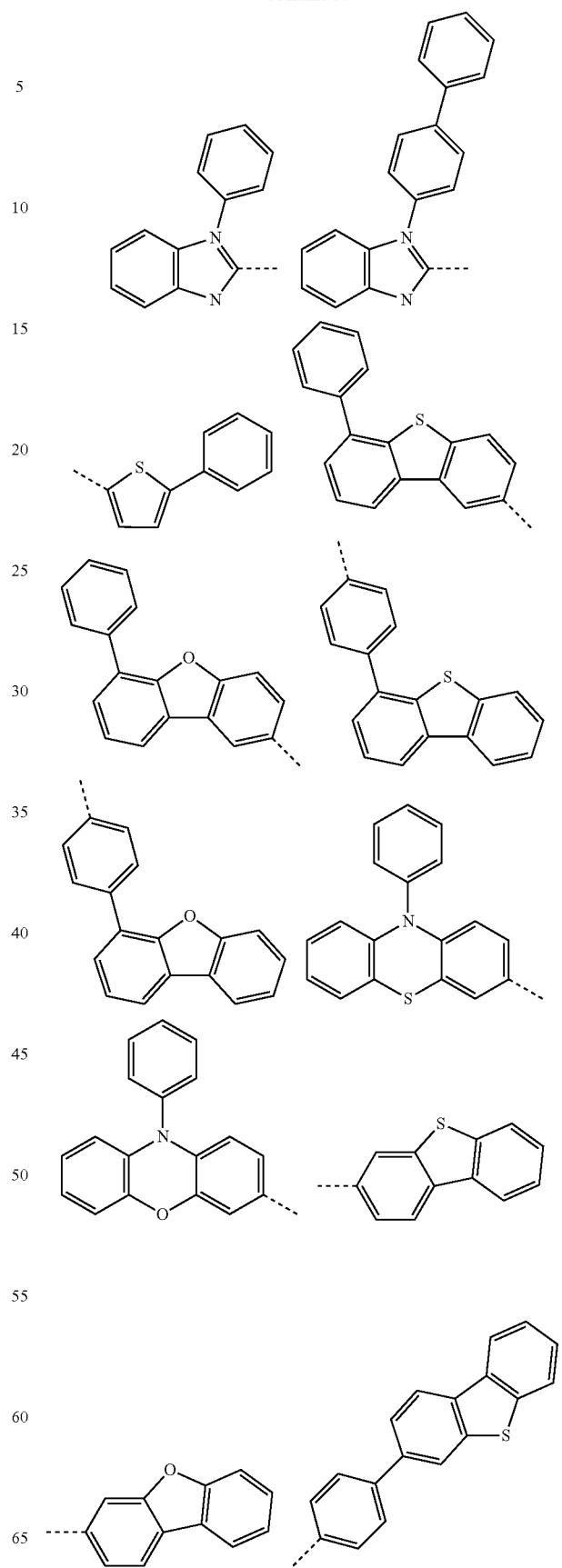

257
-continued

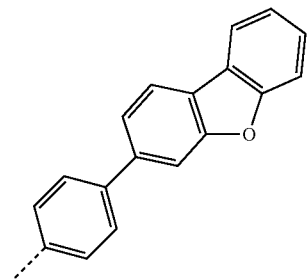

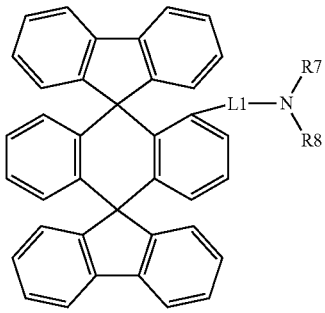

wherein, in the structural formulae, --- means a site bonding to L1 of Chemical Formula 1-1.

4. The double Spiro structure compound of claim 1, wherein Chemical Formula 1-1 is represented by any one of the following Chemical Formulae 1-2 to 1-6:

[Chemical Formula 1-2]

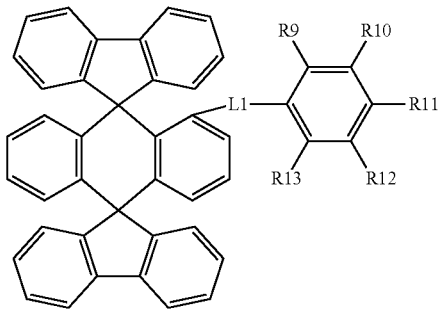

[Chemical Formula 1-3]

258
-continued

[Chemical Formula 1-4]

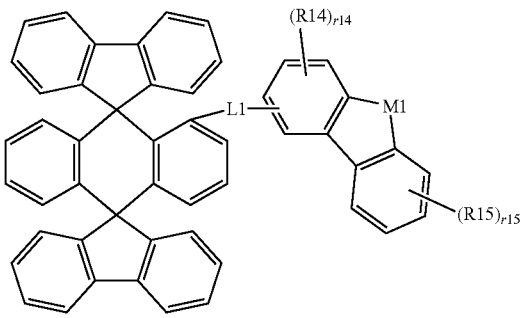

[Chemical Formula 1-5]

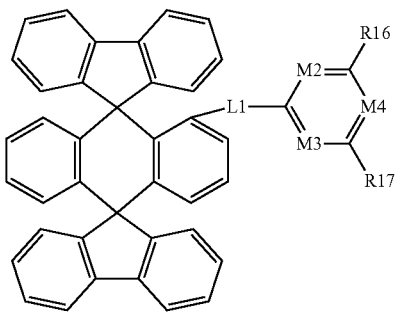

[Chemical Formula 1-6]

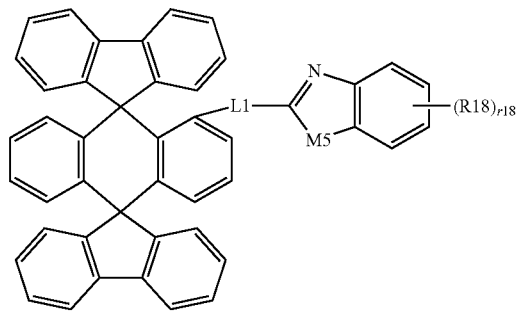

wherein, in Chemical Formulae 1-2 to 1-6,
a definition of L1 is the same as in Chemical Formula 1-1;
M1 and M5 are the same as or different from each other, and each independently O, S, NR19 or CR20R21;
M2 is N or CR22, M3 is N or CR23, M4 is N or CR24;
at least one of M2 to M4 is N;
R7 to R24 are the same as or different from each other, and each independently hydrogen; deuterium; a nitrile group; a substituted or unsubstituted alkyl group; a substituted or unsubstituted silyl group; a substituted or unsubstituted amine group; a substituted or unsubstituted aryl group; or a substituted or unsubstituted heteroaryl group, or adjacent groups bond to each other to form a substituted or unsubstituted ring;
r14, r15 and r18 are each an integer of 1 to 4; and
when r14, r15 and r18 are each 2 or more, R14s, R15s and R18s are each independently the same as or different from each other,
wherein the term "the substituted or unsubstituted" means being substituted with one, two or more substituents selected from the group consisting of deuterium; a halogen group; a nitrile group; a nitro group; an imide group; an amide group; a carbonyl group; an ester group; a hydroxyl group; an alkyl group; a cycloalkyl group; an alkoxy group; an aryloxy group; an alkylthioxy group; an arylthioxy group; an alkylsulfoxy group; an arylsulfoxy group; an alkenyl group; a silyl group; a boron group; an amine group; an arylphosphine group; an aryl group; and a heterocyclic group, or being substituted linking two or more substituents among the substituents illustrated above, or having no substituents.

5. The double spiro structure compound of claim 1, wherein Chemical Formula 1-1 is represented by any one of the following compounds:

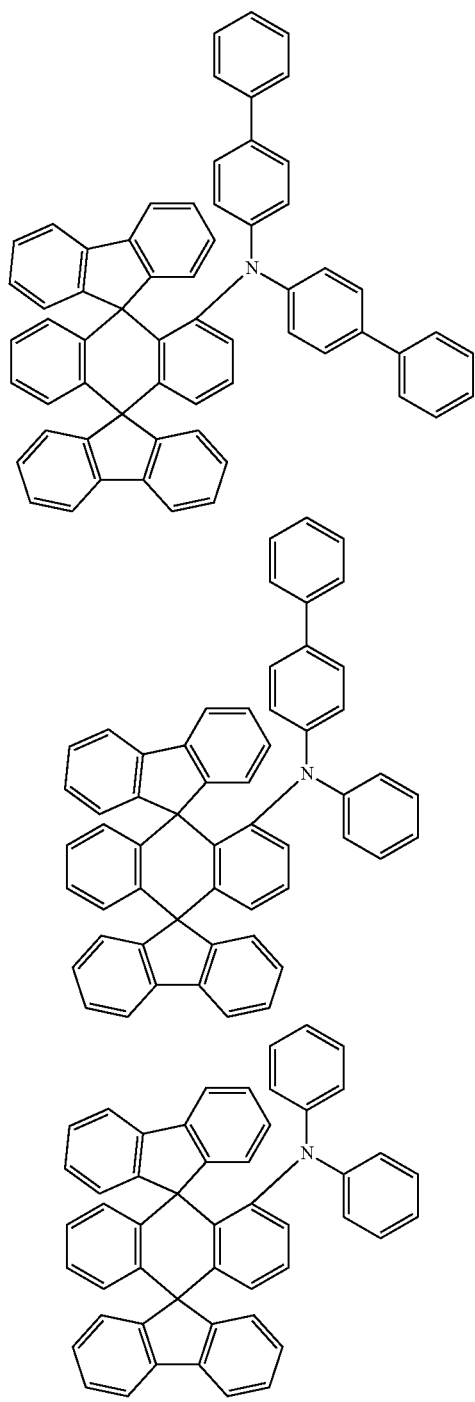

-continued

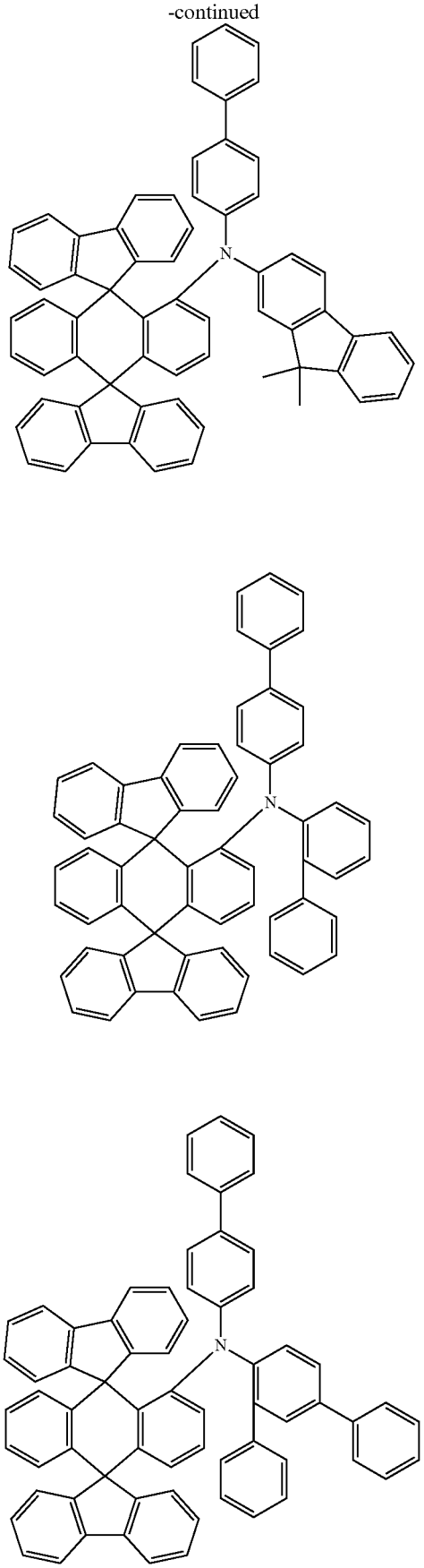

-continued
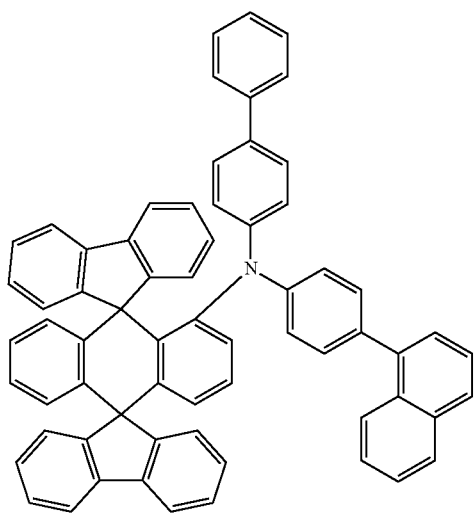
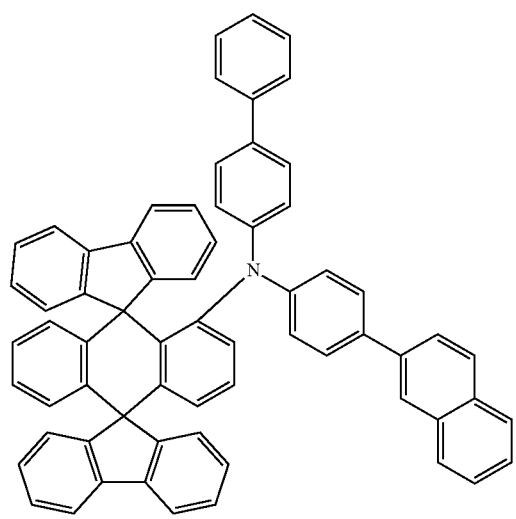
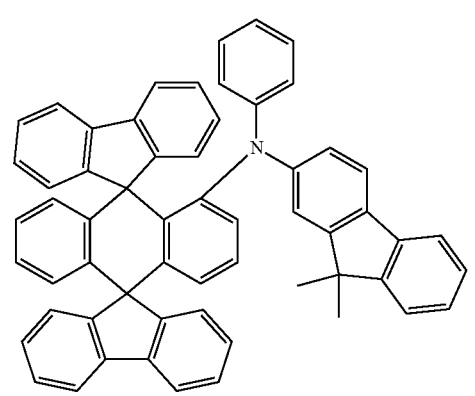
-continued
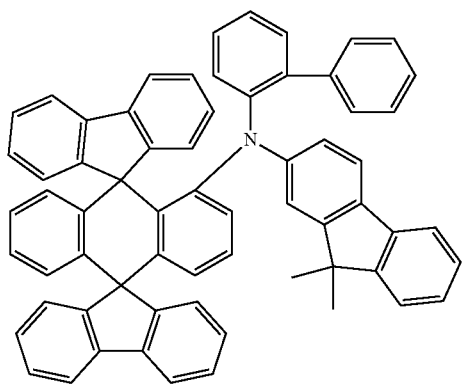
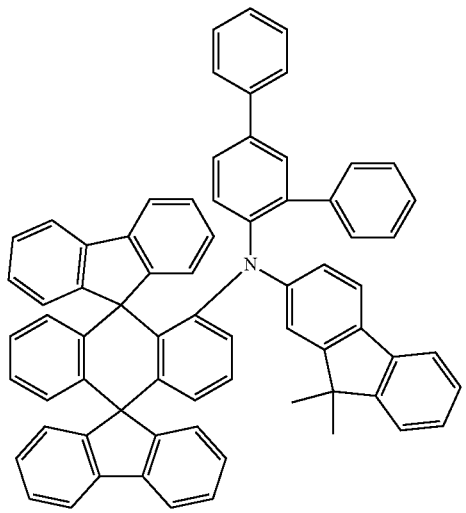
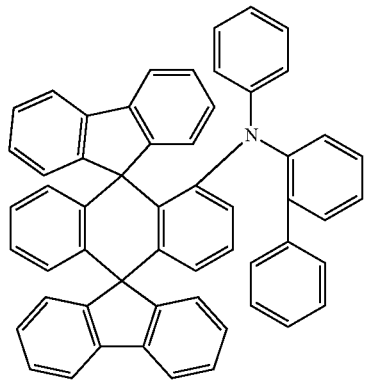
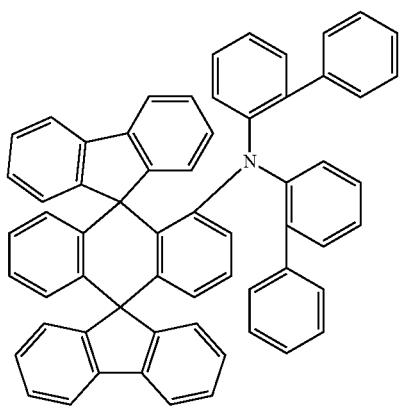

263
-continued
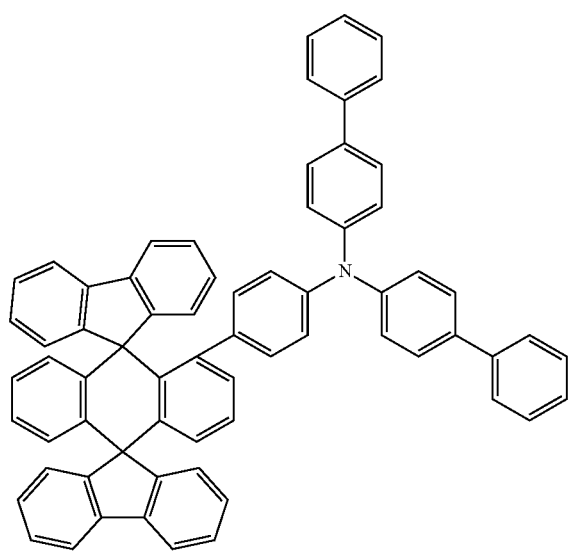
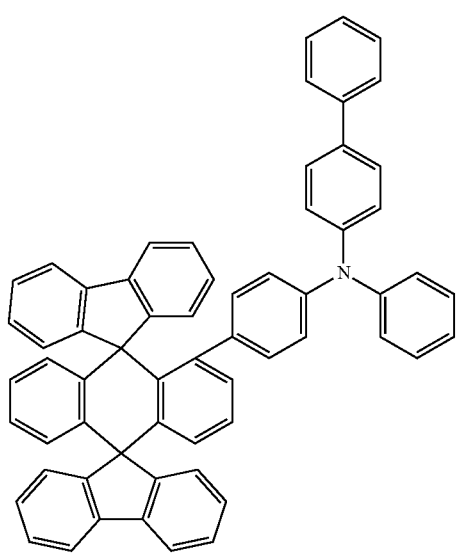
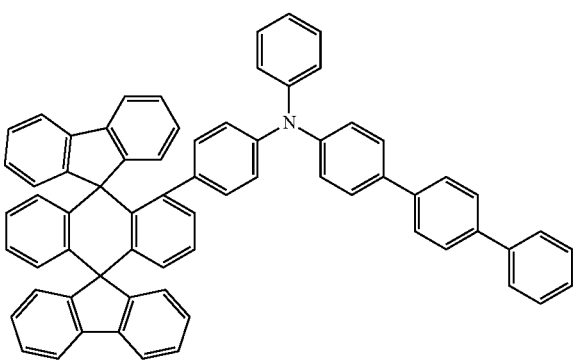
264
-continued
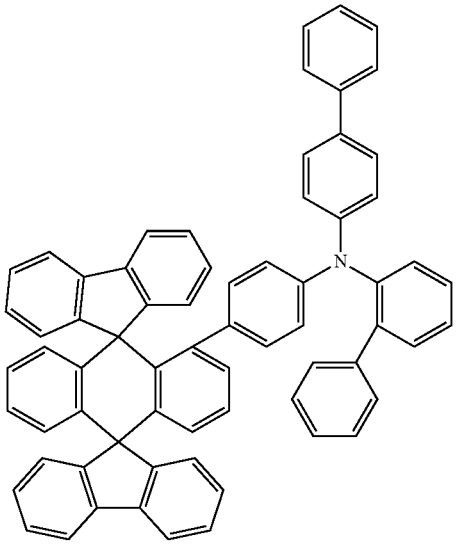
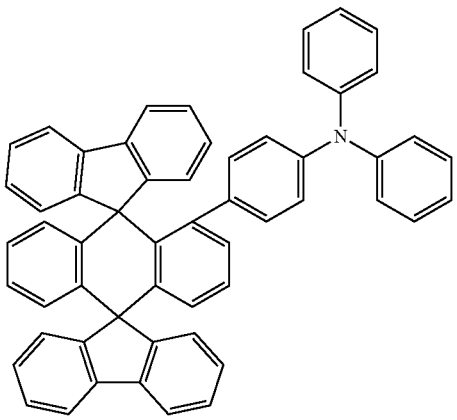
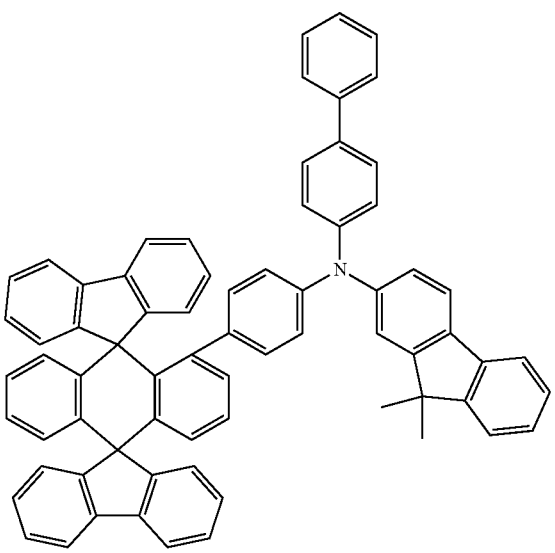

265
-continued
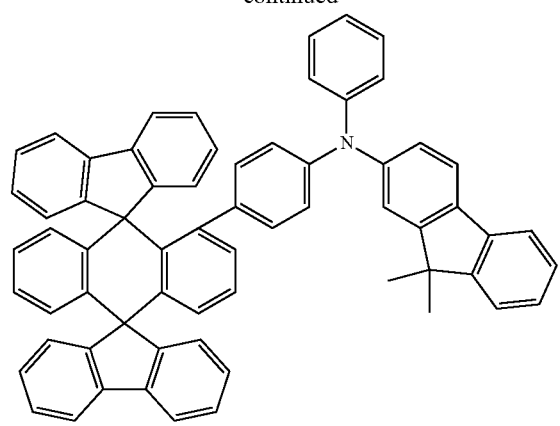
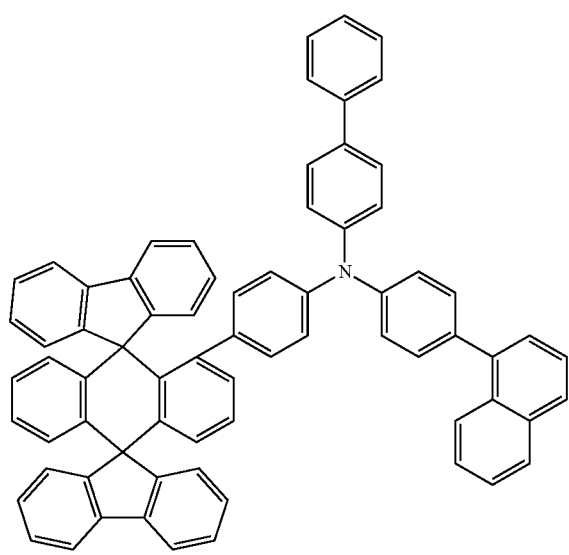
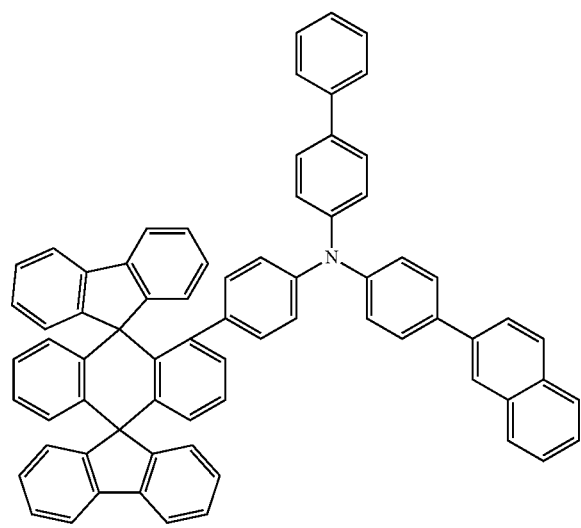
266
-continued
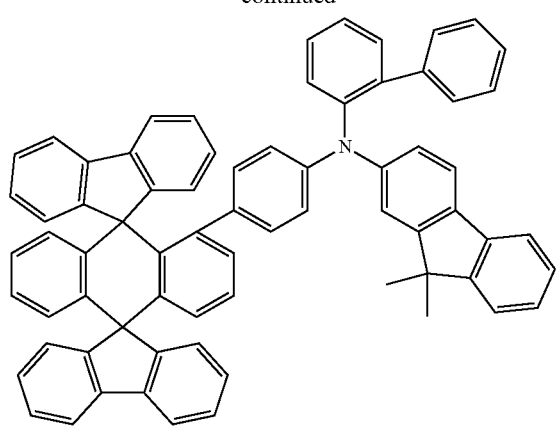
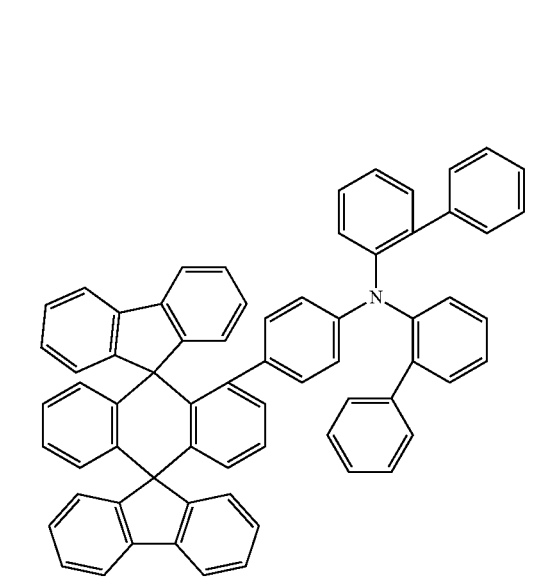

267
-continued
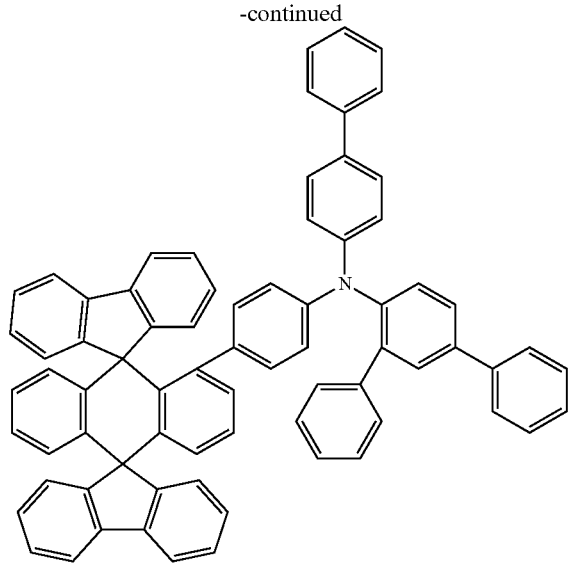
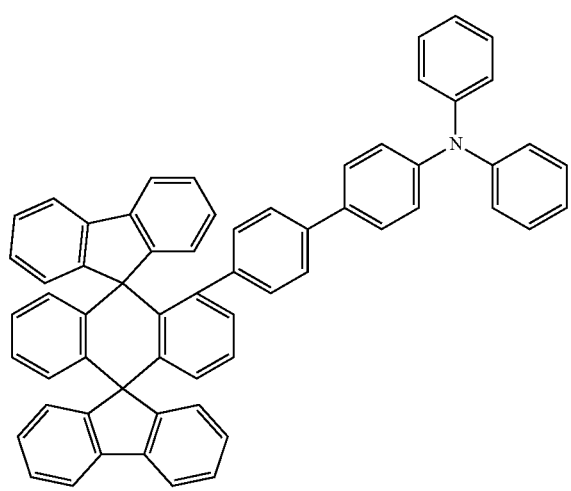
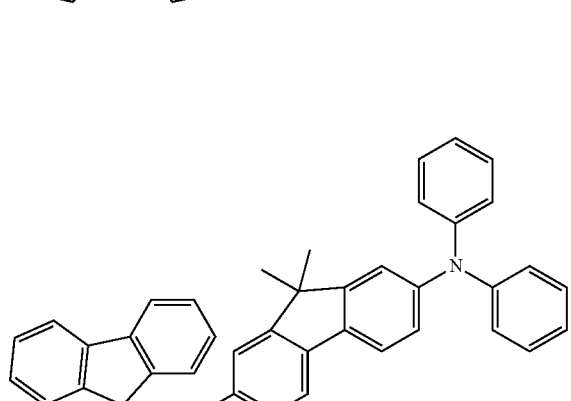
268
-continued
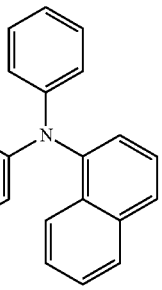
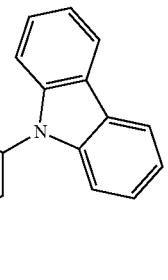
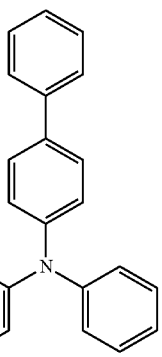

269
-continued
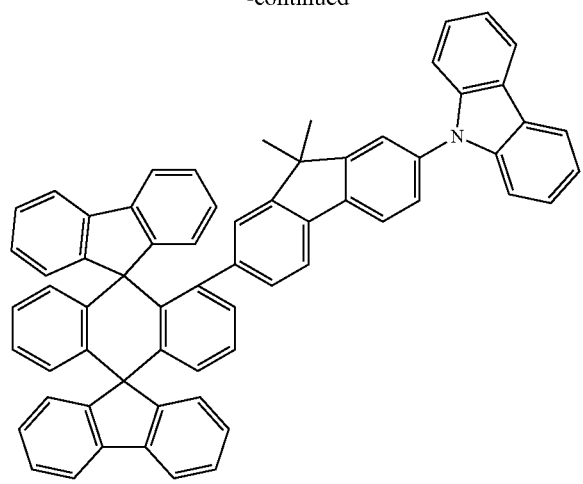
270
-continued
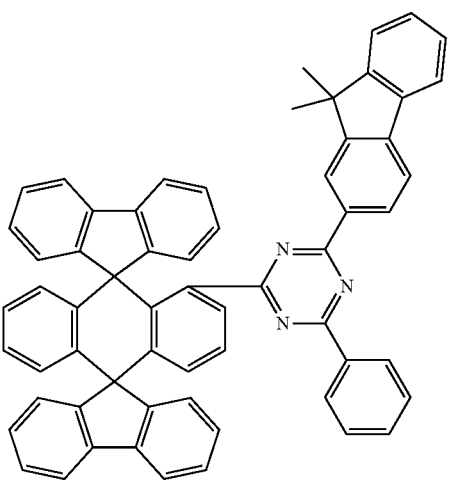
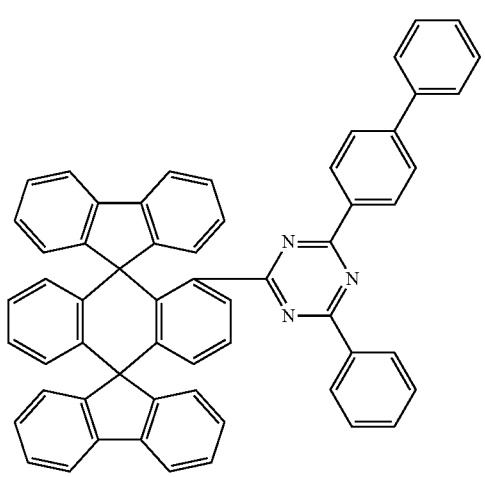
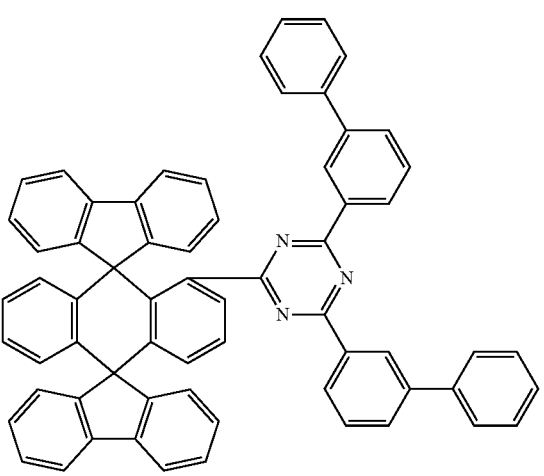
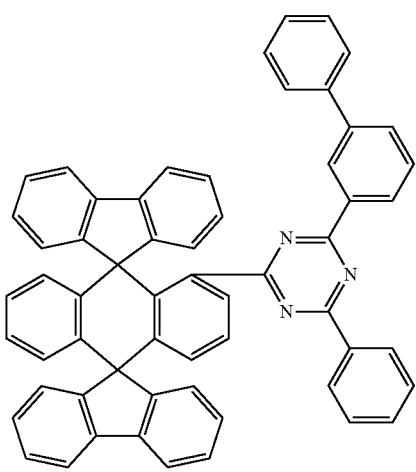
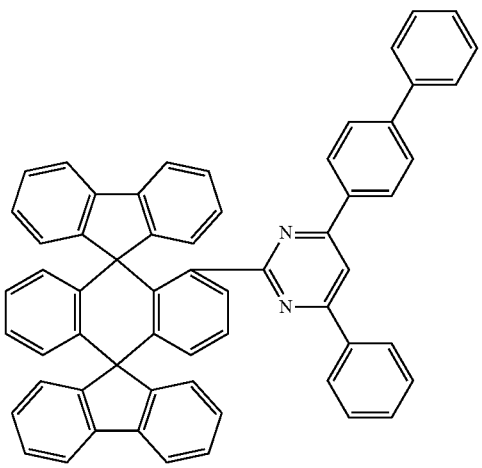

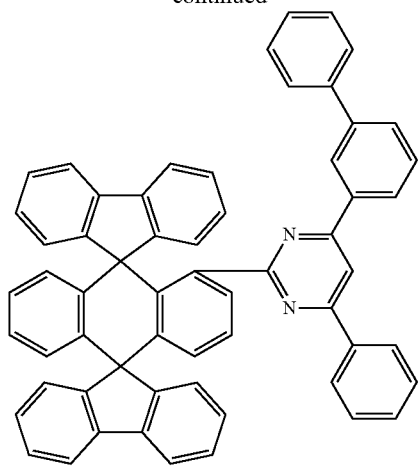
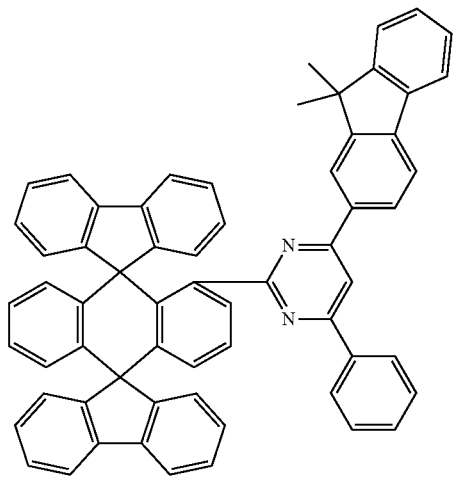
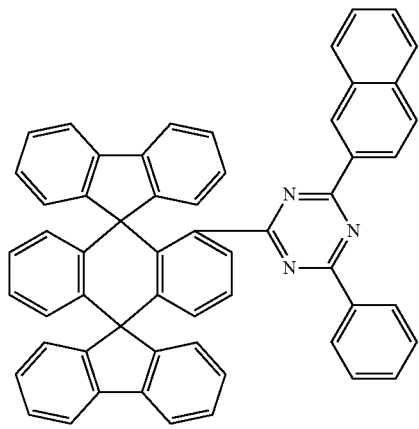
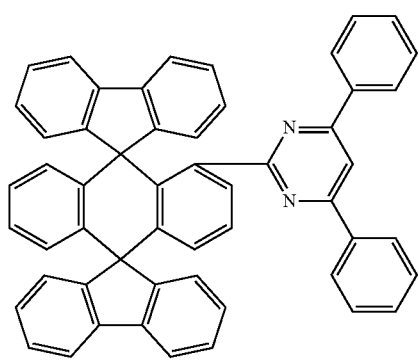
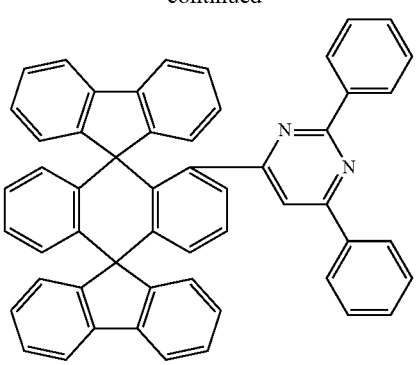
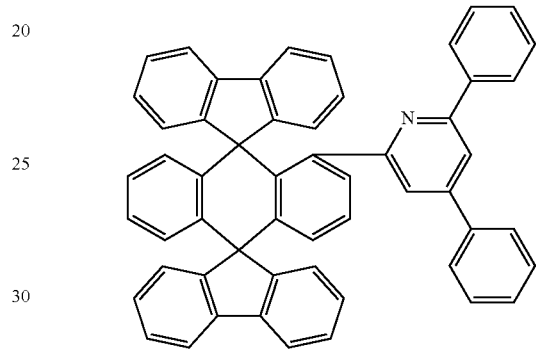
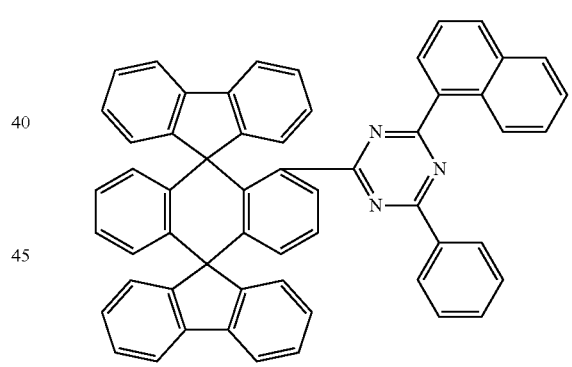
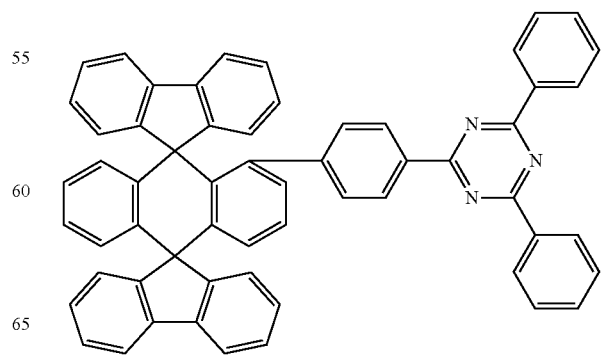

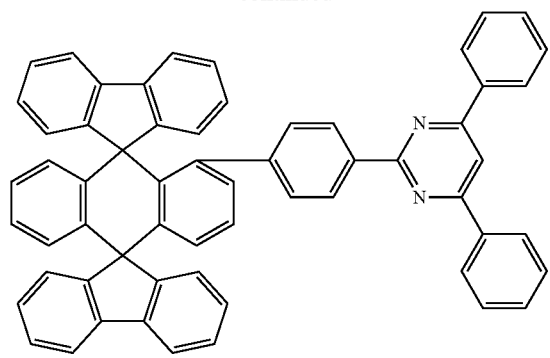
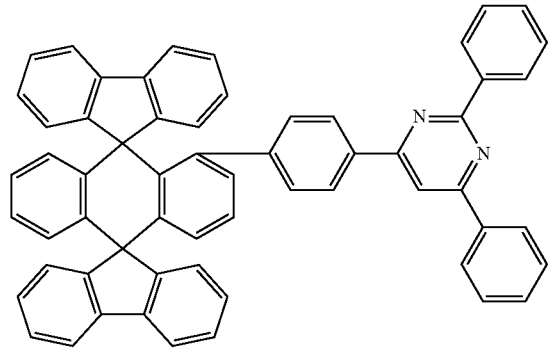
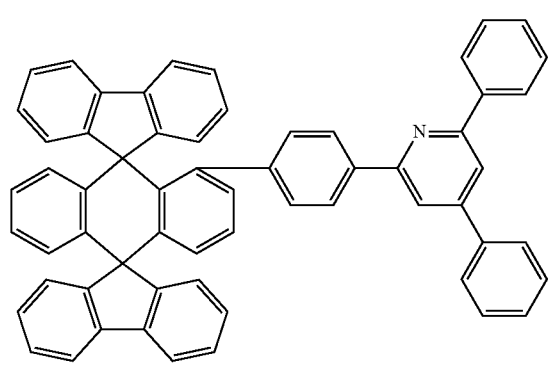
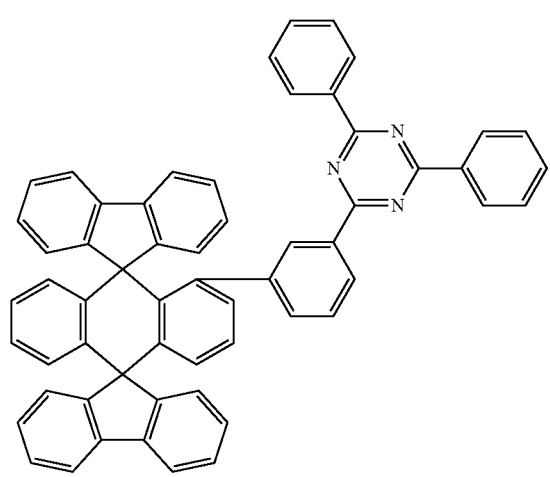
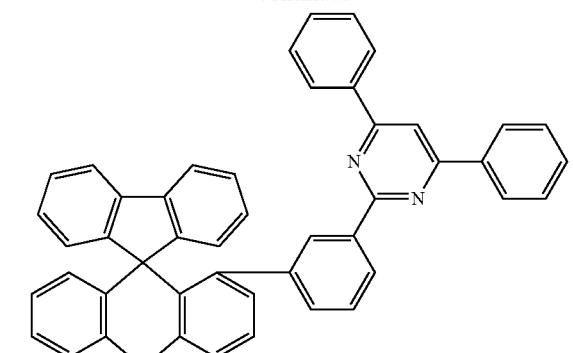
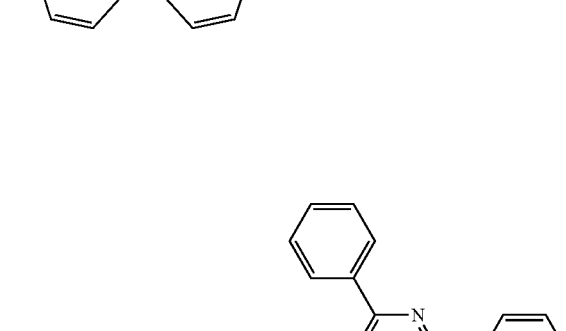
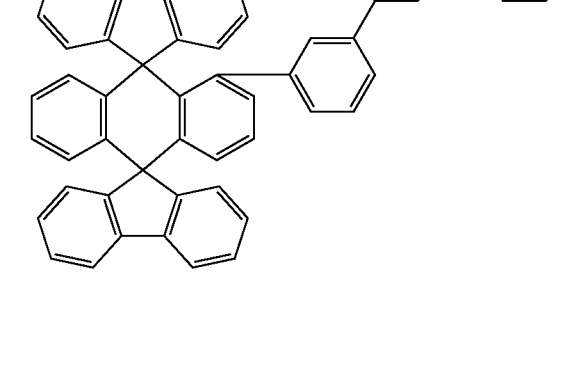
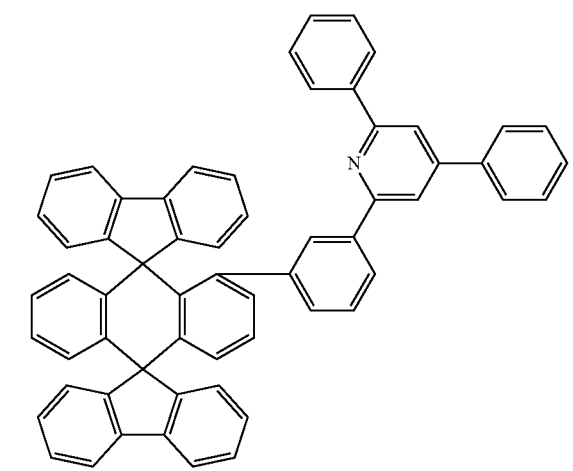

275
-continued
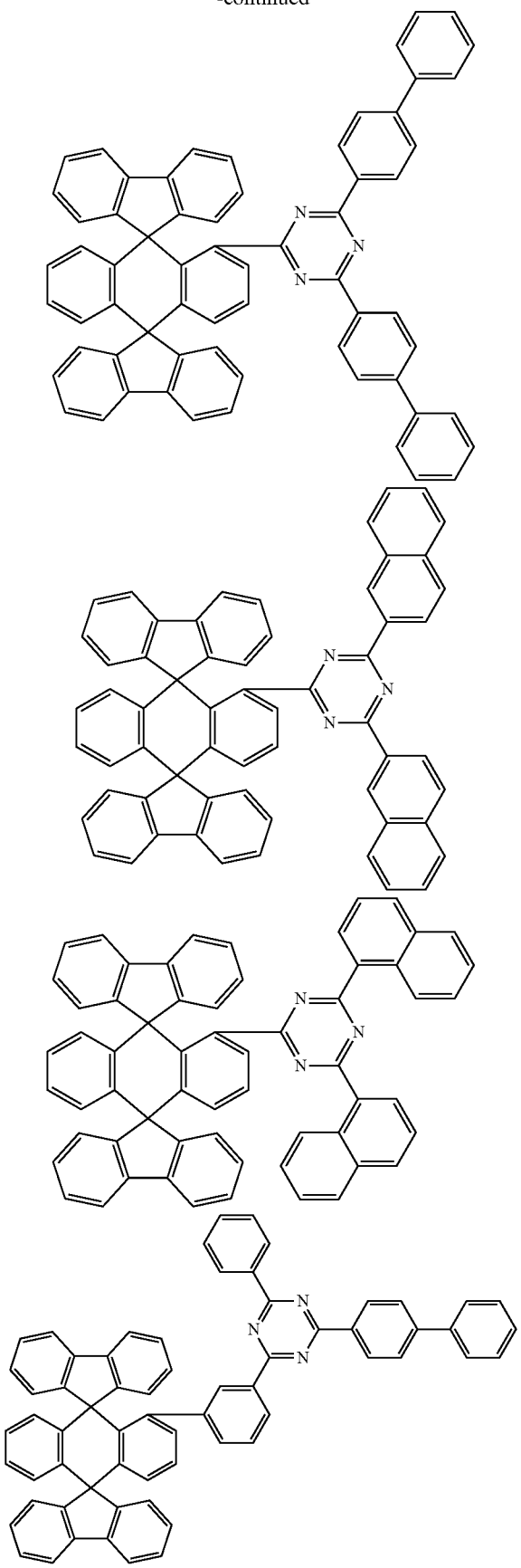
276
-continued
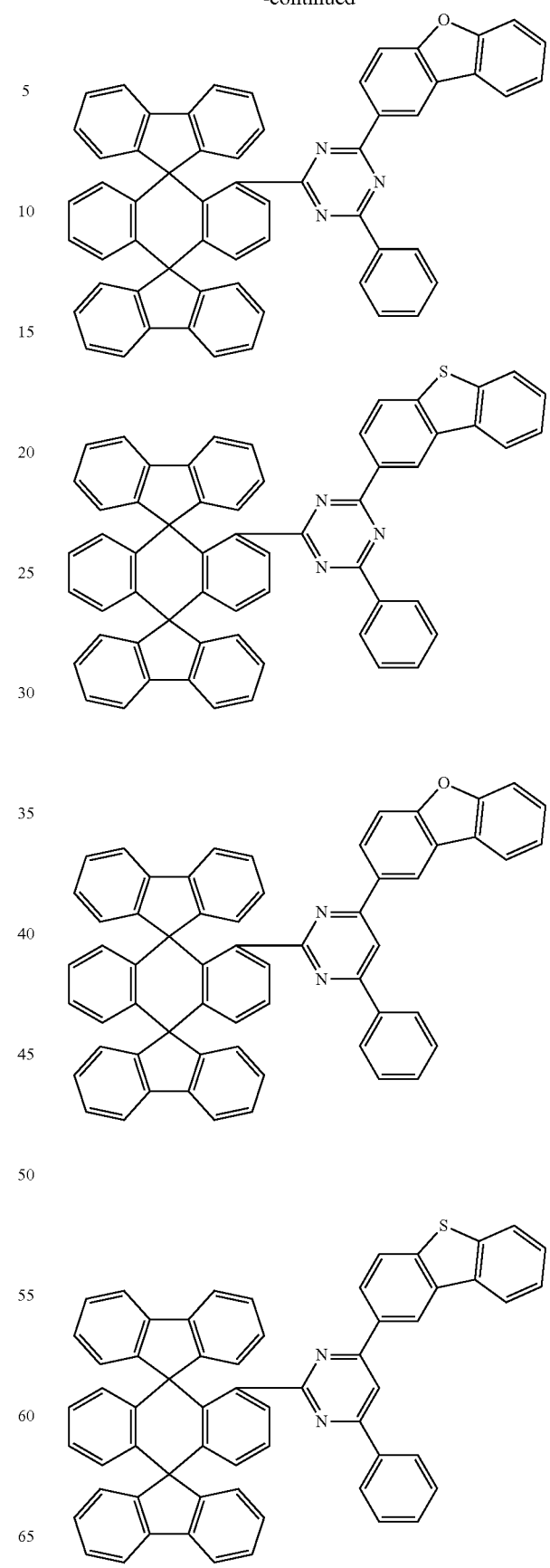

277
-continued
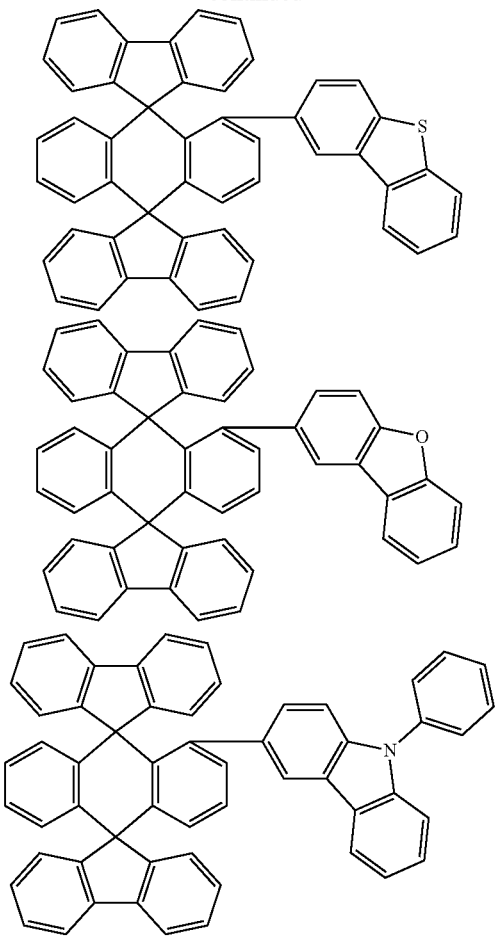
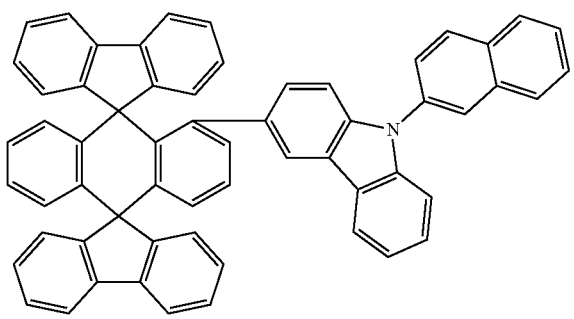
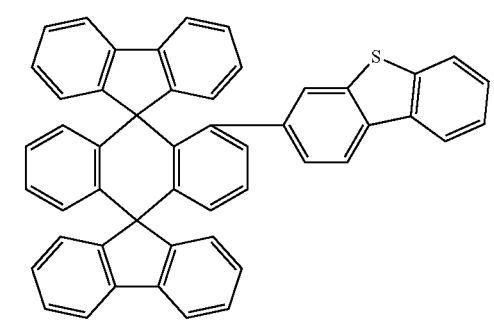
278
-continued
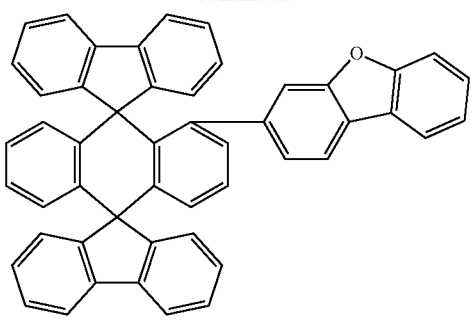
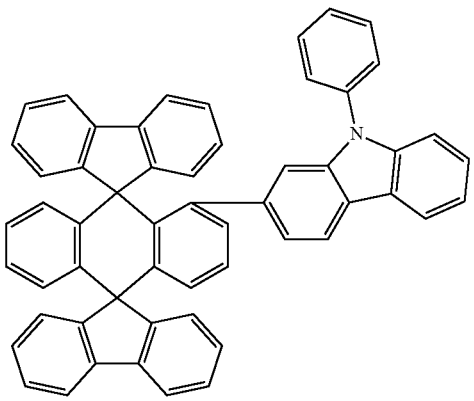
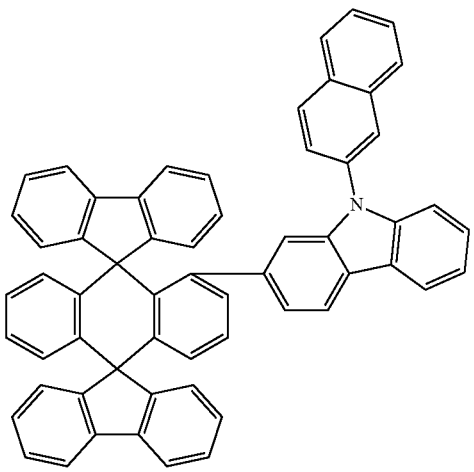
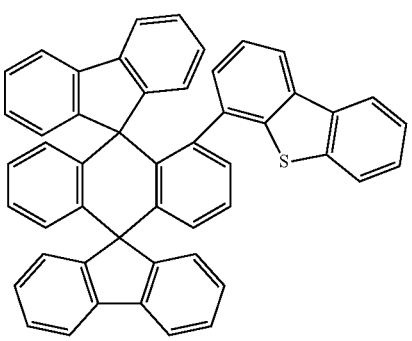

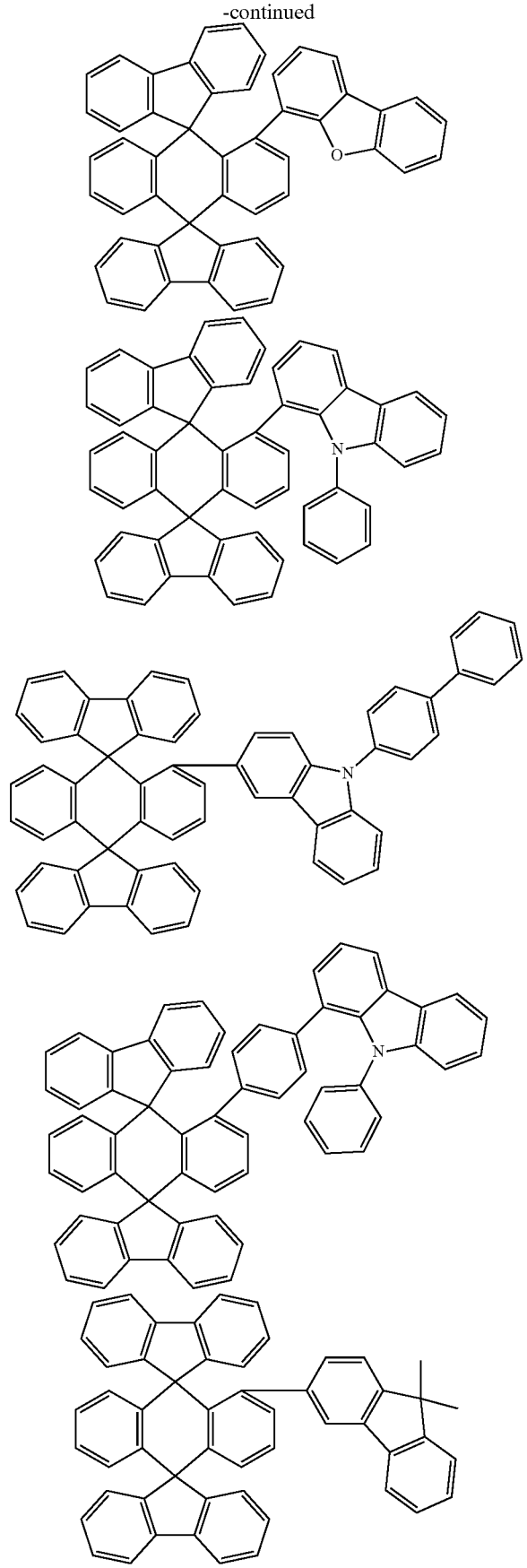

281
-continued
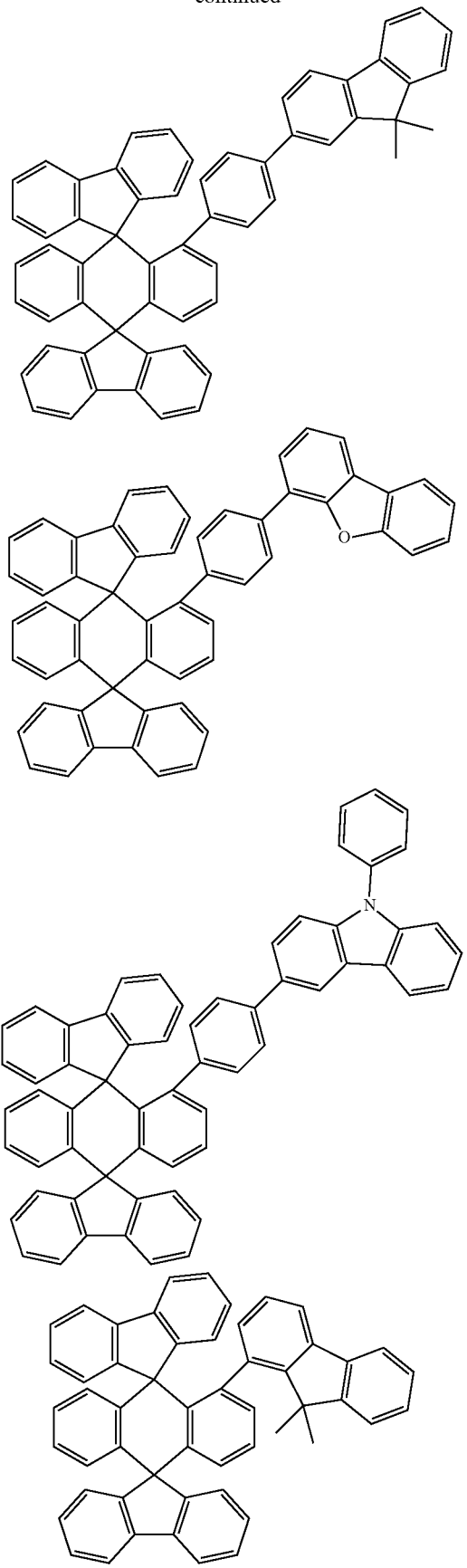
282
-continued
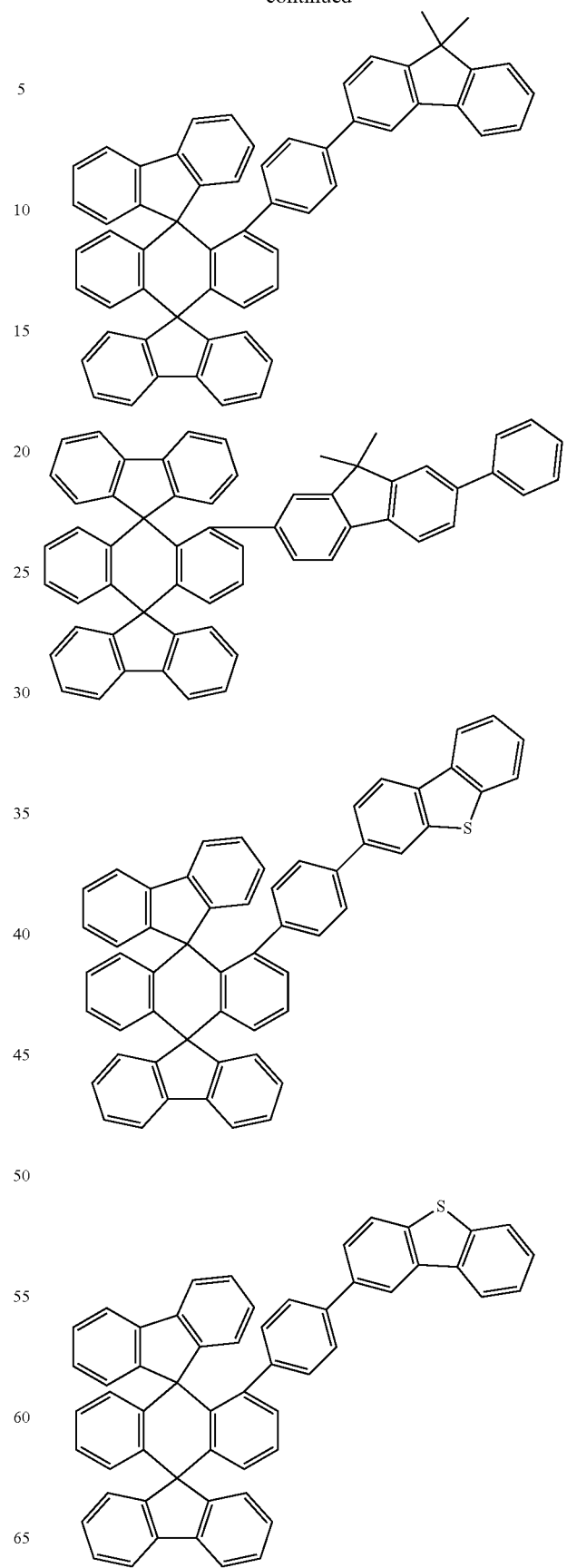

283
-continued
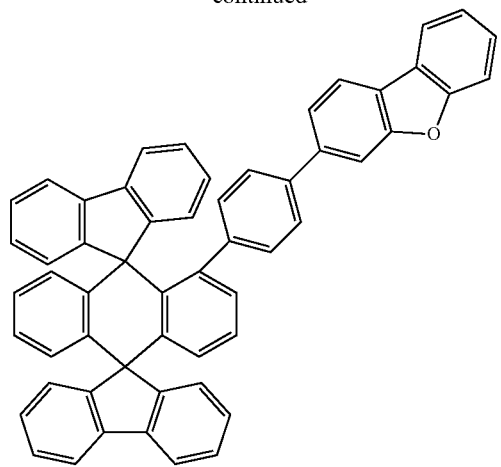
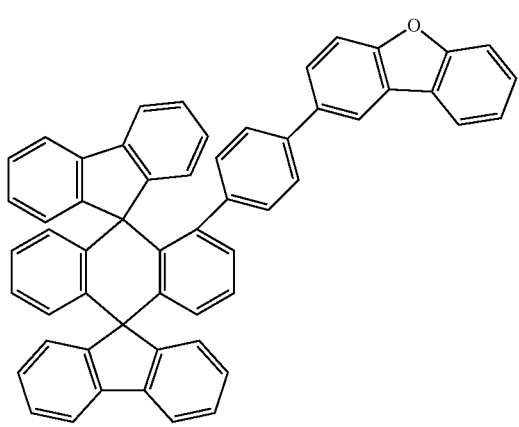
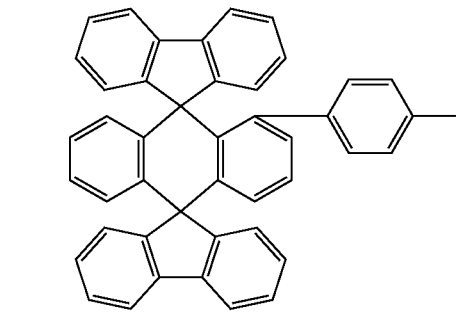
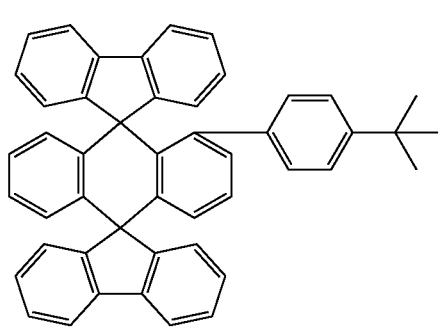
284
-continued
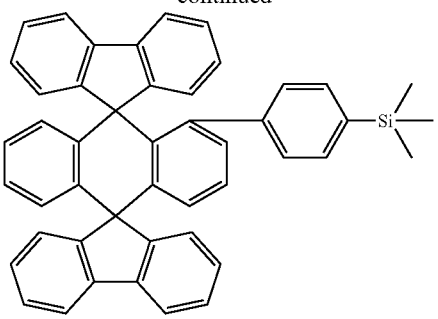
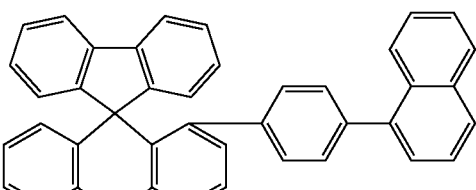
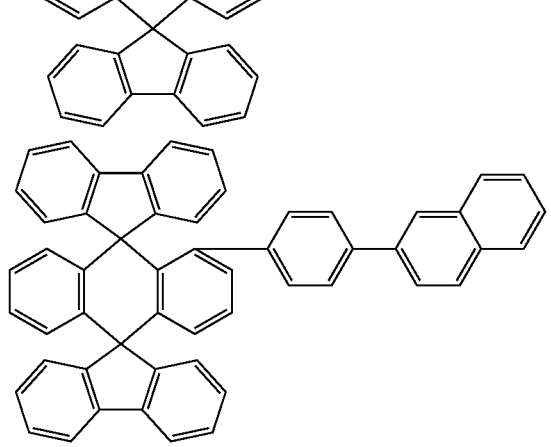
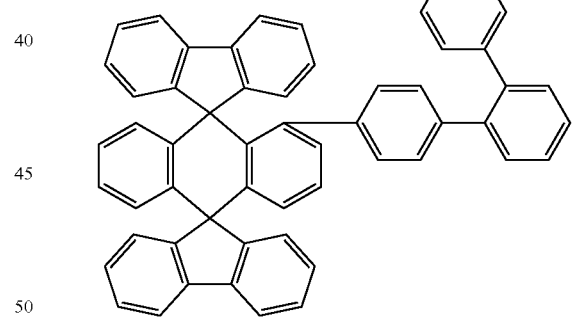
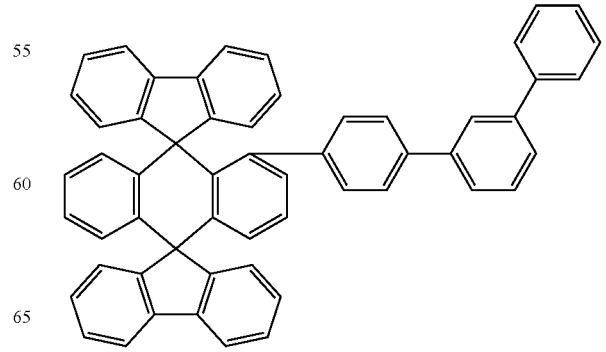

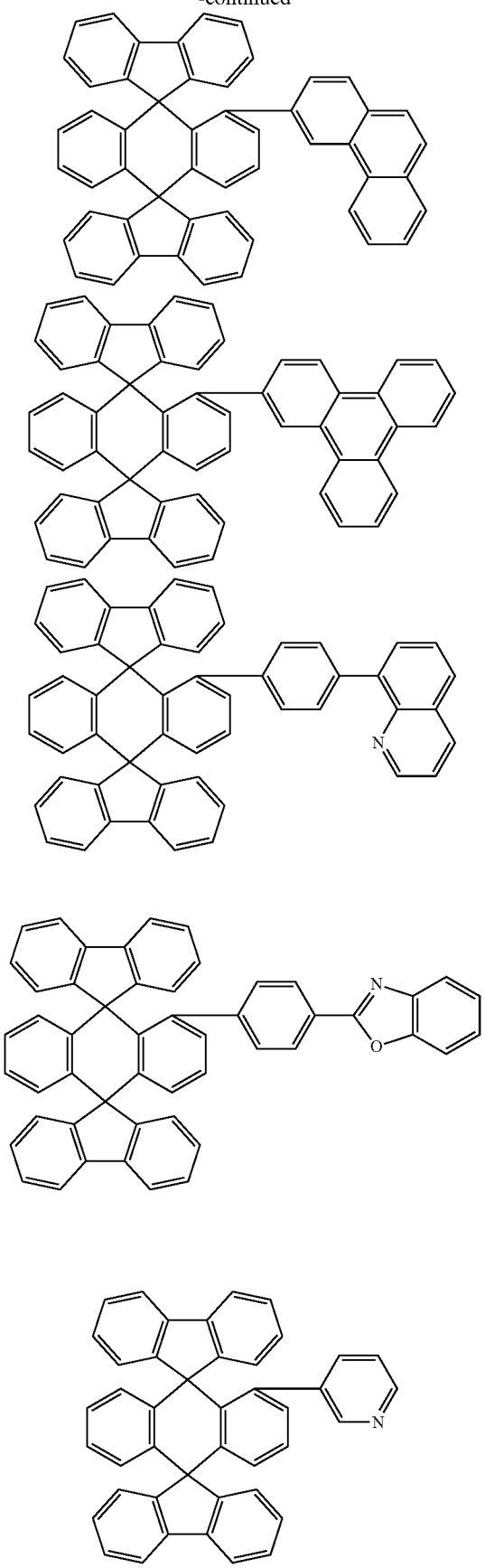
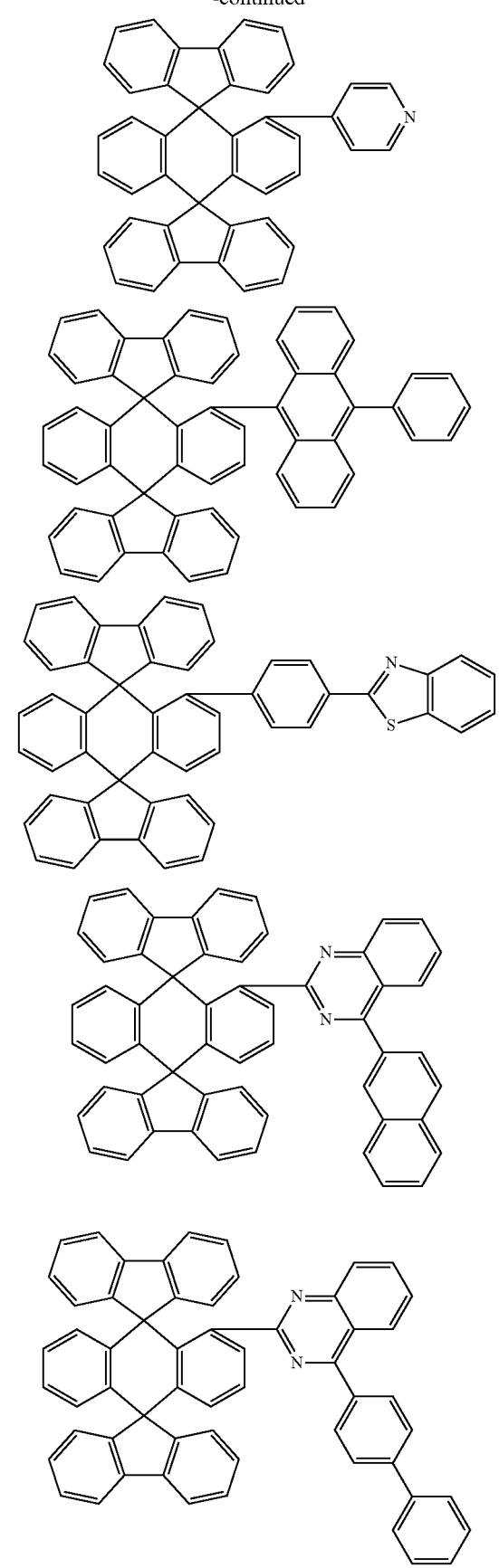

287
-continued
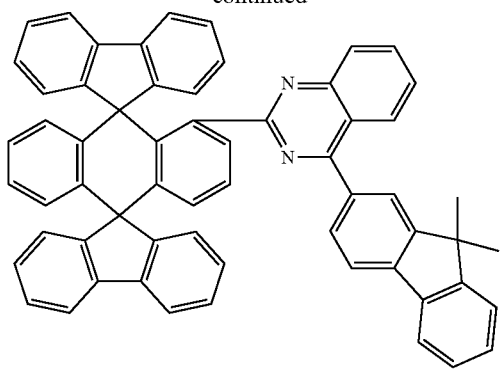
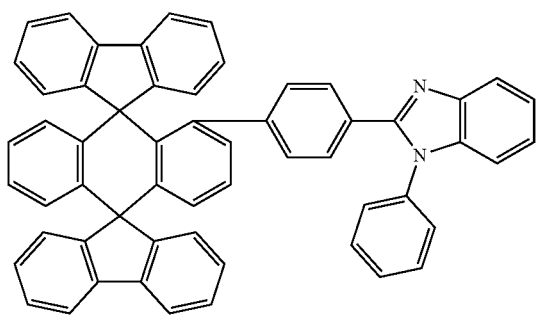
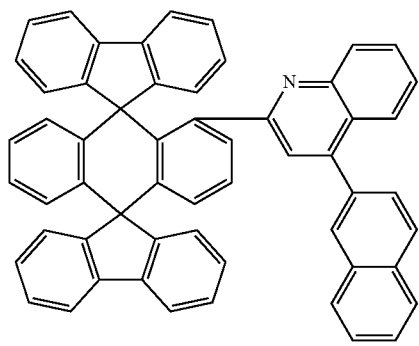
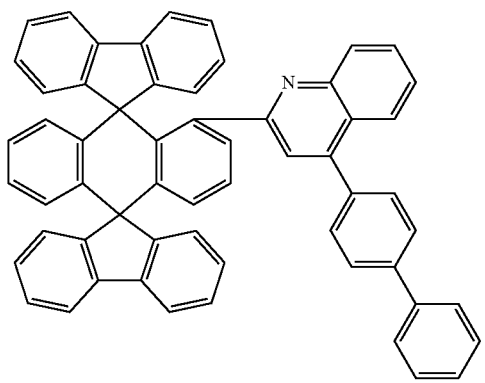
288
-continued
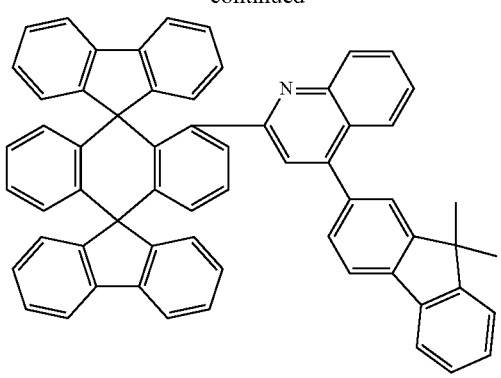
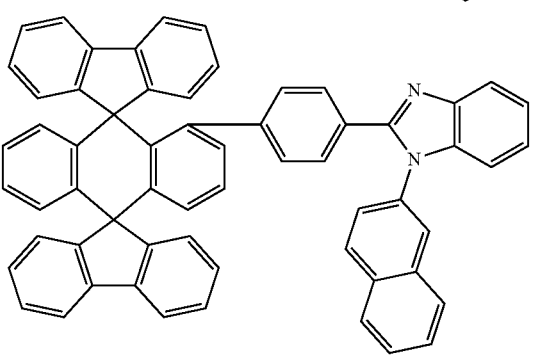
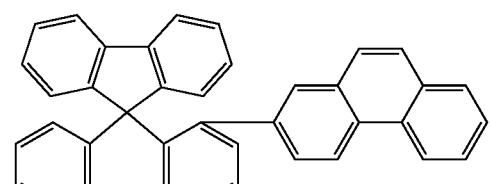
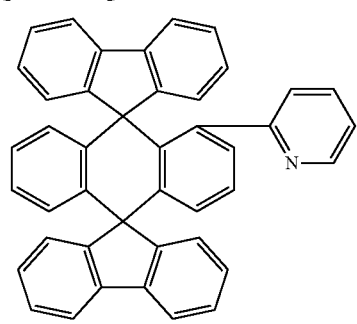
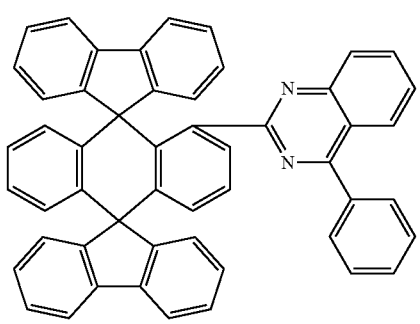

289
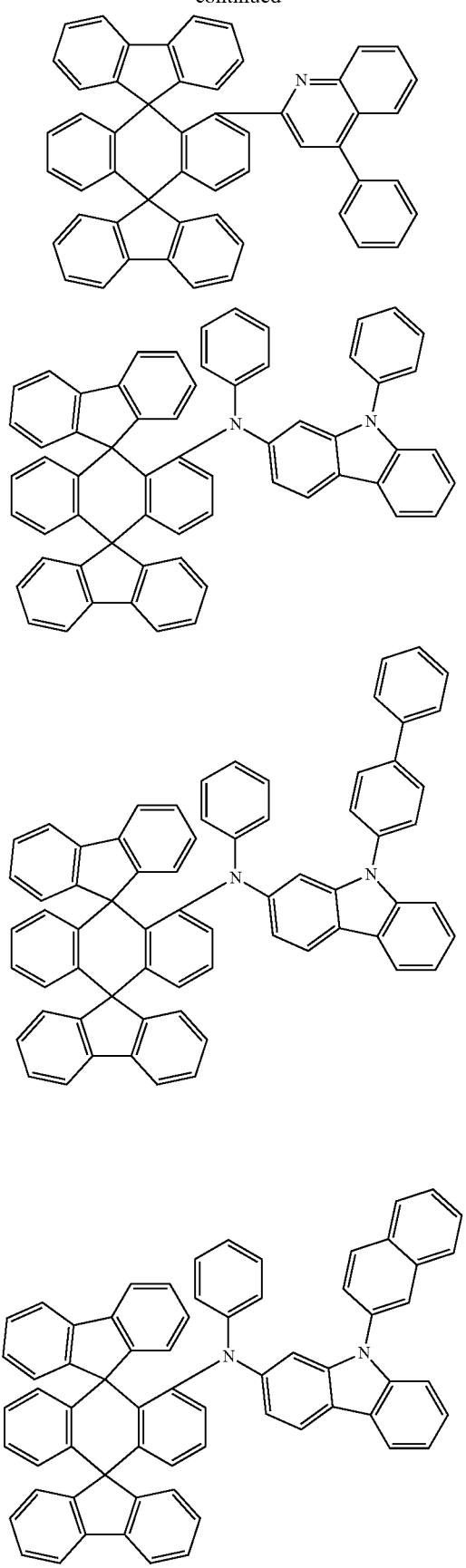
290
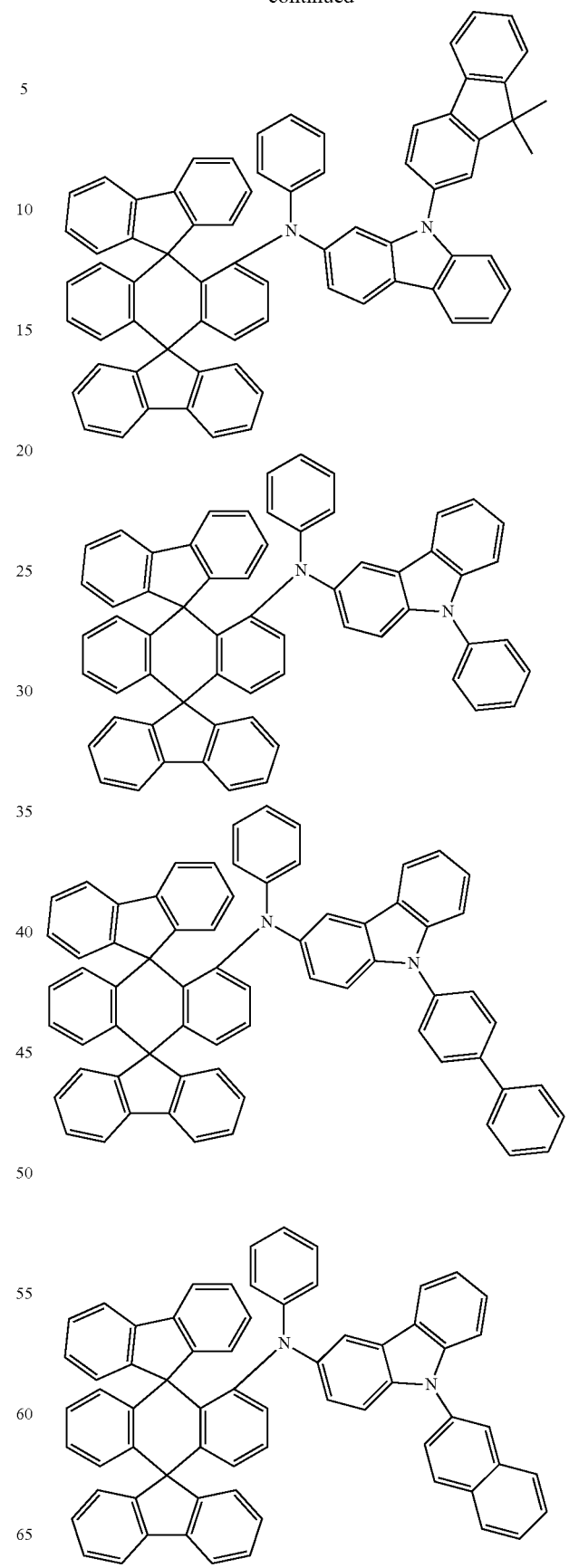

291
-continued
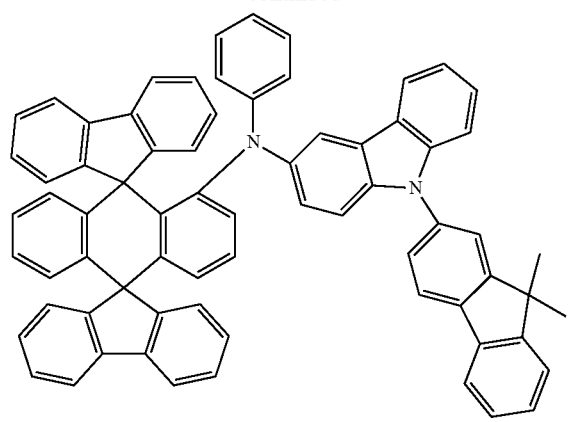
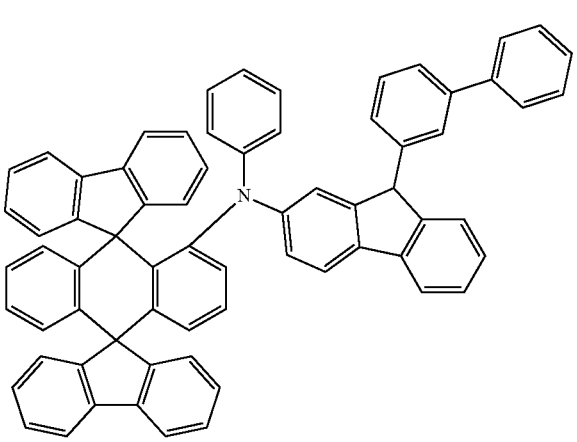
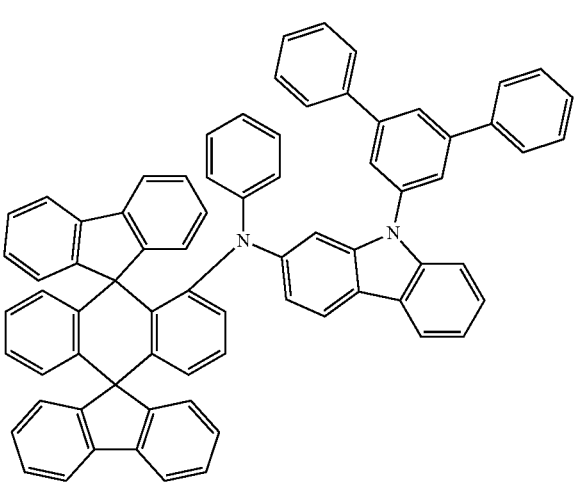
292
-continued
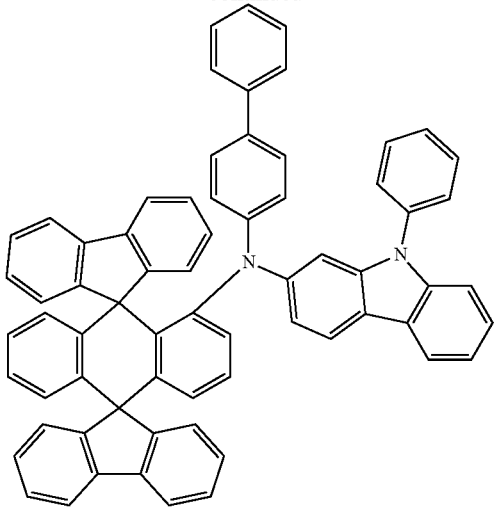
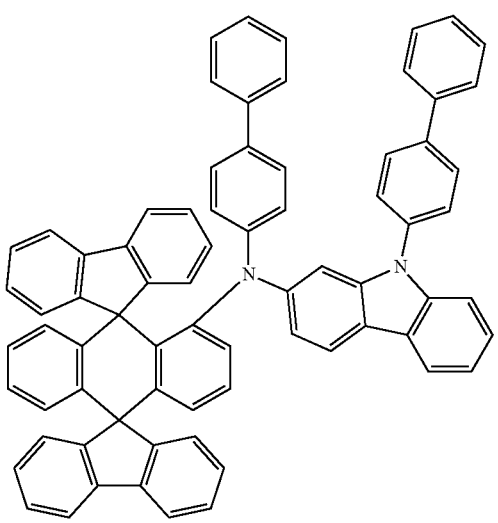
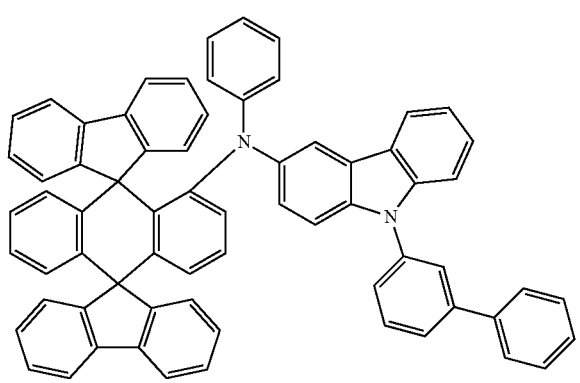

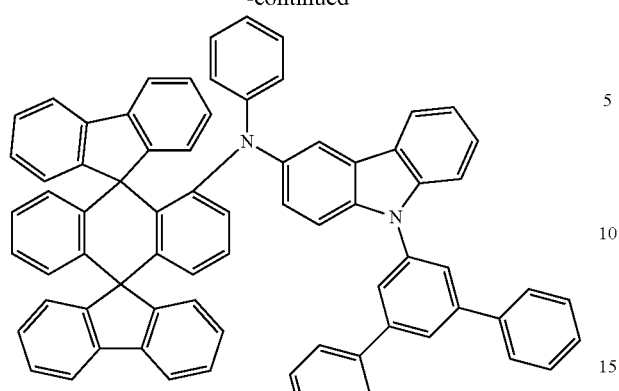
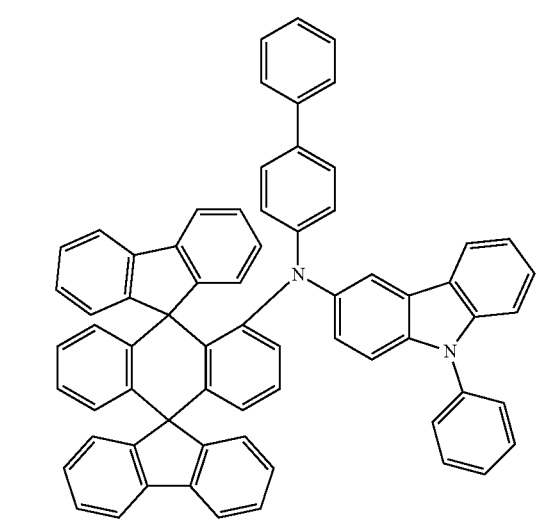
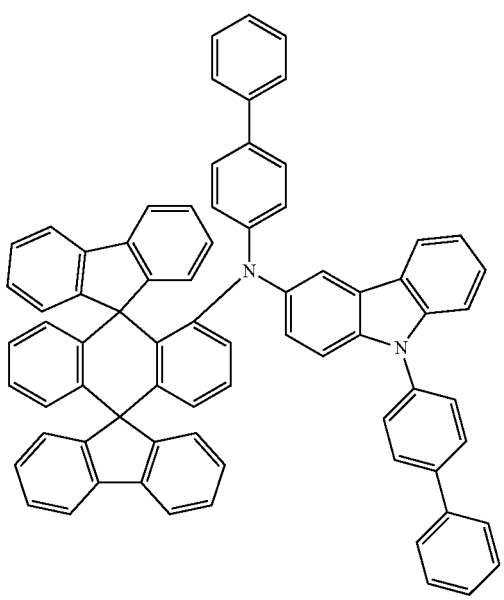
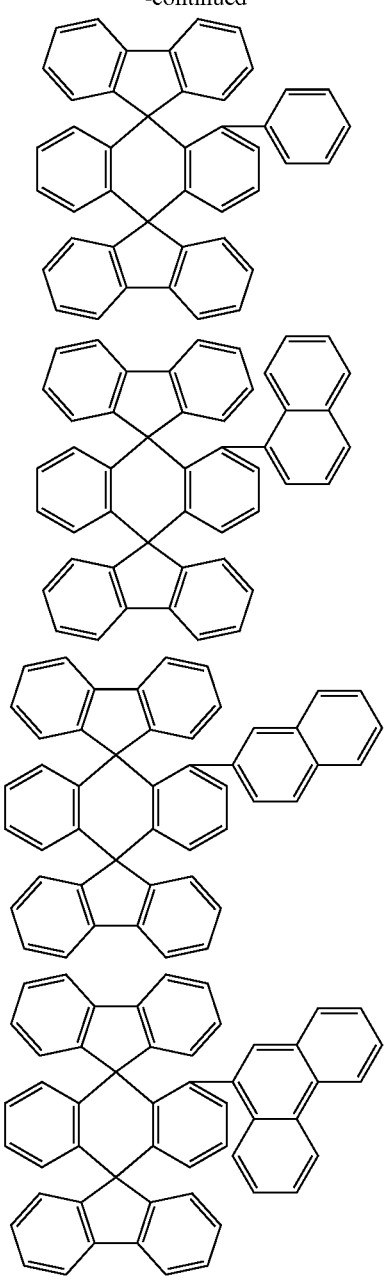
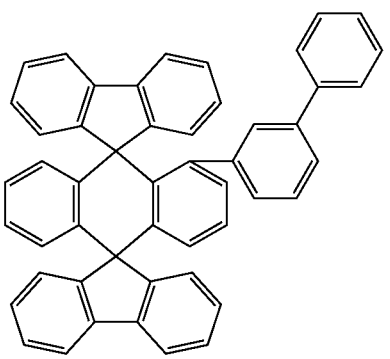

295
-continued
296
-continued
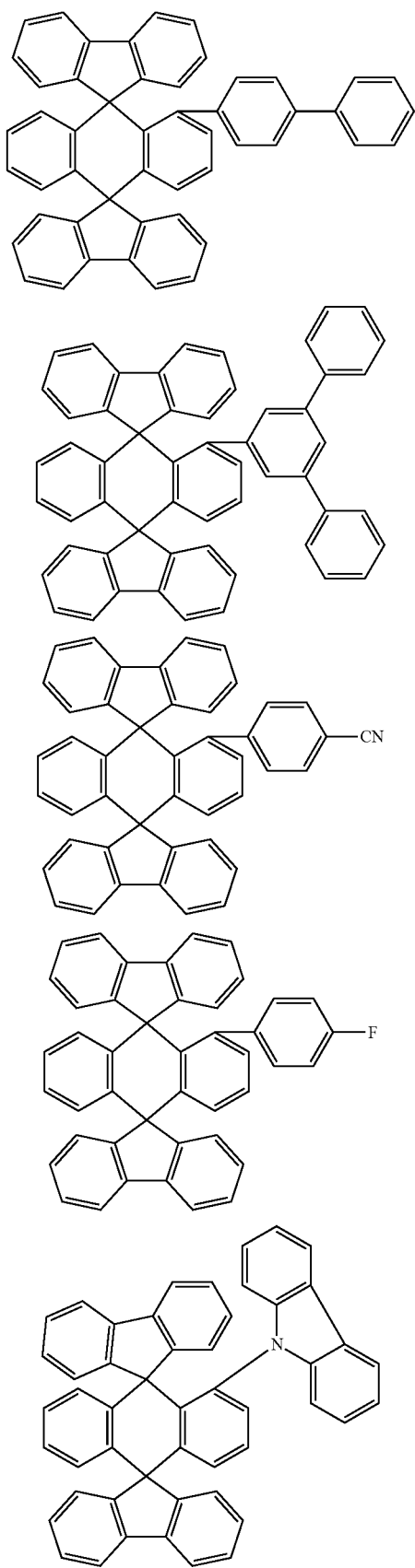
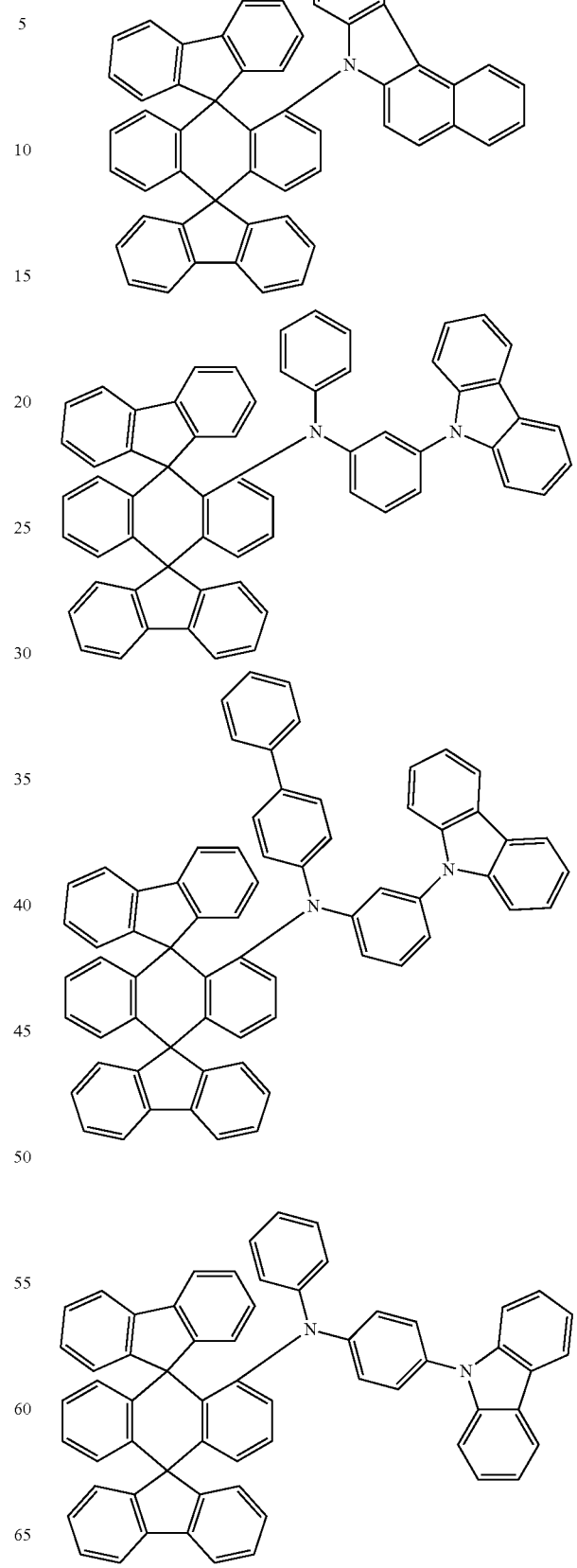

-continued

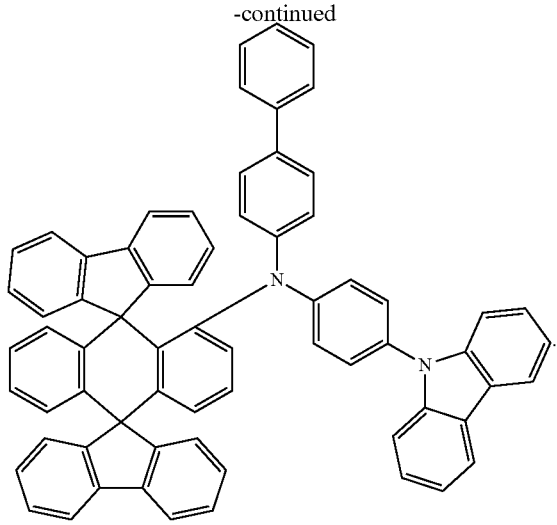

6. An organic light emitting device comprising:
a first electrode;
a second electrode provided opposite to the first electrode; and
one or more organic material layers provided between the first electrode and the second electrode,
wherein one or more layers of the organic material layers include the compound of claim 1.

7. The organic light emitting device of claim 6, wherein the organic material layer includes a hole injection layer or a hole transfer layer, and the hole injection layer or the hole transfer layer includes the compound.

8. The organic light emitting device of claim 6, wherein the organic material layer includes an electron blocking layer, and the electron blocking layer includes the compound.

9. The organic light emitting device of claim 6, wherein the organic material layer includes a light emitting layer, and the light emitting layer includes the compound.

10. The organic light emitting device of claim 6, wherein the organic material layer includes a hole blocking layer, and the hole blocking layer includes the compound.

11. The organic light emitting device of claim 6, wherein the organic material layer includes an electron transfer layer, an electron injection layer or a layer carrying out electron transfer and electron injection at the same time, and the electron transfer layer, the electron injection layer or the layer carrying out electron transfer and electron injection at the same time includes the compound.

12. The organic light emitting device of claim 6, wherein the organic material layer includes a light emitting layer, and the light emitting layer includes a compound represented by the following Chemical Formula 1-A:

[Chemical Formula 1-A]

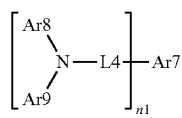

wherein, in Chemical Formula 1-A,
n1 is an integer of 1 or more;
Ar7 is a substituted or unsubstituted monovalent or more benzofluorene group; a substituted or unsubstituted monovalent or more fluoranthen group; a substituted or unsubstituted monovalent or more pyrene group; or a substituted or unsubstituted monovalent or more crycene group;
L4 is a direct bond; a substituted or unsubstituted arylene group; or a substituted or unsubstituted heteroarylene group;
Ar8 and Ar9 are the same as or different from each other, and each independently a substituted or unsubstituted aryl group; a substituted or unsubstituted silyl group; a substituted or unsubstituted germanium group; a substituted or unsubstituted alkyl group; a substituted or unsubstituted arylalkyl group; or a substituted or unsubstituted heteroaryl group, or bond to each other to form a substituted or unsubstituted ring; and
when n1 is 2 or more, each of

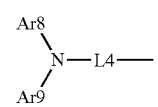

is the same as or different from each other.

13. The organic light emitting device of claim 12, wherein L4 is a direct bond, Ar7 is a divalent pyrene group, Ar8 and Ar9 are the same as or different from each other, and each independently an aryl group unsubstituted or substituted with a germanium group substituted with an alkyl group, and n1 is 2.

14. The organic light emitting device of claim 6, wherein the organic material layer includes a light emitting layer, and the light emitting layer includes a compound represented by the following Chemical Formula 2-A:

[Chemical Formula 2-A]

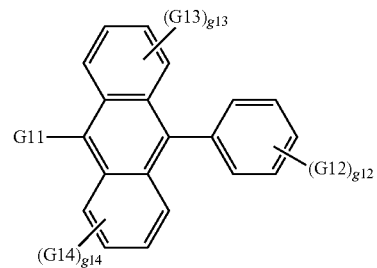

wherein, in Chemical Formula 2-A,
G11 is a 1-naphthyl group, a 2-naphthyl group, a 1-anthryl group, a 2-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 3-methyl-2-naphthyl group, a 4-methyl-1-naphthyl group, or the following chemical formula

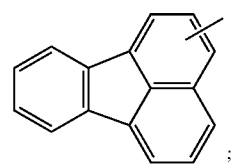

G12 is a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, an o-tolyl group, a m-tolyl group, a p-tolyl group, a p-t-butylphenyl group, a p-(2-phenylpropyl) phenyl group, a 3-methyl-2-naphthyl group, a 4-methyl-1-naphthyl group, a 4-methyl-1-anthryl group, a 4'-methylbiphenylyl group, a 4''-t-butyl-p-terphenyl-4-yl group, or a 3-fluoranthenyl group;

G13 and G14 are the same as or different from each other, and each independently hydrogen; a substituted or unsubstituted alkyl group; a substituted or unsubstituted alkoxy group; a substituted or unsubstituted aryl group; or a substituted or unsubstituted heteroaryl group;

g12 is an integer of 1 to 5;

g13 and g14 are each an integer of 1 to 4; and when g12 to g14 are each 2 or more, G12s to G14s are each independently the same as or different from each other.

15. The organic light emitting device of claim 14, wherein G11 is a phenyl group or a 1-naphthyl group, and G12 is a 2-naphthyl group.

16. The organic light emitting device of claim 12, wherein the light emitting layer includes a compound represented by the following Chemical Formula 2-A:

[Chemical Formula 2-A]

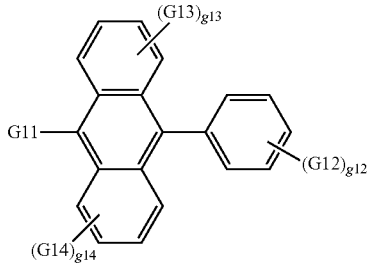

wherein, in Chemical Formula 2-A,

G11 is a phenyl group, a 1-naphthyl group, a 2-naphthyl group, a 1-anthryl group, a 2-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 3-methyl-2-naphthyl group, a 4-methyl-1-naphthyl group, or the following chemical formula

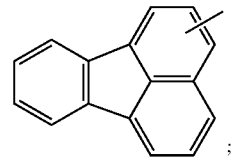

G12 is a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, an o-tolyl group, a m-tolyl group, a p-tolyl group, a p-t-butylphenyl group, a p-(2-phenylpropyl) phenyl group, a 3-methyl-2-naphthyl group, a 4-methyl-1-naphthyl group, a 4-methyl-1-anthryl group, a 4'-methylbiphenylyl group, a 4''-t-butyl-p-terphenyl-4-yl group or a 3-fluoranthenyl group;

G13 and G14 are the same as or different from each other, and each independently hydrogen; a substituted or unsubstituted alkyl group; a substituted or unsubstituted alkoxy group; a substituted or unsubstituted aryl group; or a substituted or unsubstituted heteroaryl group;

g12 is an integer of 1 to 5;

g13 and g14 are each an integer of 1 to 4; and when g12 to g14 are each 2 or more, G12s to G14s are each independently the same as or different from each other.

* * * * *